US007335814B2

(12) United States Patent

Bowles et al.

(10) Patent No.: US 7,335,814 B2

(45) Date of Patent: Feb. 26, 2008

(54) TRANSGENIC CELLS EXPRESSING GLUCOSYLTRANSFERASE NUCLEIC ACIDS

(75) Inventors: Diana Joy Bowles, Heslington (GB); Yi Li, Heslington (GB); Eng-Kiat Lim, Heslington (JP)

(73) Assignee: The University of York, Heslington (GB)

( * ) Notice: Subject to any disclaimer, the term of this patent is extended or adjusted under 35 U.S.C. 154(b) by 107 days.

(21) Appl. No.: 10/203,319

(22) PCT Filed: Feb. 8, 2001

(86) PCT No.: PCT/GB01/00477

§ 371 (c)(1), (2), (4) Date: Dec. 3, 2002

(87) PCT Pub. No.: WO01/59140

PCT Pub. Date: Aug. 16, 2001

(65) Prior Publication Data

US 2003/0226162 A1 Dec. 4, 2003

(30) Foreign Application Priority Data

Feb. 9, 2000 (GB) ................................ 0002814.2

(51) Int. Cl.

| | |
|---|---|
| *C12N 15/82* | (2006.01) |
| *A01H 5/00* | (2006.01) |
| *B30B 3/04* | (2006.01) |

(52) U.S. Cl. ....................... 800/298; 800/290; 162/100

(58) Field of Classification Search ................ 800/298, 800/290, 278, 319; 435/468; 162/100

See application file for complete search history.

(56) References Cited

U.S. PATENT DOCUMENTS

| | | | | |
|---|---|---|---|---|
| 5,981,837 A * | 11/1999 | Chapple | ..................... | 800/278 |
| 5,985,666 A * | 11/1999 | Loiselle et al. | ............. | 435/419 |

FOREIGN PATENT DOCUMENTS

| | | |
|---|---|---|
| EP | 0 967 283 A1 * | 12/1999 |
| EP | 0967283 | 12/1999 |
| WO | 97/16559 | 5/1997 |
| WO | 97/21816 | 6/1997 |
| WO | 00/00626 | 1/2000 |

OTHER PUBLICATIONS

Merriam Webster Online Dictionary. 2005, www.m-w.com/home.html.*

Lim et al (2003, Biochem. J. 373:987-992).*

Fourgoux-Nicol et al (1999, Plant Molecular Biology 40 :857-872).*

Kajita et al (1997, Plant Science 128 :109-118).*

Franke et al (2000), Plant Journal 22(3):223-234).*

Fourgoux-Nicol et al (1999, Plant Molecular Biology 40 :857-872) 10203319.*

C. Johnson-Hopson, et al., "Genomic Squence for *Arabidopsis thaliana* BAC T25N20 from chromosome I—unpublished" Database EMBL Sequence Library Online!. Jun. 18, 1998.

Y. Nakamura, et al., "Structural Analysis of *Arabidopsis thaliana* chromosome 3.1. Squence features of the regions of 4.504.864 Bp covered by sixty P1 and TAC clones" Database EMBL Sequence Library Online!, Nov. 16, 1998.

M. Bevan, et al., "EU Arabidopsis sequencing project-chromosome 4" Database EMBL Sequence Library Online!. Jul. 4, 1997.

M. Bevan, et al., "EU Arabidopsis sequencing project" Database EMBL Sequence Library Only!. Feb. 23, 1998.

Y. Nakamura, et al., "*Arabidopsis thaliana* genomic DNA, chromosome 5" Database EMBL Sequence Library Online!. Oct. 7, 1998.

X. Lin, et al., "Sequence analysis of chromosoem 2 of the plant *Arabodpsis thaliana*" Database EMBL Sequence Library Online!, Aug. 19. 1998.

X, Lin, et al., "Sequence analysis of chromosoem 2 of the plant *Arabodpsis thaliana*" Database EMBL Sequence Library Online!, Aug. 8, 1997.

Richard Graham, et al., "DNA sequence of UDP glucose indole-3-acetatebeta-D-glucosyltransferase from *Arabidopsis thaliana*" Plant Physiology, vol. 113, No. 3, 1997.

Rosamond Jackson, et al., "Identification and biochemical characterization of an Arabidopsis indole-3-acetic acid glucosyltransferase" Journal of Biological Chemistry. vol. 276, No. 6, Feb. 9, 2001.

Eng-Kiat Lim, et al., "Identification of glucosyltransferase genes involved in synthesis in Arabidopsis" Journal of Biological Chemistry, vol. 276, No. 6, Feb. 9, 2001.

Yi Li, et al., "Phylogenetic analysis of the UDP-glycosyltransferase multigene family of *Arabidopsis thaliana*" Journal of Biological Chemistry, vol. 276, No. 6, Feb. 9, 2001.

* cited by examiner

*Primary Examiner*—Stuart F. Baum

(74) *Attorney, Agent, or Firm*—Crowell & Moring LLP

(57) ABSTRACT

The invention relates to transgenic cells which have been transformed with nucleic acids encoding glucosyltransferase polypeptides (GTases) and vectors for use in transformation of said cells.

8 Claims, 59 Drawing Sheets

FIGURE 1A A062 SENSE NUCLEOTIDE SEQUENCE

Figure 33:
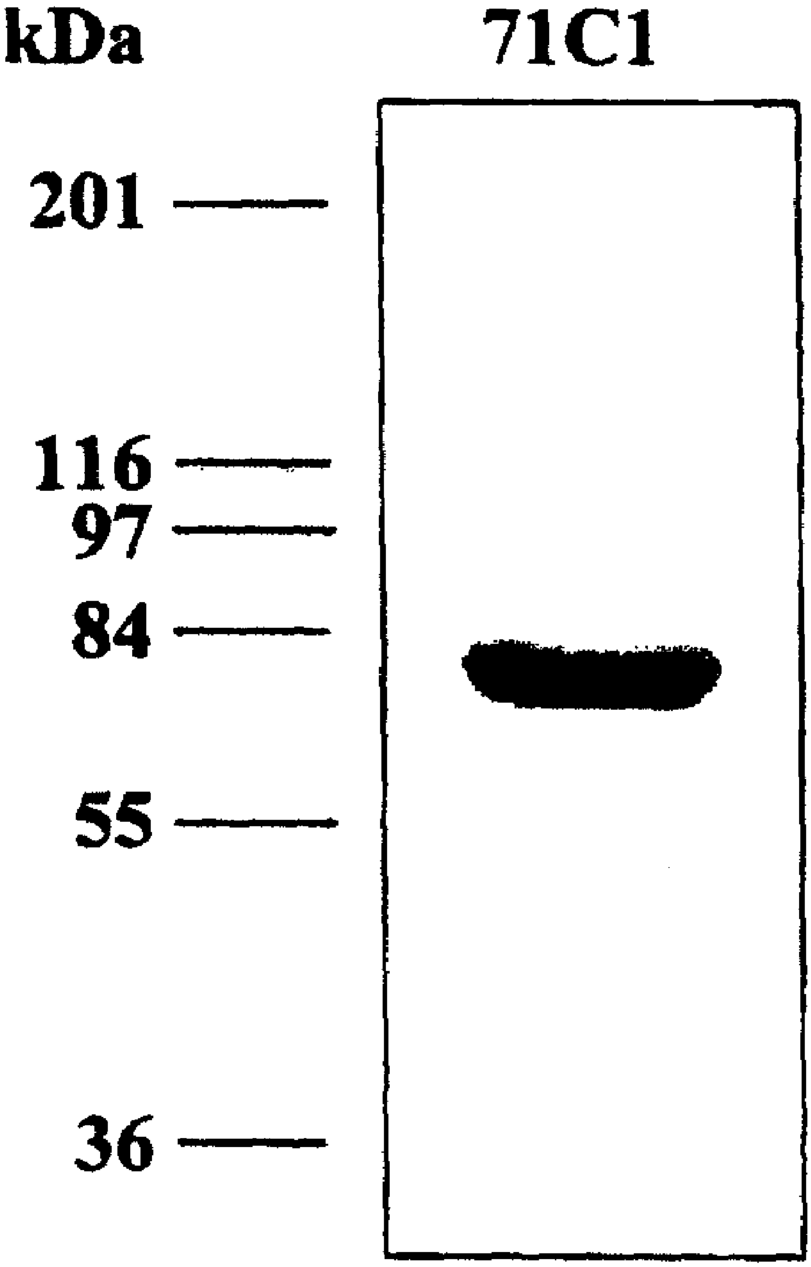

```
   1  ATGGCGCCAC CGCATTTTCT ACTGGTAACG TTTCCGGCGC AAGGTCACGT
  51  GAACCCATCT CTCCGTTTTG CTCGTCGGCT CATCAAAAGA ACCGGCGCAC
 101  GTGTCACTTT CGTCACTTGT GTCTCCGTCT TCCACAACTC CATGATCGCA
 151  AACCACAACA AAGTCGAAAA TCTCTCTTTC CTTACTTTCT CCGACGGTTT
 201  CGACGATGGA GGCATTTCCA CCTACGAAGA CCGTCAGAAA AGGTCGGTGA
 251  ATCTCAAGGT TAACGGCGAT AAGGCACTAT CGGATTTCAT CGAAGCTACT
 301  AAGAATGGTG ACTCTCCCGT GACTTGCTTG ATCTACACGA TTCTTCTCAA
 351  TTGGGCTCCA AAAGTAGCAC GTAGATTTCA ACTTCCCTCC GCTCTTCTCT
 401  GGATCCAACC GGCTTTGGTT TTCAACATCT ATTACACTCA TTTCATGGGA
 451  AACAAGTCCG TTTTCGAGTT ACCTAATCTG TCTTCTCTGG AAATCAGAGA
 501  TCTTCCATCT TTCCTCACAC CTTCCAACAC AAACAAAGGC GCATACGATG
 551  CGTTTCAAGA AATGATGGAG TTTCTCATAA AAGAAACCAA ACCGAAAATT
 601  CTCATCAACA CTTTCGATTC GCTGGAACCA GAGGCCTTAA CGGCTTTCCC
 651  GAATATCGAT ATGGTGGCGG TTGGTCCTTT ACTTCCCACG GAGATTTTCT
 701  CAGGAAGCAC CAACAAATCA GTTAAAGATC AAAGTAGTAG TTATACACTT
 751  TGGCTAGACT CGAAAACAGA GTCCTCTGTT ATTTACGTTT CCTTTGGAAC
 801  AATGGTTGAG TTGTCCAAGA AACAGATAGA GGAACTAGCG AGAGCACTCA
 851  TAGAAGGGAA ACGACCGTTT TTGTGGGTTA TAACTGATAA ATCCAACAGA
 901  GAAACGAAAA CAGAAGGAGA AGAAGAGACA GAGATTGAGA AGATAGCTGG
 951  ATTCAGACAC GAGCTTGAAG AGGTTGGGAT GATTGTGTCG TGGTGTTCGC
1001  AGATAGAGGT TTTAAGTCAC CGAGCCGTAG GTTGTTTTGT GACTCATTGT
1051  GGGTGGAGCT CGACGCTGGA GAGTTTGGTT CTTGGCGTTC CGGTTGTGGC
1101  GTTTCCGATG TGGTCGGATC AACCGACGAA CGCGAAGCTA CTGGAAGAAA
1151  GTTGGAAGAC TGGTGTGAGG GTAAGAGAGA ACAAGGATGG TTTGGTGGAG
1201  AGAGGAGAGA TCAGGAGGTG TTTGGAAGCC GTGATGGAGG AGAAGTCGGT
1251  GGAGTTGAGG GAAAACGCAA AGAAATGGAA GCGTTTAGCG ATGGAAGCGG
1301  GTAGAGAAGG AGGATCTTCG GATAAGAACA TGGAGGCTTT TGTGGAGGAT
1351  ATTTGTGGAG AATCTCTTAT TCAAAACTTG TGTGAAGCAG AGGAGGTAAA
1401  AGTAAAGTAA
```

FIGURE 1B A062 AMINO ACID SEQUENCE

```
  1 MAPPHFLLVT FPAQGHVNPS LRFARRLIKR TGARVTFVTC VSVFHNSMIA
 51 NHNKVENLSF LTFSDGFDDG GISTYEDRQK RSVNLKVNGD KALSDFIEAT
101 KNGDSPVTCL IYTILLNWAP KVARRFQLPS ALLWIQPALV FNIYYTHFMG
151 NKSVFELPNL SSLEIRDLPS FLTPSNTNKG AYDAFQEMME FLIKETKPKI
201 LINTFDSLEP EALTAFPNID MVAVGPLLPT EIFSGSTNKS VKDQSSSYTL
251 WLDSKTESSV IYVSFGTMVE LSKKQIEELA RALIEGKRPF LWVITDKSNR
301 ETKTEGEEET EIEKIAGFRH ELEEVGMIVS WCSQIEVLSH RAVGCFVTHC
351 GWSSTLESLV LGVPVVAFPM WSDQPTNAKL LEESWKTGVR VRENKDGLVE
401 RGEIRRCLEA VMEEKSVELR ENAKKWKRLA MEAGREGGSS DKNMEAFVED
451 ICGESLIQNL CEAEEVKVK
```

FIGURE 1C A062 ANTISENSE NUCLEOTIDE SEQUENCE

```
1     TTACTTTACT TTTACCTCCT CTGCTTCACA CAAGTTTTGA ATAAGAGATT
51    CTCCACAAAT ATCCTCCACA AAAGCCTCCA TGTTCTTATC CGAAGATCCT
101   CCTTCTCTAC CCGCTTCCAT CGCTAAACGC TTCCATTTCT TTGCGTTTTC
151   CCTCAACTCC ACCGACTTCT CCTCCATCAC GGCTTCCAAA CACCTCCTGA
201   TCTCTCCTCT CTCCACCAAA CCATCCTTGT TCTCTCTTAC CCTCACACCA
251   GTCTTCCAAC TTTCTTCCAG TAGCTTCGCG TTCGTCGGTT GATCCGACCA
301   CATCGGAAAC GCCACAACCG GAACGCCAAG AACCAAACTC TCCAGCGTCG
351   AGCTCCACCC ACAATGAGTC ACAAAACAAC CTACGGCTCG GTGACTTAAA
401   ACCTCTATCT GCGAACACCA CGACACAATC ATCCCAACCT CTTCAAGCTC
451   GTGTCTGAAT CCAGCTATCT TCTCAATCTC TGTCTCTTCT TCTCCTTCTG
501   TTTTCGTTTC TCTGTTGGAT TTATCAGTTA TAACCCACAA AAACGGTCGT
551   TTCCCTTCTA TGAGTGCTCT CGCTAGTTCC TCTATCTGTT TCTTGGACAA
601   CTCAACCATT GTTCCAAAGG AAACGTAAAT AACAGAGGAC TCTGTTTTCG
651   AGTCTAGCCA AAGTGTATAA CTACTACTTT GATCTTTAAC TGATTTGTTG
701   GTGCTTCCTG AGAAAATCTC CGTGGGAAGT AAAGGACCAA CCGCCACCAT
751   ATCGATATTC GGGAAAGCCG TTAAGGCCTC TGGTTCCAGC GAATCGAAAG
801   TGTTGATGAG AATTTTCGGT TTGGTTTCTT TTATGAGAAA CTCCATCATT
851   TCTTGAAACG CATCGTATGC GCCTTTGTTT GTGTTGGAAG GTGTGAGGAA
901   AGATGGAAGA TCTCTGATTT CCAGAGAAGA CAGATTAGGT AACTCGAAAA
951   CGGACTTGTT TCCCATGAAA TGAGTGTAAT AGATGTTGAA AACCAAAGCC
1001  GGTTGGATCC AGAGAAGAGC GGAGGGAAGT TGAAATCTAC GTGCTACTTT
1051  TGGAGCCCAA TTGAGAAGAA TCGTGTAGAT CAAGCAAGTC ACGGGAGAGT
1101  CACCATTCTT AGTAGCTTCG ATGAAATCCG ATAGTGCCTT ATCGCCGTTA
1151  ACCTTGAGAT TCACCGACCT TTTCTGACGG TCTTCGTAGG TGGAAATGCC
1201  TCCATCGTCG AAACCGTCGG AGAAAGTAAG GAAAGAGAGA TTTTCGACTT
1251  TGTTGTGGTT TGCGATCATG GAGTTGTGGA AGACGGAGAC ACAAGTGACG
1301  AAAGTGACAC GTGCGCCGGT TCTTTTGATG AGCCGACGAG CAAAACGGAG
1351  AGATGGGTTC ACGTGACCTT GCGCCGGAAA CGTTACCAGT AGAAAATGCG
1401  GTGGCGCCAT
```

FIGURE 2A A320 SENSE NUCLEOTIDE SEQUENCE

```
   1 ATGGAGCTAG AATCTTCTCC TCCTCTACCT CCTCATGTGA TGCTCGTATC
  51 TTTTCCAGGG CAAGGCCACG TTAATCCACT TCTTCGTCTT GGTAAGCTCT
 101 TAGCTTCAAA GGGTTTGCTC ATAACCTTCG TCACCACTGA GTCATGGGGC
 151 AAAAAGATGC GAATCTCCAA CAAAATCCAA GACCGTGTCC TCAAACCGGT
 201 TGGTAAAGGC TATCTCCGGT ATGATTTCTT CGACGACGGG CTTCCTGAAG
 251 ACGACGAAGC TAGCAGAACC AACTTAACCA TCCTCCGACC ACATCTAGAG
 301 CTGGTCGGCA AAAGAGAGAT CAAGAACCTT GTGAAACGTT ACAAGGAAGT
 351 AACGAAACAG CCCGTGACAT GTCTTATCAA CAACCCTTTC GTCTCTTGGG
 401 TCTGTGACGT GGCAGAAGAT CTTCAAATCC CTTGTGCTGT TCTTTGGGTT
 451 CAATCTTGTG CCTGCTTAGC TGCTTATTAC TATTACCACC ACAACCTAGT
 501 TGACTTCCCG ACCAAAACAG AACCCGAGAT CGATGTCCAA ATCTCTGGCA
 551 TGCCTCTCTT GAAACATGAC GAGATCCCTT CTTTCATTCA CCCTTCAAGT
 601 CCTCACTCCG CTTTGCGAGA AGTGATCATA GATCAGATTA AACGGCTTCA
 651 CAAGACTTTC TCCATTTTCA TCGACACTTT CAACTCATTG GAGAAAGACA
 701 TCATTGACCA CATGTCGACG CTCTCTCTCC CCGGTGTTAT CAGACCGCTA
 751 GGACCACTCT ACAAAATGGC TAAAACCGTA GCTTATGATG TCGTTAAAGT
 801 AAACATCTCT GAGCCAACGG ATCCTTGCAT GGAGTGGTTA GACTCGCAGC
 851 CAGTTTCCTC CGTTGTTTAC ATCTCATTCG GGACCGTTGC TTACTTGAAA
 901 CAAGAACAAA TAGACGAGAT CGCTTACGGT GTGTTAAACG CCGACGTTAC
 951 GTTCTTGTGG GTGATTAGAC AACAAGAGTT AGGTTTCAAC AAAGAGAAAC
1001 ATGTTTTGCC GGAAGAAGTT AAAGGGAAAG GGAAGATCGT TGAATGGTGT
1051 TCACAAGAGA AAGTATTATC TCATCCTTCA GTGGCATGTT TCGTGACTCA
1101 CTGTGGATGG AACTCAACGA TGGAAGCTGT GTCTTCCGGA GTCCCGACGG
1151 TTTGTTTTCC TCAATGGGGA GATCAAGTCA CGGACGCCGT TTACATGATC
1201 GATGTTTGGA AGACGGGAGT GAGGCTAAGC CGTGGAGAGG CGGAGGAGAG
1251 GTTAGTGCCG AGGGAGGAAG TTGCGGAGAG GTTGAGAGAG GTTACTAAAG
1301 GAGAGAAAGC GATCGAGTTG AAAAAGAATG CTTTGAAGTG GAAGGAAGAG
1351 GCGGAGGCGG CGGTTGCTCG CGGTGGTTCG TCGGATAGGA ATCTTGAAAA
1401 GTTTGTGGAG AAGTTGGGTG CCAAACCTGT GGGGAAAGTA CAAAACGGGA
1451 GTCATAATCA TGTCTTGGCT GGATCAATCA AAAGCTTTTA A
```

FIGURE 2B A320 AMINO ACID SEQUENCE

```
  1  MELESSPPLP PHVMLVSFPG QGHVNPLLRL GKLLASKGLL ITFVTTESWG
 51  KKMRISNKIQ DRVLKPVGKG YLRYDFFDDG LPEDDEASRT NLTILRPHLE
101  LVGKREIKNL VKRYKEVTKQ PVTCLINNPF VSWVCDVAED LQIPCAVLWV
151  QSCACLAAYY YYHHNLVDFP TKTEPEIDVQ ISGMPLLKHD EIPSFIHPSS
201  PHSALREVII DQIKRLHKTF SIFIDTFNSL EKDIIDHMST LSLPGVIRPL
251  GPLYKMAKTV AYDVVKVNIS EPTDPCMEWL DSQPVSSVVY ISFGTVAYLK
301  QEQIDEIAYG VLNADVTFLW VIRQQELGFN KEKHVLPEEV KGKGKIVEWC
351  SQEKVLSHPS VACFVTHCGW NSTMEAVSSG VPTVCFPQWG DQVTDAVYMI
401  DVWKTGVRLS RGEAEERLVP REEVAERLRE VTKGEKAIEL KKNALKWKEE
451  AEAAVARGGS SDRNLEKFVE KLGAKPVGKV QNGSHNHVLA GSIKSF
```

FIGURE 2C A320 ANTISENSE NUCLEOTIDE SEQUENCE

1 TTAAAAGCTT TTGATTGATC CAGCCAAGAC ATGATTATGA CTCCCGTTTT
51 GTACTTTCCC CACAGGTTTG GCACCCAACT TCTCCACAAA CTTTTCAAGA
101 TTCCTATCCG ACGAACCACC GCGAGCAACC GCCGCCTCCG CCTCTTCCTT
151 CCACTTCAAA GCATTCTTTT TCAACTCGAT CGCTTTCTCT CCTTTAGTAA
201 CCTCTCTCAA CCTCTCCGCA ACTTCCTCCC TCGGCACTAA CCTCTCCTCC
251 GCCTCTCCAC GGCTTAGCCT CACTCCCGTC TTCCAAACAT CGATCATGTA
301 AACGGCGTCC GTGACTTGAT CTCCCCATTG AGGAAAACAA ACCGTCGGGA
351 CTCCGGAAGA CACAGCTTCC ATCGTTGAGT TCCATCCACA GTGAGTCACG
401 AAACATGCCA CTGAAGGATG AGATAATACT TTCTCTTGTG AACACCATTC
451 AACGATCTTC CCTTTCCCTT TAACTTCTTC CGGCAAAACA TGTTTCTCTT
501 TGTTGAAACC TAACTCTTGT TGTCTAATCA CCCACAAGAA CGTAACGTCG
551 GCGTTTAACA CACCGTAAGC GATCTCGTCT ATTTGTTCTT GTTTCAAGTA
601 AGCAACGGTC CCGAATGAGA TGTAAACAAC GGAGGAAACT GGCTGCGAGT
651 CTAACCACTC CATGCAAGGA TCCGTTGGCT CAGAGATGTT TACTTTAACG
701 ACATCATAAG CTACGGTTTT AGCCATTTTG TAGAGTGGTC CTAGCGGTCT
751 GATAACACCG GGGAGAGAGA GCGTCGACAT GTGGTCAATG ATGTCTTTCT
801 CCAATGAGTT GAAAGTGTCG ATGAAAATGG AGAAAGTCTT GTGAAGCCGT
851 TTAATCTGAT CTATGATCAC TTCTCGCAAA GCGGAGTGAG GACTTGAAGG
901 GTGAATGAAA GAAGGGATCT CGTCATGTTT CAAGAGAGGC ATGCCAGAGA
951 TTTGGACATC GATCTCGGGT TCTGTTTTGG TCGGGAAGTC AACTAGGTTG
1001 TGGTGGTAAT AGTAATAAGC AGCTAAGCAG GCACAAGATT GAACCCAAAG
1051 AACAGCACAA GGGATTTGAA GATCTTCTGC CACGTCACAG ACCCAAGAGA
1101 CGAAAGGGTT GTTGATAAGA CATGTCACGG GCTGTTTCGT TACTTCCTTG
1151 TAACGTTTCA CAAGGTTCTT GATCTCTCTT TTGCCGACCA GCTCTAGATG
1201 TGGTCGGAGG ATGGTTAAGT TGGTTCTGCT AGCTTCGTCG TCTTCAGGAA
1251 GCCCGTCGTC GAAGAAATCA TACCGGAGAT AGCCTTTACC AACCGGTTTG
1301 AGGACACGGT CTTGGATTTT GTTGGAGATT CGCATCTTTT TGCCCCATGA
1351 CTCAGTGGTG ACGAAGGTTA TGAGCAAACC CTTTGAAGCT AAGAGCTTAC
1401 CAAGACGAAG AAGTGGATTA ACGTGGCCTT GCCCTGGAAA AGATACGAGC
1451 ATCACATGAG GAGGTAGAGG AGGAGAAGAT TCTAGCTCCA T

FIGURE 3A A41 SENSE NUCLEOTIDE SEQUENCE

```
   1 ATGGGATCCA TATCAGAAAT GGTGTTCGAA ACTTGTCCAT CTCCAAACCC
  51 AATTCATGTA ATGCTCGTCT CGTTTCAAGG ACAAGGCCAC GTCAACCCTC
 101 TTCTTCGTCT CGGCAAGTTA ATTGCTTCAA AGGGTTTACT CGTTACCTTC
 151 GTTACAACGG AGCTTTGGGG CAAGAAAATG AGACAAGCCA ACAAAATCGT
 201 TGACGGTGAA CTTAAACCGG TTGGTTCCGG TTCAATCCGG TTTGAGTTCT
 251 TTGATGAAGA ATGGGCAGAG GATGATGACC GGAGAGCTGA TTTCTCTTTG
 301 TACATTGCTC ACCTAGAGAG CGTTGGGATA CGAGAAGTGT CTAAGCTTGT
 351 GAGAAGATAC GAGGAAGCGA ACGAGCCTGT CTCGTGTCTT ATCAATAACC
 401 CGTTTATCCC ATGGGTCTGC CACGTGGCGG AAGAGTTCAA CATTCCTTGT
 451 GCGGTTCTCT GGGTTCAGTC TTGTGCTTGT TTCTCTGCTT ATTACCATTA
 501 CCAAGATGGC TCTGTTTCAT TCCCTACGGA AACAGAGCCT GAGCTCGATG
 551 TGAAGCTTCC TTGTGTTCCT GTCTTGAAGA ACGACGAGAT TCCTAGCTTT
 601 CTCCATCCTT CTTCTAGGTT CACGGGTTTT CGACAAGCGA TTCTTGGGCA
 651 ATTCAAGAAT CTGAGCAAGT CCTTCTGTGT TCTAATCGAT TCTTTTGACT
 701 CATTGGAACA AGAAGTTATC GATTACATGT CAAGTCTTTG TCCGGTTAAA
 751 ACCGTTGGAC CGCTTTTCAA AGTTGCTAGG ACAGTTACTT CTGACGTAAG
 801 CGGTGACATT TGCAAATCAA CAGATAAATG CCTCGAGTGG TTAGACTCGA
 851 GGCCTAAATC GTCAGTTGTC TACATTTCGT TCGGGACAGT TGCATATTTG
 901 AAGCAAGAAC AGATCGAAGA GATCGCTCAC GGAGTTTTGA AGTCGGGTTT
 951 ATCGTTCTTG TGGGTGATTA GACCTCCACC ACACGATCTG AAGGTCGAGA
1001 CACATGTCTT GCCTCAAGAA CTTAAAGAGA GTAGTGCTAA AGGTAAAGGG
1051 ATGATTGTGG ATTGGTGCCC ACAAGAGCAA GTCTTGTCTC ATCCTTCAGT
1101 GGCATGCTTC GTGACTCATT GTGGATGGAA CTCGACAATG GAATCTTTGT
1151 CTTCAGGTGT TCCGGTGGTT TGTTGTCCGC AATGGGGAGA TCAAGTGACT
1201 GATGCAGTGT ATTTGATCGA TGTTTTCAAG ACCGGGGTTA GACTAGGCCG
1251 TGGAGCGACC GAGGAGAGGG TAGTGCCAAG GGAGGAAGTG GCGGAGAAGC
1301 TTTTGGAAGC GACAGTTGGG GAGAAGGCAG AGGAGTTGAG AAAGAACGCT
1351 TTGAAATGGA AGGCGGAGGC GGAAGCAGCG GTGGCTCCAG GAGGTTCGTC
1401 GGATAAGAAT TTTAGGGAGT TTGTGGAGAA GTTAGGTGCG GGAGTAACGA
1451 AGACTAAAGA TAATGGATAC TAG
```

FIGURE 3B  A41 AMINO ACID SEQUENCE

```
  1  MVFETCPSPN  PIHVMLVSFQ  GQGHVNPLLR  LGKLIASKGL  LVTFVTTELW
 51  GKKMRQANKI  VDGELKPVGS  GSIRFEFFDE  EWAEDDDRRA  DFSLYIAHLE
101  SVGIREVSKL  VRRYEEANEP  VSCLINNPFI  PWVCHVAEEF  NIPCAVLWVQ
151  SCACFSAYYH  YQDGSVSFPT  ETEPELDVKL  PCVPVLKNDE  IPSFLHPSSR
201  FTGFRQAILG  QFKNLSKSFC  VLIDSFDSLE  QEVIDYMSSL  CPVKTVGPLF
251  KVARTVTSDV  SGDICKSTDK  CLEWLDSRPK  SSVVYISFGT  VAYLKQEQIE
301  EIAHGVLKSG  LSFLWVIRPP  PHDLKVETHV  LPQELKESSA  KGKGMIVDWC
351  PQEQVLSHPS  VACFVTHCGW  NSTMESLSSG  VPVVCCPQWG  DQVTDAVYLI
401  DVFKTGVRLG  RGATEERVVP  REEVAEKLLE  ATVGEKAEEL  RKNALKWKAE
451  AEAAVAPGGS  SDKNFREFVE  KLGAGVTKTK  DNGY
```

FIGURE 3C A41 ANTISENSE NUCLEOTIDE SEQUENCE

1 CTAGTATCCA TTATCTTTAG TCTTCGTTAC TCCCGCACCT AACTTCTCCA
51 CAAACTCCCT AAAATTCTTA TCCGACGAAC CTCCTGGAGC CACCGCTGCT
101 TCCGCCTCCG CCTTCCATTT CAAAGCGTTC TTTCTCAACT CCTCTGCCTT
151 CTCCCCAACT GTCGCTTCCA AAAGCTTCTC CGCCACTTCC TCCCTTGGCA
201 CTACCCTCTC CTCGGTCGCT CCACGGCCTA GTCTAACCCC GGTCTTGAAA
251 ACATCGATCA AATACACTGC ATCAGTCACT TGATCTCCCC ATTGCGGACA
301 ACAAACCACC GGAACACCTG AAGACAAAGA TTCCATTGTC GAGTTCCATC
351 CACAATGAGT CACGAAGCAT GCCACTGAAG GATGAGACAA GACTTGCTCT
401 TGTGGGCACC AATCCACAAT CATCCCTTTA CCTTTAGCAC TACTCTCTTT
451 AAGTTCTTGA GGCAAGACAT GTGTCTCGAC CTTCAGATCG TGTGGTGGAG
501 GTCTAATCAC CCACAAGAAC GATAAACCCG ACTTCAAAAC TCCGTGAGCG
551 ATCTCTTCGA TCTGTTCTTG CTTCAAATAT GCAACTGTCC CGAACGAAAT
601 GTAGACAACT GACGATTTAG GCCTCGAGTC TAACCACTCG AGGCATTTAT
651 CTGTTGATTT GCAAATGTCA CCGCTTACGT CAGAAGTAAC TGTCCTAGCA
701 ACTTTGAAAA GCGGTCCAAC GGTTTTAACC GGACAAAGAC TTGACATGTA
751 ATCGATAACT TCTTGTTCCA ATGAGTCAAA AGAATCGATT AGAACACAGA
801 AGGACTTGCT CAGATTCTTG AATTGCCCAA GAATCGCTTG TCGAAAACCC
851 GTGAACCTAG AAGAAGGATG GAGAAAGCTA GGAATCTCGT CGTTCTTCAA
901 GACAGGAACA CAAGGAAGCT TCACATCGAG CTCAGGCTCT GTTTCCGTAG
951 GGAATGAAAC AGAGCCATCT TGGTAATGGT AATAAGCAGA GAAACAAGCA
1001 CAAGACTGAA CCCAGAGAAC CGCACAAGGA ATGTTGAACT CTTCCGCCAC
1051 GTGGCAGACC CATGGGATAA ACGGGTTATT GATAAGACAC GAGACAGGCT
1101 CGTTCGCTTC CTCGTATCTT CTCACAAGCT TAGACACTTC TCGTATCCCA
1151 ACGCTCTCTA GGTGAGCAAT GTACAAAGAG AAATCAGCTC TCCGGTCATC
1201 ATCCTCTGCC CATTCTTCAT CAAAGAACTC AAACCGGATT GAACCGGAAC
1251 CAACCGGTTT AAGTTCACCG TCAACGATTT TGTTGGCTTG TCTCATTTTC
1301 TTGCCCCAAA GCTCCGTTGT AACGAAGGTA ACGAGTAAAC CCTTTGAAGC
1351 AATTAACTTG CCGAGACGAA GAAGAGGGTT GACGTGGCCT TGTCCTTGAA
1401 ACGAGACGAG CATTACATGA ATTGGGTTTG GAGATGGACA AGTTTCGAAC
1451 ACCATTTCTG ATATGGATCC CAT

FIGURE 4A A42 SENSE NUCLEOTIDE SEQUENCE

```
   1 ATGGACCCGT CTCGTCATAC TCATGTGATG CTCGTATCTT TCCCCGGCCA
  51 AGGTCACGTA AACCCTCTAC TTCGTCTCGG AAAGCTCATA GCCTCTAAAG
 101 GCTTACTCGT CACCTTTGTC ACCACAGAGA AGCCATGGGG CAAGAAGATG
 151 CGTCAAGCCA ACAAGATTCA AGACGGTGTG CTCAAACCGG TCGGTCTAGG
 201 TTTCATCCGG TTTGAGTTCT TCTCTGACGG CTTCGCCGAC GACGATGAAA
 251 AAAGATTCGA CTTCGATGCC TTCCGACCAC ACCTTGAAGC TGTCGGAAAA
 301 CAAGAGATCA AGAATCTCGT TAAGAGATAT AACAAGGAGC CGGTGACGTG
 351 TCTCATAAAC AACGCTTTTG TCCCATGGGT ATGTGATGTC GCCGAGGAGC
 401 TTCACATCCC TTCGGCTGTT CTATGGGTCC AGTCTTGTGC TTGTCTCACG
 451 GCTTATTACT ATTACCACCA CCGGTTAGTT AAGTTCCCGA CCAAAACCGA
 501 GCCGGACATC AGCGTTGAAA TCCCTTGCTT GCCATTGTTA AAGCATGACG
 551 AGATCCCAAG CTTTCTTCAC CCTTCGTCTC CGTATACAGC TTTTGGAGAT
 601 ATCATTTTAG ACCAGTTAAA GAGATTCGAA AACCACAAGT CTTTCTATCT
 651 TTTCATCGAC ACTTTTCGCG AACTAGAAAA AGACATCATG GACCACATGT
 701 CACAACTTTG TCCTCAAGCC ATCATCAGTC CTGTCGGTCC GCTCTTCAAG
 751 ATGGCTCAAA CCTTGAGTTC TGACGTTAAG GGAGATATAT CCGAGCCAGC
 801 GAGTGACTGC ATGGAATGGC TTGACTCAAG AGAACCATCC TCAGTCGTTT
 851 ACATCTCCTT TGGGACTATA GCCAACTTGA AGCAAGAGCA GATGGAGGAG
 901 ATCGCTCATG GCGTTTTGAG CTCTGGCTTG TCGGTCTTAT GGGTGGTTCG
 951 GCCTCCCATG GAAGGGACAT TTGTAGAACC ACATGTTTTG CCTCGAGAGC
1001 TCGAAGAAAA GGGTAAAATC GTGGAATGGT GTCCCCAAGA GAGAGTCTTG
1051 GCTCATCCTG CGATTGCTTG TTTCTTAAGT CACTGCGGAT GGAACTCGAC
1101 AATGGAGGCT TTAACTGCCG GAGTCCCCGT TGTTTGTTTT CCGCAATGGG
1151 GAGATCAAGT GACTGATGCG GTGTACTTGG CTGATGTTTT CAAGACAGGA
1201 GTGAGACTAG GCCGCGGAGC CGCTGAGGAG ATGATTGTTT CGAGGGAGGT
1251 TGTAGCAGAG AAGCTGCTTG AGGCCACAGT TGGGGAAAAG GCGGTGGAGC
1301 TGAGAGAAAA CGCTCGGAGG TGGAAGGCGG AGGCCGAGGC CGCCGTGGCG
1351 GACGGTGGAT CATCTGATAT GAACTTTAAA GAGTTTGTGG ACAAGTTGGT
1401 TACGAAACAT GTGACGAGAG AAGACAACGG AGAACACTAG
```

FIGURE 4B A42 AMINO ACID SEQUENCE

1 MDPSRHTHVM LVSFPGQGHV NPLLRLGKLI ASKGLLVTFV TTEKPWGKKM

51 RQANKIQDGV LKPVGLGFIR FEFFSDGFAD DDEKRFDFDA FRPHLEAVGK

101 QEIKNLVKRY NKEPVTCLIN NAFVPWVCDV AEELHIPSAV LWVQSCACLT

151 AYYYYHHRLV KFPTKTEPDI SVEIPCLPLL KHDEIPSFLH PSSPYTAFGD

201 IILDQLKRFE NHKSFYLFID TFRELEKDIM DHMSQLCPQA IISPVGPLFK

251 MAQTLSSDVK GDISEPASDC MEWLDSREPS SVVYISFGTI ANLKQEQMEE

301 IAHGVLSSGL SVLWVVRPPM EGTFVEPHVL PRELEEKGKI VEWCPQERVL

351 AHPAIACFLS HCGWNSTMEA LTAGVPVVCF PQWGDQVTDA VYLADVFKTG

401 VRLGRGAAEE MIVSREVVAE KLLEATVGEK AVELRENARR WKAEAEAAVA

451 DGGSSDMNFK EFVDKLVTKH VTREDNGEH

FIGURE 4C A42 ANTISENSE NUCLEOTIDE SEQUENCE

```
   1 CTAGTGTTCT CCGTTGTCTT CTCTCGTCAC ATGTTTCGTA ACCAACTTGT
  51 CCACAAACTC TTTAAAGTTC ATATCAGATG ATCCACCGTC CGCCACGGCG
 101 GCCTCGGCCT CCGCCTTCCA CCTCCGAGCG TTTTCTCTCA GCTCCACCGC
 151 CTTTTCCCCA ACTGTGGCCT CAAGCAGCTT CTCTGCTACA ACCTCCCTCG
 201 AAACAATCAT CTCCTCAGCG GCTCCGCGGC CTAGTCTCAC TCCTGTCTTG
 251 AAAACATCAG CCAAGTACAC CGCATCAGTC ACTTGATCTC CCCATTGCGG
 301 AAAACAAACA ACGGGGACTC CGGCAGTTAA AGCCTCCATT GTCGAGTTCC
 351 ATCCGCAGTG ACTTAAGAAA CAAGCAATCG CAGGATGAGC CAAGACTCTC
 401 TCTTGGGGAC ACCATTCCAC GATTTTACCC TTTTCTTCGA GCTCTCGAGG
 451 CAAAACATGT GGTTCTACAA ATGTCCCTTC CATGGGAGGC CGAACCACCC
 501 ATAAGACCGA CAAGCCAGAG CTCAAAACGC CATGAGCGAT CTCCTCCATC
 551 TGCTCTTGCT TCAAGTTGGC TATAGTCCCA AAGGAGATGT AAACGACTGA
 601 GGATGGTTCT CTTGAGTCAA GCCATTCCAT GCAGTCACTC GCTGGCTCGG
 651 ATATATCTCC CTTAACGTCA GAACTCAAGG TTTGAGCCAT CTTGAAGAGC
 701 GGACCGACAG GACTGATGAT GGCTTGAGGA CAAAGTTGTG ACATGTGGTC
 751 CATGATGTCT TTTTCTAGTT CGCGAAAAGT GTCGATGAAA AGATAGAAAG
 801 ACTTGTGGTT TTCGAATCTC TTTAACTGGT CTAAAATGAT ATCTCCAAAA
 851 GCTGTATACG GAGACGAAGG GTGAAGAAAG CTTGGGATCT CGTCATGCTT
 901 TAACAATGGC AAGCAAGGGA TTTCAACGCT GATGTCCGGC TCGGTTTTGG
 951 TCGGGAACTT AACTAACCGG TGGTGGTAAT AGTAATAAGC CGTGAGACAA
1001 GCACAAGACT GGACCCATAG AACAGCCGAA GGGATGTGAA GCTCCTCGGC
1051 GACATCACAT ACCCATGGGA CAAAAGCGTT GTTTATGAGA CACGTCACCG
1101 GCTCCTTGTT ATATCTCTTA ACGAGATTCT TGATCTCTTG TTTTCCGACA
1151 GCTTCAAGGT GTGGTCGGAA GGCATCGAAG TCGAATCTTT TTTCATCGTC
1201 GTCGGCGAAG CCGTCAGAGA AGAACTCAAA CCGGATGAAA CCTAGACCGA
1251 CCGGTTTGAG CACACCGTCT TGAATCTTGT TGGCTTGACG CATCTTCTTG
1301 CCCCATGGCT TCTCTGTGGT GACAAAGGTG ACGAGTAAGC CTTTAGAGGC
1351 TATGAGCTTT CCGAGACGAA GTAGAGGGTT TACGTGACCT TGGCCGGGGA
1401 AAGATACGAG CATCACATGA GTATGACGAG ACGGGTCCAT
```

FIGURE 5A A43 SENSE NUCLEOTIDE SEQUENCE

```
   1 ATGGAGATGG AATCGTCGTT ACCTCATGTG ATGCTCGTAT CATTCCCAGG
  51 GCAAGGTCAC ATAAGCCCTC TTCTTCGTCT CGGAAAGATC ATTGCCTCTA
 101 AAGGCTTAAT CGTCACCTTT GTAACCACAG AGGAACCATT GGGCAAGAAG
 151 ATGCGTCAAG CCAACAATAT TCAAGACGGT GTGCTCAAAC CGGTCGGGCT
 201 AGGTTTTCTC CGGTTCGAGT TCTTCGAGGA TGGATTTGTC TACAAAGAAG
 251 ACTTTGATTT GTTACAAAAA TCACTTGAAG TTTCCGGAAA ACGAGAGATC
 301 AAGAATCTTG TCAAGAAATA TGAGAAGCAA CCAGTGAGAT GTCTCATAAA
 351 TAATGCCTTT GTTCCATGGG TTTGTGACAT AGCCGAGGAG CTTCAAATCC
 401 CATCAGCTGT TCTTTGGGTC CAGTCTTGTG CTTGCCTCGC CGCTTATTAC
 451 TATTACCACC ACCAGTTAGT TAAGTTTCCG ACCGAAACCG AGCCGGAAAT
 501 AACCGTTGAC GTCCCTTTCA AGCCATTAAC ATTGAAGCAT GACGAGATCC
 551 CTAGCTTTCT TCACCCTTCC TCTCCGCTGT CCTCTATAGG AGGTACCATT
 601 TTAGAGCAGA TCAAGCGACT TCACAAGCCT TTCTCTGTTC TCATCGAAAC
 651 TTTTCAAGAA CTTGAAAAAG ATACCATTGA CCACATGTCC CAGCTCTGCC
 701 CTCAAGTCAA CTTCAACCCC ATCGGTCCGC TTTTTACTAT GGCTAAAACC
 751 ATAAGGTCTG ACATCAAGGG AGACATCTCC AAGCCAGATA GTGACTGCAT
 801 AGAGTGGCTT GACTCGAGAG AACCATCCTC CGTTGTTTAC ATCTCTTTTG
 851 GGACTTTGGC TTTCTTGAAG CAAAACCAGA TCGACGAGAT TGCTCACGGC
 901 ATTCTCAACT CCGGGTTGTC CTGCTTATGG GTTTTGCGGC CTCCCTTAGA
 951 AGGCTTAGCC ATAGAACCGC ATGTCTTGCC TCTAGAGCTT GAAGAGAAAG
1001 GGAAGATTGT GGAATGGTGT CAACAAGAGA AAGTTTTGGC TCATCCTGCG
1051 GTTGCTTGCT TCTTAAGTCA CTGTGGATGG AACTCAACCA TGGAGGCTTT
1101 AACTTCAGGA GTTCCCGTTA TTTGTTTCCC GCAGTGGGGA GATCAGGTGA
1151 CAAATGCGGT GTACATGATT GATGTTTTCA AGACAGGATT GAGACTCAGC
1201 CGTGGAGCTT CCGATGAGAG GATTGTTCCA AGGGAGGAGG TTGCTGAGCG
1251 ACTGCTTGAG GCCACCGTTG GAGAGAAGGC GGTGGAGCTG AGAGAAAACG
1301 CTCGGAGGTG GAAGGAGGAG GCGGAGTCTG CCGTGGCTTA CGGTGGAACA
1351 TCGGAAAGGA ATTTTCAAGA GTTTGTTGAC AAGTTGGTTG ATGTCAAGAC
1401 AATGACAAAC ATTAATAATG TCGTGTAAGT
```

FIGURE 5B A43 AMINO ACID SEQUENCE

```
  1 MEMESSLPHV MLVSFPGQGH ISPLLRLGKI IASKGLIVTF VTTEEPLGKK
 51 MRQANNIQDG VLKPVGLGFL RFEFFEDGFV YKEDFDLLQK SLEVSGKREI
101 KNLVKKYEKQ PVRCLINNAF VPWVCDIAEE LQIPSAVLWV QSCACLAAYY
151 YYHHQLVKFP TETEPEITVD VPFKPLTLKH DEIPSFLHPS SPLSSIGGTI
201 LEQIKRLHKP FSVLIETFQE LEKDTIDHMS QLCPQVNFNP IGPLFTMAKT
251 IRSDIKGDIS KPDSDCIEWL DSREPSSVVY ISFGTLAFLK QNQIDEIAHG
301 ILNSGLSCLW VLRPPLEGLA IEPHVLPLEL EEKGKIVEWC QQEKVLAHPA
351 VACFLSHCGW NSTMEALTSG VPVICFPQWG DQVTNAVYMI DVFKTGLRLS
401 RGASDERIVP REEVAERLLE ATVGEKAVEL RENARRWKEE AESAVAYGGT
451 SERNFQEFVD KLVDVKTMTN INNVV
```

FIGURE 5C A43 ANTISENSE NUCLEOTIDE SEQUENCE

```
   1 ACTTACACGA CATTATTAAT GTTTGTCATT GTCTTGACAT CAACCAACTT
  51 GTCAACAAAC TCTTGAAAAT TCCTTTCCGA TGTTCCACCG TAAGCCACGG
 101 CAGACTCCGC CTCCTCCTTC CACCTCCGAG CGTTTTCTCT CAGCTCCACC
 151 GCCTTCTCTC CAACGGTGGC CTCAAGCAGT CGCTCAGCAA CCTCCTCCCT
 201 TGGAACAATC CTCTCATCGG AAGCTCCACG GCTGAGTCTC AATCCTGTCT
 251 TGAAAACATC AATCATGTAC ACCGCATTTG TCACCTGATC TCCCCACTGC
 301 GGGAAACAAA TAACGGGAAC TCCTGAAGTT AAAGCCTCCA TGGTTGAGTT
 351 CCATCCACAG TGACTTAAGA AGCAAGCAAC CGCAGGATGA GCCAAAACTT
 401 TCTCTTGTTG ACACCATTCC ACAATCTTCC CTTTCTCTTC AAGCTCTAGA
 451 GGCAAGACAT GCGGTTCTAT GGCTAAGCCT TCTAAGGGAG GCCGCAAAAC
 501 CCATAAGCAG GACAACCCGG AGTTGAGAAT GCCGTGAGCA ATCTCGTCGA
 551 TCTGGTTTTG CTTCAAGAAA GCCAAAGTCC CAAAAGAGAT GTAAACAACG
 601 GAGGATGGTT CTCTCGAGTC AAGCCACTCT ATGCAGTCAC TATCTGGCTT
 651 GGAGATGTCT CCCTTGATGT CAGACCTTAT GGTTTTAGCC ATAGTAAAAA
 701 GCGGACCGAT GGGGTTGAAG TTGACTTGAG GGCAGAGCTG GGACATGTGG
 751 TCAATGGTAT CTTTTTCAAG TTCTTGAAAA GTTTCGATGA GAACAGAGAA
 801 AGGCTTGTGA AGTCGCTTGA TCTGCTCTAA AATGGTACCT CCTATAGAGG
 851 ACAGCGGAGA GGAAGGGTGA AGAAAGCTAG GGATCTCGTC ATGCTTCAAT
 901 GTTAATGGCT TGAAAGGGAC GTCAACGGTT ATTTCCGGCT CGGTTTCGGT
 951 CGGAAACTTA ACTAACTGGT GGTGGTAATA GTAATAAGCG GCGAGGCAAG
1001 CACAAGACTG GACCCAAAGA ACAGCTGATG GGATTTGAAG CTCCTCGGCT
1051 ATGTCACAAA CCCATGGAAC AAAGGCATTA TTTATGAGAC ATCTCACTGG
1101 TTGCTTCTCA TATTTCTTGA CAAGATTCTT GATCTCTCGT TTTCCGGAAA
1151 CTTCAAGTGA TTTTTGTAAC AAATCAAAGT CTTCTTTGTA GACAAATCCA
1201 TCCTCGAAGA ACTCGAACCG GAGAAAACCT AGCCCGACCG GTTTGAGCAC
1251 ACCGTCTTGA ATATTGTTGG CTTGACGCAT CTTCTTGCCC AATGGTTCCT
1301 CTGTGGTTAC AAAGGTGACG ATTAAGCCTT TAGAGGCAAT GATCTTTCCG
1351 AGACGAAGAA GAGGGCTTAT GTGACCTTGC CCTGGGAATG ATACGAGCAT
1401 CACATGAGGT AACGACGATT CCATCTCCAT
```

FIGURE 6A A911 SENSE NUCLEOTIDE SEQUENCE

```
   1 ATGGGCAGTA GTGAGGGTCA AGAAACACAT GTCCTAATGG TAACACTACC
  51 ATTCCAAGGT CACATCAATC CAATGCTCAA ACTCGCAAAA CATCTCTCGT
 101 TATCATCAAA GAACCTACAC ATCAATCTCG CCACTATTGA GTCAGCCCGT
 151 GATCTCCTCT CCACCGTAGA AAAACCTCGT TATCCGGTGG ACCTCGTGTT
 201 CTTCTCCGAT GGTCTACCTA AAGAAGATCC AAAGGCCCCT GAAACTCTTT
 251 TGAAGTCATT GAATAAAGTC GGAGCCATGA ACTTGTCTAA AATCATCGAA
 301 GAAAAGAGAT ACTCTTGTAT CATCTCTTCG CCTTTTACTC CATGGGTTCC
 351 AGCTGTTGCA GCCTCTCATA ACATCTCTTG TGCAATACTT TGGATCCAAG
 401 CTTGTGGAGC TTACTCGGTT TATTACCGTT ACTACATGAA GACAAACTCT
 451 TTCCCTGATC TTGAAGATCT GAATCAAACG GTGGAGTTAC CAGCTTTACC
 501 ATTGTTGGAA GTTCGAGATC TTCCATCGTT TATGTTACCT TCTGGTGGTG
 551 CTCACTTCTA TAATCTAATG GCGGAATTTG CAGATTGTTT GAGGTATGTG
 601 AAATGGGTTT TGGTTAATTC ATTCTATGAA CTCGAATCAG AGATAATCGA
 651 ATCGATGGCT GATTTAAAAC CTGTAATTCC AATTGGTCCT CTGGTTTCTC
 701 CATTTCTGTT GGGCGATGGT GAGGAGGAAA CCCTAGACGG TAAAAACCTA
 751 GATTTTTGTA AATCTGATGA TTGTTGTATG GAGTGGCTTG ACAAGCAAGC
 801 TAGGTCTTCT GTTGTGTACA TATCTTTCGG AAGTATGCTC GAAACATTGG
 851 AGAATCAGGT CGAGACCATA GCGAAGGCGC TGAAGAACAG AGGACTTCCA
 901 TTTCTTTGGG TGATAAGGCC AAAGGAGAAA GCCCAAAACG TTGCTGTTTT
 951 GCAGGAGATG GTGAAAGAAG GACAAGGGGT TGTTCTCGAG TGGAGTCCAC
1001 AAGAGAAGAT TTTGAGCCAC GAGGCAATCT CTTGTTTTGT CACGCATTGC
1051 GGCTGGAACT CGACTATGGA GACGGTGGTG GCTGGTGTTC CTGTGGTAGC
1101 GTACCCTAGC TGGACGGATC AGCCCATTGA CGCGCGGTTG CTTGTTGATG
1151 TGTTTGGAAT CGGAGTAAGG ATGAGGAATG ACAGTGTCGA TGGCGAGCTT
1201 AAGGTCGAAG AAGTAGAAAG ATGCATTGAG GCCGTGACGG AGGGACCCGC
1251 TGCCGTGGAT ATAAGAAGGA GAGCGGCGGA GCTAAAGCGC GTGGCGAGAT
1301 TGGCGTTGGC ACCTGGTGGA TCTTCGACAC GGAATTTAGA CTTGTTCATT
1351 AGTGATATCA CAATCGCCTA ACTCTTTACT TCAACTAGTA CAAAATGTAT
1401 GAATACAAGG TTTGATATAA CCACTATCAA TTGTTAG
```

FIGURE 6B A911 AMINO ACID SEQUENCE

```
  1 MGSSEGQETH VLMVTLPFQG HINPMLKLAK HLSLSSKNLH INLATIESAR
 51 DLLSTVEKPR YPVDLVFFSD GLPKEDPKAP ETLLKSLNKV GAMNLSKIIE
101 EKRYSCIISS PFTPWVPAVA ASHNISCAIL WIQACGAYSV YYRYYMKTNS
151 FPDLEDLNQT VELPALPLLE VRDLPSFMLP SGGAHFYNLM AEFADCLRYV
201 KWVLVNSFYE LESEIIESMA DLKPVIPIGP LVSPFLLGDG EEETLDGKNL
251 DFCKSDDCCM EWLDKQARSS VVYISFGSML ETLENQVETI AKALKNRGLP
301 FLWVIRPKEK AQNVAVLQEM VKEGQGVVLE WSPQEKILSH EAISCFVTHC
351 GWNSTMETVV AGVPVVAYPS WTDQPIDARL LVDVFGIGVR MRNDSVDGEL
401 KVEEVERCIE AVTEGPAAVD IRRRAAELKR VARLALAPGG SSTRNLDLFI
451 SDITIA
```

FIGURE 6C A911 ANTISENSE NUCLEOTIDE SEQUENCE

```
   1 CTAACAATTG ATAGTGGTTA TATCAAACCT TGTATTCATA CATTTTGTAC
  51 TAGTTGAAGT AAAGAGTTAG GCGATTGTGA TATCACTAAT GAACAAGTCT
 101 AAATTCCGTG TCGAAGATCC ACCAGGTGCC AACGCCAATC TCGCCACGCG
 151 CTTTAGCTCC GCCGCTCTCC TTCTTATATC CACGGCAGCG GGTCCCTCCG
 201 TCACGGCCTC AATGCATCTT TCTACTTCTT CGACCTTAAG CTCGCCATCG
 251 ACACTGTCAT TCCTCATCCT TACTCCGATT CCAAACACAT CAACAAGCAA
 301 CCGCGCGTCA ATGGGCTGAT CCGTCCAGCT AGGGTACGCT ACCACAGGAA
 351 CACCAGCCAC CACCGTCTCC ATAGTCGAGT TCCAGCCGCA ATGCGTGACA
 401 AAACAAGAGA TTGCCTCGTG GCTCAAAATC TTCTCTTGTG GACTCCACTC
 451 GAGAACAACC CCTTGTCCTT CTTTCACCAT CTCCTGCAAA ACAGCAACGT
 501 TTTGGGCTTT CTCCTTTGGC CTTATCACCC AAAGAAATGG AAGTCCTCTG
 551 TTCTTCAGCG CCTTCGCTAT GGTCTCGACC TGATTCTCCA ATGTTTCGAG
 601 CATACTTCCG AAAGATATGT ACACAACAGA AGACCTAGCT TGCTTGTCAA
 651 GCCACTCCAT ACAACAATCA TCAGATTTAC AAAAATCTAG GTTTTTACCG
 701 TCTAGGGTTT CCTCCTCACC ATCGCCCAAC AGAAATGGAG AAACCAGAGG
 751 ACCAATTGGA ATTACAGGTT TTAAATCAGC CATCGATTCG ATTATCTCTG
 801 ATTCGAGTTC ATAGAATGAA TTAACCAAAA CCCATTTCAC ATACCTCAAA
 851 CAATCTGCAA ATTCCGCCAT TAGATTATAG AAGTGAGCAC CACCAGAAGG
 901 TAACATAAAC GATGGAAGAT CTCGAACTTC CAACAATGGT AAAGCTGGTA
 951 ACTCCACCGT TTGATTCAGA TCTTCAAGAT CAGGGAAAGA GTTTGTCTTC
1001 ATGTAGTAAC GGTAATAAAC CGAGTAAGCT CCACAAGCTT GGATCCAAAG
1051 TATTGCACAA GAGATGTTAT GAGAGGCTGC AACAGCTGGA ACCCATGGAG
1101 TAAAAGGCGA AGAGATGATA CAAGAGTATC TCTTTTCTTC GATGATTTTA
1151 GACAAGTTCA TGGCTCCGAC TTTATTCAAT GACTTCAAAA GAGTTTCAGG
1201 GGCCTTTGGA TCTTCTTTAG GTAGACCATC GGAGAAGAAC ACGAGGTCCA
1251 CCGGATAACG AGGTTTTTCT ACGGTGGAGA GGAGATCACG GGCTGACTCA
1301 ATAGTGGCGA GATTGATGTG TAGGTTCTTT GATGATAACG AGAGATGTTT
1351 TGCGAGTTTG AGCATTGGAT TGATGTGACC TTGGAATGGT AGTGTTACCA
1401 TTAGGACATG TGTTTCTTGA CCCTCACTAC TGCCCAT
```

FIGURE 7A A119 SENSE NUCLEOTIDE SEQUENCE

1 ATGCATATCA CAAAACCACA CGCCGCCATG TTTTCCAGTC CCGGAATGGG
51 CCATGTCATC CCGGTGATCG AGCTTGGAAA GCGTCTCTCC GCTAACAACG
101 GCTTCCACGT CACCGTCTTC GTCCTCGAAA CCGACGCAGC CTCCGCTCAA
151 TCCAAGTTCC TAAACTCAAC CGGCGTCGAC ATCGTCAAAC TTCCATCGCC
201 GGACATTTAT GGTTTAGTGG ACCCCGACGA CCATGTAGTG ACCAAGATCG
251 GAGTCATTAT GCGTGCAGCA GTTCCAGCCC TCCGATCCAA GATCGCTGCC
301 ATGCATCAAA AGCCAACGGC TCTGATCGTT GACTTGTTTG GCACAGATGC
351 GTTATGTCTC GCAAAGGAAT TTAACATGTT GAGTTATGTG TTTATCCCTA
401 CCAACGCACG TTTTCTCGGA GTTTCGATTT ATTATCCAAA TTTGGACAAA
451 GATATCAAGG AAGAGCACAC AGTGCAAAGA AACCCACTCG CTATACCGGG
501 GTGTGAACCG GTTAGGTTCG AAGATACTCT GGATGCATAT CTGGTTCCCG
551 ACGAACCGGT GTACCGGGAT TTTGTTCGTC ATGGTCTGGC TTACCCAAAA
601 GCCGATGGAA TTTTGGTAAA TACATGGGAA GAGATGGAGC CCAAATCATT
651 GAAGTCCCTT CTAAACCCAA AGCTCTTGGG CCGGGTTGCT CGTGTACCGG
701 TCTATCCAAT CGGTCCCTTA TGCAGACCGA TACAATCATC CGAAACCGAT
751 CACCCGGTTT TGGATTGGTT AAACGAACAA CCGAACGAGT CGGTTCTCTA
801 TATCTCCTTC GGGAGTGGTG GTTGTCTATC GGCGAAACAG TTAACTGAAT
851 TGGCGTGGGG ACTCGAGCAG AGCCAGCAAC GGTTCGTATG GGTGGTTCGA
901 CCACCGGTCG ACGGTTCGTG TTGTAGCGAG TATGTCTCGG CTAACGGTGG
951 TGGAACCGAA GACAACACGC CAGAGTATCT ACCGGAAGGG TTCGTGAGTC
1001 GTACTAGTGA TAGAGGTTTC GTGGTCCCCT CATGGGCCCC ACAAGCTGAA
1051 ATCCTGTCCC ATCGGGCCGT TGGTGGGTTT TTGACCCATT GCGGTTGGAG
1101 CTCGACGTTG GAAAGCGTCG TTGGCGGCGT TCCGATGATC GCATGGCCAC
1151 TTTTTGCCGA GCAGAATATG AATGCGGCGT TGCTCAGCGA CGAACTGGGA
1201 ATCGCAGTCA GATTGGATGA TCCAAAGGAG GATATTTCTA GGTGGAAGAT
1251 TGAGGCGTTG GTGAGGAAGG TTATGACTGA GAAGGAAGGT GAAGCGATGA
1301 GAAGGAAAGT GAAGAAGTTG AGAGACTCGG CGGAGATGTC ACTGAGCATT
1351 GACGGTGGTG GTTTGGCGCA CGAGTCGCTT TGCAGAGTCA CCAAGGAGTG
1401 TCAACGGTTT TTGGAACGTG TCGTGGACTT GTCACGTGGT GCTTAG

FIGURE 7B A119 AMINO ACID SEQUENCE

```
  1 MHITKPHAAM FSSPGMGHVI PVIELGKRLS ANNGFHVTVF VLETDAASAQ
 51 SKFLNSTGVD IVKLPSPDIY GLVDPDDHVV TKIGVIMRAA VPALRSKIAA
101 MHQKPTALIV DLFGTDALCL AKEFNMLSYV FIPTNARFLG VSIYYPNLDK
151 DIKEEHTVQR NPLAIPGCEP VRFEDTLDAY LVPDEPVYRD FVRHGLAYPK
201 ADGILVNTWE EMEPKSLKSL LNPKLLGRVA RVPVYPIGPL CRPIQSSETD
251 HPVLDWLNEQ PNESVLYISF GSGGCLSAKQ LTELAWGLEQ SQQRFVWVVR
301 PPVDGSCCSE YVSANGGGTE DNTPEYLPEG FVSRTSDRGF VVPSWAPQAE
351 ILSHRAVGGF LTHCGWSSTL ESVVGGVPMI AWPLFAEQNM NAALLSDELG
401 IAVRLDDPKE DISRWKIEAL VRKVMTEKEG EAMRRKVKKL RDSAEMSLSI
451 DGGGLAHESL CRVTKECQRF LERVVDLSRG A
```

FIGURE 7C A119 ANTISENSE NUCLEOTIDE SEQUENCE

```
   1 CTAAGCACCA CGTGACAAGT CCACGACACG TTCCAAAAAC CGTTGACACT
  51 CCTTGGTGAC TCTGCAAAGC GACTCGTGCG CCAAACCACC ACCGTCAATG
 101 CTCAGTGACA TCTCCGCCGA GTCTCTCAAC TTCTTCACTT TCCTTCTCAT
 151 CGCTTCACCT TCCTTCTCAG TCATAACCTT CCTCACCAAC GCCTCAATCT
 201 TCCACCTAGA AATATCCTCC TTTGGATCAT CCAATCTGAC TGCGATTCCC
 251 AGTTCGTCGC TGAGCAACGC CGCATTCATA TTCTGCTCGG CAAAAAGTGG
 301 CCATGCGATC ATCGGAACGC CGCCAACGAC GCTTTCCAAC GTCGAGCTCC
 351 AACCGCAATG GGTCAAAAAC CCACCAACGG CCCGATGGGA CAGGATTTCA
 401 GCTTGTGGGG CCCATGAGGG GACCACGAAA CCTCTATCAC TAGTACGACT
 451 CACGAACCCT TCCGGTAGAT ACTCTGGCGT GTTGTCTTCG GTTCCACCAC
 501 CGTTAGCCGA GACATACTCG CTACAACACG AACCGTCGAC CGGTGGTCGA
 551 ACCACCCATA CGAACCGTTG CTGGCTCTGC TCGAGTCCCC ACGCCAATTC
 601 AGTTAACTGT TTCGCCGATA GACAACCACC ACTCCCGAAG GAGATATAGA
 651 GAACCGACTC GTTCGGTTGT TCGTTTAACC AATCCAAAAC CGGGTGATCG
 701 GTTTCGGATG ATTGTATCGG TCTGCATAAG GGACCGATTG GATAGACCGG
 751 TACACGAGCA ACCCGGCCCA AGAGCTTTGG GTTTAGAAGG GACTTCAATG
 801 ATTTGGGCTC CATCTCTTCC CATGTATTTA CCAAAATTCC ATCGGCTTTT
 851 GGGTAAGCCA GACCATGACG AACAAAATCC CGGTACACCG GTTCGTCGGG
 901 AACCAGATAT GCATCCAGAG TATCTTCGAA CCTAACCGGT TCACACCCCG
 951 GTATAGCGAG TGGGTTTCTT TGCACTGTGT GCTCTTCCTT GATATCTTTG
1001 TCCAAATTTG GATAATAAAT CGAAACTCCG AGAAAACGTG CGTTGGTAGG
1051 GATAAACACA TAACTCAACA TGTTAAATTC CTTTGCGAGA CATAACGCAT
1101 CTGTGCCAAA CAAGTCAACG ATCAGAGCCG TTGGCTTTTG ATGCATGGCA
1151 GCGATCTTGG ATCGGAGGGC TGGAACTGCT GCACGCATAA TGACTCCGAT
1201 CTTGGTCACT ACATGGTCGT CGGGGTCCAC TAAACCATAA ATGTCCGGCG
1251 ATGGAAGTTT GACGATGTCG ACGCCGGTTG AGTTTAGGAA CTTGGATTGA
1301 GCGGAGGCTG CGTCGGTTTC GAGGACGAAG ACGGTGACGT GGAAGCCGTT
1351 GTTAGCGGAG AGACGCTTTC CAAGCTCGAT CACCGGGATG ACATGGCCCA
1401 TTCCGGGACT GGAAAACATG GCGGCGTGTG GTTTTGTGAT ATGCAT
```

FIGURE 8A A233 SENSE NUCLEOTIDE SEQUENCE

```
   1  ATGAGTAGTG ATCCTCATCG TAAGCTCCAT GTTGTGTTCT TCCCTTTCAT
  51  GGCTTATGGT CACATGATAC CAACTCTAGA CATGGCTAAG CTTTTCTCTA
 101  GCAGAGGAGC CAAATCTACA ATCCTCACCA CACCTCTCAA CTCCAAGATC
 151  TTCCAAAAAC CCATCGAAAG ATTCAAGAAC CTGAATCCGA GTTTCGAAAT
 201  CGACATCCAG ATCTTCGATT TCCCTTGCGT GGATCTCGGG TTACCAGAAG
 251  GATGCGAAAA CGTCGATTTC TTCACCTCAA ACAACAATGA TGATAGACAG
 301  TATCTGACCT TGAAGTTCTT TAAGTCGACA AGGTTTTTCA AAGATCAGCT
 351  TGAGAAGCTC CTCGAGACAA CGAGACCAGA CTGTCTTATC GCCGACATGT
 401  TCTTCCCCTG GGCTACGGAA GCTGCTGAGA AGTTCAATGT GCCAAGACTT
 451  GTGTTCCACG GTACTGGCTA CTTTTCTTTA TGCTCTGAAT ATTGCATCAG
 501  AGTGCATAAC CCACAAAACA TAGTAGCTTC AAGGTACGAG CCATTTGTGA
 551  TTCCTGATCT CCCGGGGAAC ATAGTGATAA CTCAAGAACA GATAGCAGAC
 601  CGTGACGAAG AAAGCGAGAT GGGGAAGTTT ATGATTGAGG TCAAAGAATC
 651  TGATGTGAAG AGCTCAGGTG TTATTGTAAA CAGCTTCTAC GAGCTTGAAC
 701  CTGATTACGC CGACTTTTAC AAGAGTGTTG TACTGAAGAG AGCGTGGCAT
 751  ATCGGTCCGC TTTCGGTTTA CAACAGAGGA TTTGAGGAGA AGGCTGAGAG
 801  AGGAAAGAAA GCAAGCATTA ATGAGGTTGA ATGCCTCAAA TGGCTTGACT
 851  CCAAGAAACC AGATTCAGTC ATTTACATTT CTTTTGGGAG CGTGGCTTGC
 901  TTCAAGAACG AGCAGCTATT CGAGATCGCT GCAGGATTAG AAACTTCTGG
 951  AGCAAATTTC ATCTGGGTTG TTAGGAAAAA CATAGGTATT GAAAAAGAAG
1001  AATGGTTACC AGAAGGGTTC GAAGAGAGGG TGAAAGGAAA AGGGATGATT
1051  ATAAGAGGAT GGGCACCACA GGTGCTCATA CTTGATCATC AAGCAACTTG
1101  TGGGTTTGTG ACCCATTGCG GCTGGAACTC GCTTCTGGAA GGAGTGGCTG
1151  CAGGGCTACC AATGGTGACA TGGCCTGTAG CAGCGGAGCA ATTCTACAAT
1201  GAGAAATTGG TTACGCAAGT GCTCAGAACA GGAGTGAGCG TGGGAGCGAA
1251  AAAGAATGTA AGAACTACGG GAGATTTCAT TAGCAGAGAG AAAGTGGTTA
1301  AAGCGGTGAG GGAGGTGTTG GTTGGGGAAG AGGCGGATGA GAGGCGGGAG
1351  AGGGCAAAGA AGTTGGCAGA GATGGCTAAA GCTGCCGTGG AAGGAGGGTC
1401  TTCTTTCAAC GATCTAAACA GCTTCATAGA AGAGTTTACC TCGTAA
```

FIGURE 8B A233 AMINO ACID SEQUENCE

```
  1  MSSDPHRKLH VVFFPFMAYG HMIPTLDMAK LFSSRGAKST ILTTPLNSKI
 51  FQKPIERFKN LNPSFEIDIQ IFDFPCVDLG LPEGCENVDF FTSNNNDDRQ
101  YLTLKFFKST RFFKDQLEKL LETTRPDCLI ADMFFPWATE AAEKFNVPRL
151  VFHGTGYFSL CSEYCIRVHN PQNIVASRYE PFVIPDLPGN IVITQEQIAD
201  RDEESEMGKF MIEVKESDVK SSGVIVNSFY ELEPDYADFY KSVVLKRAWH
251  IGPLSVYNRG FEEKAERGKK ASINEVECLK WLDSKKPDSV IYISFGSVAC
301  FKNEQLFEIA AGLETSGANF IWVVRKNIGI EKEEWLPEGF EERVKGKGMI
351  IRGWAPQVLI LDHQATCGFV THCGWNSLLE GVAAGLPMVT WPVAAEQFYN
401  EKLVTQVLRT GVSVGAKKNV RTTGDFISRE KVVKAVREVL VGEEADERRE
451  RAKKLAEMAK AAVEGGSSFN DLNSFIEEFT S
```

FIGURE 8C A233 ANTISENSE NUCLEOTIDE SEQUENCE

```
   1 TTACGAGGTA AACTCTTCTA TGAAGCTGTT TAGATCGTTG AAAGAAGACC
  51 CTCCTTCCAC GGCAGCTTTA GCCATCTCTG CCAACTTCTT TGCCCTCTCC
 101 CGCCTCTCAT CCGCCTCTTC CCCAACCAAC ACCTCCCTCA CCGCTTTAAC
 151 CACTTTCTCT CTGCTAATGA AATCTCCCGT AGTTCTTACA TTCTTTTTCG
 201 CTCCCACGCT CACTCCTGTT CTGAGCACTT GCGTAACCAA TTTCTCATTG
 251 TAGAATTGCT CCGCTGCTAC AGGCCATGTC ACCATTGGTA GCCCTGCAGC
 301 CACTCCTTCC AGAAGCGAGT TCCAGCCGCA ATGGGTCACA AACCCACAAG
 351 TTGCTTGATG ATCAAGTATG AGCACCTGTG GTGCCCATCC TCTTATAATC
 401 ATCCCTTTTC CTTTCACCCT CTCTTCGAAC CCTTCTGGTA ACCATTCTTC
 451 TTTTTCAATA CCTATGTTTT TCCTAACAAC CCAGATGAAA TTTGCTCCAG
 501 AAGTTTCTAA TCCTGCAGCG ATCTCGAATA GCTGCTCGTT CTTGAAGCAA
 551 GCCACGCTCC CAAAAGAAAT GTAAATGACT GAATCTGGTT TCTTGGAGTC
 601 AAGCCATTTG AGGCATTCAA CCTCATTAAT GCTTGCTTTC TTTCCTCTCT
 651 CAGCCTTCTC CTCAAATCCT CTGTTGTAAA CCGAAAGCGG ACCGATATGC
 701 CACGCTCTCT TCAGTACAAC ACTCTTGTAA AAGTCGGCGT AATCAGGTTC
 751 AAGCTCGTAG AAGCTGTTTA CAATAACACC TGAGCTCTTC ACATCAGATT
 801 CTTTGACCTC AATCATAAAC TTCCCCATCT CGCTTTCTTC GTCACGGTCT
 851 GCTATCTGTT CTTGAGTTAT CACTATGTTC CCCGGGAGAT CAGGAATCAC
 901 AAATGGCTCG TACCTTGAAG CTACTATGTT TTGTGGGTTA TGCACTCTGA
 951 TGCAATATTC AGAGCATAAA GAAAAGTAGC CAGTACCGTG GAACACAAGT
1001 CTTGGCACAT TGAACTTCTC AGCAGCTTCC GTAGCCCAGG GGAAGAACAT
1051 GTCGGCGATA AGACAGTCTG GTCTCGTTGT CTCGAGGAGC TTCTCAAGCT
1101 GATCTTTGAA AAACCTTGTC GACTTAAAGA ACTTCAAGGT CAGATACTGT
1151 CTATCATCAT TGTTGTTTGA GGTGAAGAAA TCGACGTTTT CGCATCCTTC
1201 TGGTAACCCG AGATCCACGC AAGGGAAATC GAAGATCTGG ATGTCGATTT
1251 CGAAACTCGG ATTCAGGTTC TTGAATCTTT CGATGGGTTT TTGGAAGATC
1301 TTGGAGTTGA GAGGTGTGGT GAGGATTGTA GATTTGGCTC CTCTGCTAGA
1351 GAAAAGCTTA GCCATGTCTA GAGTTGGTAT CATGTGACCA TAAGCCATGA
1401 AAGGGAAGAA CACAACATGG AGCTTACGAT GAGGATCACT ACTCAT
```

FIGURE 9A A407 SENSE NUCLEOTIDE SEQUENCE

```
   1 ATGCATATCA CAAAACCACA CGCCGCCATG TTTTCCAGTC CCGGAATGGG
  51 CCATGTCCTC CCGGTGATCG AGCTAGCTAA GCGTCTCTCC GCTAACCACG
 101 GCTTCCACGT CACCGTCTTC GTCCTTGAAA CTGACGCAGC CTCCGTTCAG
 151 TCCAAGCTCC TTAACTCAAC CGGTGTTGAC ATCGTCAACC TTCCATCGCC
 201 CGACATTTCT GGCTTGGTAG ACCCCAACGC CCATGTGGTG ACCAAGATCG
 251 GAGTCATTAT GCGTGAAGCT GTTCCAACCC TCCGATCCAA GATCGTTGCC
 301 ATGCATCAAA ACCCAACGGC TCTGATCATT GACTTGTTTG GCACAGATGC
 351 GTTATGTCTT GCAGCGGAGT TAAACATGTT GACTTATGTC TTTATCGCTT
 401 CCAACGCGCG TTATCTCGGA GTTTCGATAT ATTATCCAAC TTTGGACGAA
 451 GTTATCAAAG AAGAGCACAC AGTGCAACGA AAACCGCTCA CTATACCGGG
 501 GTGTGAACCG GTTAGATTTG AAGATATTAT GGATGCATAT CTGGTTCCGG
 551 ACGAACCGGT GTACCACGAT TTGGTTCGTC ACTGTCTGGC CTACCCAAAA
 601 GCGGATGGAA TCTTGGTGAA TACATGGGAA GAGATGGAGC CCAAATCATT
 651 AAAGTCCCTT CAAGACCCGA AACTTTTGGG CCGGGTCGCT CGTGTACCGG
 701 TTTATCCGGT TGGTCCGTTA TGCAGACCGA TACAATCATC CACGACCGAT
 751 CACCCGGTTT TTGATTGGTT AAACAAACAA CCAAACGAGT CGGTTCTCTA
 801 CATTTCCTTC GGGAGTGGTG GTTCTCTAAC GGCTCAACAG TTAACCGAAT
 851 TGGCGTGGGG GCTCGAGGAG AGCCAGCAAC GGTTTATATG GGTGGTTCGA
 901 CCGCCCGTTG ACGGCTCGTC TTGCAGTGAT TATTTCTCGG CTAAAGGCGG
 951 TGTAACCAAA GACAACACGC CAGAGTATCT ACCAGAAGGG TTCGTGACTC
1001 GTACTTGCGA TAGAGGTTTC ATGATCCCAT CATGGGCACC GCAAGCTGAA
1051 ATCCTAGCCC ATCAGGCCGT TGGTGGGTTT TTAACACATT GTGGTTGGAG
1101 CTCGACGTTG GAAAGCGTCC TTTGCGGCGT TCCAATGATA GCGTGGCCGC
1151 TTTTCGCCGA GCAGAATATG AACGCGGCGT TGCTTAGCGA TGAACTGGGA
1201 ATCTCTGTTA GAGTGGATGA TCCAAAGGAG GCGATTTCTA GGTCGAAGAT
1251 TGAGGCGATG GTGAGGAAGG TTATGGCTGA GGACGAAGGT GAAGAGATGA
1301 GAAGGAAAGT GAAGAAGTTG AGAGACACGG CGGAGATGTC ACTTAGTATT
1351 CACGGTGGTG GTTCGGCGCA TGAGTCGCTT TGCAGAGTCA CGAAGGAGTG
1401 TCAACGGTTT TTGGAATGTG TCGGGGACTT GGGACGTGGT GCTTAG
```

FIGURE 9B A407 AMINO ACID SEQUENCE

```
  1 MHITKPHAAM FSSPGMGHVL PVIELAKRLS ANHGFHVTVF VLETDAASVQ
 51 SKLLNSTGVD IVNLPSPDIS GLVDPNAHVV TKIGVIMREA VPTLRSKIVA
101 MHQNPTALII DLFGTDALCL AAELNMLTYV FIASNARYLG VSIYYPTLDE
151 VIKEEHTVQR KPLTIPGCEP VRFEDIMDAY LVPDEPVYHD LVRHCLAYPK
201 ADGILVNTWE EMEPKSLKSL QDPKLLGRVA RVPVYPVGPL CRPIQSSTTD
251 HPVFDWLNKQ PNESVLYISF GSGGSLTAQQ LTELAWGLEE SQQRFIWVVR
301 PPVDGSSCSD YFSAKGGVTK DNTPEYLPEG FVTRTCDRGF MIPSWAPQAE
351 ILAHQAVGGF LTHCGWSSTL ESVLCGVPMI AWPLFAEQNM NAALLSDELG
401 ISVRVDDPKE AISRSKIEAM VRKVMAEDEG EEMRRKVKKL RDTAEMSLSI
451 HGGGSAHESL CRVTKECQRF LECVGDLGRG A
```

FIGURE 9C A407 ANTISENSE NUCLEOTIDE SEQUENCE

```
   1 CTAAGCACCA CGTCCCAAGT CCCCGACACA TTCCAAAAAC CGTTGACACT
  51 CCTTCGTGAC TCTGCAAAGC GACTCATGCG CCGAACCACC ACCGTGAATA
 101 CTAAGTGACA TCTCCGCCGT GTCTCTCAAC TTCTTCACTT TCCTTCTCAT
 151 CTCTTCACCT TCGTCCTCAG CCATAACCTT CCTCACCATC GCCTCAATCT
 201 TCGACCTAGA AATCGCCTCC TTTGGATCAT CCACTCTAAC AGAGATTCCC
 251 AGTTCATCGC TAAGCAACGC CGCGTTCATA TTCTGCTCGG CGAAAAGCGG
 301 CCACGCTATC ATTGGAACGC CGCAAAGGAC GCTTTCCAAC GTCGAGCTCC
 351 AACCACAATG TGTTAAAAAC CCACCAACGG CCTGATGGGC TAGGATTTCA
 401 GCTTGCGGTG CCCATGATGG GATCATGAAA CCTCTATCGC AAGTACGAGT
 451 CACGAACCCT TCTGGTAGAT ACTCTGGCGT GTTGTCTTTG GTTACACCGC
 501 CTTTAGCCGA GAAATAATCA CTGCAAGACG AGCCGTCAAC GGGCGGTCGA
 551 ACCACCCATA TAAACCGTTG CTGGCTCTCC TCGAGCCCCC ACGCCAATTC
 601 GGTTAACTGT TGAGCCGTTA GAGAACCACC ACTCCCGAAG GAAATGTAGA
 651 GAACCGACTC GTTTGGTTGT TTGTTTAACC AATCAAAAAC CGGGTGATCG
 701 GTCGTGGATG ATTGTATCGG TCTGCATAAC GGACCAACCG GATAAACCGG
 751 TACACGAGCG ACCCGGCCCA AAAGTTTCGG GTCTTGAAGG GACTTTAATG
 801 ATTTGGGCTC CATCTCTTCC CATGTATTCA CCAAGATTCC ATCCGCTTTT
 851 GGGTAGGCCA GACAGTGACG AACCAAATCG TGGTACACCG GTTCGTCCGG
 901 AACCAGATAT GCATCCATAA TATCTTCAAA TCTAACCGGT TCACACCCCG
 951 GTATAGTGAG CGGTTTTCGT TGCACTGTGT GCTCTTCTTT GATAACTTCG
1001 TCCAAAGTTG GATAATATAT CGAAACTCCG AGATAACGCG CGTTGGAAGC
1051 GATAAAGACA TAAGTCAACA TGTTTAACTC CGCTGCAAGA CATAACGCAT
1101 CTGTGCCAAA CAAGTCAATG ATCAGAGCCG TTGGGTTTTG ATGCATGGCA
1151 ACGATCTTGG ATCGGAGGGT TGGAACAGCT TCACGCATAA TGACTCCGAT
1201 CTTGGTCACC ACATGGGCGT TGGGGTCTAC CAAGCCAGAA ATGTCGGGCG
1251 ATGGAAGGTT GACGATGTCA ACACCGGTTG AGTTAAGGAG CTTGGACTGA
1301 ACGGAGGCTG CGTCAGTTTC AAGGACGAAG ACGGTGACGT GGAAGCCGTG
1351 GTTAGCGGAG AGACGCTTAG CTAGCTCGAT CACCGGGAGG ACATGGCCCA
1401 TTCCGGGACT GGAAAACATG GCGGCGTGTG GTTTTGTGAT ATGCAT
```

FIGURE 10A A961 SENSE NUCLEOTIDE SEQUENCE

```
      ATGGGGAAGC AAGAAGATGC AGAGCTCGTC ATCATACCTT TCCCTTTCTC
  51  CGGACACATT CTCGCAACAA TCGAACTCGC CAAACGTCTC ATAAGTCAAG
 101  ACAATCCTCG GATCCACACC ATCACCATCC TCTATTGGGG ATTACCTTTT
 151  ATTCCTCAAG CTGACACAAT CGCTTTCCTC CGATCCCTAG TCAAAAATGA
 201  GCCTCGTATC CGTCTCGTTA CGTTGCCCGA AGTCCAAGAC CCTCCACCAA
 251  TGGAACTCTT TGTGGAATTT GCCGAATCTT ACATTCTTGA ATACGTCAAG
 301  AAAATGGTTC CCATCATCAG AGAAGCTCTC TCCACTCTCT TGTCTTCCCG
 351  CGATGAATCG GGTTCAGTTC GTGTGGCTGG ATTGGTTCTT GACTTCTTCT
 401  GCGTCCCTAT GATCGATGTA GGAAACGAGT TTAATCTCCC TTCTTACATT
 451  TTCTTGACGT GTAGCGCAGG GTTCTTGGGT ATGATGAAGT ATCTTCCAGA
 501  GAGACACCGC GAAATCAAAT CGGAATTCAA CCGGAGCTTC AACGAGGAGT
 551  TGAATCTCAT TCCTGGTTAT GTCAACTCTG TTCCTACTAA GGTTTTGCCG
 601  TCAGGTCTAT TCATGAAAGA GACCTACGAG CCTTGGGTCG AACTAGCAGA
 651  GAGGTTTCCT GAAGCTAAGG GTATTTTGGT TAATTCATAC ACAGCTCTCG
 701  AGCCAAACGG TTTTAAATAT TTCGATCGTT GTCCGGATAA CTACCCAACC
 751  ATTTACCCAA TCGGGCCGAT ATTATGCTCC AACGACCGTC CGAATTTGGA
 801  CTCATCGGAA CGAGATCGGA TCATAACTTG GCTAGATGAC CAACCCGAGT
 851  CATCGGTCGT GTTCCTCTGT TTCGGGAGCT TGAAGAATCT CAGCGCTACT
 901  CAGATCAACG AGATAGCTCA AGCCTTAGAG ATCGTTGACT GCAAATTCAT
 951  CTGGTCGTTT CGAACCAACC CGAAGGAGTA CGCGAGCCCT TACGAGGCTC
1001  TACCACACGG GTTCATGGAC CGGGTCATGG ATCAAGGCAT TGTTTGTGGT
1051  TGGGCTCCTC AAGTTGAAAT CCTAGCCCAT AAAGCTGTGG GAGGATTCGT
1101  ATCTCATTGT GGTTGGAACT CGATATTGGA GAGTTTGGGT TTCGGCGTTC
1151  CAATCGCCAC GTGGCCGATG TACGCGGAAC AACAACTAAA CGCGTTCACG
1201  ATGGTGAAGG AGCTTGGTTT AGCCTTGGAG ATGCGGTTGG ATTACGTGTC
1251  GGAAGATGGA GATATAGTGA AAGCTGATGA GATCGCAGGA ACCGTTAGAT
1301  CTTTAATGGA CGGTGTGGAT GTGCCGAAGA GTAAAGTGAA GGAGATTGCT
1351  GAGGCGGGAA AAGAAGCTGT GGACGGTGGA TCTTCGTTTC TTGCGGTTAA
1401  AAGATTCATC GGTGACTTGA TCGACGGCGT TTCTATAAGT AAGTAG
```

FIGURE 10B A961 AMINO ACID SEQUENCE

```
  1 MGKQEDAELV IIPFPFSGHI LATIELAKRL ISQDNPRIHT ITILYWGLPF
 51 IPQADTIAFL RSLVKNEPRI RLVTLPEVQD PPPMELFVEF AESYILEYVK
101 KMVPIIREAL STLLSSRDES GSVRVAGLVL DFFCVPMIDV GNEFNLPSYI
151 FLTCSAGFLG MMKYLPERHR EIKSEFNRSF NEELNLIPGY VNSVPTKVLP
201 SGLFMKETYE PWVELAERFP EAKGILVNSY TALEPNGFKY FDRCPDNYPT
251 IYPIGPILCS NDRPNLDSSE RDRIITWLDD QPESSVVFLC FGSLKNLSAT
301 QINEIAQALE IVDCKFIWSF RTNPKEYASP YEALPHGFMD RVMDQGIVCG
351 WAPQVEILAH KAVGGFVSHC GWNSILESLG FGVPIATWPM YAEQQLNAFT
401 MVKELGLALE MRLDYVSEDG DIVKADEIAG TVRSLMDGVD VPKSKVKEIA
451 EAGKEAVDGG SSFLAVKRFI GDLIDGVSIS K
```

FIGURE 10C A961 ANTISENSE NUCLEOTIDE SEQUENCE

```
      CTACTTACTT ATAGAAACGC CGTCGATCAA GTCACCGATG AATCTTTTAA
  51  CCGCAAGAAA CGAAGATCCA CCGTCCACAG CTTCTTTTCC CGCCTCAGCA
 101  ATCTCCTTCA CTTTACTCTT CGGCACATCC ACACCGTCCA TTAAAGATCT
 151  AACGGTTCCT GCGATCTCAT CAGCTTTCAC TATATCTCCA TCTTCCGACA
 201  CGTAATCCAA CCGCATCTCC AAGGCTAAAC CAAGCTCCTT CACCATCGTG
 251  AACGCGTTTA GTTGTTGTTC CGCGTACATC GGCCACGTGG CGATTGGAAC
 301  GCCGAAACCC AAACTCTCCA ATATCGAGTT CCAACCACAA TGAGATACGA
 351  ATCCTCCCAC AGCTTTATGG GCTAGGATTT CAACTTGAGG AGCCCAACCA
 401  CAAACAATGC CTTGATCCAT GACCCGGTCC ATGAACCCGT GTGGTAGAGC
 451  CTCGTAAGGG CTCGCGTACT CCTTCGGGTT GGTTCGAAAC GACCAGATGA
 501  ATTTGCAGTC AACGATCTCT AAGGCTTGAG CTATCTCGTT GATCTGAGTA
 551  GCGCTGAGAT TCTTCAAGCT CCCGAAACAG AGGAACACGA CCGATGACTC
 601  GGGTTGGTCA TCTAGCCAAG TTATGATCCG ATCTCGTTCC GATGAGTCCA
 651  AATTCGGACG GTCGTTGGAG CATAATATCG GCCCGATTGG GTAAATGGTT
 701  GGGTAGTTAT CCGGACAACG ATCGAAATAT TTAAAACCGT TTGGCTCGAG
 751  AGCTGTGTAT GAATTAACCA AAATACCCTT AGCTTCAGGA AACCTCTCTG
 801  CTAGTTCGAC CCAAGGCTCG TAGGTCTCTT TCATGAATAG ACCTGACGGC
 851  AAAACCTTAG TAGGAACAGA GTTGACATAA CCAGGAATGA GATTCAACTC
 901  CTCGTTGAAG CTCCGGTTGA ATTCCGATTT GATTTCGCGG TGTCTCTCTG
 951  GAAGATACTT CATCATACCC AAGAACCCTG CGCTACACGT CAAGAAAATG
1001  TAAGAAGGGA GATTAAACTC GTTTCCTACA TCGATCATAG GGACGCAGAA
1051  GAAGTCAAGA ACCAATCCAG CCACACGAAC TGAACCCGAT TCATCGCGGG
1101  AAGACAAGAG AGTGGAGAGA GCTTCTCTGA TGATGGGAAC CATTTTCTTG
1151  ACGTATTCAA GAATGTAAGA TTCGGCAAAT TCCACAAAGA GTTCCATTGG
1201  TGGAGGGTCT TGGACTTCGG GCAACGTAAC GAGACGGATA CGAGGCTCAT
1251  TTTTGACTAG GGATCGGAGG AAAGCGATTG TGTCAGCTTG AGGAATAAAA
1301  GGTAATCCCC AATAGAGGAT GGTGATGGTG TGGATCCGAG GATTGTCTTG
1351  ACTTATGAGA CGTTTGGCGA GTTCGATTGT TGCGAGAATG TGTCCGGAGA
1401  AAGGGAAAGG TATGATGACG AGCTCTGCAT CTTCTTGCTT CCCCAT
```

FIGURE 11A A962 SENSE NUCLEOTIDE SEQUENCE

```
   1 ATGGCGAAGC AGCAAGAAGC AGAGCTCATC TTCATCCCAT TTCCAATCCC
  51 CGGACACATT CTCGCCACAA TCGAACTCGC GAAACGTCTC ATCAGTCACC
 101 AACCTAGTCG GATCCACACC ATCACCATCC TCCATTGGAG CTTACCTTTT
 151 CTTCCTCAAT CTGACACTAT CGCCTTCCTC AAATCCCTAA TCGAAACAGA
 201 GTCTCGTATC CGTCTCATTA CCTTACCCGA TGTCCAAAAC CCTCCACCAA
 251 TGGAGCTATT TGTGAAAGCT TCCGAATCTT ACATTCTTGA ATACGTCAAG
 301 AAAATGGTTC CTTTGGTCAG AAACGCTCTC TCCACTCTCT TGTCTTCTCG
 351 TGATGAATCG GATTCAGTTC ATGTCGCCGG ATTAGTTCTT GATTTCTTCT
 401 GTGTCCCTTT GATCGATGTC GGAAACGAGT TTAATCTCCC TTCTTACATC
 451 TTCTTGACGT GTAGCGCAAG TTTCTTGGGT ATGATGAAGT ATCTTCTGGA
 501 GAGAAACCGC GAAACCAAAC CGGAACTTAA CCGGAGCTCT GACGAGGAAA
 551 CAATATCAGT TCCTGGTTTT GTTAACTCCG TTCCGGTTAA AGTTTTGCCA
 601 CCGGGTTTGT TCACGACTGA GTCTTACGAA GCTTGGGTCG AAATGGCGGA
 651 AAGGTTCCCT GAAGCCAAGG GTATTTTGGT CAATTCATTT GAATCTCTAG
 701 AACGTAACGC TTTTGATTAT TTCGATCGTC GTCCGGATAA TTACCCACCC
 751 GTTTACCCAA TCGGGCCAAT TCTATGCTCC AACGATCGTC CGAATTTGGA
 801 TTTATCGGAA CGAGACCGGA TCTTGAAATG GCTCGATGAC CAACCCGAGT
 851 CATCTGTTGT GTTTCTCTGC TTCGGGAGCT TGAAGAGTCT CGCTGCGTCT
 901 CAGATTAAAG AGATCGCTCA AGCCTTAGAG CTCGTCGGAA TCAGATTCCT
 951 CTGGTCGATT CGAACGGACC CGAAGGAGTA CGCGAGCCCG AACGAGATTT
1001 TACCGGACGG GTTTATGAAC CGAGTCATGG GTTTGGGCCT TGTTTGTGGT
1051 TGGGCTCCTC AAGTTGAAAT TCTGGCCCAT AAAGCAATTG GAGGGTTCGT
1101 GTCACACTGC GGTTGGAACT CGATATTGGA GAGTTTGCGT TTCGGAGTTC
1151 CAATTGCCAC GTGGCCAATG TACGCGGAAC AACAACTAAA CGCGTTCACG
1201 ATTGTGAAGG AGCTTGGTTT GGCGTTGGAG ATGCGGTTGG ATTACGTGTC
1251 GGAATATGGA GAAATCGTGA AAGCTGATGA AATCGCAGGA GCCGTACGAT
1301 CTTTGATGGA CGGTGAGGAT GTGCCGAGGA GGAAACTGAA GGAGATTGCG
1351 GAGGCGGGAA AAGAGGCTGT GATGGACGGT GGATCTTCGT TTGTTGCGGT
1401 TAAAAGATTC ATAGATGGGC TTTGA
```

FIGURE 11B A962 AMINO ACID SEQUENCE

```
  1  MAKQQEAELI FIPFPIPGHI LATIELAKRL ISHQPSRIHT ITILHWSLPF
 51  LPQSDTIAFL KSLIETESRI RLITLPDVQN PPPMELFVKA SESYILEYVK
101  KMVPLVRNAL STLLSSRDES DSVHVAGLVL DFFCVPLIDV GNEFNLPSYI
151  FLTCSASFLG MMKYLLERNR ETKPELNRSS DEETISVPGF VNSVPVKVLP
201  PGLFTTESYE AWVEMAERFP EAKGILVNSF ESLERNAFDY FDRRPDNYPP
251  VYPIGPILCS NDRPNLDLSE RDRILKWLDD QPESSVVFLC FGSLKSLAAS
301  QIKEIAQALE LVGIRFLWSI RTDPKEYASP NEILPDGFMN RVMGLGLVCG
351  WAPQVEILAH KAIGGFVSHC GWNSILESLR FGVPIATWPM YAEQQLNAFT
401  IVKELGLALE MRLDYVSEYG EIVKADEIAG AVRSLMDGED VPRRKLKEIA
451  EAGKEAVMDG GSSFVAVKRF IDGL
```

FIGURE 11C A962 ANTISENSE NUCLEOTIDE SEQUENCE

```
   1  TCAAAGCCCA TCTATGAATC TTTTAACCGC AACAAACGAA GATCCACCGT
  51  CCATCACAGC CTCTTTTCCC GCCTCCGCAA TCTCCTTCAG TTTCCTCCTC
 101  GGCACATCCT CACCGTCCAT CAAAGATCGT ACGGCTCCTG CGATTTCATC
 151  AGCTTTCACG ATTTCTCCAT ATTCCGACAC GTAATCCAAC CGCATCTCCA
 201  ACGCCAAACC AAGCTCCTTC ACAATCGTGA ACGCGTTTAG TTGTTGTTCC
 251  GCGTACATTG GCCACGTGGC AATTGGAACT CCGAAACGCA AACTCTCCAA
 301  TATCGAGTTC CAACCGCAGT GTGACACGAA CCCTCCAATT GCTTTATGGG
 351  CCAGAATTTC AACTTGAGGA GCCCAACCAC AAACAAGGCC CAAACCCATG
 401  ACTCGGTTCA TAAACCCGTC CGGTAAAATC TCGTTCGGGC TCGCGTACTC
 451  CTTCGGGTCC GTTCGAATCG ACCAGAGGAA TCTGATTCCG ACGAGCTCTA
 501  AGGCTTGAGC GATCTCTTTA ATCTGAGACG CAGCGAGACT CTTCAAGCTC
 551  CCGAAGCAGA GAAACACAAC AGATGACTCG GGTTGGTCAT CGAGCCATTT
 601  CAAGATCCGG TCTCGTTCCG ATAAATCCAA ATTCGGACGA TCGTTGGAGC
 651  ATAGAATTGG CCCGATTGGG TAAACGGGTG GGTAATTATC CGGACGACGA
 701  TCGAAATAAT CAAAAGCGTT ACGTTCTAGA GATTCAAATG AATTGACCAA
 751  AATACCCTTG GCTTCAGGGA ACCTTTCCGC CATTTCGACC CAAGCTTCGT
 801  AAGACTCAGT CGTGAACAAA CCCGGTGGCA AAACTTTAAC CGGAACGGAG
 851  TTAACAAAAC CAGGAACTGA TATTGTTTCC TCGTCAGAGC TCCGGTTAAG
 901  TTCCGGTTTG GTTTCGCGGT TTCTCTCCAG AAGATACTTC ATCATACCCA
 951  AGAAACTTGC GCTACACGTC AAGAAGATGT AAGAAGGGAG ATTAAACTCG
1001  TTTCCGACAT CGATCAAAGG GACACAGAAG AAATCAAGAA CTAATCCGGC
1051  GACATGAACT GAATCCGATT CATCACGAGA AGACAAGAGA GTGGAGAGAG
1101  CGTTTCTGAC CAAAGGAACC ATTTTCTTGA CGTATTCAAG AATGTAAGAT
1151  TCGGAAGCTT TCACAAATAG CTCCATTGGT GGAGGGTTTT GGACATCGGG
1201  TAAGGTAATG AGACGGATAC GAGACTCTGT TTCGATTAGG GATTTGAGGA
1251  AGGCGATAGT GTCAGATTGA GGAAGAAAAG GTAAGCTCCA ATGGAGGATG
1301  GTGATGGTGT GGATCCGACT AGGTTGGTGA CTGATGAGAC GTTTCGCGAG
1351  TTCGATTGTG GCGAGAATGT GTCCGGGGAT TGGAAATGGG ATGAAGATGA
1401  GCTCTGCTTC TTGCTGCTTC GCCAT
```

UGT71B5 Figure 12

ATGAAGATTGAGCTTGTGTTCATACCTTTGCCGGGGATTGGTCATCTCAGGCCAACCGTGAAGCTAGCG
AAGCAACTCATAGGCAGCGAAAACCGTCTTTCGATCACCATAATCATCATCCCTTCAAGATTTGACGCC
GGTGATGCATCCGCCTGTATCGCATCTCTCACCACGTTGTCTCAAGATGATCGCCTCCATTACGAATCC
ATATCCGTCGCAAAACAACCACCAACCTCCGACCCGGATCCTGTTCCGGCTCAAGTGTACATAGAGAAA
CAAAAGACGAAAGTGAGAGATGCAGTCGCGGCGAGAATCGTCGATCCAACAAGAAAGCTCGCGGGATTC
GTGGTGGACATGTTCTGTTCCTCGATGATCGATGTAGCTAACGAGTTTGGAGTTCCGTGTTATATGGTA
TACACATCGAACGCTACGTTTTTAGGAACCATGCTTCACGTTCAACAAATGTACGATCAAAAGAAGTAT
GACGTCAGCGAGTTAGAAAACTCGGTCACCGAGTTGGAGTTTCCGTCTCTGACTCGTCCTTATCCAGTG
AAGTGTCTTCCTCATATCCTCACTTCAAAGGAGTGGTTACCTCTCTCTCTAGCTCAAGCTAGGTGTTTC
CGGAAGATGAAGGGTATTTTGGTAAATACAGTTGCTGAGCTTGAACCTCACGCTTTGAAAATGTTCAAT
ATTAATGGTGACGATCTTCCTCAAGTTTATCCTGTTGGACCAGTGTTGCATCTCGAAAACGGCAATGAC
GATGATGAGAAGCAATCGGAAATTTTGCGGTGGCTCGACGAGCAACCGTCTAAATCTGTTGTGTTTCTC
TGCTTTGGGAGCTTGGGAGGTTTCACTGAAGAACAAACAAGAGAAACCGCTGTGGCCCTAGATAGAAGC
GGTCAGCGGTTTCTTTGGTGTCTTCGTCACGCATCGCCAAATATAAAAACAGATCGTCCCAGAGATTAC
ACGAATCTTGAGGAGGTTTTACCGGAGGGGTTCTTGGAACGGACTTTGGATAGAGGGAAAGTGATTGGA
TGGGCACCACAAGTGGCGGTACTAGAGAAGCCGGCGATAGGAGGGTTTGTCACTCACTGCGGTTGGAAC
TCTATTTTAGAGAGCTTGTGGTTCGGTGTTCCAATGGTGACGTGGCCGCTATACGCGGAACAGAAGGTT
AACGCGTTTGAGATGGTTGAGGAGCTGGGTTTGGCGGTGGAGATACGGAAGTACTTAAAAGGAGATTTG
TTCGCCGGAGAGATGGAGACGGTTACCGCGGAGGATATAGAGAGAGCCATTAGGCGTGTGATGGAGCAA
GACAGTGACGTTAGGAACAACGTGAAAGAGATGGCGGAGAAGTGCCACTTCGCGTTAATGGACGGTGGA
TCTTCGAAGGCGGCTTTGGAAAAGTTTATTCAAGACGTGATAGAGAATATGGATTAA

UGT71C3 Figure 13

ATGAAAGCAGAAGCAGAGATCATCTTCGTTACATATCCATCCCCTGGTCATCTTCTTGTCTCCATTGAA
TTCGCTAAATCTCTCATCAAACGTGATGATCGCATCCACACCATCACCATCCTCTACTGGGCTTTACCT
CTCGCTCCTCAAGCCCACCTTTTCGCTAAGTCCCTCGTTGCTTCACAGCCTCGAATCCGTCTCCTTGCG
TTGCCTGATGTTCAAAACCCTCCACCATTGGAACTCTTCTTTAAAGCTCCCGAAGCTTATATTCTTGAG
TCCACCAAGAAAACAGTTCCTTTAGTCAGAGACGCTCTCTCCACTCTAGTTTCTTCACGTAAAGAATCC
GGTTCGGTTCGTGTAGTCGGTTTGGTTATCGATTTTTTTTGTGTTCCAATGATCGAAGTGGCAAACGAG
CTTAACCTTCCTTCTTACATCTTCCTAACGTGTAACGCTGGGTTTTTAAGTATGATGAAGTATCTCCCT
GAGAGACATCGCATAACCACTTCTGAGCTAGATTTAAGCTCCGGCAACGTAGAACATCCAATTCCTGGC
TACGTCTGCTCCGTGCCGACGAAGGTTTTGCCTCCAGGTCTATTCGTGAGAGAGTCCTACGAGGCTTGG
GTCGAGATTGCAGAGAAGTTCCCTGGAGCCAAGGGCATTTTGGTAAACTCAGTCACATGTCTTGAGCAG
AATGCATTTGATTACTTCGCTCGTCTTGATGAGAACTATCCTCCGGTTTACCCGGTCGGACCGGTTCTT
AGTTTGAAGGATCGTCCGTCTCCAAATCTGGACGCATCGGACCGGGATCGGATCATGAGATGGCTCGAG
GACCAGCCGGAGTCGTCAATTGTGTATATCTGCTTCGGAAGCCTCGGAATCATTGGCAAGCTGCAGATT
GAAGAGATAGCTGAAGCCTTGGAACTCACCGGCCACAGGTTTCTTTGGTCAATACGTACAAATCCGACG
GAGAAAGCGAGCCCGTACGATCTGTTGCCGGAGGGATTTCTCGATCGGACGGCCAGTAAGGGATTGGTG
TGTGATTGGGCCCCGCAAGTAGAAGTTCTGGCCCATAAAGCGCTCGGAGGATTCGTGTCTCACTGCGGT
TGGAACTCTGTACTGGAGAGCTTATGGTTCGGTGTTCCGATCGCCACGTGGCCAATGTACGCTGAGCAA
CAGTTAAACGCATTCTCGATGGTGAAGGAGTTAGGGTTAGCCGTGGAGCTGCGTTTAGACTACGTTTCG
GCGTACGGAGAGATAGTAAAAGCTGAGGAGATCGCGGGAGCCATACGATCATTGATGGACGGTGAGGAT
ACGCCGAGGAAGAGAGTGAAGGAGATGGCGGAAGCGGCGAGGAATGCTTTGATGGACGGAGGATCTTCG
TTTGTTGCGGTTAAACGATTTCTCGACGAGTTGATCGGCGGAGATGTTTAG

UGT71C5 Figure 14

ATGAAGACAGCAGAGCTCATATTCGTTCCTCTGCCGGAGACCGGCCATCTCTTGTCAACGATCGAGTTT
GGAAAGCGTCTACTCAATCTAGACCGTCGGATTTCTATGATTACAATCCTCTCCATGAATCTTCCTTAC
GCTCCTCACGCCGACGCTTCTCTTGCTTCGCTAACAGCCTCCGAGCCTGGTATCCGAATCATCAGTCTC
CCGGAGATCCACGATCCACCTCCGATCAAGCTTCTTGACACTTCCTCCGAGACTTACATCCTCGATTTC
ATCCATAAAAACATACCTTGTCTCAGAAAAACCATCCAAGATTTAGTCTCATCATCATCATCTTCCGGA
GGTGGTAGTAGTCATGTCGCCGGCTTGATTCTTGATTTCTTCTGCGTTGGTTTGATCGACATCGGCCGT
GAGGTAAACCTTCCTTCCTATATCTTCATGACTTCCAACTTTGGTTTCTTAGGGGTTCTACAGTATCTC
CCGGAACGACAACGTTTGACTCCGTCGGAGTTCGATGAGAGCTCCGGCGAGGAAGAGTTACATATTCCG
GCGTTTGTGAACCGTGTTCCCGCCAAGGTTCTGCCGCCAGGTGTGTTCGATAAACTCTCTTACGGGTCT
CTGGTCAAAATCGGCGAGCGATTACATGAAGCCAAGGGTATTTTGGTTAATTCATTTACCCAAGTGGAG
CCTTATGCTGCTGAACATTTTTCTCAAGGACGAGATTACCCTCACGTGTATCCTGTTGGGCCGGTTCTC
AACTTAACGGGCCGTACAAATCCGGGTCTAGCTTCGGCCCAATATAAAGAGATGATGAAGTGGCTTGAC
GAGCAACCAGACTCGTCGGTTTTGTTCCTGTGTTTCGGGAGCATGGGAGTCTTCCCTGCACCTCAGATC
ACAGAGATTGCTCACGCGCTCGAGCTTATCGGGTGCAGGTTCATCTGGGCGATCCGTACGAACATGGCG
GGAGATGGCGATCCTCAGGAGCCGCTTCCAGAAGGATTTGTCGATCGAACAATGGGCCGTGGAATTGTG
TGTAGTTGGGCTCCACAAGTGGATATCTTGGCCCACAAGGCAACAGGTGGATTCGTTTCTCACTGCGGG
TGGAATTCCGTCCAAGAGAGTCTATGGTACGGTGTACCTATTGCAACGTGGCCAATGTATGCGGAGCAA
CAACTGAACGCATTTGAGATGGTGAAGGAGTTGGGCTTAGCAGTGGAGATAAGGCTTGACTACGTGGCG
GATGGTGATAGGGTTACTTTGGAGATCGTGTCAGCCGATGAAATAGCCACAGCCGTCCGATCATTGATG
GATAGTGATAACCCCGTGAGAAAGAAGGTTATAGAAAAATCTTCAGTGGCGAGGAAAGCTGTTGGTGAT
GGTGGGTCTTCTACGGTGGCCACATGTAATTTTATCAAAGATATTCTTGGGGATCACTTTTGA

UGT71D1 Figure 15

ATGCGGAATGTAGAGCTCATCTTCATCCCCACACCAACCGTTGGTCATCTTGTTCCGTTTCTTGAATTT
GCTAGGCGTCTCATTGAGCAAGATGATAGGATCCGTATCACAATCCTCTTGATGAAACTACAAGGTCAG
TCTCATCTAGACACTTATGTTAAATCAATTGCCTCCTCTCAACCGTTTGTTAGATTCATTGATGTCCCT
GAGTTAGAGGAGAAACCTACACTTGGTAGTACACAATCTGTGGAAGCTTATGTGTATGATGTTATTGAG
AGAAATATCCCTCTTGTGAGGAATATAGTCATGGATATTTTAACTTCTCTTGCATTGGATGGAGTTAAG
GTCAAGGGATTAGTTGTTGACTTTTTCTGTCTCCCTATGATTGACGTTGCTAAAGATATAAGTCTCCCT
TTCTATGTGTTCTTGACTACAAATTCCGGGTTCTTAGCTATGATGCAGTATCTAGCAGATCGACATAGT
AGAGATACATCGGTTTTTGTAAGAAACTCGGAAGAAATGTTGTCGATACCTGGATTTGTAAACCCTGTC
CCAGCCAATGTTCTGCCGTCAGCTCTGTTTGTTGAAGATGGTTATGATGCTTACGTTAAGCTGGCCATA
TTGTTTACAAAGGCCAATGGAATCCTAGTGAATAGCTCCTTTGATATTGAGCCTTACTCTGTGAATCAT
TTTCTTCAAGAACAGAATTATCCTTCTGTTTATGCTGTTGGCCCCATATTTGACTTGAAAGCCCAGCCT
CATCCAGAGCAGGACCTAACCCGTCGTGACGAGTTGATGAAATGGCTTGATGATCAACCCGAGGCATCG
GTTGTATTCCTTTGTTTTGGGAGTATGGCAAGGTTAAGAGGTTCTCTAGTGAAGGAAATAGCTCATGGA
CTTGAGCTATGTCAATATAGATTCCTCTGGTCACTCCGTAAAGAAGAGGTGACAAAGGATGATTTGCCA
GAGGGGTTCCTTGACCGTGTCGATGGACGTGGAATGATATGTGGTTGGTCTCCTCAGGTAGAAATACTG
GCCCATAAGGCAGTGGGAGGCTTTGTTTCTCACTGTGGATGGAACTCAATAGTAGAGAGTTTGTGGTTT
GGCGTGCCAATTGTGACATGGCCAATGTATGCAGAGCAACAACTCAATGCGTTTCTGATGGTGAAGGAA
CTGAAGCTAGCTGTGGAGCTGAAGCTTGATTACAGGGTACATAGTGATGAGATAGTAAACGCAAACGAG
ATAGAGACCGCTATTCGTTATGTAATGGACACGGATAATAATGTTGTGAGGAAACGAGTGATGGATATC
TCGCAGATGATCCAGAGAGCTACGAAGAATGGTGGATCTTCGTTTGCCGCAATTGAGAAATTCATATAT
GACGTGATAGGAATTAAGCCCTAG

UGT73B1 Figure 16

ATGGGAACTCCTGTCGAAGTCTCTAAGCTCCATTTCTTGCTCTTCCCTTTCATGGCTCATGGCCATATG
ATACCAACTCTAGACATGGCTAAGCTCTTTGCCACCAAAGGAGCTAAATCCACTATCCTCACTACACCT
CTCAATGCCAAGCTCTTCTTCGAGAAACCCATCAAATCATTCAACCAAGACAACCCGGGACTCGAAGAC
ATCACCATCCAGATCCTTAATTTCCCTTGCACAGAGCTTGGTTTGCCTGATGGCTGTGAGAATACTGAT
TTCATCTTCTCCACACCTGACCTAAACGTAGGTGACTTGAGTCAAAAGTTTTTACTCGCAATGAAATAT
TTCGAAGAGCCACTAGAGGAGCTCCTCGTGACAATGAGACCAGACTGTCTTGTCGGTAACATGTTCTTC
CCTTGGTCCACTAAAGTTGCTGAGAAGTTCGGAGTACCGAGACTTGTGTTCCACGGCACAGGCTACTTC
TCTTTATGTGCTTCTCATTGCATAAGGCTCCCTAAGAATGTGGCAACAAGTTCTGAGCCCTTTGTGATT
CCTGATCTCCCGGGAGACATTTTGATTACAGAGGAACAGGTCATGGAGACAGAAGAAGAGTCTGTAATG
GGGAGGTTTATGAAGGCAATAAGAGACTCAGAGAGAGATAGCTTTGGCGTGTTGGTGAACAGCTTCTAC
GAGCTTGAACAGGCTTACTCAGATTATTTCAAGAGCTTTGTGGCGAAAAGAGCGTGGCATATCGGTCCG
CTTTCCTTAGGAAATAGAAAGTTCGAGGAGAAAGCAGAAAGAGGCAAAAAGGCAAGCATTGATGAGCAT
GAATGTTTGAAATGGCTCGACTCCAAGAAATGTGATTCAGTGATTTACATGGCCTTTGGAACCATGTCT
AGCTTTAAAAACGAGCAGCTGATAGAGATTGCAGCTGGTTTAGATATGTCAGGACATGATTTTGTCTGG
GTGGTTAACAGAAAAGGCAGCCAAGGTACCATAGACATCACTCTCTTTGCAGCAAAATCCTCTGTTTTT
GTTTTAGAGAAAAACCAATGATCTAATTAGGATTCTACTGTTTCAAACTCTAACTTTTGCGTTTGCATT
ACATATAAATAGTTGAGAAGGAAGATTGGTTACCAGAGGGGTTTGAAGAGAAGACCAAGGGAAAAGGAT
TGATAATCCGAGGGTGGGCGCCACAAGTGCTGATACTTGAGCACAAAGCAATTGGCGGATTTTTGACGC
ATTGTGGATGGAACTCGTTATTAGAAGGGGTGGCAGCGGGCCTGCCAATGGTGACATGGCCCGTGGGAG
CCGAGCAGTTCTACAACGAGAAATTGGTGACACAAGTGTTGAAAACAGGAGTGAGTGTGGGAGTGAAGA
AGATGATGCAAGTAGTTGGAGACTTCATTAGCAGAGAGAAAGTGGAGGGAGCGGTGAGGGAAGTGATGG
TTGGAGAAGAGAGGAGGAAACGGGCCAAGGAGTTAGCAGAAATGGCGAAAAATGCGGTGAAAGAAGGAG
GATCTTCAGATCTAGAGGTAGATAGGTTGATGGAAGAGCTTACGTTAGTTAAACTGCAAAAAGAGAAGG
TATAA

UGT73B2 Figure 17

ATGGGTAGTGATCATCATCATCGAAAGCTCCACGTTATGTTCTTCCCTTTCATGGCTTATGGTCACATG
ATACCAACTCTAGACATGGCTAAGCTTTTCTCTAGCAGAGGAGCCAAATCCACAATCCTCACCACATCT
CTCAACTCCAAGATCCTCCAAAAACCCATCGACACATTCAAGAATCTGAATCCGGGTCTCGAAATCGAC
ATCCAGATCTTCAATTTCCCTTGCGTGGAGCTGGGGTTACCAGAAGGATGTGAAAACGTTGATTTCTTC
ACTTCAAACAACAATGATGATAAAAACGAGATGATCGTGAAATTCTTTTTCTCGACAAGGTTTTTCAAA
GACCAGCTTGAGAAACTCCTCGGGACAACGAGACCAGACTGTCTTATCGCCGACATGTTCTTCCCCTGG
GCTACTGAAGCTGCTGGGAAGTTCAATGTGCCAAGACTTGTGTTCCACGGCACTGGCTACTTCTCTTTA
TGCGCTGGTTATTGCATCGGAGTGCATAAACCACAGAAGAGAGTGGCTTCAAGCTCTGAGCCATTTGTG
ATTCCCGAGCTCCCTGGGAACATTGTGATAACTGAAGAACAGATCATAGATGGCGATGGAGAATCCGAC
ATGGGAAAGTTTATGACTGAAGTTAGGGAATCGGAAGTGAAGAGCTCAGGAGTTGTTTTGAATAGTTTC
TACGAGCTAGAACATGATTACGCCGATTTTTACAAAAGTTGTGTACAAAAGAGAGCGTGGCATATCGGT
CCGCTATCGGTTTACAACAGGGGATTTGAGGAGAAGGCTGAGAGAGGAAAGAAAGCGAACATTGATGAG
GCTGAATGCCTCAAATGGCTTGACTCCAAGAAACCAAATTCAGTCATTTATGTTTCCTTTGGGAGCGTG
GCTTTCTTCAAGAATGAACAGTTATTCGAGATCGCTGCAGGGTTAGAAGCTTCCGGTACAAGTTTCATT
TGGGTTGTTAGGAAAACCAAAGGTATTGAAATTGACGTTTGAAGCCTATATTATATAGCTGTAATTTGG
GTAGCTTTGATTTTAATCTGACACAAGATTTGGTGTGAACAGATGATAGAGAAGAATGGTTACCAGAAG
GGTTCGAAGAGAGGGTGAAAGGGAAAGGTATGATAATAAGAGGATGGGCACCACAGGTGCTGATACTTG
ACCACCAAGCAACCGGTGGGTTTGTGACCCATTGCGGCTGGAACTCGCTTCTTGAAGGAGTGGCTGCAG
GGCTACCAATGGTGACATGGCCTGTAGGAGCGGAGCAATTCTACAATGAGAAATTGGTTACGCAAGTGC
TCAGAACAGGAGTGAGCGTGGGAGCGAGCAAGCATATGAAAGTTATGATGGGAGATTTCATTAGCAGAG
AGAAAGTGGATAAAGCGGTGAGGGAGGTTTTGGCTGGGGAAGCAGCAGAGGAGAGGCGGAGACGGGCAA
AGAAGCTAGCGGCGATGGCTAAAGCTGCCGTGGAAGAAGGAGGGTCTTCCTTCAACGATCTAAACAGCT
TCATGGAAGAGTTTAGTTCATAA

UGT73B4 Figure 18

ATGAACAGAGAGCAAATTCATATTTTGTTCTTCCCCTTCATGGCTCATGGCCACATGATTCCACTCTTA
GACATGGCCAAGCTTTTCGCTAGAAGAGGAGCCAAATCAACTCTCCTCACAACCCCAATAAATGCTAAG
ATCTTGGAGAAACCCATTGAAGCATTCAAAGTTCAAAATCCTGATCTCGAAATCGGAATCAAGATCCTC
AATTTCCCTTGTGTAGAGCTTGGATTGCCAGAAGGATGCGAGAACCGTGACTTCATTAACTCATACCAA
AAATCTGACTCATTTGACTTGTTCTTGAAGTTTCTTTTCTCTACCAAGTATATGAAACAGCAGTTGGAG
AGTTTCATTGAAACAACCAAACCGAGTGCTCTTGTAGCCGATATGTTCTTCCCTTGGGCAACAGAATCC
GCGGAGAAGATCGGTGTTCCAAGACTTGTGTTCCACGGCACATCATCCTTTGCCTTGTGTTGTTCGTAT
AACATGAGGATTCATAAGCCACACAAGAAAGTCGCTTCGAGTTCTACTCCATTTGTAATCCCTGGTCTC
CCTGGAGACATAGTTATTACAGAAGACCAAGCCAATGTCACCAACGAAGAAACTCCATTCGGAAAGTTT
TGGAAAGAAGTCAGGGAATCAGAGACCAGTAGCTTTGGTGTTTTGGTGAATAGCTTCTACGAGCTGGAA
TCATCTTATGCTGATTTTTACCGTAGTTTTGTGGCGAAAAAAGCGTGGCATATAGGTCCACTTTCACTA
TCCAACAGAGGGATTGCAGAGAAAGCCGGAAGAGGGAAAAAGGCAAACATTGATGAGCAAGAATGCCTC
AAATGGCTTGACTCTAAGACACCTGGCTCAGTAGTTTACTTGTCCTTTGGTAGCGGAACCGGCTTACCC
AACGAACAGCTGTTAGAGATTGCTTTCGGCCTTGAAGGCTCTGGACAAAATTTCATTTGGGTGGTTAGC
AAAAATGAAAACCAAGGTAATTTTTTTCCTCCTTAACCATTATTAATCAATGTAGTCTTTATTAGTATA
TTTCCAAAAATATTAACATTTGTGTATACATTTTCCTATTGCCAAATATGCTATGATGCCATAGCAATG
AGTAGATTGGTTTGTGTACTTTATATATTACTTTGTAGAACTTCTAACAATTATGACTTGGTGTTGGTG
TAGTTGGGACAGGTGAAAATGAAGATTGGTTGCCTAAAGGGTTTGAAGAGAGGAATAAAGGAAAAGGGC
TGATAATACGCGGATGGGCCCCGCAAGTGCTGATACTTGACCACAAAGCAATCGGAGGATTTGTGACGC
ATTGCGGATGGAACTCGACTTTGGAGGGCATTGCCGCAGGGCTGCCTATGGTGACTTGGCCGATGGGGG
CAGAACAGTTCTACAACGAGAAGTTATTGACAAAAGTGTTGAGAATAGGAGTGAACGTTGGAGCTACCG
AGTTGGTGAAAAAAGGAAAGTTGATTAGTAGAGCACAAGTGGAGAAGGCAGTAAGGGAAGTGATTGGTG
GTGAGAAGGCAGAGGAAAGGCGGCTAAGGGCTAAGGAGCTGGGCGAGATGGCTAAAGCCGCTGTGGAAG
AAGGAGGGTCTTCTTATAATGATGTGAACAAGTTTATGGAAGAGCTGAATGGTAGAAAGTAG

UGT73B5 Figure 19

ATGAACAGAGAAGTCTCTGAGAGAATTCATATTTTGTTCTTCCCCTTCATGGCTCAAGGCCACATGATT
CCAATTTTGGACATGGCCAAGCTTTTCTCGAGGAGAGGAGCCAAGTCAACCCTTCTCACAACCCCAATC
AACGCTAAGATCTTCGAGAAACCTATTGAAGCATTCAAAAATCAAAACCCTGATCTCGAAATCGGAATC
AAGATCTTCAATTTCCCTTGTGTAGAGCTTGGATTGCCTGAAGGATGCGAGAACGCTGACTTTATCAAC
TCATACCAAAAATCTGACTCAGGTGACTTGTTCTTGAAGTTTCTTTTCTCTACCAAGTATATGAAACAA
CAGTTGGAGAGTTTCATTGAAACAACCAAACCAAGTGCTCTTGTTGCCGATATGTTCTTCCCTTGGGCG
ACAGAATCTGCTGAGAAGCTCGGTGTACCAAGACTTGTGTTCCACGGTACATCTTTCTTTTCTTTGTGT
TGTTCGTATAACATGAGGATTCATAAGCCACACAAGAAAGTCGCTACGAGTTCTACTCCTTTTGTAATC
CCTGGTCTCCCAGGAGACATAGTTATTACAGAAGACCAAGCCAATGTTGCCAAAGAAGAAACGCCAATG
GGAAAGTTTATGAAAGAGGTTAGGGAATCAGAGACCAATAGCTTTGGTGTATTGGTTAATAGCTTCTAC
GAGCTGGAATCAGCTTATGCTGATTTTTATCGTAGTTTTGTGGCGAAAAGAGCTTGGCATATCGGTCCG
CTTTCGCTATCTAACAGAGAGTTAGGAGAGAAAGCCAGAAGAGGGAAAAAGGCTAACATTGATGAGCAA
GAATGCCTAAAATGGCTGGACTCTAAGACACCTGGTTCAGTAGTTTACTTGTCCTTTGGGAGCGGAACT
AATTTCACCAACGACCAGCTGTTAGAGATCGCTTTTGGTCTTGAAGGTTCTGGACAAAGTTTCATCTGG
GTGGTTAGGAAAAATGAAAACCAAGGTAAATTGTTTCTCCCCAGCCATTATTAACCAACATAGTAATGT
TAATATTTGTGTATATATTCGTATTGCCAAATATGCTCTGATACCATGGCAAGTAATAGATTGGCTCAT
GTATTTTATTTGTGATCATGTAGAATTTTCTTAACAGTTATGACTTGGTGTTGGTATGGTTGGGACAGG
TGACAATGAAGAGTGGTTGCCTGAAGGGTTTAAAGAGAGGACAACAGGGAAAGGGCTAATAATACCTGG
ATGGGCGCCGCAAGTGCTGATACTTGACCATAAAGCAATTGGAGGATTTGTGACTCATTGCGGATGGAA
CTCGGCTATAGAGGGCATTGCCGCGGGGCTGCCTATGGTAACATGGCCAATGGGGGCAGAACAGTTCTA
CAATGAGAAGCTATTGACAAAAGTGTTGAGAATAGGAGTGAACGTTGGAGCTACCGAGTTGGTGAAAAA
AGGAAAGTTGATTAGTAGAGCACAAGTGGAGAAGGCAGTAAGGGAAGTGATTGGTGGTGAGAAGGCAGA
GGAAAGGCGGCTATGGGCTAAGAAGCTGGGCGAGATGGCTAAAGCCGCTGTGGAAGAAGGAGGGTCCTC
TTATAATGATGTGAACAAGTTTATGGAAGAGCTGAATGGTAGAAAGTAG

UGT73C1 Figure 20

ATGGCATCGGAATTTCGTCCTCCTCTTCATTTTGTTCTCTTCCCTTTCATGGCTCAAGGCCACATGATC
CCAATGGTAGATATTGCAAGGCTCCTGGCTCAGCGCGGGGTGACTATAACCATTGTCACTACACCTCAA
AACGCAGGCCGGTTCAAGAACGTTCTTAGCCGGGCTATCCAATCCGGCTTGCCCATCAATCTCGTGCAA
GTAAAGTTTCCATCTCAAGAATCGGGTTCACCGGAAGGACAGGAGAATTTGGACTTGCTCGATTCATTG
GGGGCTTCATTAACCTTCTTCAAAGCATTTAGCCTGCTCGAGGAACCAGTCGAGAAGCTCTTGAAAGAG
ATTCAACCTAGGCCAAACTGCATAATCGCTGACATGTGTTTGCCTTATACAAACAGAATTGCCAAGAAT
CTTGGTATACCAAAAATCATCTTTCATGGCATGTGTTGCTTCAATCTTCTTTGTACGCACATAATGCAC
CAAAACCACGAGTTCTTGGAAACTATAGAGTCTGACAAGGAATACTTCCCCATTCCTAATTTCCCTGAC
AGAGTTGAGTTCACAAAATCTCAGCTTCCAATGGTATTAGTTGCTGGAGATTGGAAAGACTTCCTTGAC
GGAATGACAGAAGGGGATAACACTTCTTATGGTGTGATTGTTAACACGTTTGAAGAGCTCGAGCCAGCT
TATGTTAGAGACTACAAGAAGGTTAAAGCGGGTAAGATATGGAGCATCGGACCGGTTTCCTTGTGCAAC
AAGTTAGGAGAAGACCAAGCTGAGAGGGGAAACAAGGCGGACATTGATCAAGACGAGTGTATTAAATGG
CTTGATTCTAAAGAAGAAGGGTCGGTGCTATATGTTTGCCTTGGAAGTATATGCAATCTTCCTCTGTCT
CAGCTCAAAGAGCTCGGCTTAGGCCTCGAGGAATCCCAAAGACCTTTCATTTGGGTCATAAGAGGTTGG
GAGAAGTATAACGAGTTACTTGAATGGATCTCAGAGAGCGGTTATAAGGAAAGAATCAAAGAAAGAGGC
CTTCTCATAACAGGATGGTCGCCTCAAATGCTTATCCTTACACATCCTGCCGTTGGAGGATTCTTGACA
CATTGTGGATGGAACTCTACTCTTGAAGGAATCACTTCAGGCGTTCCATTACTCACGTGGCCACTGTTT
GGAGACCAATTCTGCAATGAGAAATTGGCGGTGCAGATACTAAAAGCCGGTGTGAGAGCTGGGGTTGAA
GAGTCCATGAGATGGGGAGAAGAGGAGAAAATAGGAGTACTGGTGGATAAAGAAGGAGTAAAGAAGGCA
GTGGAGGAATTGATGGGTGATAGTAATGATGCTAAGGAGAGAAGAAAAAGAGTGAAAGAGCTTGGAGAA
TTAGCTCACAAGGCTGTGGAAGAAGGAGGCTCTTCTCATTCCAACATCACATTCTTGCTACAAGACATA
ATGCAATTAGAACAACCCAAGAAATGA

UGT731C Figure 21

ATGGCTACGGAAAAAACCCACCAATTTCATCCTTCTCTTCACTTTGTCCTCTTCCCTTTCATGGCTCAA
GGCCACATGATTCCCATGATTGATATTGCAAGACTCTTGGCTCAGCGTGGTGTGACCATAACAATTGTC
ACGACACCTCACAACGCAGCAAGGTTTAAGAATGTCCTAAACCGAGCGATCGAGTCTGGCTTGGCCATC
AACATACTGCATGTGAAGTTTCCATATCAAGAGTTTGGTTTGCCAGAAGGAAAAGAGAATATAGATTCG
TTAGACTCAACGGAGTTGATGGTACCTTTCTTCAAAGCGGTGAACTTGCTTGAAGATCCGGTCATGAAG
CTCATGGAAGAGATGAAACCTAGACCTAGCTGTCTAATTTCTGATTGGTGTTTGCCTTATACAAGCATA
ATCGCCAAGAACTTCAATATACCAAAGATAGTTTTCCACGGCATGGGTTGCTTTAATCTTTTGTGTATG
CATGTTCTACGCAGAAACTTAGAGATCCTAGAGAATGTAAAGTCGGATGAAGAGTATTTCTTGGTTCCT
AGTTTTCCTGATAGAGTTGAATTTACAAAGCTTCAACTTCCTGTGAAAGCAAATGCAAGTGGAGATTGG
AAAGAGATAATGGATGAAATGGTAAAAGCAGAATACACATCCTATGGTGTGATCGTCAACACATTTCAG
GAGTTGGAGCCACCTTATGTCAAAGACTACAAAGAGGCAATGGATGGAAAAGTATGGTCCATTGGACCC
GTTTCCTTGTGTAACAAGGCAGGTGCAGACAAAGCTGAGAGGGGAAGCAAGGCCGCCATTGATCAAGAT
GAGTGTCTTCAATGGCTTGATTCTAAAGAAGAAGGTTCGGTGCTCTATGTTTGCCTTGGAAGTATATGT
AATCTTCCTTTGTCTCAGCTCAAGGAGCTGGGGCTAGGCCTTGAGGAATCTCGAAGATCTTTTATTTGG
GTCATAAGAGGTTCGGAAAAGTATAAAGAACTATTTGAGTGGATGTTGGAGAGCGGTTTTGAAGAAAGA
ATCAAAGAGAGAGGACTTCTCATTAAAGGGTGGGCACCTCAAGTCCTTATCCTTTCACATCCTTCCGTT
GGAGGATTCCTGACACACTGTGGATGGAACTCGACTCTCGAAGGAATCACCTCAGGCATTCCACTGATC
ACTTGGCCGCTGTTTGGAGACCAATTCTGCAACCAAAAACTGGTCGTTCAAGTACTAAAAGCCGGTGTA
AGTGCCGGGGTTGAAGAAGTCATGAAATGGGGAGAAGAAGATAAAATAGGAGTGTTAGTGGATAAAGAA
GGAGTGAAAAAGGCTGTGGAAGAATTGATGGGTGATAGTGATGATGCAAAAGAGAGGAGAAGAAGAGTC
AAAGAGCTTGGAGAATTAGCTCACAAAGCTGTGGAAAAAGGAGGCTCTTCTCATTCTAACATCACACTC
TTGCTACAAGACATAATGCAACTAGCACAATTCAAGAATTGA

UGT73C5 Figure 22

ATGGTTTCCGAAACAACCAAATCTTCTCCACTTCACTTTGTTCTCTTCCCTTTCATGGCTCAAGGCCAC
ATGATTCCCATGGTTGATATTGCAAGGCTCTTGGCTCAGCGTGGTGTGATCATAACAATTGTCACGACG
CCTCACAATGCAGCGAGGTTCAAGAATGTCCTAAACCGTGCCATTGAGTCTGGCTTGCCCATCAACTTA
GTGCAAGTCAAGTTTCCATATCTAGAAGCTGGTTTGCAAGAAGGACAAGAGAATATCGATTCTCTTGAC
ACAATGGAGCGGATGATACCTTTCTTTAAAGCGGTTAACTTTCTCGAAGAACCAGTCCAGAAGCTCATT
GAAGAGATGAACCCTCGACCAAGCTGTCTAATTTCTGATTTTTGTTTGCCTTATACAAGCAAAATCGCC
AAGAAGTTCAATATCCCAAAGATCCTCTTCCATGGCATGGGTTGCTTTTGTCTTCTGTGTATGCATGTT
TTACGCAAGAACCGTGAGATCTTGGACAATTTAAAGTCAGATAAGGAGCTTTTCACTGTTCCTGATTTT
CCTGATAGAGTTGAATTCACAAGAACGCAAGTTCCGGTAGAAACATATGTTCCAGCTGGAGACTGGAAA
GATATCTTTGATGGTATGGTAGAAGCGAATGAGACATCTTATGGTGTGATCGTCAACTCATTTCAAGAG
CTCGAGCCTGCTTATGCCAAAGACTACAAGGAGGTAAGGTCCGGTAAAGCATGGACCATTGGACCCGTT
TCCTTGTGCAACAAGGTAGGAGCCGACAAAGCAGAGAGGGGAAACAAATCAGACATTGATCAAGATGAG
TGCCTTAAATGGCTCGATTCTAAGAAACATGGCTCGGTGCTTTACGTTTGTCTTGGAAGTATCTGTAAT
CTTCCTTTGTCTCAACTCAAGGAGCTGGGACTAGGCCTAGAGGAATCCCAAAGACCTTTCATTTGGGTC
ATAAGAGGTTGGGAGAAGTACAAAGAGTTAGTTGAGTGGTTCTCGGAAAGCGGCTTTGAAGATAGAATC
CAAGATAGAGGACTTCTCATCAAAGGATGGTCCCCTCAAATGCTTATCCTTTCACATCCATCAGTTGGA
GGGTTCCTAACACACTGTGGTTGGAACTCGACTCTTGAGGGGATAACTGCTGGTCTACCGCTACTTACA
TGGCCGCTATTCGCAGACCAATTCTGCAATGAGAAATTGGTCGTTGAGGTACTAAAAGCCGGTGTAAGA
TCCGGGGTTGAACAGCCTATGAAATGGGGAGAAGAGGAGAAAATAGGAGTGTTGGTGGATAAAGAAGGA
GTGAAGAAGGCAGTGGAAGAATTAATGGGTGAGAGTGATGATGCAAAAGAGAGAAGAAGAAGAGCCAAA
GAGCTTGGAGATTCAGCTCACAAGGCTGTGGAAGAAGGAGGCTCTTCTCATTCTAACATCTCTTTCTTG
CTACAAGACATAATGGAACTGGCAGAACCCAATAATTGA

UGT73C6 Figure 23

ATGGCTTTCGAAAAAAACAACGAACCTTTTCCTCTTCACTTTGTTCTCTTCCCTTTCATGGCTCAAGGC
CACATGATTCCCATGGTTGATATTGCAAGGCTCTTGGCTCAGCGAGGTGTGCTTATAACAATTGTCACG
ACGCCTCACAATGCAGCAAGGTTCAAGAATGTCCTAAACCGTGCCATTGAGTCTGGTTTGCCCATCAAC
CTAGTGCAAGTCAAGTTTCCATATCAAGAAGCTGGTCTGCAAGAAGGACAAGAAAATATGGATTTGCTT
ACCACGATGGAGCAGATAACATCTTTCTTTAAAGCGGTTAACTTACTCAAAGAACCAGTCCAGAACCTT
ATTGAAGAGATGAGCCCGCGACCAAGCTGTCTAATCTCTGATATGTGTTTGTCGTATACAAGCGAAATC
GCCAAGAAGTTCAAAATACCAAAGATCCTCTTCCATGGCATGGGTTGCTTTTGTCTTCTGTGTGTTAAC
GTTCTGCGCAAGAACCGTGAGATCTTGGACAATTTAAAGTCTGATAAGGAGTACTTCATTGTTCCTTAT
TTTCCTGATAGAGTTGAATTCACAAGACCTCAAGTTCCGGTGGAAACATATGTTCCTGCAGGCTGGAAA
GAGATCTTGGAGGATATGGTAGAAGCGGATAAGACATCTTATGGTGTTATAGTCAACTCATTTCAAGAG
CTCGAACCTGCGTATGCCAAAGACTTCAAGGAGGCAAGGTCTGGTAAAGCATGGACCATTGGACCTGTT
TCCTTGTGCAACAAGGTAGGAGTAGACAAAGCAGAGAGGGGAAACAAATCAGATATTGATCAAGATGAG
TGCCTTGAATGGCTCGATTCTAAGGAACCGGGATCTGTGCTCTACGTTTGCCTTGGAAGTATTTGTAAT
CTTCCTCTGTCTCAGCTCCTTGAGCTGGGACTAGGCCTAGAGGAATCCCAAAGACCTTTCATCTGGGTC
ATAAGAGGTTGGGAGAAATACAAAGAGTTAGTTGAGTGGTTCTCGGAAAGCGGCTTTGAAGATAGAATC
CAAGATAGAGGACTTCTCATCAAAGGATGGTCCCCTCAAATGCTTATCCTTTCACATCCTTCTGTTGGA
GGGTTCTTAACGCACTGCGGATGGAACTCGACTCTTGAGGGGATAACTGCTGGTCTACCAATGCTTACA
TGGCCACTATTTGCAGACCAATTCTGCAACGAGAAACTGGTCGTACAAATACTAAAAGTCGGTGTAAGT
GCCGAGGTTAAAGAGGTCATGAAATGGGGAGAAGAAGAGAAGATAGGAGTGTTGGTGGATAAAGAAGGA
GTGAAGAAGGCAGTGGAAGAACTAATGGGTGAGAGTGATGATGCAAAAGAGAGAAGAAGAAGAGCCAAA
GAGCTTGGAGAATCAGCTCACAAGGCTGTGGAAGAAGGAGGCTCCTCTCATTCTAATATCACTTTCTTG
CTACAAGACATAATGCAACTAGCACAGTCCAATAATTGA

UGT73C7 Figure 24

ATGTGTTCTCATGATCCTCTTCACTTCGTCGTAATACCCTTTATGGCCCAAGGCCATATGATCGCATTG
GTCGACATCTCTAGGCTCTTGTCCCAGCGCCAAGGCGTGACTGTCTGCATCATCACAACTACTCAAAAT
GTAGCCAAGATCAAGACTTCACTCTCATTTTCCTCTTTGTTTGCGACTATCAACATCGTTGAAGTTAAG
TTTCTGTCTCAACAAACGGGTTTGCCAGAAGGGTGCGAGAGTTTAGATATGTTGGCTTCAATGGGCGAT
ATGGTGAAGTTCTTTGATGCTGCCAACTCACTTGAGGAGCAAGTTGAGAAAGCTATGGAAGAGATGGTT
CAGCCGCGGCCAAGCTGCATCATTGGAGACATGAGCCTTCCTTTCACTTCAAGACTTGCCAAGAAATTC
AAGATCCCCAAACTTATCTTCCATGGGTTTTCTTGTTTCAGCCTCATGTCTATACAAGTGGTTCGAGAA
AGCGGGATCTTGAAAATGATAGAATCAAACGACGAGTATTTTGATTTGCCCGGCTTGCCTGACAAAGTT
GAGTTCACGAAACCTCAGGTCTCTGTGTTGCAACCTGTTGAAGGAAATATGAAAGAGAGTACGGCCAAG
ATTATTGAAGCTGATAATGACTCTTATGGTGTTATTGTGAACACTTTTGAAGAGTTAGAGGTTGATTAT
GCAAGAGAATATAGGAAAGCAAGGGCTGGAAAAGTTTGGTGCGTTGGACCTGTTTCCTTGTGCAATAGG
TTAGGGTTAGACAAAGCTAAAAGAGGAGATAAGGCTTCTATTGGTCAAGACCAATGTCTTCAATGGCTT
GACTCTCAAGAAACTGGTTCAGTGCTCTACGTTTGCCTTGGAAGTCTATGTAATCTTCCCTTGGCTCAG
CTCAAAGAGCTGGGACTAGGCCTTGAGGCATCTAATAAACCTTTCATATGGGTTATAAGAGAATGGGGA
AAATATGGAGATTTAGCAAATTGGATGCAACAAAGCGGATTTGAAGAGCGGATCAAAGATAGAGGACTG
GTGATCAAAGGTTGGGCGCCGCAAGTTTTCATCCTCTCACACGCATCCATTGGAGGGTTTTTGACTCAC
TGTGGATGGAACTCGACACTAGAAGGAATTACTGCAGGAGTTCCATTATTGACATGGCCTTTGTTTGCT
GAACAATTCTTGAATGAGAAGTTAGTTGTGCAGATACTAAAAGCAGGGTTAAAGATAGGAGTAGAGAAA
TTGATGAAATATGGAAAAGAAGAGGAGATAGGAGCGATGGTGAGCAGAGAATGTGTGAGAAAAGCTGTG
GATGAGCTAATGGGTGATAGTGAAGAAGCAGAAGAGAGAAGAAGAAAAGTTACAGAACTTAGTGACTTG
GCAAATAAGGCTTTGGAAAAAGGAGGATCTTCAGATTCTAATATCACATTGCTCATTCAAGATATTATG
GAGCAATCACAAAATCAATTTTAA

UGT74F2 Figure 25

ATGGAGCATAAGAGAGGACATGTATTAGCAGTGCCGTACCCAACGCAAGGACACATCACACCATTCCGC
CAATTCTGCAAACGACTTCACTTCAAAGGTCTCAAAACCACTCTCGCTCTCACCACTTTCGTCTTCAAC
TCCATCAATCCTGACCTATCCGGTCCAATCTCCATAGCCACCATCTCCGATGGCTATGACCATGGGGGT
TTCGAGACAGCTGACTCCATCGACGACTACCTCAAAGACTTTAAAACTTCCGGCTCGAAAACCATTGCA
GACATCATCCAAAAACACCAGACTAGTGATAACCCCATCACTTGTATCGTCTATGATGCTTTCCTGCCT
TGGGCACTTGACGTTGCTAGAGAGTTTGGTTTAGTTGCGACTCCTTTCTTTACGCAGCCTTGTGCTGTT
AACTATGTTTATTATCTTTCTTACATAAACAATGGAAGCTTGCAACTTCCCATTGAGGAATTGCCTTTT
CTTGAGCTCCAAGATTTGCCTTCTTTCTTCTCTGTTTCTGGCTCTTATCCTGCTTACTTTGAGATGGTG
CTTCAACAGTTCATAAATTTCGAAAAAGCTGATTTCGTTCTCGTTAATAGCTTCCAAGAGTTGGAACTG
CATGTTAGATCTCTCTCTATCTCTTTCTTACAATTCTTAAACCATCTCTTGTTCTTGTGCATGTACTAA
CTGCTCTTTTTTTGTTTACAGGAGAATGAATTGTGGTCGAAAGCTTGTCCTGTGTTGACAATTGGTCCA
ACTATTCCATCAATTTACTTAGACCAACGTATCAAATCAGACACCGGCTATGATCTTAATCTCTTTGAA
TCGAAAGATGATTCCTTCTGCATTAACTGGCTCGACACAAGGCCACAAGGGTCGGTGGTGTACGTAGCA
TTCGGAAGCATGGCTCAGCTGACTAATGTGCAGATGGAGGAGCTTGCTTCAGCAGTAAGCAACTTCAGC
TTCCTGTGGGTGGTCAGATCTTCAGAGGAGGAAAAACTCCCATCAGGGTTTCTTGAGACAGTGAATAAA
GAAAAGAGCTTGGTCTTGAAATGGAGTCCTCAGCTTCAAGTTCTGTCAAACAAAGCCATCGGTTGTTTC
TTGACTCACTGTGGCTGGAACTCAACCATGGAGGCTTTGACCTTCGGGGTTCCCATGGTGGCAATGCCC
CAATGGACTGATCAACCGATGAACGCAAAGTACATACAAGATGTGTGGAAGGCTGGAGTTCGTGTGAAG
ACAGAGAAGGAGAGTGGGATTGCCAAGAGAGAGGAGATTGAGTTTAGCATTAAGGAAGTGATGGAAGGA
GAGAGGAGCAAAGAGATGAAGAAGAACGTGAAGAAATGGAGAGACTTGGCTGTCAAGTCACTCAATGAA
GGAGGTTCTACGGATACTAACATTGATACATTTGTATCAAGGGTTCAGAGCAAATAG

UGT76E1 Figure 26

ATGGAAGAACTAGGAGTGAAGAGAAGGATAGTATTGGTTCCAGTTCCAGCACAAGGTCATGTAACTCCG
ATTATGCAACTCGGGAAGGCTCTTTACTCCAAGGGCTTCTCCATCACTGTTGTTCTCACACAGTATAAT
CGAGTTAGCTCATCCAAGGACTTCTCTGATTTTCATTTCCTCACCATCCCAGGCAGCTTGACCGAGTCT
GATCTCAAAAACCTTGGACCATTCAAGTTTCTCTTCAAGCTCAATCAAATTTGCGAGGCAAGCTTCAAG
CAATGTATTGGTCAACTATTGCAGGAGCAAGGTAATGATATCGCTTGTGTCGTCTACGATGAGTACATG
TACTTCTCCCAAGCTGCAGTTAAAGAGTTTCAACTTCCTAGCGTCCTCTTCAGCACGACAAGTGCTACT
GCCTTTGTCTGTCGCTCTGTTTTGTCTAGAGTCAACGCAGAGTCATTCTTGCTTGACATGAAAGGTACT
CAAGATTTTTTAGCTTGTTAACTCAAACTTTAAAAGTGCATTTAGGTATATAAACCAATCCAAATGCTG
TTGTTTGCTTTGCAGATCCCAAAGTGTCAGACAAGGAATTTCCAGGGTTGCATCCGCTAAGGTACAAGG
ACCTGCCAACTTCAGCATTTGGGCCATTAGAGAGTATACTCAAGGTTTACAGTGAGACTGTCAACATTC
GAACAGCTTCGGCAGTTATCATCAACTCAACAAGCTGTCTAGAGAGCTCATCTTTGGCATGGTTACAAA
AACAACTGCAAGTTCCAGTGTATCCTATAGGCCCACTTCACATTGCAGCTTCAGCGCCTTCTAGTTTAC
TTGAAGAGGACAGGAGTTGCCTTGAGTGGTTGAACAAGCAAAAAATAGGCTCAGTGATTTACATAAGTT
TGGGAAGCTTGGCTCTAATGGAAACTAAAGACATGTTGGAGATGGCTTGGGGTTTACGTAATAGCAACC
AACCTTTCTTATGGGTGATCCGACCGGGTTCTATTCCCGGCTCGGAATGGACAGAGTCTTTACCGGAGG
AATTCAGTAGGTTGGTTTCAGAAAGAGGTTACATTGTGAAATGGGCACCACAGATAGAAGTTCTCAGAC
ATCCTGCAGTGGGAGGGTTTTGGAGTCACTGCGGATGGAACTCGACCCTAGAGAGCATCGGGGAAGGAG
TTCCGATGATCTGTAGGCCTTTTACGGGAGATCAGAAAGTCAATGCGAGGTACTTAGAGAGAGTTTGGA
GAATTGGGGTTCAATTGGAAGGAGAGCTGGATAAAGGAACAGTGGAGAGAGCTGTAGAGAGATTGATTA
TGGATGAAGAAGGAGCAGAAATGAGGAAGAGAGTTATCAACTTGAAAGAGAAGCTTCAAGCCTCTGTCA
AGAGTAGAGGTTCCTCATTCAGCTCATTAGACAACTTTGTCAATTCCTTAAAAATGATGAATTTCATGT
AG

UGT76E11 Figure 27

ATGGAGGAAAAGCCGGCGGGCAGAAGAGTAGTGTTGGTTGCAGTTCCAGCTCAAGGACATATCTCTCCA
ATAATGCAACTTGCAAAAACACTTCACTTGAAGGGTTTCTCAATCACAATCGCTCAGACAAAGTTCAAT
TACTTTAGCCCTTCAGATGACTTCACTGATTTTCAGTTTGTCACCATTCCAGAAAGCTTACCAGAGTCT
GATTTTGAGGATCTCGGGCCAATAGAGTTTCTGCATAAGCTCAACAAAGAGTGTCAGGTGAGCTTCAAA
GACTGTTTGGGTCAGTTGTTGCTGCAACAAGGTAATGAGATAGCCTGTGTTGTCTACGACGAGTTCATG
TACTTTGCTGAAGCTGCAGCCAAAGAGTTTAAGCTTCCAAACGTCATTTTCAGCACCACAAGTGCCACG
GCTTTTGTTTGCCGCTCTGCATTCGACAAACTTTATGCAAACAGTATCCTGACTCCCTTGAAAGGTACT
CTTGAATTCTCTGTCTTCTATTCTTGCTGGTTTCTATAATCTGTAACAGCATGGTTCTTGACCTTTTTG
CAGAACCCAAAGGACAACAAAACGAGCTAGTGCCAGAGTTTCATCCCCTGAGATGCAAAGACTTTCCGG
TTTCACATTGGGCATCATTAGAAAGCATGATGGAGCTGTATAGGAATACAGTTGACAAACGGACAGCTT
CCTCGGTGATAATCAACACAGCGAGCTGTCTAGAGAGCTCATCTCTGTCTCGTCTGCAGCAACAGCTAC
AAATTCCAGTTTATCCTATAGGCCCTCTTCACCTGGTGGCATCAGCTTCTACGAGTCTTCTTGAAGAGA
ACAAGAGCTGTATTGAATGGTTGAACAAACAAAAGAAAAACTCTGTGATATTCGTAAGCTTGGGAAGCT
TAGCTTTGATGGAAATCAATGAGGTGATAGAAACTGCTTTGGGATTGGATAGTAGCAAGCAACAGTTCT
TGTGGGTCATTCGGCCAGGGTCAGTACGTGGTTCGGAATGGATAGAGAACTTGCCTAAGGAGTTTAGTA
AGATAATTTCGGGTCGAGGTTACATTGTGAAATGGGCTCCACAGAAGGAAGTACTTTCTCATCCTGCAG
TAGGAGGATTTTGGAGCCATTGCGGATGGAACTCGACACTAGAGAGCATCGGGGAAGGAGTTCCAATGA
TTTGCAAGCCGTTTTCCAGTGATCAAATGGTGAATGCGAGATACTTGGAGTGTGTATGGAAAATTGGGA
TTCAAGTTGAGGGTGATCTAGACAGAGGAGCGGTCGAGAGAGCTGTGAGGAGGTTAATGGTGGAGGAAG
AAGGGGAGGGGATGAGGAAGAGAGCTATCAGTTTGAAAGAGCAACTTAGAGCCTCTGTTATAAGTGGAG
GTTCTTCACACAACTCGCTAGAGGAGTTTGTACACTACATGAGGACTCTATGA

UGT76E12 Figure 28

ATGCAGGTTTTGGGAATGGAGGAAAAGCCTGCAAGGAGAAGCGTAGTGTTGGTTCCATTTCCAGCACAA
GGACATATATCTCCAATGATGCAACTTGCCAAAACCCTTCACTTAAAGGGTTTCTCGATCACAGTTGTT
CAGACTAAGTTCAATTACTTTAGCCCTTCAGATGACTTCACTCATGATTTTCAGTTCGTCACCATTCCA
GAAAGCTTACCAGAGTCTGATTTCAAGAATCTCGGACCAATACAGTTTCTGTTTAAGCTCAACAAAGAG
TGTAAGGTGAGCTTCAAGGACTGTTTGGGTCAGTTGGTGCTGCAACAAAGTAATGAGATCTCATGTGTC
ATCTACGATGAGTTCATGTACTTTGCTGAAGCTGCAGCCAAAGAGTGTAAGCTTCCAAACATCATTTTC
AGCACAACAAGTGCCACGGCTTTCGCTTGCCGCTCTGTATTTGACAAACTATATGCAAACAATGTCCAA
GCTCCCTTGAAAGGTACTCTAAAACTCTCTGTTTCGTGGTTTCCGCGAGTGGCTATAAGATTGAAACAG
CATTGTTTTTGACCTTTTTTGCAGAAACTAAAGGACAACAAGAAGAGCTAGTTCCGGAGTTTTATCCCT
TGAGATATAAAGACTTTCCAGTTTCACGGTTTGCATCATTAGAGAGCATAATGGAGGTGTATAGGAATA
CAGTTGACAAACGGACAGCTTCCTCGGTGATAATCAACACTGCGAGCTGTCTAGAGAGCTCATCTCTGT
CTTTTCTGCAACAACAACAGCTACAAATTCCAGTGTATCCTATAGGCCCTCTTCACATGGTGGCCTCAG
CTCCTACAAGTCTGCTTGAAGAGAACAAGAGCTGCATCGAATGGTTGAACAAACAAAAGGTAAACTCGG
TGATATACATAAGCATGGGAAGCATAGCTTTAATGGAAATCAACGAGATAATGGAAGTCGCGTCAGGAT
TGGCTGCTAGCAACCAACACTTCTTATGGGTGATCCGACCAGGGTCAATACCTGGTTCCGAGTGGATAG
AGTCCATGCCTGAAGAGTTTAGTAAGATGGTTTTGGACCGAGGTTACATTGTGAAATGGGCTCCACAGA
AGGAAGTACTTTCTCATCCTGCAGTAGGAGGGTTTTGGAGCCATTGTGGATGGAACTCGACACTAGAAA
GCATCGGCCAAGGAGTTCCAATGATCTGCAGGCCATTTTCGGGTGATCAAAAGGTGAACGCTAGATACT
TGGAGTGTGTATGGAAAATTGGGATTCAAGTGGAGGGTGAGCTAGACAGAGGAGTGGTCGAGAGAGCTG
TGAAGAGGTTAATGGTTGACGAAGAAGGAGAGGAGATGAGGAAGAGAGCTTTCAGTTTAAAAGAGCAAC
TTAGAGCCTCTGTTAAAAGTGGAGGCTCTTCACACAACTCGCTAGAAGAGTTTGTACACTTCATAAGGA
CTCTATGA

UGT76E2 Figure 29

ATGGAGGAAAAGCAAGTGAAGGAGACAAGGATAGTGTTGGTTCCAGTTCCAGCTCAAGGTCATGTAACT
CCGATGATGCAACTAGGAAAAGCTCTTCACTCAAAGGGTTTCTCCATCACTGTTGTTCTGACACAGTCT
AATCGAGTTAGCTCTTCCAAAGACTTCTCTGATTTCCATTTCCTCACCATCCCAGGCAGCTTAACTGAG
TCTGATCTCCAAAACCTAGGACCACAAAAGTTTGTGCTCAAGCTCAATCAAATTTGTGAGGCAAGCTTC
AAGCAGTGTATAGGTCAACTATTGCATGAACAATGTAATAATGATATTGCTTGTGTCGTCTACGATGAG
TACATGTACTTCTCTCATGCTGCAGTAAAAGAGTTTCAACTTCCTAGTGTCGTCTTTAGCACGACAAGT
GCTACTGCTTTTGTCTGTCGCTCTGTTTTGTCTAGAGTCAACGCAGAGTCGTTCTTGATCGACATGAAA
GGTATTCAAGATTCTAGCTTGTTTTATCTTAATTCAAAATCCTATTTATAGAAACTAATCCAAATGATC
GATGTTATCTTTTCAGATCCTGAAACACAAGACAAAGTATTTCCAGGGTTGCATCCTCTGAGGTACAAG
GATCTACCAACTTCAGTATTTGGGCCAATAGAGAGTACGCTCAAGGTTTACAGTGAGACTGTGAACACT
CGAACAGCTTCCGCTGTTATCATCAACTCAGCAAGCTGTTTAGAGAGCTCATCTTTGGCAAGGTTGCAA
CAACAACTGCAAGTTCCGGTGTATCCTATAGGCCCACTTCATATTACAGCTTCAGCGCCTTCTAGTTTA
CTAGAAGAAGACAGGAGTTGCGTTGAGTGGTTGAACAAGCAAAAATCAAATTCAGTTATTTACATAAGC
TTGGGAAGCTTGGCTCTAATGGACACCAAAGACATGTTGGAGATGGCTTGGGGATTAAGTAATAGCAAC
CAACCTTTCTTATGGGTGGTCAGACCGGGCTCTATTCCGGGGTCAGAATGGACAGAGTCCTTACCAGAG
GAATTCAATAGGTTGGTTTCAGAAAGAGGTTACATTGTGAAATGGGCTCCGCAGATGGAAGTTCTCAGA
CATCCTGCAGTAGGAGGGTTTTGGAGTCACTGTGGATGGAACTCAACAGTAGAGAGCATCGGGGAAGGA
GTTCCGATGATATGTAGGCCTTTCACCGGGGATCAGAAAGTCAATGCGAGGTACTTAGAGAGAGTTTGG
AGAATTGGGGTTCAATTGGAGGGAGATCTGGATAAAGAAACTGTGGAGAGAGCTGTAGAGTGGTTGCTT
GTGGATGAAGAAGGAGCAGAAATGAGGAAGAGAGCCATTGACTTGAAAGAAAAGATTGAAACCTCTGTT
AGAAGTGGAGGTTCCTCATGCAGCTCACTAGACGACTTTGTTAATTCCATGTGA

UGT78D1 Figure 30

ATGACCAAATTCTCCGAGCCAATCAGAGACTCCCACGTGGCAGTTCTCGCGTTTTTCCCCGTTGGCGCT
CATGCCGGTCCTCTCTTAGCCGTCACTCGCCGTCTCGCCGCCGCTTCTCCCTCCACCATCTTTTCTTTC
TTCAACACCGCAAGATCAAACGCGTCGTTGTTCTCCTCTGATCATCCCGAGAACATCAAGGTCCACGAC
GTCTCTGACGGTGTTCCGGAGGGAACCATGCTCGGGAATCCACTGGAGATGGTCGAGCTGTTTCTCGAA
GCGGCTCCACGTATTTTCCGGAGCGAAATCGCGGCGGCAGAGATAGAAGTTGGAAAGAAAGTGACATGC
ATGCTAACAGATGCCTTCTTCTGGTTCGCAGCGGACATAGCGGCTGAGCTGAACGCGACTTGGGTTGCC
TTCTGGGCCGGCGGAGCAAACTCACTCTGTGCTCATCTCTACACTGATCTCATCAGAGAAACCATCGGT
CTCAAAGGTAACTAGCTTTTTAGCGTTTAGTGATTATTCCACAAATTCAGCTACTACACTTTGTATGTA
TTTATGGTTATTATTATTATTTATCTCCTGGTAGATGTGAGTATGGAAGAGACATTAGGGTTTATACCA
GGAATGGAGAATTACAGAGTTAAAGATATACCAGAGGAAGTTGTATTTGAAGATTTGGACTCTGTTTTC
CCAAAGGCTTTATACCAAATGAGTCTTGCTTTACCTCGTGCCTCTGCTGTTTTCATCAGTTCCTTTGAA
GAGTTAGAACCTACATTGAACTATAACCTAAGATCCAAACTTAAACGTTTCTTGAACATCGCCCCTCTC
ACGTTATTATCTTCTACATCGGAGAAAGAGATGCGTGATCCTCATGGCTGCTTTGCTTGGATGGGGAAG
AGATCAGCTGCTTCTGTAGCGTACATTAGCTTCGGCACCGTCATGGAACCTCCTCCTGAAGAGCTTGTG
GCGATAGCACAAGGGTTGGAATCAAGCAAAGTGCCGTTTGTTTGGTCGCTGAAGGAGAAGAACATGGTT
CATCTACCAAAAGGGTTTTTGGATCGGACAAGAGAGCAAGGGATAGTGGTTCCTTGGGCTCCACAAGTG
GAACTGCTGAAACACGAGGCAATGGGTGTGAATGTGACACATTGTGGATGGAACTCAGTGTTGGAGAGT
GTGTCGGCAGGTGTACCGATGATCGGCAGACCGATTTTGGCGGATAATAGGCTCAACGGAAGAGCAGTG
GAGGTTGTGTGGAAGGTTGGAGTGATGATGGATAATGGAGTCTTCACGAAAGAAGGATTTGAGAAGTGT
TTGAATGATGTTTTTGTTCATGATGATGGTAAGACGATGAAGGCTAATGCCAAGAAGCTTAAAGAAAAA
CTCCAAGAAGATTTCTCCATGAAAGGAAGCTCTTTAGAGAATTTCAAAATATTGTTGGACGAAATTGTG
AAAGTTTAG

UGT89B1 Figure 31

ATGAAAGTGAACGAGGAAAACAACAAGCCGACAAAGACCCATGTCTTAATCTTCCCATTTCCGGCGCAA
GGTCACATGATTCCCCTCCTCGACTTCACCCACCGCCTTGCTCTCCGCGGCGGCGCCGCCTTAAAAATA
ACCGTCCTAGTCACTCCAAAAAACCTTCCTTTTCTCTCTCCGCTTCTCTCCGCCGTAGTTAACATCGAA
CCACTTATCCTCCCTTTTCCCTCCCACCCTTCAATCCCCTCCGGCGTCGAAAACGTCCAAGACTTACCT
CCTTCAGGCTTCCCTTTAATGATCCACGCGCTTGGTAATCTCCACGCGCCGCTTATCTCTTGGATTACT
TCTCACCCTTCTCCTCCAGTAGCCATCGTATCTGATTTCTTCCTTGGTTGGACCAAAAACCTCGGAATC
CCTCGTTTCGATTTCTCTCCCTCCGCTGCTATCACTTGCTGCATACTCAATACTCTCTGGATCGAAATG
CCCACCAAGATCAACGAAGATGACGATAACGAGATCCTCCACTTTCCCAAGATCCCGAATTGTCCAAAA
TACCGTTTTGATCAGATCTCCTCTCTTTACAGAAGTTACGTTCACGGAGATCCAGCTTGGGAGTTCATA
AGAGACTCCTTTAGAGATAACGTGGCGAGTTGGGGACTCGTCGTGAACTCGTTCACCGCCATGGAAGGT
GTTTATCTCGAACATCTTAAGCGAGAGATGGGCCATGATCGTGTATGGGCTGTAGGCCCAATTATTCCG
TTATCTGGGGATAACCGTGGTGGCCCGACTTCTGTTTCTGTTGATCACGTGATGTCGTGGCTTGACGCA
CGTGAGGATAACCACGTGGTGTACGTGTGCTTTGGAAGTCAAGTAGTTTTGACTAAAGAGCAGACTCTT
GCACTCGCCTCTGGGCTTGAGAAAAGCGGCGTCCATTTCATATGGGCCGTAAAGGAGCCCGTTGAGAAA
GACTCAACACGTGGCAACATCCTGGACGGTTTCGACGATCGCGTGGCTGGGAGAGGTCTGGTGATCAGA
GGATGGGCTCCACAAGTAGCTGTGCTACGTCACCGAGCCGTTGGCGCGTTTTTAACGCACTGTGGTTGG
AACTCTGTGGTGGAGGCGGTTGTCGCCGGCGTTTTGATGCTGACGTGGCCGATGAGAGCTGACCAGTAC
ACTGACGCGTCTCTGGTGGTTGATGAGTTGAAAGTAGGTGTGCGTGCTTGCGAAGGACCTGACACGGTG
CCTGACCCGGACGAGTTAGCTCGAGTTTTCGCTGATTCCGTGACCGGAAATCAAACGGAGAGGATCAAA
GCCGTGGAGCTGAGGAAAGCAGCGTTGGATGCGATTCAAGAACGTGGGAGCTCAGTGAATGATTTAGAT
GGATTTATCCAACATGTCGTTAGTTTAGGACTAAACAAATGA

72B3 ORF Figure 32

ATGAGCATAGATATTTTTCAAGAAATAAGAATAAAGAAAATTCTACTCTTAATGGCGGAAGCAAACACT
CCACACATAGCAATCATGCCGAGTCCCGGTATGGGTCACCTTATCCCATTCGTCGAGTTAGCAAAGCGA
CTCGTTCAGCACGACTGTTTCACCGTCACAATGATCATCTCCGGTGAAACTTCGCCGTCTAAGGCACAA
AGATCCGTTCTCAACTCTCTCCCTTCCTCCATAGCCTCCGTATTTCTCCCTCCCGCCGATCTTTCCGAT
GTTCCCTCCACAGCGCGAATCGAAACTCGGGCCATGCTCACCATGACTCGTTCCAATCCGGCGCTCCGG
GAGCTTTTTGGCTCTTTATCAACGAAGAAAAGTCTCCCGGCGGTTCTCGTCGTCGATATGTTTGGTGCG
GATGCGTTCGACGTGGCCGTTGACTTCCACGTGTCACCATACATTTTCTATGCATCCAATGCAAACGTC
TTGTCGTTTTTTCTTCACTTGCCGAAACTAGACAAAACGGTGTCGTGTGAGTTTAGGTACTTAACCGAA
CCGCTTAAGATTCCCGGCTGTGTCCCGATAACCGGTAAGGACTTTCTTGATACGGTTCAAGACCGAAAC
GACGACGCATACAAATTGCTTCTCCATAACACCAAGAGGTACAAAGAAGCTAAAGGGATTCTAGTGAAT
TCCTTCGTTGATTTAGAGTCGAATGCAATAAAGGCCTTACAAGAACCGGCTCCTGATAAACCAACGGTA
TACCCGATTGGGCCGCTGGTTAACACAAGTTCATCTAATGTTAACTTGGAAGACAAGTTCGGATGTTTA
AGTTGGCTAGACAACCAACCATTCGGCTCGGTTCTATACATATCATTTGGAAGCGGCGGAACACTTACA
TGTGAGCAGTTTAATGAGCTTGCTATTGGTCTTGCGGAGAGCGGAAAACGGTTTATTTGGGTCATACGA
AGTCCAAGCGAGATAGTTAGTTCGTCGTATTTCAATCCACACAGCGAGACAGACCCCTTTTCGTTTTTA
CCAATTGGGTTCTTAGACCGAACCAAAGAGAAAGGTTTGGTGGTTCCATCATGGGCTCCACAGGTTCAA
ATCCTGGCTCATCCATCCACATGCGGGTTTTTAACACACTGTGGATGGAATTCGACCTTAGAAAGCATT
GTAAACGGTGTACCACTCATAGCGTGGCCTTTATTCGCGGAGCAAAAGATGAATACATTGCTACTCGTG
GAGGATGTTGGAGCGGCTCTAAGAATCCATGCGGGTGAAGATGGGATTGTACGGAGGGAAGAAGTGGTG
AGAGTGGTGAAGGCACTGATGGAAGGTGAAGAGGGAAAAGCCATAGGAAATAAAGTGAAGGAGTTGAAA
GAAGGAGTTGTTAGAGTCTTGGGTGACGATGGATTGTCCAGCAAGTCATTTGGTGAAGTTTTGTTAAAG
TGGAAAACGCACCAGCGAGATATCAACCAAGAGACGTCCCACTAA

A
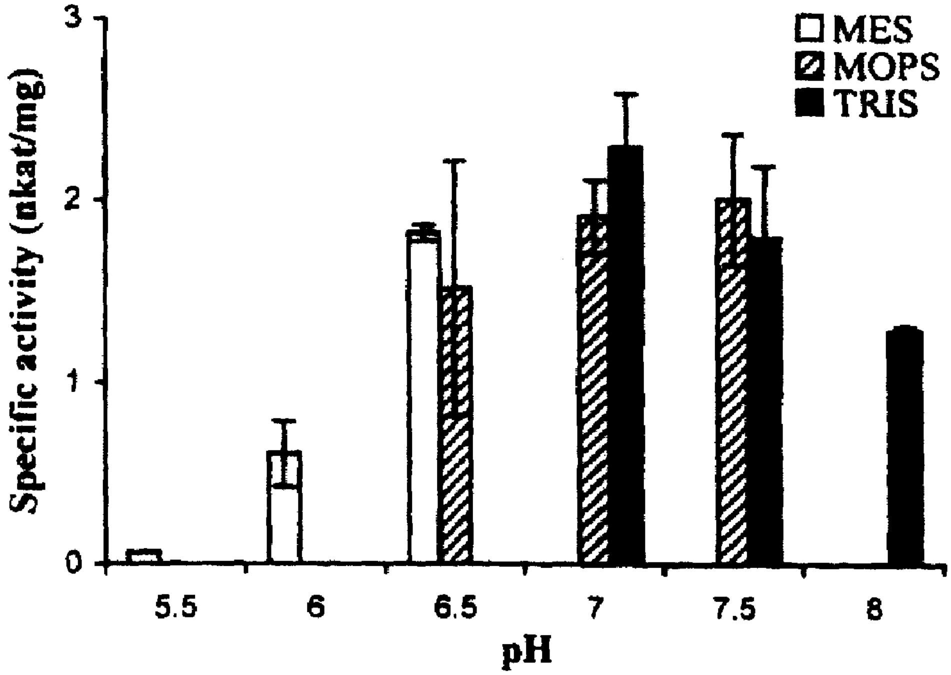
B
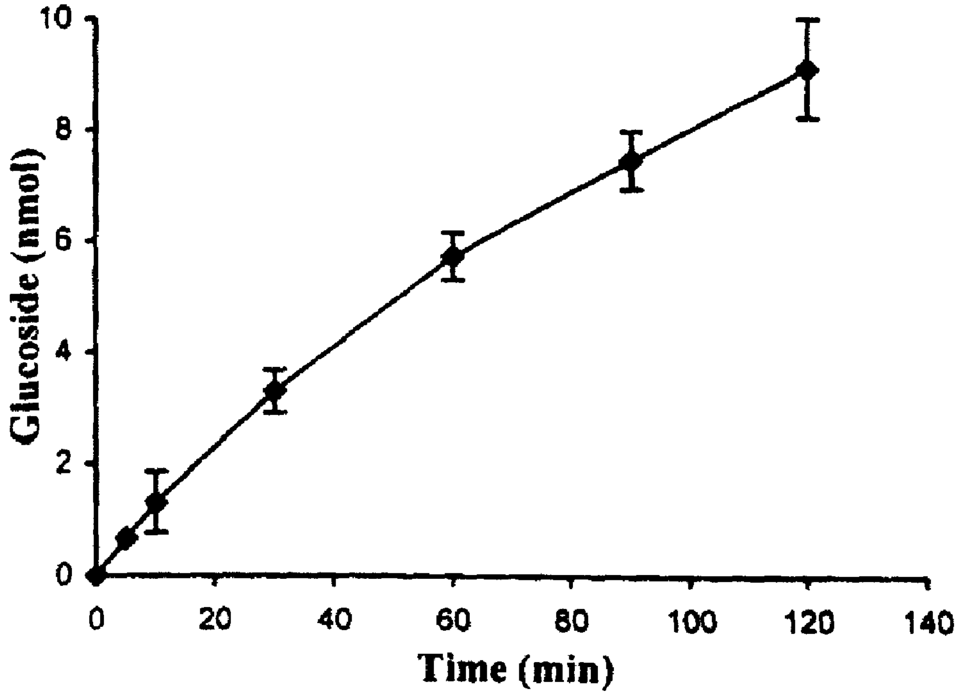
Figure 35

| UGT | Figure | LUTEOLIN | QUERCETIN | CATECHIN | CYANIDIN | CAFFEIC ACID |
|---|---|---|---|---|---|---|
| 71B5 | 12 | | + | | | - |
| 71C1 | 10A | + | ++ | | | + |
| 71C2 | 11A | + | | | | - |
| 71C3 | 13 | | + | | | |
| 71C5 | 14 | | + | | | |
| 71D1 | 15 | | ++ | | | - |
| 72B3 | 32 | | + | | | |
| 72E2 | 7A | | | | | + |
| 72E3 | 9A | | | | | + |
| 73B1 | 16 | + | + | | | - |
| 73B2 | 17 | + | + | | | - |
| 73B3 | 8A | + | ++ | | | + |
| 73B4 | 18 | + | ++ | | | |
| 73B5 | 19 | | ++ | | | |
| 73C1 | 20 | + | | | | - |
| 73C3 | 21 | + | | | | - |
| 73C5 | 22 | + | + | | | - |
| 73C6 | 23 | + | + | | | - |
| 73C7 | 24 | + | | | | |
| | | | | | | |
| 74F2 | 25 | + | | | | - |
| 75B1 | 1A | | | | | + |
| 76E1 | 26 | + | | | | |
| 76E11 | 27 | + | + | | | |
| 76E12 | 28 | + | ++ | | | |
| 76E2 | 29 | + | | | | |
| 78D1 | 30 | | + | | | |
| 84A1 | 4A | | | | | + |
| 84A4 | 3A | | | | | + |
| 84B1 | 5A | + | + | | | + |
| 89B1 | 31 | +++ | ++ | | | |

+++ = highest activity

++ = more than 20% activity

\+ = less than 20% activity

Figure 37

TRANSGENIC CELLS EXPRESSING GLUCOSYLTRANSFERASE NUCLEIC ACIDS

The invention relates to transgenic cells which have been transformed with glucosyltransferase (GTases) nucleic acids.

GTases are enzymes which post-translationally transfer glucosyl residues from an activated nucleotide sugar to monomeric and polymeric acceptor molecules such as other sugars, proteins, lipids and other organic substrates. These glucosylated molecules take part in diverse metabolic pathways and processes. The transfer of a glucosyl moiety can alter the acceptor's bioactivity, solubility and transport properties within the cell and throughout the plant. One family of GTases in higher plants is defined by the presence of a C-terminal consensus sequence. The GTases of this family function in the cytosol of plant cells and catalyse the transfer of glucose to small molecular weight substrates, such as phenylpropanoid derivatives, coumarins, flavonoids, other secondary metabolites and molecules known to act as plant hormones. Available evidence indicates that GTases enzymes can be highly specific, such as the maize and *Arabidopsis* GTases that glucosylate indole-3-acetic acid (IAA).

The production and use of paper has increased in the last 10 years. For example, between 1989 and 1999 the production of paper and board in the UK has increased from 4.6 to 6.6 million tonnes. Worldwide consumption has also reflected a general increase in paper usage. For example, in the UK per capita consumption of paper is over 200 kg per annum. In the USA this figure is over 300 kg per annum.

Wood used in the paper industry is initially particulated, typically by chipping, before conversion to a pulp which can be utilised to produce paper. The pulping process involves the removal of lignin. Lignin is a major non-carbohydrate component of wood and comprises approximately one quarter of the raw material in wood pulp. The removal of lignin is desirable since the quality of the paper produced from the pulp is largely determined by the lignin content. Many methods have been developed to efficiently and cost effectively remove lignin from wood pulp. These methods can be chemical, mechanical or biological. For example, chemical methods to pulp wood are disclosed in WO9811294, EP0957198 and WO0047812. Although chemical methods are efficient means to remove lignin from pulp it is known that chemical treatments can result in degradation of polysaccharides and is expensive. Moreover, to remove residual lignin from pulp it is necessary to use strong bleaching agents which require removal before the pulp can be converted into paper. These agents are also damaging to the environment.

Biological methods to remove lignin are known. There are however disadvantages associated with such methods. For example it is important to provide micro-organisms (eg bacteria and/or fungi) which only secrete ligninolytic enzymes which do not affect cellulose fibres. This method is also very time consuming (can take 3-4 weeks) and expensive due to the need to provide bioreactors. Biological treatment can also include pre-treatment of wood chips to make them more susceptible to further biological or chemical pulping.

It is therefore desirable to provide further means by which lignin can be efficiently and cost effectively removed from wood pulp which do not have the disadvantages associated with prior art methods.

For the sake of clarity reference herein to transgenic means a plant which has been genetically modified to include a nucleic acid sequence not naturally found in said plant. For example, by over-expression of monolignol glucosyltransferases in planta, plant cell wall properties may be altered through increasing the flux through biosynthetic intermediates that are obligatory for incorporation and assembly of the lignin polymer. Conversely, reduction of the monolignol glucoside pools, such as through the use of nucleic acid comprising GTase sequences in antisense configuration may lead to altered properties through reducing the flux through specific intermediates. Changes in lignin composition, such as with decreased ratios of coniferyl alcohol to sinapyl alcohol are highly desirable in paper and pulping processes, because the more highly methylated lignin (sinapyl alcohol) is more easily removed during pulping processes (Chiang et al (1988) TAPPI J. 71, 173-176).

In some applications it may be desirable to change lignin composition and increase the lignin content of a plant cell to increase the mechanical strength of wood. This would have utility in, for example the construction industry or in furniture making.

Both lignin content and the level of cross-linking of polysaccharide polymers within plant cell walls, also play an important role in determining texture and quality of raw materials through altering the cell walls and tissue mechanical properties. For example, there is considerable interest in reducing cell separation in edible tissues since this would prevent over-softening and loss of juiciness. Phenolics, such as ferulic acid, play an important role in cell adhesion since they can be esterified to cell wall polysaccharides during synthesis and oxidatively cross-linked in the wall, thereby increasing rigidity. Most non-lignified tissues contain these phenolic components and their levels can be modified by altering flux through the same metabolic pathways as those culminating in lignin. Therefore, in the same way as for the manipulation of lignin composition and content, GTase nucleic acid in sense and/or antisense configurations can be used to affect levels of ferulic acid and related phenylpropanoid derivatives that function in oxidative cross-linking. These changes in content have utility in the control of raw material quality of edible plant tissues.

Lignin and oxidative cross-linking in plant cell walls also play important roles in stress and defence responses of most plant species. For example, when non-woody tissues are challenged by pests or pathogen attack, or suffer abiotic stress such as through mechanical damage or UV radiation, the plant responds by localised and systemic alteration in cell wall and cytosolic properties, including changes in lignin content and composition and changes in cross-linking of other wall components. Therefore, it can also be anticipated that cell- or tissue-specific changes in these responses brought about by changed levels of the relevant GTase activities will have utility in protecting the plant to biotic attack and biotic/abiotic stresses.

GTases also have utility with respect to the modification of antioxidants. Reactive oxygen species are produced in all aerobic organisms during respiration and normally exist in a cell in balance with biochemical anti-oxidants. Environmental challenges, such as by pollutants, oxidants, toxicants, heavy metals and so on, can lead to excess reactive oxygen species which perturb the cellular redox balance, potentially leading to wide-ranging pathological conditions. In animals and humans, cardiovascular diseases, cancers, inflammatory and degenerative disorders are linked to events arising from oxidative damage.

Because of the current prevalence of these diseases, there is considerable interest in anti-oxidants, consumed in the diet or applied topically such as in UV-screens. Anti-oxidant micronutrients obtained from vegetables and fruits, teas, herbs and medicinal plants are thought to provide significant protection against health problems arising from oxidative stress. Well known anti-oxidants from plant tissues include for example: quercetin, luteolin and the catechin, epicatechin and cyanidin groups of compounds.

Caffeic acid (3,4-dihydroxycinnamic acid) is a further example of an anti-oxidant with beneficial therapeutic properties.

Certain plant species, organs and tissues are known to have relatively high levels of one or more compounds with anti-oxidant activity. Greater accumulation of these compounds in those species, their wider distribution in crop plants and plant parts already used for food and drink production, and the increased bioavailability of anti-oxidants (absorption. metabolic conversions and excretion rate) are three features considered to be highly desirable.

It will be apparent that changed levels of the relevant GTase activities capable of glucosylating anti-oxidant compounds in *planta* will allow the production of anti-oxidants with beneficial properties. GTase sequences can also be expressed in prokaryotes or simple eukaryotes, such as yeast, to produce enzymes for biotransformations in those cells, or as in vitro processing systems.

STATEMENTS OF INVENTION

According to an aspect of the invention there is provided a transgenic cell comprising a nucleic acid molecule which encodes a polypeptide which has:

i) glucosyltransferase activity:

ii) is selected from the group comprising sequences of FIGS. 1A, 2A, 3A, 4A, 5A, 6A, 7A, 8A, 9A, 10A, 11A, 12, 13, 14, 15, 16, 17, 18, 19, 20, 21, 22, 23, 24, 25, 26, 27, 28, 29, 30, 31, 32 iii) nucleic acids which hybridise to the sequences represented in (ii) above; and iv) nucleic acid sequences which are degenerate as a result of the genetic code to the sequences defined in (i) and (ii) above.

In a further preferred embodiment of the invention said nucleic acid molecule anneals under stringent hybridisation conditions to the sequence presented in FIGS. 1A, 2A, 3A, 4A, 5A, 6A, 7A, 8A, 9A, 10A, 11A, 12, 13, 14, 15, 16, 17, 18, 19, 20, 21, 22, 23, 24, 25, 26, 27, 28, 29, 30, 31, 32

More preferably still said nucleic acid molecule is selected from FIGS. 7A, 8A, 9A, 10A, 15, 18, 19, 28 or 31.

Stringent hybridisation/washing conditions are well known in the art. For example, nucleic acid hybrids that are stable after washing in 0.1×SSC,0.1% SDS at 60° C. It is well known in the art that optimal hybridisation conditions can be calculated if the sequence of the nucleic acid is known. For example, hybridisation conditions can be determined by the GC content of the nucleic acid subject to hybridisation. Please see Sambrook et al (1989) Molecular Cloning; A Laboratory Approach. A common formula for calculating the stringency conditions required to achieve hybridisation between nucleic acid molecules of a specified homology is:

$$T_m=81.5° \text{ C.}+16.6 \text{ Log } [Na^-]+0.41[\% \ G+C]-0.63 \ (\%\text{formamide}).$$

In a preferred embodiment of the invention said transgenic cell is a eukaryotic cell. Preferably said eukaryotic cell is a plant cell or yeast cell.

In an alternative embodiment of the invention said transgenic cell is a prokaryotic cell.

In a further preferred embodiment of the invention the nucleic acid molecule is selected from the group comprising: antisense sequences of the sequences of any one of FIGS. 1C, 2C, 3C, 4C, 5C, 6C, 7C, 8C, 9C, 10C and 11C or parts thereof, or antisense sequences of the sense sequences presented in FIGS. 12-32. More preferably still said antisense sequence is selected from FIG. 7C or 9C In a further preferred embodiment of the invention said nucleic acid is cDNA.

In a yet further preferred embodiment of the invention said nucleic acid is genomic DNA.

In yet still a further preferred embodiment of the invention said plant is a woody plant selected from: poplar; eucalyptus; Douglas fir; pine; walnut; ash; birch; oak; teak; spruce. Preferably said woody plant is a plant used typically in the paper industry, for example poplar.

Methods to transform woody species of plant are well known in the art. For example the transformation of poplar is disclosed in U.S. Pat No. 4,795,855 and WO9118094. The transformation of eucalyptus is disclosed in EP1050209 and WO9725434. Each of these patents is incorporated in their entirety by reference.

In a still further preferred embodiment of the invention said plant is selected from: corn (*Zea mays*), canola (*Brassica napus, Brassica rapa* ssp.), alfalfa (*Medicago sativa*), rice (*Oryza sativa*), rye (*Secale cerale*), sorghum (*Sorghum bicolor, Sorghum vulgare*), sunflower (*helianthus annuas*), wheat (*Tritium aestivum*), soybean (*Glycine max*), tobacco (*Nicotiana tabacum*), potato (*Solanum tuberosum*), peanuts (*Arachis hypogaea*), cotton (*Gossypium hirsutum*), sweet potato (*lopmoea batatus*). cassava (*Manihot esculenta*), coffee (*Cofea* spp.), coconut (*Cocos nucifera*), pineapple (*Anana comosus*), citris tree (*Citrus* spp.) cocoa (*Theobroma cacao*), tea (*Camellia senensis*), banana (*Musa* spp.), avacado (*Persea americana*), fig (*Ficus casica*), guava (*Psidium guajava*), mango (*Mangifer indica*), olive (*Olea europaea*), papaya (*Carica papaya*), cashew (*Anacardium occidentale*), macadamia (*Macadamia intergrifolia*), almond (*Prunus amygdalus*), sugar beets (*Beta vulgaris*), oats, barley, vegetables and ornamentals.

Preferably, plants of the present invention are crop plants (for example, cereals and pulses, maize, wheat, potatoes, tapioca, rice, sorghum, millet, cassava, barley, pea, and other root, tuber or seed crops. Important seed crops are oil-seed rape, sugar beet, maize, sunflower, soybean, and sorghum. Horticultural plants to which the present invention may be applied may include lettuce, endive, and vegetable brassicas including cabbage, broccoli, and cauliflower, and carnations and geraniums. The present invention may be applied in tobacco, cucurbits, carrot, strawberry, sunflower, tomato, pepper, chrysanthemum.

Grain plants that provide seeds of interest include oil-seed plants and leguminous plants. Seeds of interest include grain seeds, such as corn, wheat, barley, rice, sorghum, rye, etc. Oil-seed plants include cotton, soybean, safflower, sunflower, Brassica, maize, alfalfa, palm, coconut, etc. Leguminous plants include beans and peas. Beans include guar, locust bean, fenugreek, soybean, garden beans, cowpea, mungbean, lima bean, fava been, lentils, chickpea, etc.

According to a further aspect of the invention there is provided a vector comprising the nucleic acid according to the invention operably linked to a promoter.

"Vector" includes, inter alia, any plasmid, cosmid, phage or *Agrobacterium* binary vector in double or single stranded linear or circular form which may or may not be selftransmissable or mobilizable, and which can transform a prokaryotic or eukaryotic host either by integration into the cellular genome or exist extrachromosomally (e.g. autonomous replicating plasmid with an origin of replication ie an episomal vector).

Suitable vectors can constructed, containing appropriate regulatory sequences. including promoter sequences, terminator fragments, polyadenylation sequences, enhancer sequences, marker genes and other sequences as appropriate. For further details see, for example, Molecular Cloning: Laboratory Manual: $2^{nd}$ edition, Sambrook et al. 1989, Cold Spring Habor Laboratory Press or Current Protocols in Molecular Biology, Second Edition, Ausubel et al. Eds. John Wiley & Sons, 1992.

Specifically included are shuttle vectors by which is meant a DNA vehicle capable, naturally or by design, of replication in two different host organisms, which may be selected from actinomycetes and related species, bacteria and eukaryotic (e.g. higher plant, mammalian, yeast or fungal cells).

A vector including nucleic acid according to the invention need not include a promoter or other regulatory sequence, particularly if the vector is to be used to introduce the nucleic acid into cells for recombination into the gene.

Preferably the nucleic acid in the vector is under the control of, and operably linked to, an appropriate promoter or other regulatory elements for transcription in a host cell such as a microbial, (e.g. bacterial), or plant cell. The vector may be a bi-functional expression vector which functions in multiple hosts. In the case of GTase genomic DNA this may contain its own promoter or other regulatory elements and in the case of cDNA this may be under the control of an appropriate promoter or other regulatory elements for expression in the host cell.

By "promoter" is meant a nucleotide sequence upstream from the transcriptional initiation site and which contains all the regulatory regions required for transcription. Suitable promoters include constitutive, tissue-specific, inducible, developmental or other promoters for expression in plant cells comprised in plants depending on design. Such promoters include viral, fungal, bacterial, animal and plant-derived promoters capable of functioning in plant cells.

Constitutive promoters include, for example CaMV 35S promoter (Odell et al. (1985) Nature 313, 9810-812); rice actin (McElroy et al. (1990) Plant Cell 2: 163-171); ubiquitin (Christian et al. (1989) Plant Mol. Biol. 18 (675-689); pEMU (Last et al. (1991) Theor Appl. Genet. 81: 581-588); MAS (Velten et al. (1984) EMBO J. 3. 2723-2730); ALS promoter (U.S. application Ser. No. 08/409,297), and the like. Other constitutive promoters include those in U.S. Pat. Nos. 5,608,149; 5,608,144; 5,604,121; 5,569,597; 5,466,785; 5,399,680, 5,268,463; and 5,608,142.

Chemical-regulated promoters can be used to modulate the expression of a gene in a plant through the application of an exogenous chemical regulator. Depending upon the objective, the promoter may be a chemical-inducible promoter, where application of the chemical induced gene expression, or a chemical-repressible promoter, where application of the chemical represses gene expression. Chemical-inducible promoters are known in the art and include but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena et al. (1991) Proc. Natl. Acad. Sci. USA 88: 10421-10425 and McNellis et al. (1998) Plant J. 14(2): 247-257) and tetracycline-inducible and tetracycline-repressible promoters (see, for example, Gatz et al. (1991) Mol. Gen. Genet. 227: 229-237, and U.S. Pat. Nos. 5,814,618 and 5,789,156, herein incorporated by reference.

Where enhanced expression in particular tissues is desired, tissue-specific promoters can be utilised. Tissue-specific promoters include those described by Yamamoto et al. (1997) Plant J. 12(2): 255-265; Kawamata et al. (1997) Plant Cell Physiol. 38(7): 792-803; Hansen et al. (1997) Mol. Gen. Genet. 254(3): 337-343; Russell et al. (1997) Transgenic Res. 6(2): 157-168; Rinehart et al. (1996) Plant Physiol. 112(3): 1331-1341; Van Camp et al. (1996) Plant Physiol. 112(2): 525-535; Canevascni et al. (1996) Plant Physiol. 112(2): 513-524; Yamamoto et al. (1994) Plant Cell Physiol. 35(5): 773-778; Lam (1994) Results Probl. Cell Differ. 20: 181-196; Orozco et al. (1993) Plant Mol. Biol. 23(6): 1129-1138; Mutsuoka et al. (1993) Proc. Natl. Acad. Sci. USA 90 (20): 9586-9590: and Guevara-Garcia et al (1993) Plant J. 4(3): 495-50.

"Operably linked" means joined as part of the same nucleic acid molecule, suitably positioned and oriented for transcription to be initiated from the promoter. DNA operably linked to a promoter is "under transcriptional initiation regulation" of the promoter. In a preferred aspect, the promoter is an inducible promoter or a developmentally regulated promoter.

Particular of interest in the present context are nucleic acid constructs which operate as plant vectors. Specific procedures and vectors previously used with wide success upon plants are described by Guerineau and Mullineaux (1993) (Plant transformation and expression vectors.

In: Plant Molecular Biology Labfax (Croy RRD ed) Oxford, BIOS Scientific Publishers, pp 121-148. Suitable vectors may include plant viral-derived vectors (see e.g. EP-A-194809). If desired, selectable genetic markers may be included in the construct, such as those that confer selectable phenotypes such as resistance to antibodies or herbicides (e.g. kanamycin, hygromycin, phosphinotricin, chlorsulfuron, methotrexate, gentamycin, spectinomycin, imidazolinones and glyphosate).

According to a further aspect of the invention there is provided a method of enhancing monolignol glucoside synthesis in a plant comprising causing or allowing expression of at least one GTase nucleic acid according to the invention in a plant. Preferably the plant is a woody plant species.

According to a further aspect of the invention there is provided a method of inhibiting monolignol glucoside synthesis in a plant comprising causing or allowing expression of at least one GTase antisense nucleic acid according to the invention in a plant. Preferably the plant is a woody plant species.

Inhibition of GTase expression may, for instance, be achieved using anti-sense technology.

In using anti-sense genes or partial gene sequences to down-regulate gene expression, a nucleotide sequence is placed under the control of a promoter in a "reverse orientation" such that transcription yields RNA which is complementary to normal mRNA transcribed from the "sense" strand of the target gene. See, for example, Rothstein et al, 1987; Smith et al, (1998), Nature 334, 724-726; Zhang et al (1992) The Plant Cell 4, 1575-1588, English et al. (1996) The Plant Cell 8, 179 188. Antisense technology is also reviewed in Bourque (1995), Plant Science 105, 125-149, and Flavell (1994) PNAS USA 91, 3490-3496.

According to a further aspect of the invention there is provided a nucleotide sequence encoding an antisense RNA molecule complementary to a sense mRNA molecule encoding for a polypeptide having a glucosyl transferase activity in the biosynthesis of at least a monolignol glucoside in lignin biosynthesis in a plant, which nucleotide sequence is under transcriptional control of a promoter and a terminator, both promoter and terminator capable of functioning in plant cells.

Suitable promoters and terminators are referred to hereinabove.

According to a further aspect of the invention there is provided a nucleotide sequence according to the invention comprising a transcriptional regulatory sequence, a sequence under the transcriptional control thereof which encodes an RNA which consists of a plurality of subsequences, characterised in that the RNA subsequences are antisense RNAs to mRNAs of proteins having a GTase activity in the lignin biosynthesis pathway in plant cells, In particular, the said RNA subsequences are antisense RNAs to mRNAs of GTase having a GTase activity in the lignin biosynthesis pathway in plant cells. such as the GTase of FIGS. 1-11(C)

The nucleotide sequence may encode an RNA having any number of subsequences. Preferably, the number of subsequences lies between 2 and 7 (inclusive) and more preferably lies between 2-4.

According to a further aspect of the invention there is provided a host cell transformed with nucleic acid or a vector according to the invention, preferably a plant or a microbial cell. The microbial cell may be prokaryotic (eg *Escherchia coli, Bacillus subtilis*) or eukaryotic (eg *Saccharomyces cerevisiae*).

In the transgenic plant cell the transgene may be on an extra-genomic vector or incorporated, preferably stably, into the genome. There may be more than one heterologous nucleotide sequence per haploid genome.

According to a yet further aspect of the invention there is provided a method of transforming a plant cell comprising introduction of a vector into a plant cell and causing or allowing recombination between the vector and the plant cell genome to introduce a nucleic acid according to the invention into the genome.

Plants transformed with a DNA construct of the invention may be produced by standard techniques known in the art for the genetic manipulation of plants. DNA can be introduced into plant cells using any suitable technology, such as a disarmed Ti-plasmid vector carried by Agrobacterium exploiting its natural gene transferability (EP-A-270355, EP-A-0116718, NAR 12(22):8711-87215 (1984), Townsend et al,. U.S. Pat. No. 5,563,055); particle or microprojectile bombardment (U.S. Pat. No. 5,100,792, EP-A-444882, EP-A-434616; Sanford et al, U.S. Pat. No. 4,945,050; Tomes et al. (1995) "Direct DNA Transfer into Intact Plant Cells via Microprojectile Bombardment", in Plant Cell, Tissue and Organ Culture: Fundamental Methods, ed. Gamborg and Phillips (Springer-Verlag, Berlin); and McCabe et al. (1988) Biotechnology 6: 923-926); microinjection (WO 92/09696, WO 94/00583, EP 331083, EP 175966, Green et al. 91987) Plant Tissue and Cell Culture, Academic Press, Crossway et al. (1986) Biotechniques 4:320-334); electroporation (EP 290395, WO 8706614, Riggs et al. (1986) Proc. Natl. Acad. Sci. USA 83:5602-5606; D'Halluin et al. 91992). Plant Cell 4:1495-1505) other forms of direct DNA uptake (DE 4005152, WO 9012096. U.S. Pat. No. 4,684,611, Paszkowski et al. (1984) EMBO J. 3:2717-2722); liposome-mediated DNA uptake (e.g. Freeman et al (1984) Plant Cell Physiol, 29:1353); or the vortexing method (e.g. Kindle (1990) Proc. Nat. Acad. Sci. USA 87:1228). Physical methods for the transformation of plant cells are reviewed in Oard (1991) Biotech. Adv. 9:1-11. See generally, Weissinger et al. (1988) Ann. Rev. Genet. 22:421-477; Sanford et al. (1987) Particulate Sciences and Technology 5:27-37; Christou et al. (1988) Plant Physiol. 87:671-674; McCabe et al. (1988) Bio/Technology 6:923-926: Finer and McMullen (1991) In Vitro Cell Dev. Biol. 27P:175-182: Singh et al. (1988) Theor. Appl. Genet. 96:319-324: Datta et al. (1990) Biotechnology 8:736-740; Klein et al. (1988) Proc. Natl. Acad. Sci. USA 85: 4305-4309; Klein et al. (1988) Biotechnology 6:559-563; Tomes, U.S. Pat. No. 5,240,855; Buising et al. U.S. Pat. Nos. 5,322,783 and 5,324,646; Klein et al. (1988) Plant Physiol 91: 440-444; Fromm et al (1990) Biotechnology 8:833-839; Hooykaas-Von Slogteren et al. 91984). Nature (London) 311:763-764; Bytebier et al. (1987) Proc. Natl. Acad. Sci. USA 84:5345-5349; De Wet et al. (1985) in The Experimental Manipuation of Ovule Tissues ed. Chapman et al. (Longman, New York), pp. 197-209; Kaeppler et al. (1990) Plant Cell Reports 9:415-418 and Kaeppler et al. (1992) Theor. Appl. Genet. 84:560-566; Li et al. (1993) Plant Cell Reports 12: 250-255 and Christou and Ford (1995) Annals of Botany 75: 407-413; Osjoda et al. (1996) Nature Biotechnology 14:745-750, all of which are herein incorporated by reference.

*Agrobacterium* transformation is widely used by those skilled in the art to transform dicotyledonous species. Recently. there has been substantial progress towards the routine production of stable, fertile transgenic plants in almost all economically relevant monocot plants (Toriyama et al. (1988) Bio/Technology 6: 1072-1074; Zhang et al. (1988) Plant Cell rep. 7379-384; Zhang et al. (1988) Theor. Appl. Genet. 76:835-840; Shimamoto et al. (1989) Nature 338:274-276; Datta et al. (1990) Bio/Technology 8: 736-740; Christou et al. (1991) Bio/Technology 9:957-962; Peng et al (1991) International Rice Research Institute, Manila, Philippines, pp.563-574; Cao et al. (1992) Plant Cell Rep. 11: 585-591; Li et al. (1993) Plant Cell Rep. 12: 250-255: Rathore et al. (1993) Plant Mol. Biol. 21:871-884; Fromm et al (1990) Bio/Technology 8:833-839; Gordon Kamm et al. (1990) Plant Cell 2:603-618; D'Halluin et al. (1992) Plant Cell 4:1495-1505; Walters et al. (1992) Plant Mol. Biol. 18:189-200: Koziel et al. (1993). Biotechnology 11194-200; Vasil, I. K. (1994) Plant Mol. Biol. 25:925-937; Weeks et al (1993) Plant Physiol. 102:1077-1084: Somers et al. (1992) Bio/Technology 10:1589-1594; WO 92/14828. In particular, *Agrobacterium* mediated transformation is now emerging also as an highly efficient transformation method in monocots. (Hiei, et al. (1994) The Plant Journal 6:271-282). See also, Shimamoto, K. (1994) Current Opinion in Biotechnology 5:158-162; Vasil, et al. (1992) Bio/Technology 10:667-674; Vain, et al. (1995) Biotechnology Advances 13(4):653-671: Vasil, et al. (1996) Nature Biotechnology 14: 702).

Microprojectile bombardment, electroporation and direct DNA uptake are preferred where *Agrobacterium* is inefficient or ineffective. Alternatively, a combination of different techniques may be employed to enhance the efficiency of the transformation process, e.g. bombardment with Agrobacterium-coated microparticles (EP-A-486234) or microprojectile bombardment to induce wounding followed by co-cultivation with Agrobacterium (EP-A-486233).

Plants which include a plant cell according to the invention are also provided.

In addition to the regenerated plant, the present invention embraces all of the following: a clone of such a plant, seed, selfed of hybrid progeny and descendants (e.g. F1 and F2 descendants).

According to a further aspect of the invention there is provided an isolated nucleic acid molecule obtainable from *Arabidopsis thaliana* which comprises a nucleic acid sequence encoding a polypeptide having (1) GTase functionality; and (2) is capable of adding a glucosyl group via an O-glucosidic linkage to form (a) a glucosyl ester of at least one of:

cinnamic acid; p-coumaric acid; caffeic acid; ferulic acid; and sinapic acid; and/or (b) a 4-O-glucoside of at least one of:

cinnamic acid; p-coumaric acid; caffeic acid; ferulic acid; sinapic acid; p-coumaryl aldehyde; coniferyl aldehyde; sinapyl aldehyde; p-coumaryl alcohol; coniferyl alcohol; and sinapyl alcohol.

In a further aspect of the invention there is provided a polypeptide encoded by an isolated nucleic acid molecule of the present invention wherein the said polypeptide is selected from the polypeptides of FIGS. 1B, 2B, 3B, 4B, 5B, 6B, 7B, 8B, 9B, 10B and 11B or functional variants and/or parts thereof. Preferably the polypeptide is selected from the group of polypeptides of FIGS. 2B, 3B, 4B, 6B, 7B and 9B or functional variants and/or parts thereof. Preferably still the polypeptide is selected from the group of polypeptides selected from FIGS. 2B, 3B, 7B and 9B or functional variants and/or parts thereof. Most preferably the polypeptide is one of the polypeptides shown in FIGS. 2B, 3B, 7B or 9B. Polypeptides encoded by the sense nucleic acid sequences presented in FIGS. 12-32 are also provided and readily derived from these sense sequences.

Variants of sequences having substantial identity or homology with the GTase molecules of the invention may be utilized in the practices of the invention. That is, the GTase of FIGS. 1A-11A may be modified yet still remain functional. Generally, the GTase will comprise at least about 40%-60%, preferably about 60%-80%, more preferably about 80%-95% sequence identity with a GTase nucleotide sequence of FIGS. 1A-32 herein.

The activity of functional variant polypeptides may be assessed by transformation into a host capable of expressing the nucleic acid of the invention. Methodology for such transformation is described in more detail below.

In a further aspect of the invention there is disclosed a method of producing a derivative nucleic acid comprising the step of modifying any of the sequences disclosed above, particularly the coding sequence of FIGS. 1A, 2A, 3A, 4A, 5A, 6A, 7A, 8A, 9A, 10A, 11A, 12, 13, 14, 15, 16, 17, 18, 19, 20, 21, 22, 23, 24, 25, 26, 27, 28, 29, 30, 31, 32

Alternatively, changes to a sequence may produce a derivative by way of one or more of addition, insertion, deletion or substitution of one or more nucleotides in the nucleic acid, leading to the addition, insertion, deletion or substitution or one or more amino acids in the encoded polypeptide.

Other desirable mutations may be random or site directed mutagenesis in order to alter the activity (e.g. specificity) or stability of the encoded polypeptide or to produce dominant negative variants which may alter the flux through lignin biosynthetic pathways to alter the amount of lignin or an intermediate in the lignin biosynthetic pathway.

The invention will now be described with reference to the following Figures and Examples which are not to be construed as limiting the invention.

Scheme 1: The major intermediates in lignin biosynthesis pathway.

Figure 34:
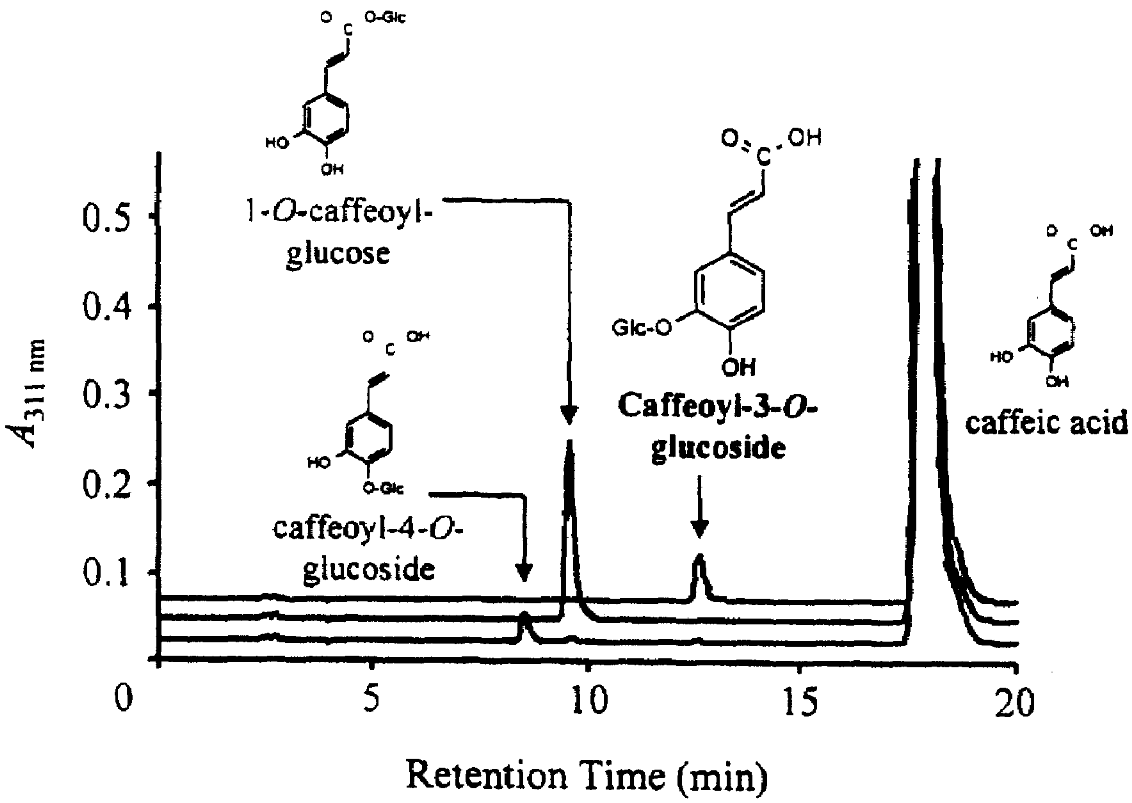

FIG. 1A: Sense nucleotide sequence of A062 (SEQ ID NO:1). The coding region starts from the first nucleotide and ends at the last nucleotide;

FIG. 1B: The amino acid sequence of A062 (SEQ ID NO: 2);

FIG. 1C: The antisense nucleotide sequence of A062 (SEQ ID NO:3);

FIG. 2A Sense nucleotide sequence of A320 (SEQ ID NO: 4). The coding region starts from the first nucleotide and ends at the last nucleotide;

FIG. 2B The amino acid sequence of A320 (SEQ ID NO: 5);

FIG. 2C: The antisense nucleotide sequence of A320 (SEQ ID NO: 6);

FIG. 3A: Sense nucleotide sequence of A41 (SEQ ID NO: 7). The coding region starts from the first nucleotide and ends at the last nucleotide;

FIG. 3B: The amino acid sequence of A41 (SEQ ID NO: 8);

FIG. 3C: The antisense nucleotide sequence of A41 (SEQ ID NO: 9);

FIG. 4A: Sense nucleotide sequence of A42 (SEQ ID NO: 10). The coding region starts from the first nucleotide and ends at the last nucleotide;

FIG. 4B: The amino acid sequence of A42 (SEQ ID NO: 11);

FIG. 4C: The antisense nucleotide sequence of A42 (SEQ ID NO: 12);

FIG. 5A: Sense nucleotide sequence of A43 (SEQ ID NO: 13). The coding region starts from the first nucleotide and ends at the last nucleotide;

FIG. 5B: The amino acid sequence of A43 (SEQ ID NO: 14);

FIG. 5C: The antisense nucleotide sequence of A43 (SEQ ID NO: 15);

FIG. 6A: Sense nucleotide sequence of A911 (SEQ ID NO: 16). The coding region starts from the first nucleotide and ends at the last nucleotide;

FIG. 6B: The amino acid sequence of A911 (SEQ ID NO: 17);

FIG. 6C: The antisense nucleotide sequence of A911 (SEQ ID NO: 18);

FIG. 7A: Sense nucleotide sequence of A119 (SEQ ID NO: 19). The coding region starts from the first nucleotide and ends at the last nucleotide;

FIG. 7B: The amino acid sequence of A119 (SEQ ID NO: 20);

FIG. 7C: The antisense nucleotide sequence of A119 (SEQ ID NO: 21);

FIG. 8A: Sense nucleotide sequence of A233 (SEQ ID NO: 22). The coding region starts from the first nucleotide and ends at the last nucleotide;

FIG. 8B: The amino acid sequence of A233 (SEQ ID NO: 23);

FIG. 8C: The antisense nucleotide sequence of A233 (SEQ ID NO: 24);

FIG. 9A: Sense nucleotide sequence of A407 (SEQ ID NO: 25). The coding region starts from the first nucleotide and ends at the last nucleotide;

FIG. 9B: The amino acid sequence of A407 (SEQ ID NO: 26);

FIG. 9C: The antisense nucleotide sequence of A407 (SEQ ID NO: 27);

FIG. 10A: Sense nucleotide sequence of A961 (SEQ ID NO: 28). The coding region starts from the first nucleotide and ends at the last nucleotide;

FIG. 10B: The amino acid sequence of A961 (SEQ ID NO: 29);

FIG. 10C: The antisense nucleotide sequence of A961 (SEQ ID NO: 30);

FIG. 11A: Sense nucleotide sequence of A962 (SEQ ID NO: 31). The coding region starts from the first nucleotide and ends at the last nucleotide;

FIG. 11B: The amino acid sequence of A962 (SEQ ID NO: 32);

FIG. 11C: The antisense nucleotide sequence of A962. (SEQ ID NO: 33);

FIG. 12: The sense nucleotide sequence of UGT71B5 (SEQ ID NO: 34);

FIG. 13 The sense nucleotide sequence of UGT71C3 (SEQ ID NO: 35);

FIG. 14 The sense nucleotide sequence of UGT71C5 (SEQ ID NO: 36);

FIG. 15 The sense nucleotide sequence of UGT71D1 (SEQ ID NO: 37);

FIG. 16 The sense nucleotide sequence of UGT73B1 (SEQ ID NO: 38);

FIG. 17 The sense nucleotide sequence of UGT73B2 (SEQ ID NO: 39);

FIG. 18 The sense nucleotide sequence of UGT73B4 (SEQ ID NO: 40);

FIG. 19 The sense nucleotide sequence of UGT73B5 (SEQ ID NO: 41);

FIG. 20 The sense nucleotide sequence of UGT73C1 (SEQ ID NO: 42);

FIG. 21 The sense nucleotide sequence of UGT731C (SEQ ID NO: 43);

FIG. 22 The sense nucleotide sequence of UGT73C5 (SEQ ID NO: 44);

FIG. 23 The sense nucleotide sequence of UGT73C6 (SEQ ID NO: 45);

FIG. 24 The sense nucleotide sequence of UGT73C7 (SEQ ID NO: 46);

FIG. 25 The sense nucleotide sequence of UGT74F2 (SEQ ID NO: 47);

FIG. 26 The sense nucleotide sequence of UGT76E1 (SEQ ID NO: 48);

FIG. 27 The sense nucleotide sequence of UGT76E11 (SEQ ID NO: 49);

FIG. 28 The sense nucleotide sequence of UGT76E12 (SEQ ID NO: 50);

FIG. 29 The sense nucleotide sequence of UGT76E2 (SEQ ID NO: 51);

FIG. 30 The sense nucleotide sequence of UGT78D1 (SEQ ID NO: 52);

FIG. 31 The sense nucleotide sequence of UGT89B1 (SEQ ID NO: 53);

FIG. 32 The sense nucleotide sequence of UGT72B3 (SEQ ID NO: 54);

FIG. 33 shows recombinant GST-UGT71C1 fusion protein purified from *E. coli* using glutathione-coupled Sepharose. The protein (5 µg) was analyzed using 10% SDS-PAGE and was visualized with Coomassive staining;

FIG. 34 shows three different glucose conjugates of caffeic acid, (caffeoyl-3-O-glucoside, caffeoyl-4-O-glucoside and 1-O-caffeoylglucose), obtained from the glucosyltransferase reactions containing the recombinant UGT71 C1, UGT73B3 and UGT84A1 respectively. Each assay contained 1-2 µg of recombinant UGT, 1 mM caffeic acid, 5 mM UDP-glucose, 1.4 mM 2-mercaptoethanol and 50 mM TRIS-HCl, pH 7.0. The mix was incubated at 30° C. for 30 min and was analyzed by reverse-phase HPLC subsequently. Linear gradient (10-16%) of acetonitrile in $H_2O$ at 1 ml/min over 20 min was used to separate the glucose conjugates from caffeic acid.

Figure 36:
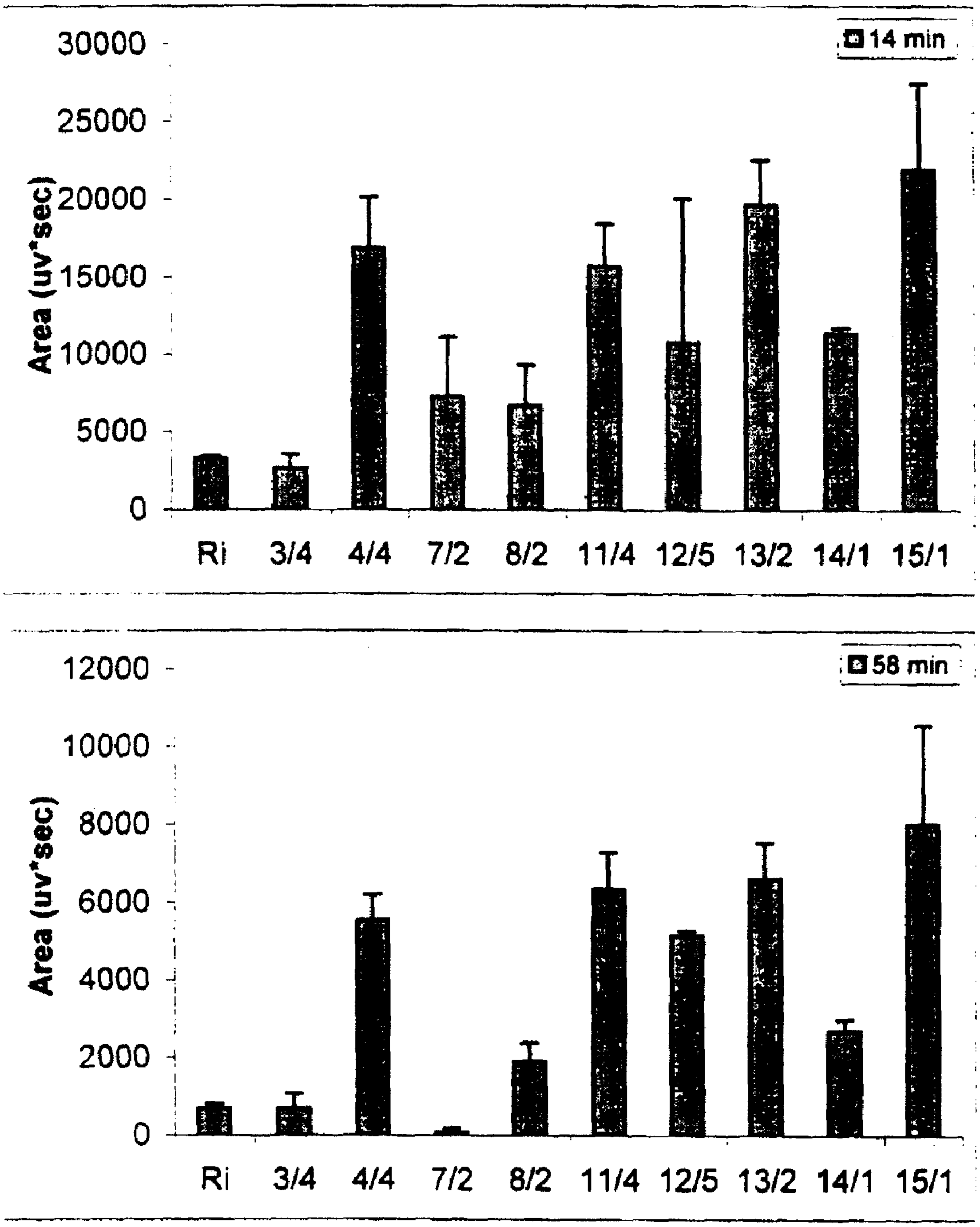

FIG. 35A shows the pH optima of UGT71C1 glucosyltransferase activity measured over the range pH 5.5-8.0 in the reactions containing 50 mM buffer, 1 µg of UGT71C1, 1 mM caffeic acid, 5 mM UDP-glucose and 1.4 mM 2-mercaptoethanol. The mix was incubated at 30° C. for 30 mm. The reaction was stopped by the addition of 20 µl of trichloroacetic acid (240 mg/ml) and was analyzed by reverse-phase HPLC subsequently. The specific enzyme activity was expressed as nanomoles of caffeic acid glucosylated per second (nkat) by 1 mg of protein in 30 min of reaction time at 30° C. FIG. 35B, the time course of UGT71C1 glucosyltransferase activity was studied by measuring the amount of caffeic acid glucosylated by 1 µg of UGT71C1 in 50 mM TRIS-HCl, pH 7.0. The reactions were carried out and analyzed as described in A;

FIG. 36 shows UGT71C1 transgenic *Arabidopsis thaliana* plants and their ability to glucosylate caffeic acid; and FIG. 37 summarises the GTase activities of various GTase polypeptides with respect to various anti-oxidant substrates.

EXAMPLES

Materials and Methods

Transformation of Woody Plant Species

The transformation of woody plant species is known in the art. See U.S. Pat. No. 4,795,855 and WO9118094; EP1050209 and WO9725434. Each of these patents are incorporated in their entirety by reference.

Transformation of Non-Woody Plant Species

Methods used in the transformation of plant species other than woody species are well known in the art and are extensively referenced herein.

Identification of GTase Sequences

The GTase sequence identification was carried out using GCG software (Wisconsin package, version 8.1). Blasta programme was used to search *Arabidopsis* protein sequences containing a PSPG (plant secondary product UDP-glucose glucosyltransferase) signature motif (Hughes and Hughes (1994) DNA Sequence 5, 41-49) in EMBL and GenBank sequence database. The database information on the GTases described in the present invention are listed in Table 1.

Amplification and Cloning of the GTase Sequences

The GTase sequences were amplified from *Arabidopsis thaliana* Columbia genomic DNA with specific primers (Table 2), following standard methodologies (Sambrook et al (1989) Molecular Cloning: A Laboratory Manual, $2^{nd}$ Ed., Cold Spring Harbor Laboratory, Cold Spring Harbor, N.Y.). 50 ng of genomic DNA isolated from *Arabidopsis thaliana* Columbia were incubated with 1xpfu PCR buffer (Stratagene), 250 µM dNTPS, 50 pmole primer for each end, and 5 units of pfu DNA polymerase (Stratagene) in a total of 100 µl. The PCR reactions were carried out as outlined in the programme described in Table 3.

After PCR amplification, the products were double digested by appropriate restriction enzymes listed in Table 2 (bold type). The digested DNA fragments were purified using an electro-eluction method (Sambrook et al (1989) Molecular Cloning: A Laboratory Manual, $2^{nd}$ Ed., Cold Spring Harbor Laboratory, Cold Spring Harbor, N.Y.) and ligated into the corresponding cloning site on pGEX2T plasmid DNA (Pharmacia) by T4 DNA ligase (NEB) at 16°

C. overnight. The resulting recombinant plasmid DNA was amplified in *E. coli* XLI-blue cells and was confirmed with the restriction enzymes listed in Table 2 (bold type) following the method described by Sambrook et al (1989) Molecular Cloning: A Laboratory Manual, 2nd Ed., Cold Spring Habor Laboratory, Cold Spring Harbor, N.Y.).

Preparation of Glucosyltransferase Recombinant Proteins

*E. coli* cells carrying recombinant plasmid DNA as described above were grown at 37° C. overnight on 2YT (16 g bacto tryptone, 10 g bacto-yeast extract, 5 g NaCl per litre) agar (1.8% w/v) plate which contained 50 μg/ml ampicillin. A single colony was picked into 2 ml of 2YT containing the same concentration of ampicillin. The bacterial culture was incubated at 37° C. with moderate agitation for 6 h. The bacterial culture was transferred into 1 L of 2 YT and incubated at 20° C. subsequently. 0.1 mM IPTG was added when the culture reached logarithmic growth phase ($A_{600\ nm}$~0.5). The bacterial culture was incubated for another 24 h. The cells were collected by a centrifugation at 7,000×g for 5 min at 4° C. and resuspended in 5 ml spheroblast buffer (0.5 mM EDTA, 750 mM sucrose, 200 mM Tris, pH 8.0). Lysozyme solution was added to a final concentration of 1 mg/ml. 7-fold volume of 0.5×spheroblast buffer was poured into the suspension immediately and the suspension was incubated for 4° C. for 30 min under gentle shaking. The spheroblasts were collected by a centrifugation at 12,000×g for 5 min at 4° C., and resuspended in 5 ml ice cold PBL buffer (140 mM NaCl, 80 mM, $NA_2$ $HPO_4$, 15 mM $KH_2PO4$). 2 mM of PMSF was added into suspension immediately and the suspension was centrifuged at 12,000×g for 20 min at 4° C. in order to remove the cell debris. After the centrifugation, the supernatant was transferred to a 15 ml tube. 200 μl of 50% (v/v) slurry of Glutathione-coupled Sepharose 4B were added into the tube and the mixture was mixed gently for 30 min at room temperature. The mixture was then centrifuged at a very slow speed (500×g) for 1 min. the supernatant was discarded. The beads were washed with 5 ml ice cold PBS buffer three times. After each wash, a short centrifugation was applied as described above to sediment the Sepharose beads. To recover the expressed protein from Sepharose beads, 100 μl of 20 mM reduced glutathione were used to resuspend the beads. After 10 min incubation at room temperature, the beads were collected and the supernatant containing the expressed protein was collected. The elution step was repeated once, and both supernatant fractions were combined and stored at 4° C. for protein assay and further studies.

Protein Concentration Assay

The protein assays were carried out by adding 10 μl of protein solution into 900 μl of distilled water and 200 μl of Bio-Rad Protein Assay Dye. The absorbance at 595 nm was read. A series of BSA (bovine serium albumin) at different concentration was used as standard. Regression line was plotted based on the coordinates of the BSA concentration against the reading at 595 nm. The concentration of protein sample was therefore estimated from the regression line after the protein assay.

Assay for Enzyme Activity

A standard glucosylation reaction was set up by mixing 2 μg of recombinant proteins with 14 mM 2-mercaptoethanol, 5 mM UDP-glucose. 1 mM of various lignin or antioxidant substrate, 100 mM Tris, pH 7.0, to a total volume of 200 μl. The reaction was carried out at 30° C. for 30 min and stopped by the addition of 20 μl trichloroacetic acid (240 mg/ml). All the samples were stored at −20° C. before the liquid chromatographic assay.

High-Performance Liquid Chromatographic

Reverse-phase HPLC (Waters Separator 2690 and Waters Tunable Absorbance Detector 486, Waters Limited. Herts, UK) using a Columbus 5μ $C_{18}$ column (250×4.60 mm, Phenomenex). Linear gradient of acetonitrile in $H_2O$ (all solutions contained 0.1% trifluoroacetic acid) at 1 ml/min over 20 min. was used to separate the glucose conjugates from their aglycone. The HPLC methods were described as the following: cinnamic acid, $\lambda_{288\ mn}$, 10-55% acetonitrile; p-coumaric acid, $\lambda_{311\ nm}$, 10-25% acetonitrile; caffeic acid, $\lambda_{311\ nm}$, 10-16% acetonitrile; ferulic acid, $\lambda_{311\ nm}$, 10-35% acetonitrile; sinapic acid, $\lambda_{306\ nm}$, 10-40% acetonitrile; p-coumaryl aldehyde, $\lambda_{315\ nm}$, 10-46% acetonitrile; coniferyl aldehyde, $\lambda_{283\ nm}$, 10-47% acetonitrile; sinapyl aldehyde, $\lambda_{280\ nm}$, 10-47% acetonitrile; p-coumaryl alcohol. $\lambda_{283\ nm}$, 10-27% acetonitrile; coniferyl alcohol, $\lambda_{306\ nm}$, 10-25% acetonitrile; sinapyl alcohol, $\lambda_{285\ nm}$, 10-25% acetonitrile. The retention time ($R_t$) of the glucose conjugates analysed is listed in the following: cinnamoylglucose, $R_t$=12.3 min; p-coumaroylglucose, $R_t$=10.6 min; caffeoylglucose, $R_t$=8.5 min; feruloylglucose, $R_t$=10.3 min; sinapoylglucose, $R_t$=9.7 min; caffeoyl-4-O-glucoside, $R_t$=6.8 min; feruloyl-4-O-glucoside, $R_t$=7.8 min: sinapoyl-4-O-glucoside. $R_t$=8.2 min: coniferin. $R_t$=8.2 min: syringin, $R_t$=9.1 min.

The recombinant GTases were shown to have GTase activity towards the major intermediates of the lignin biosynthesis pathway (Tables 5 and 6). It is clear from these results that the GTases display different specific activity reaction profiles relative to each other on the various lignin precursor substrates utilised.

Michaelis-Menten kinetics were also studied on several of the GTases against their preferred substrates (Tables 7 and 8). It is clear from these results that the GTases display different enzyme kinetics for different substrates.

The results (in total) indicate that certain GTases show a greater potential for use in the alteration of lignin biosynthesis in *planta* than others.

Reducing the Formation of Monolilnol Glucosides in *Planta*

In one approach to reduce the formation of monolignol glucosides in *planta*, A119 and A407 are down regulated using an antisense strategy (A). Expression of the A119 and A407 antisense sequences is driven by the gene's own promoter. An alternative approach (B) is to modify the UDP-glucose binding motif through an in vitro mutagenesis method (Lim et al., 1998) such that the mutant protein is able to bind the monolignol substrates but loses its catalytic activity. Such mutant proteins are thought to compete with the functional native protein by binding specifically to monolignols, thereby reducing the formation of monolignol glucosides.

Anti-Sense Approach

Amplification and Cloning of the A119 and A407 Promoter Sequences

Approximately 2 kb of the 5' flanking sequences of A119 and A407 are amplified directly from genomic DNA by PCR. The promoter fragments are then cloned into a pBluescript plasmid vector (Sambrook et al., 1989).

Construct Chimaeric Genes of A119 and A407 Promoter and their ORF Region in Antisense Orientation.

The A119 and A407 cDNA fragments are amplified from pGEXA119 and pGEXA407 by PCR. The fragments are then ligated correspondingly into the A119 and A407 promoter constructs described in (A)-(1) with the ORF region in the antisense orientation.

Preparation of Binary Construct Containing the A119 and A407 Antisense Chimaeric Gene The DNA fragments containing the A119 and A407 antisense chimaeric genes are amplified by PCR from the chimaeric constructs described in (A)-(2). The fragments are then ligated into a binary vector (Sambrook et al., 1989). The final constructs are transformed into plants subsequently.

Mutant Gene Approach

In Vitro Site Mutagenesis to Modify the UDPglucose Binding Motif in A119 and A407

In vitro site mutagenesis is carried by PCR to modify the sequences encoding the UDPglucose binding motif in A119 and A407 (Lim et al. 1998). The constructs pGEXA119 and pGEXA407 are used in the DNA templates in the PCR reaction.

Construct Chimaeric Mutant Genes Regulated by A119 and A407 Promoters

The A119 and A407 mutant genes are amplified from the pGEXA119 and pGEXA407 mutant constructs described in (B)-(1) by PCR. The A 119 and A407 mutant gene fragments are then ligated into the A119 and A407 promoter constructs described in (A)-(1) with the ORF region in the sense orientation.

Preparation of Binary Construct Containing the Chimaeric Mutant Genes A119 and A407

The DNA fragments containing the A119 and A407 mutant chimaeric genes are amplified by PCR from the chimaeric constructs described in (B)-(2). The fragments are then ligated into a binary vector (Sambrook et al., 1989). The final constructs are transformed into plants subsequently.

Enhancing the Formation of Monolignol Glucosides in *Planta*

The CaMV 35S promoter fragment is used to drive the expression of A119 and A497. DNA fragments containing A119 and A407 ORF sequences are amplified from pGEXA119 and pGEXA407 correspondingly by PCR. The DNA fragments are ligated downstream of the CaMV 35S promoter. The constructs are used to transform plants such that the lignin content and composition is altered.

TABLE 1

Database information on eleven Arabidopsis GTase genes

| Gene name | protein_id | chromosome | DataBase acc. no. | BAC/P1 clone | gene name in database |
|---|---|---|---|---|---|
| A062 | Gi\|3935156 | I | ac005106 | T25N20 | T25N20.20 |
| A320 | Not annotated | III | ab019232 | MIL23 | not annotated |
| A41 | Emb\|CAB10326.1 | IV | z97339 | FCA4 | d13780c |
| A42 | Emb\|CAB10327.1 | IV | z97339 | FCA4 | d13785c |
| A43 | Emb\|CAB10328.1 | IV | z97339 | FCA4 | d13790c |
| A911 | Gi\|2642451 | II | ac002391 | T20D16 | T20D16.11 |
| A119 | Not annotated | V | ab018119 | MSN2 | not annotated |
| A233 | Wrongly annotated | IV | a1021961 | F28A23 | wrongly annotated |
| A407 | Gi\|3319344 | V | af077407 | F9D12 | F9D12.4 |
| A961 | Gi\|3582329 | II | ac005496 | T27A16 | T27A16.15 |
| A962 | Gi\|3582341 | II | ac005496 | T27A16 | T27A16.16 |

Parameters used for the search of the above *Arabidopsis* sequences and the programme used are as follows:

NETBLAST with the default settings:

Infile2=nr

Matrix=Blosum 62

Translate=1

Dbtranslate=1

TABLE 2

DNA sequences and restriction enzyme sites in primers used in amplification of 11 Arabidopsis Gtase sequences from genomic DNA.

Sequence complementary to either end of the ORFs are underlined. Restriction enzyme sites that were used in making expression constructs were in BOLD type.

| primer | DNA sequence (5'→3') | restriction enzyme sites |
|---|---|---|
| A062 5' (SEQ ID NO: 55) | CGGGTGATCAGGTACC<u>ATGGCGCCACCGCATTTTC</u> | BclI and KpnI |
| A062 3' (SEQ ID NO: 56) | CGGAATTCGTCGAC<u>TTACTTTACTTTTACCTCCTC</u> | EcoRI and SalI |
| A320 5' (SEQ ID NO: 57) | CCCCCGGGTACC<u>ATGGAGCTAGAATCTTCTCTCC</u> | SmaI and KpnI |

TABLE 2-continued

DNA sequences and restriction enzyme sites in primers used in amplification of 11 Arabidopsis Gtase sequences from genomic DNA.

Sequence complementary to either end of the ORFs are underlined. Restriction enzyme sites that were used in making expression constructs were in BOLD type.

| primer | DNA sequence (5'→3') | restriction enzyme sites |
|---|---|---|
| A320 3' (SEQ ID NO: 58) | CGGAATTCTCGAGTTAAAAGCTTTTGATTGATCC | EcoRI and XhoI |
| A41 5' (SEQ ID NO: 59) | TGGGATCCATATCAGAAATGGTGTTC | BamHI |
| A41 3' (SEQ ID NO: 60) | GGGAATTCCTAGTATCCATTATCTTTAGTC | EcoRI |
| A42 5' (SEQ ID NO: 61) | GGGGATCCATGGACCCGTCTCGTCATACTC | BamHI |
| A42 3' (SEQ ID NO: 62) | GGGAATTCCACTAGTGTTCTCCGTTGTCTTC | EcoRI |
| A43 5' (SEQ ID NO: 63) | GGGGATCCAATATGGAGATGGAATCGTCGTTAC | BamHI |
| A43 3' (SEQ ID NO: 64) | GGGAATTCCTTACACGACATTATTAATGTTTG | EcoRI |
| A911 5' (SEQ ID NO: 65) | GGGGTACCTGATCAATAATGGGCAGTAGTGAGGG | KpnI and BclI |
| A911 3' (SEQ ID NO: 66) | CGGAATTCGTCGACGAGTTAGGCGATTGTGATATC | EcoRI and SalI |
| A119 5' (SEQ ID NO: 67) | CGGGATCCGGTACCATGCATATCACAAAACCACAC | BamHI and KpnI |
| A119 3' (SEQ ID NO: 68) | CGGAATTCGCTAGCTAAGCACCACGTGACAAGTCC | EcoRI and Nhel |
| A233 5' (SEQ ID NO: 69) | CGGGATCCGGTACCATGAGTAGTGATCCTCATCGT | BamHI and KpnI |
| A233 3' (SEQ ID NO: 70) | CGGGATCCGAATTCTACGAGGTAAACTCTTCTATG | BamHI and EcoRI |
| A407 5' (SEQ ID NO: 71) | CGGGATCCGGTACCATGCATATCACAAAACCAC | BamHI and KpnI |
| A407 3' (SEQ ID NO: 72) | CGGAATTCGTCGACCTAAGCACCACGTCCCAAG | EcoRI and SalI |
| A961 5' (SEQ ID NO: 73) | GGGTGATCAGGTACCATGGGGAAGCAAGAAGATG | BclI and KpnI |
| A961 3' (SEQ ID NO: 74) | CGGAATTCGTCGACTACTTACTTATAGAAACGCCG | EcoRI and SalI |

TABLE 2-continued

DNA sequences and restriction enzyme sites in primers used in amplification of 11 Arabidopsis Gtase sequences from genomic DNA.

Sequence complementary to either end of the ORFs are underlined. Restriction enzyme sites that were used in making expression constructs were in BOLD type.

| primer | DNA sequence (5'→3') | restriction enzyme sites |
|---|---|---|
| A962 5' (SEQ ID NO: 75) | GAAGATCTGGTACCATGGCGAAGCAGCAAGAAG | BglII and KpnI |
| A962 3' (SEQ ID NO: 76) | CGGAATTCGTCGACCGATCAAAGCCCATCTATG | EcoRI and SalI |

TABLE 3

PCR programme

| Stage I (1 cycle) | | Stage II (40 cycles) | | Stage III (1 cycle) | |
|---|---|---|---|---|---|
| 95° C. | 5 min | 95° C. | 1 min | 95° C. | 2 min |
| 55° C. | 2 min | 55° C. | 1 min | 55° C. | 2 min |
| 72° C. | 3 min | 72° C. | 2 min | 72° C. | 5 min |

TABLE 4

The HPLC conditions

| Lignin Precursors | Acetonitrile Gradient (%) | Detector Wavelength (nm) |
|---|---|---|
| cinnamic acid | 10-55 | 288 |
| p-coumaric acid | 10-25 | 311 |
| caffeic acid | 10-16 | 311 |
| ferulic acid | 10-35 | 311 |
| sinapic acid | 10-40 | 306 |
| p-coumaryl aldehyde | 10-46 | 315 |
| coniferyl aldehyde | 10-47 | 283 |
| sinapyl aldehyde | 10-47 | 280 |
| p-coumaryl alcohol | 10-27 | 283 |
| coniferyl alcohol | 10-25 | 306 |
| sinapyl alcohol | 10-25 | 285 |

TABLE 5

Specific activity of the recombinant GTases producing glucose ester against lignin precursors Each assay contained 0.5 ml of potential substrates. 5 mM UDPG and 0.2 µg of recombinant GTases in a total volume of 200 µl. The reactions were incubated at 20° C. for 30 min and were stopped by addition of 20 µl TCA (240 mg/ml). Each reaction mix was then analysed using HPLC. The specific activity (nkat/mg) of the recombinant GTase is defined as the amount of substrate (nmole) converted to glucose ester per second by 1 mg of protein at 20° C. under the reaction conditions.

| | A41 | A320 | A42 | A43 | A911 | A062 |
|---|---|---|---|---|---|---|
| Cinnamic acid | 0.30 | 0.06 | 14.21 | 0.02 | 8.77 | 1.62 |
| p-coumaric acid | 13.53 | 0.05 | 4.69 | 0.03 | 4.31 | 2.54 |
| Caffeic acid | 2.61 | 0.05 | 0.62 | 0.01 | 0.77 | 0.26 |
| Ferulic acid | 6.64 | 0.54 | 15.63 | 0.04 | 2.88 | 0.08 |
| Sinapic acid | 5.35 | 15.58 | 11.97 | 0.05 | 0.15 | 0.1 |

TABLE 6

Specific activity of the recombinant GTases producing O-glucosides against lignin precursors The reactions were set up following the conditions described in Table 1. All the reactions, except those containing the aldehydes, were stopped by the addition of TCA. The aldehyde assay mixs were injected into HPLC immediately after the reactions were completed. The specific activity (nkat/mg) of the recombinant GTase is defined as the amount of substrate (nmole) converted to 4-O-glucoside per second by 1 mg of protein at 30° C. under the reaction conditions.

| | A233 | A119 | A407 | A961 | A962 |
|---|---|---|---|---|---|
| Cinnamic acid | ND[a] | ND | ND | ND | ND |
| p-coumaric acid | 0.09 | 0.02 | 0.01 | 0.01 | 0.01 |
| caffeic acid | 0.48 | 0.13 | 0.07 | 0.07 | ND |
| ferulic acid | 0.37 | 14.48 | 0.25 | ND | ND |
| sinapic acid | 0.39 | 102.56 | 65.39 | 0.01 | 0.01 |
| p-coumaryl aldehyde | ND | 0.03 | ND | 0.01 | 0.02 |
| Coniferyl aldehyde | ND | 1.08 | ND | 0.16 | 0.34 |
| sinapyl aldehyde | ND | 4.55 | ND | 0.57 | 0.50 |
| p-coumaryl alcohol | ND | ND | ND | ND | ND |
| Coniferyl alcohol | 0.46 | 67.53 | 2.78 | 0.57 | 0.49 |
| sinapyl alcohol | 0.05 | 126.16 | 114.76 | 0.35 | 0.45 |

[a]ND, not detected

TABLE 7

Kinetic studies on the recombinant GTases producing glucose esters against lignin precursors

| A41 | | A320 | | A42 | | A911 | | A062 | |
|---|---|---|---|---|---|---|---|---|---|
| $K_m$ MM | $V_{max}$ nkat/mg | $K_m$ mM | $V_{max}$ nkat/mg | $K_m$ mM | $V_{max}$ nkat/mg | $K_m$ mM | $V_{max}$ nkat/mg | $K_m$ mM | $V_{max}$ nkat/mg |
| 1.51 | — | 1.80 | — | 0.72 | — | 1.05 | — | 2.36 | — |
| — | — | — | — | 0.49 | 19.42 | 0.05 | 9.06 | 4.33 | 2.87 |
| 0.10 | 16.13 | — | — | 0.40 | 6.67 | 0.39 | 11.10 | 5.05 | 4.91 |
| 0.06 | 20.24 | — | — | 0.20 | 1.67 | 0.23 | 1.18 | — | — |
| 0.35 | 11.35 | — | — | 0.36 | 18.35 | 0.34 | 6.91 | — | — |
| 0.24 | 6.78 | 0.06 | 8.37 | 0.13 | 12.80 | — | — | — | — |

TABLE 8

Kinetic studies on the recombinant GTases producing O-glucosides against lignin precursors

| | A119 | | A407 | |
|---|---|---|---|---|
| | $K_m$ mM | $V_{max}$ nkat/mg | $K_m$ mM | $V_{max}$ nkat/mg |
| UDPG | 0.93 | — | 0.89 | — |
| ferulic acid | 0.25 | 18.87 | — | — |
| sinapic acid | 0.51 | 131.58 | 0.14 | 75.19 |
| coniferyl alcohol | 0.26 | 92.59 | — | — |
| sinapyl alcohol | 1.10 | 322.58 | 1.07 | 357.10 |

TABLE 9

$^1H$ and $^{13}C$ NMR spectra were recorded in deuterated methanol at 500 MHz and 125 MHz respectively. Chemical shifts are given on δ scale with TMS as internal standard. The position on the aromatic ring begins with the carbon joining the propanoic acid. d, doublet; dd, doublet of doublets: m, multiplet; J. coupling constant.

| | Caffeic acid | | Caffeoyl-3-O-glucoside | |
|---|---|---|---|---|
| Position | $\delta_H$ | $\delta_C$ | $\delta_H$ | $\delta_C$ |
| C1 | — | 128.1 | — | 127.6 |
| C2 | 7.02 (1H, d, J = 2.0 Hz) | 115.2 | 7.47 (1H, d, J = 2.0 Hz) | 117.0 |
| C3 | — | 146.7 | — | 146.0 |
| C4 | — | 149.4 | — | 150.6 |
| C5 | 6.77 (1H, d, J = 8.0 Hz) | 116.6 | 6.84 (1H, d, J = 8.5 Hz) | 117.8 |
| C6 | 6.92 (1H, dd, J = 8.0, 2.0 Hz) Hz) | 122.8 | 7.13 (1H, dd, J = 8.5, 2.0 Hz) | 125.6 |
| C7 | 7.53 (1H, d, J = 16.0 Hz) | 146.9 | 7.45 (1H, d, J = 14.5 Hz) | 146.6 |
| C8 | 6.21 (1H, d, J = 15.5 Hz) | 116.3 | 6.33 (1H, d, J = 14.5 Hz) | 116.1 |
| C9 | — | 171.5 | — | 170.4 |
| Glc-1 | | | ~4.86 (signal interrupted) | 103.9 |
| Glc-2 | | | } 3.40-3.50 (4H, m) | 74.5 |
| Glc-3 | | | | 78.0 |
| Glc-4 | | | | 71.0 |
| Glc-5 | | | | 77.2 |
| Glc-6 | | | 3.93 (1H, dd, J = 12.0, 2.0 Hz) 3.71 (1H, dd, J = 12.0, 5.5 Hz) | 62.4 |

TABLE 10

Each assay contained 1 g of UGT71Cl, 1 mM phenolic compound, 5 mM UDP-glucose. 1.4 mM 2-mercaptoethanol and 50 mM TRIS-HCl, pH 7.0. The mix was incubated at 30° C. for 30 min. The reaction was stopped by the addition of 20 1 of trichloroacetic acid (240 mg/ml) and was analysed by reverse-phase HPLC subsequently. The results represent the mean of three replicates ± standard deviation.

| Substrate | Specific activity nkat/mg |
|---|---|
| o-Coumaric acid | 1.5 ± 0.2 |
| m-Coumaric acid | 1.2 ± 0.2 |
| p-Coumaric acid | 0 |
| Caffeic acid | 2.9 ± 0.8 |
| Ferulic acid | 0 |
| Sinapic acid | 0 |
| Esculetin | 34.8 ± 4.2 |
| Scopoletin | 29.4 ± 3.9 |
| Salicylic acid | 0 |
| 4-hydroxybenzoic acid | 0 |
| 3,4-dihydroxybenzoic acid | 0 |
| Eriodictyol | 0 |
| Luteolin | 0.7 ± 0.1 |
| Quercetin | 1.4 ± 0.4 |
| Catechin | 0 |
| Cyanidin | 0 |

The invention is claim:

1. A transgenic plant comprising an isolated nucleic acid molecule which encodes a polypeptide which has glucosyltransferase activity and is encoded by i) the nucleic acid molecule of SEQ ID NO 19; or ii) a nucleic acid molecule that encodes the amino acid sequence of SEQ ID NO: 20 and which enhances monolignol glucoside biosynthesis.

2. A transgenic plant according to claim 1, wherein said monolignols are selected from the group consisting of: cinnamic acid; p-coumaric acid; caffeic acid; ferulic acid; sinapic acid; p-coumaryl aldehyde; coniferyl aldehyde; sinapyl aldehyde; p-coumaryl alcohol; coniferyl alcohol and sinapyl alcohol.

3. The transgenic plant according to claim 1, wherein the nucleic acid is cDNA.

4. The transgenic plant according to claim 1, wherein the nucleic acid is genomic DNA.

5. The transgenic plant according to claim 1, wherein the plant is a woody plant selected from the group consisting of poplar; eucalyptus; Douglas fir; pine; walnut; ash; birch; oak; teak and spruce.

6. The transgenic plant according to claim 5, wherein said plant is poplar.

7. The transgenic plant according to claim 1, wherein the plant is a non-woody plant species.

8. A method for the manufacture of paper or paperboard comprising:

i) pulping transgenic wood material derived from the transgenic woody plant according to claim 5; and ii) producing paper or paperboard from the pulped transgenic wood material.

* * * * *

SEQUENCE LISTING

<160> NUMBER OF SEQ ID NOS: 76

<210> SEQ ID NO 1
<211> LENGTH: 1410
<212> TYPE: DNA
<213> ORGANISM: Arabidopsis thaliana

<400> SEQUENCE: 1

```
atggcgccac cgcattttct actggtaacg tttccggcgc aaggtcacgt gaacccatct     60
ctccgttttg ctcgtcggct catcaaaaga accggcgcac gtgtcacttt cgtcacttgt    120
gtctccgtct tccacaactc catgatcgca aaccacaaca aagtcgaaaa tctctctttc    180
cttactttct ccgacggttt cgacgatgga ggcatttcca cctacgaaga ccgtcagaaa    240
aggtcggtga atctcaaggt taacggcgat aaggcactat cggatttcat cgaagctact    300
aagaatggtg actctcccgt gacttgcttg atctacacga ttcttctcaa ttgggctcca    360
aaagtagcac gtagatttca acttccctcc gctcttctct ggatccaacc ggctttggtt    420
ttcaacatct attacactca tttcatggga aacaagtccg ttttcgagtt acctaatctg    480
tcttctctgg aaatcagaga tcttccatct ttcctcacac cttccaacac aaacaaaggc    540
gcatacgatg cgtttcaaga aatgatggag tttctcataa aagaaaccaa accgaaaatt    600
ctcatcaaca ctttcgattc gctggaacca gaggccttaa cggctttccc gaatatcgat    660
atggtggcgg ttggtccttt acttcccacg gagattttct caggaagcac caacaaatca    720
gttaaagatc aaagtagtag ttatacactt tggctagact cgaaaacaga gtcctctgtt    780
atttacgttt cctttggaac aatggttgag ttgtccaaga aacagataga ggaactagcg    840
agagcactca tagaagggaa acgaccgttt ttgtgggtta taactgataa atccaacaga    900
gaaacgaaaa cagaaggaga agaagagaca gagattgaga agatagctgg attcagacac    960
gagcttgaag aggttgggat gattgtgtcg tggtgttcgc agatagaggt tttaagtcac   1020
cgagccgtag gttgttttgt gactcattgt gggtggagct cgacgctgga gagtttggtt   1080
cttggcgttc cggttgtggc gtttccgatg tggtcggatc aaccgacgaa cgcgaagcta   1140
ctggaagaaa gttggaagac tggtgtgagg gtaagagaga acaaggatgg tttggtggag   1200
agaggagaga tcaggaggtg tttggaagcc gtgatggagg agaagtcggt ggagttgagg   1260
gaaaacgcaa agaaatggaa gcgtttagcg atggaagcgg gtagagaagg aggatcttcg   1320
gataagaaca tggaggcttt tgtggaggat atttgtggag aatctcttat tcaaaacttg   1380
tgtgaagcag aggaggtaaa agtaaagtaa                                    1410
```

<210> SEQ ID NO 2
<211> LENGTH: 469
<212> TYPE: PRT
<213> ORGANISM: Arabidopsis thaliana

<400> SEQUENCE: 2

```
Met Ala Pro Pro His Phe Leu Leu Val Thr Phe Pro Ala Gln Gly His
1               5                   10                  15

Val Asn Pro Ser Leu Arg Phe Ala Arg Arg Leu Ile Lys Arg Thr Gly
            20                  25                  30

Ala Arg Val Thr Phe Val Thr Cys Val Ser Val Phe His Asn Ser Met
        35                  40                  45

Ile Ala Asn His Asn Lys Val Glu Asn Leu Ser Phe Leu Thr Phe Ser
    50                  55                  60
```

-continued

```
Asp Gly Phe Asp Asp Gly Gly Ile Ser Thr Tyr Glu Asp Arg Gln Lys
 65                  70                  75                  80

Arg Ser Val Asn Leu Lys Val Asn Gly Asp Lys Ala Leu Ser Asp Phe
                85                  90                  95

Ile Glu Ala Thr Lys Asn Gly Asp Ser Pro Val Thr Cys Leu Ile Tyr
            100                 105                 110

Thr Ile Leu Leu Asn Trp Ala Pro Lys Val Ala Arg Arg Phe Gln Leu
        115                 120                 125

Pro Ser Ala Leu Leu Trp Ile Gln Pro Ala Leu Val Phe Asn Ile Tyr
    130                 135                 140

Tyr Thr His Phe Met Gly Asn Lys Ser Val Phe Glu Leu Pro Asn Leu
145                 150                 155                 160

Ser Ser Leu Glu Ile Arg Asp Leu Pro Ser Phe Leu Thr Pro Ser Asn
                165                 170                 175

Thr Asn Lys Gly Ala Tyr Asp Ala Phe Gln Glu Met Met Glu Phe Leu
            180                 185                 190

Ile Lys Glu Thr Lys Pro Lys Ile Leu Ile Asn Thr Phe Asp Ser Leu
        195                 200                 205

Glu Pro Glu Ala Leu Thr Ala Phe Pro Asn Ile Asp Met Val Ala Val
    210                 215                 220

Gly Pro Leu Leu Pro Thr Glu Ile Phe Ser Gly Ser Thr Asn Lys Ser
225                 230                 235                 240

Val Lys Asp Gln Ser Ser Ser Tyr Thr Leu Trp Leu Asp Ser Lys Thr
                245                 250                 255

Glu Ser Ser Val Ile Tyr Val Ser Phe Gly Thr Met Val Glu Leu Ser
            260                 265                 270

Lys Lys Gln Ile Glu Glu Leu Ala Arg Ala Leu Ile Glu Gly Lys Arg
        275                 280                 285

Pro Phe Leu Trp Val Ile Thr Asp Lys Ser Asn Arg Glu Thr Lys Thr
    290                 295                 300

Glu Gly Glu Glu Glu Thr Glu Ile Glu Lys Ile Ala Gly Phe Arg His
305                 310                 315                 320

Glu Leu Glu Glu Val Gly Met Ile Val Ser Trp Cys Ser Gln Ile Glu
                325                 330                 335

Val Leu Ser His Arg Ala Val Gly Cys Phe Val Thr His Cys Gly Trp
            340                 345                 350

Ser Ser Thr Leu Glu Ser Leu Val Leu Gly Val Pro Val Val Ala Phe
        355                 360                 365

Pro Met Trp Ser Asp Gln Pro Thr Asn Ala Lys Leu Leu Glu Glu Ser
    370                 375                 380

Trp Lys Thr Gly Val Arg Val Arg Glu Asn Lys Asp Gly Leu Val Glu
385                 390                 395                 400

Arg Gly Glu Ile Arg Arg Cys Leu Glu Ala Val Met Glu Glu Lys Ser
                405                 410                 415

Val Glu Leu Arg Glu Asn Ala Lys Lys Trp Lys Arg Leu Ala Met Glu
            420                 425                 430

Ala Gly Arg Glu Gly Gly Ser Ser Asp Lys Asn Met Glu Ala Phe Val
        435                 440                 445

Glu Asp Ile Cys Gly Glu Ser Leu Ile Gln Asn Leu Cys Glu Ala Glu
    450                 455                 460

Glu Val Lys Val Lys
465
```

-continued

<210> SEQ ID NO 3
<211> LENGTH: 1410
<212> TYPE: DNA
<213> ORGANISM: Arabidopsis thaliana

<400> SEQUENCE: 3
ttactttact tttacctcct ctgcttcaca caagttttga ataagagatt ctccacaaat 60
atcctccaca aaagcctcca tgttcttatc cgaagatcct ccttctctac ccgcttccat 120
cgctaaacgc ttccatttct ttgcgttttc cctcaactcc accgacttct cctccatcac 180
ggcttccaaa cacctcctga tctctcctct ctccaccaaa ccatccttgt tctctcttac 240
cctcacacca gtcttccaac tttcttccag tagcttcgcg ttcgtcggtt gatccgacca 300
catcggaaac gccacaaccg gaacgccaag aaccaaactc tccagcgtcg agctccaccc 360
acaatgagtc acaaaacaac ctacggctcg gtgacttaaa acctctatct gcgaacacca 420
cgacacaatc atcccaacct cttcaagctc gtgtctgaat ccagctatct tctcaatctc 480
tgtctcttct tctccttctg ttttcgtttc tctgttggat ttatcagtta taacccacaa 540
aaacggtcgt ttcccttcta tgagtgctct cgctagttcc tctatctgtt tcttggacaa 600
ctcaaccatt gttccaaagg aaacgtaaat aacagaggac tctgttttcg agtctagcca 660
aagtgtataa ctactacttt gatctttaac tgatttgttg gtgcttcctg agaaaatctc 720
cgtgggaagt aaaggaccaa ccgccaccat atcgatattc gggaaagccg ttaaggcctc 780
tggttccagc gaatcgaaag tgttgatgag aattttcggt ttggtttctt ttatgagaaa 840
ctccatcatt tcttgaaacg catcgtatgc gcctttgttt gtgttggaag gtgtgaggaa 900
agatggaaga tctctgattt ccagagaaga cagattaggt aactcgaaaa cggacttgtt 960
tcccatgaaa tgagtgtaat agatgttgaa aaccaaagcc ggttggatcc agagaagagc 1020
ggagggaagt tgaaatctac gtgctacttt tggagcccaa ttgagaagaa tcgtgtagat 1080
caagcaagtc acgggagagt caccattctt agtagcttcg atgaaatccg atagtgcctt 1140
atcgccgtta accttgagat tcaccgacct tttctgacgg tcttcgtagg tggaaatgcc 1200
tccatcgtcg aaaccgtcgg agaaagtaag gaaagagaga ttttcgactt tgttgtggtt 1260
tgcgatcatg gagttgtgga agacggagac acaagtgacg aaagtgacac gtgcgccggt 1320
tcttttgatg agccgacgag caaaacggag agatgggttc acgtgacctt gcgccggaaa 1380
cgttaccagt agaaaatgcg gtggcgccat 1410

<210> SEQ ID NO 4
<211> LENGTH: 1491
<212> TYPE: DNA
<213> ORGANISM: Arabidopsis thaliana

<400> SEQUENCE: 4
atggagctag aatcttctcc tcctctacct cctcatgtga tgctcgtatc ttttccaggg 60
caaggccacg ttaatccact tcttcgtctt ggtaagctct tagcttcaaa gggtttgctc 120
ataaccttcg tcaccactga gtcatggggc aaaaagatgc gaatctccaa caaaatccaa 180
gaccgtgtcc tcaaaccggt tggtaaaggc tatctccggt atgatttctt cgacgacggg 240
cttcctgaag acgacgaagc tagcagaacc aacttaacca tcctccgacc acatctagag 300
ctggtcggca aaagagagat caagaacctt gtgaaacgtt acaaggaagt aacgaaacag 360
cccgtgacat gtcttatcaa caaccctttc gtctcttggg tctgtgacgt ggcagaagat 420
cttcaaatcc cttgtgctgt tctttgggtt caatcttgtg cctgcttagc tgcttattac 480

-continued

```
tattaccacc acaacctagt tgacttcccg accaaaacag aacccgagat cgatgtccaa    540

atctctggca tgcctctctt gaaacatgac gagatccctt ctttcattca cccttcaagt    600

cctcactccg ctttgcgaga agtgatcata gatcagatta aacggcttca caagactttc    660

tccattttca tcgacacttt caactcattg gagaaagaca tcattgacca catgtcgacg    720

ctctctctcc ccggtgttat cagaccgcta ggaccactct acaaaatggc taaaaccgta    780

gcttatgatg tcgttaaagt aaacatctct gagccaacgg atccttgcat ggagtggtta    840

gactcgcagc cagtttcctc cgttgtttac atctcattcg ggaccgttgc ttacttgaaa    900

caagaacaaa tagacgagat cgcttacggt gtgttaaacg ccgacgttac gttcttgtgg    960

gtgattagac aacaagagtt aggtttcaac aaagagaaac atgttttgcc ggaagaagtt   1020

aaagggaaag ggaagatcgt tgaatggtgt tcacaagaga aagtattatc tcatccttca   1080

gtggcatgtt tcgtgactca ctgtggatgg aactcaacga tggaagctgt gtcttccgga   1140

gtcccgacgg tttgttttcc tcaatgggga gatcaagtca cggacgccgt ttacatgatc   1200

gatgtttgga agacgggagt gaggctaagc cgtggagagg cggaggagag gttagtgccg   1260

agggaggaag ttgcggagag gttgagagag gttactaaag gagagaaagc gatcgagttg   1320

aaaaagaatg ctttgaagtg gaaggaagag gcggaggcgg cggttgctcg cggtggttcg   1380

tcggatagga atcttgaaaa gtttgtggag aagttgggtg ccaaacctgt ggggaaagta   1440

caaaacggga gtcataatca tgtcttggct ggatcaatca aaagctttta a            1491
```

<210> SEQ ID NO 5
<211> LENGTH: 496
<212> TYPE: PRT
<213> ORGANISM: Arabidopsis thaliana

<400> SEQUENCE: 5

```
Met Glu Leu Glu Ser Ser Pro Pro Leu Pro Pro His Val Met Leu Val
  1               5                  10                  15

Ser Phe Pro Gly Gln Gly His Val Asn Pro Leu Leu Arg Leu Gly Lys
             20                  25                  30

Leu Leu Ala Ser Lys Gly Leu Leu Ile Thr Phe Val Thr Thr Glu Ser
         35                  40                  45

Trp Gly Lys Lys Met Arg Ile Ser Asn Lys Ile Gln Asp Arg Val Leu
     50                  55                  60

Lys Pro Val Gly Lys Gly Tyr Leu Arg Tyr Asp Phe Phe Asp Asp Gly
 65                  70                  75                  80

Leu Pro Glu Asp Asp Glu Ala Ser Arg Thr Asn Leu Thr Ile Leu Arg
                 85                  90                  95

Pro His Leu Glu Leu Val Gly Lys Arg Glu Ile Lys Asn Leu Val Lys
            100                 105                 110

Arg Tyr Lys Glu Val Thr Lys Gln Pro Val Thr Cys Leu Ile Asn Asn
        115                 120                 125

Pro Phe Val Ser Trp Val Cys Asp Val Ala Glu Asp Leu Gln Ile Pro
    130                 135                 140

Cys Ala Val Leu Trp Val Gln Ser Cys Ala Cys Leu Ala Ala Tyr Tyr
145                 150                 155                 160

Tyr Tyr His His Asn Leu Val Asp Phe Pro Thr Lys Thr Glu Pro Glu
                165                 170                 175

Ile Asp Val Gln Ile Ser Gly Met Pro Leu Leu Lys His Asp Glu Ile
            180                 185                 190
```

-continued

```
Pro Ser Phe Ile His Pro Ser Ser Pro His Ser Ala Leu Arg Glu Val
        195                 200                 205

Ile Ile Asp Gln Ile Lys Arg Leu His Lys Thr Phe Ser Ile Phe Ile
    210                 215                 220

Asp Thr Phe Asn Ser Leu Glu Lys Asp Ile Ile Asp His Met Ser Thr
225                 230                 235                 240

Leu Ser Leu Pro Gly Val Ile Arg Pro Leu Gly Pro Leu Tyr Lys Met
                245                 250                 255

Ala Lys Thr Val Ala Tyr Asp Val Val Lys Val Asn Ile Ser Glu Pro
            260                 265                 270

Thr Asp Pro Cys Met Glu Trp Leu Asp Ser Gln Pro Val Ser Ser Val
        275                 280                 285

Val Tyr Ile Ser Phe Gly Thr Val Ala Tyr Leu Lys Gln Glu Gln Ile
    290                 295                 300

Asp Glu Ile Ala Tyr Gly Val Leu Asn Ala Asp Val Thr Phe Leu Trp
305                 310                 315                 320

Val Ile Arg Gln Gln Glu Leu Gly Phe Asn Lys Glu Lys His Val Leu
                325                 330                 335

Pro Glu Glu Val Lys Gly Lys Gly Lys Ile Val Glu Trp Cys Ser Gln
            340                 345                 350

Glu Lys Val Leu Ser His Pro Ser Val Ala Cys Phe Val Thr His Cys
        355                 360                 365

Gly Trp Asn Ser Thr Met Glu Ala Val Ser Ser Gly Val Pro Thr Val
    370                 375                 380

Cys Phe Pro Gln Trp Gly Asp Gln Val Thr Asp Ala Val Tyr Met Ile
385                 390                 395                 400

Asp Val Trp Lys Thr Gly Val Arg Leu Ser Arg Gly Glu Ala Glu Glu
                405                 410                 415

Arg Leu Val Pro Arg Glu Glu Val Ala Glu Arg Leu Arg Glu Val Thr
            420                 425                 430

Lys Gly Glu Lys Ala Ile Glu Leu Lys Lys Asn Ala Leu Lys Trp Lys
        435                 440                 445

Glu Glu Ala Glu Ala Ala Val Ala Arg Gly Gly Ser Ser Asp Arg Asn
    450                 455                 460

Leu Glu Lys Phe Val Glu Lys Leu Gly Ala Lys Pro Val Gly Lys Val
465                 470                 475                 480

Gln Asn Gly Ser His Asn His Val Leu Ala Gly Ser Ile Lys Ser Phe
                485                 490                 495
```

<210> SEQ ID NO 6
<211> LENGTH: 1491
<212> TYPE: DNA
<213> ORGANISM: Arabidopsis thaliana

<400> SEQUENCE: 6

```
ttaaaagctt ttgattgatc cagccaagac atgattatga ctcccgtttt gtactttccc      60

cacaggtttg gcacccaact tctccacaaa cttttcaaga ttcctatccg acgaaccacc     120

gcgagcaacc gccgcctccg cctcttcctt ccacttcaaa gcattctttt tcaactcgat     180

cgctttctct cctttagtaa cctctctcaa cctctccgca acttcctccc tcggcactaa     240

cctctcctcc gcctctccac ggcttagcct cactcccgtc ttccaaacat cgatcatgta     300

aacggcgtcc gtgacttgat ctccccattg aggaaaacaa accgtcggga ctccggaaga     360

cacagcttcc atcgttgagt tccatccaca gtgagtcacg aaacatgcca ctgaaggatg     420
```

-continued

```
agataatact ttctcttgtg aacaccattc aacgatcttc cctttccctt taacttcttc    480

cggcaaaaca tgtttctctt tgttgaaacc taactcttgt tgtctaatca cccacaagaa    540

cgtaacgtcg gcgtttaaca caccgtaagc gatctcgtct atttgttctt gtttcaagta    600

agcaacggtc ccgaatgaga tgtaaacaac ggaggaaact ggctgcgagt ctaaccactc    660

catgcaagga tccgttggct cagagatgtt tactttaacg acatcataag ctacggtttt    720

agccattttg tagagtggtc ctagcggtct gataacaccg gggagagaga gcgtcgacat    780

gtggtcaatg atgtctttct ccaatgagtt gaaagtgtcg atgaaaatgg agaaagtctt    840

gtgaagccgt ttaatctgat ctatgatcac ttctcgcaaa gcggagtgag gacttgaagg    900

gtgaatgaaa gaagggatct cgtcatgttt caagagaggc atgccagaga tttggacatc    960

gatctcgggt tctgttttgg tcgggaagtc aactaggttg tggtggtaat agtaataagc   1020

agctaagcag gcacaagatt gaacccaaag aacagcacaa gggatttgaa gatcttctgc   1080

cacgtcacag acccaagaga cgaaagggtt gttgataaga catgtcacgg gctgtttcgt   1140

tacttccttg taacgtttca caaggttctt gatctctctt ttgccgacca gctctagatg   1200

tggtcggagg atggttaagt tggttctgct agcttcgtcg tcttcaggaa gcccgtcgtc   1260

gaagaaatca taccggagat agcctttacc aaccggtttg aggacacggt cttggatttt   1320

gttggagatt cgcatctttt tgccccatga ctcagtggtg acgaaggtta tgagcaaacc   1380

ctttgaagct aagagcttac caagacgaag aagtggatta acgtggcctt gccctggaaa   1440

agatacgagc atcacatgag gaggtagagg aggagaagat tctagctcca t            1491
```

<210> SEQ ID NO 7
<211> LENGTH: 1473
<212> TYPE: DNA
<213> ORGANISM: Arabidopsis thaliana

<400> SEQUENCE: 7

```
atgggatcca tatcagaaat ggtgttcgaa acttgtccat ctccaaaccc aattcatgta     60

atgctcgtct cgtttcaagg acaaggccac gtcaaccctc ttcttcgtct cggcaagtta    120

attgcttcaa agggtttact cgttaccttc gttacaacgg agctttgggg caagaaaatg    180

agacaagcca acaaaatcgt tgacggtgaa cttaaaccgg ttggttccgg ttcaatccgg    240

tttgagttct ttgatgaaga atgggcagag gatgatgacc ggagagctga tttctctttg    300

tacattgctc acctagagag cgttgggata cgagaagtgt ctaagcttgt gagaagatac    360

gaggaagcga acgagcctgt ctcgtgtctt atcaataacc cgtttatccc atgggtctgc    420

cacgtggcgg aagagttcaa cattccttgt gcggttctct gggttcagtc ttgtgcttgt    480

ttctctgctt attaccatta ccaagatggc tctgtttcat tccctacgga aacagagcct    540

gagctcgatg tgaagcttcc ttgtgttcct gtcttgaaga acgacgagat tcctagcttt    600

ctccatcctt cttctaggtt cacgggtttt cgacaagcga ttcttgggca attcaagaat    660

ctgagcaagt ccttctgtgt tctaatcgat tcttttgact cattggaaca agaagttatc    720

gattacatgt caagtctttg tccggttaaa accgttggac cgcttttcaa agttgctagg    780

acagttactt ctgacgtaag cggtgacatt tgcaaatcaa cagataaatg cctcgagtgg    840

ttagactcga ggcctaaatc gtcagttgtc tacatttcgt tcgggacagt tgcatatttg    900

aagcaagaac agatcgaaga gatcgctcac ggagttttga agtcgggttt atcgttcttg    960

tgggtgatta gacctccacc acacgatctg aaggtcgaga cacatgtctt gcctcaagaa   1020

cttaaagaga gtagtgctaa aggtaaaggg atgattgtgg attggtgccc acaagagcaa   1080
```

-continued

```
gtcttgtctc atccttcagt ggcatgcttc gtgactcatt gtggatggaa ctcgacaatg   1140

gaatctttgt cttcaggtgt tccggtggtt tgttgtccgc aatggggaga tcaagtgact   1200

gatgcagtgt atttgatcga tgttttcaag accggggtta gactaggccg tggagcgacc   1260

gaggagaggg tagtgccaag ggaggaagtg gcggagaagc ttttggaagc gacagttggg   1320

gagaaggcag aggagttgag aaagaacgct ttgaaatgga aggcggaggc ggaagcagcg   1380

gtggctccag gaggttcgtc ggataagaat tttagggagt ttgtggagaa gttaggtgcg   1440

ggagtaacga agactaaaga taatggatac tag                                1473


<210> SEQ ID NO 8
<211> LENGTH: 484
<212> TYPE: PRT
<213> ORGANISM: Arabidopsis thaliana

<400> SEQUENCE: 8

Met Val Phe Glu Thr Cys Pro Ser Pro Asn Pro Ile His Val Met Leu
  1               5                  10                  15

Val Ser Phe Gln Gly Gln Gly His Val Asn Pro Leu Leu Arg Leu Gly
             20                  25                  30

Lys Leu Ile Ala Ser Lys Gly Leu Leu Val Thr Phe Val Thr Thr Glu
         35                  40                  45

Leu Trp Gly Lys Lys Met Arg Gln Ala Asn Lys Ile Val Asp Gly Glu
     50                  55                  60

Leu Lys Pro Val Gly Ser Gly Ser Ile Arg Phe Glu Phe Phe Asp Glu
 65                  70                  75                  80

Glu Trp Ala Glu Asp Asp Asp Arg Arg Ala Asp Phe Ser Leu Tyr Ile
                 85                  90                  95

Ala His Leu Glu Ser Val Gly Ile Arg Glu Val Ser Lys Leu Val Arg
            100                 105                 110

Arg Tyr Glu Glu Ala Asn Glu Pro Val Ser Cys Leu Ile Asn Asn Pro
        115                 120                 125

Phe Ile Pro Trp Val Cys His Val Ala Glu Glu Phe Asn Ile Pro Cys
    130                 135                 140

Ala Val Leu Trp Val Gln Ser Cys Ala Cys Phe Ser Ala Tyr Tyr His
145                 150                 155                 160

Tyr Gln Asp Gly Ser Val Ser Phe Pro Thr Glu Thr Glu Pro Glu Leu
                165                 170                 175

Asp Val Lys Leu Pro Cys Val Pro Val Leu Lys Asn Asp Glu Ile Pro
            180                 185                 190

Ser Phe Leu His Pro Ser Ser Arg Phe Thr Gly Phe Arg Gln Ala Ile
        195                 200                 205

Leu Gly Gln Phe Lys Asn Leu Ser Lys Ser Phe Cys Val Leu Ile Asp
    210                 215                 220

Ser Phe Asp Ser Leu Glu Gln Glu Val Ile Asp Tyr Met Ser Ser Leu
225                 230                 235                 240

Cys Pro Val Lys Thr Val Gly Pro Leu Phe Lys Val Ala Arg Thr Val
                245                 250                 255

Thr Ser Asp Val Ser Gly Asp Ile Cys Lys Ser Thr Asp Lys Cys Leu
            260                 265                 270

Glu Trp Leu Asp Ser Arg Pro Lys Ser Ser Val Val Tyr Ile Ser Phe
        275                 280                 285

Gly Thr Val Ala Tyr Leu Lys Gln Glu Gln Ile Glu Glu Ile Ala His
    290                 295                 300
```

-continued

Gly Val Leu Lys Ser Gly Leu Ser Phe Leu Trp Val Ile Arg Pro Pro
305 310 315 320

Pro His Asp Leu Lys Val Glu Thr His Val Leu Pro Gln Glu Leu Lys
325 330 335

Glu Ser Ser Ala Lys Gly Lys Gly Met Ile Val Asp Trp Cys Pro Gln
340 345 350

Glu Gln Val Leu Ser His Pro Ser Val Ala Cys Phe Val Thr His Cys
355 360 365

Gly Trp Asn Ser Thr Met Glu Ser Leu Ser Ser Gly Val Pro Val Val
370 375 380

Cys Cys Pro Gln Trp Gly Asp Gln Val Thr Asp Ala Val Tyr Leu Ile
385 390 395 400

Asp Val Phe Lys Thr Gly Val Arg Leu Gly Arg Gly Ala Thr Glu Glu
405 410 415

Arg Val Val Pro Arg Glu Glu Val Ala Glu Lys Leu Leu Glu Ala Thr
420 425 430

Val Gly Glu Lys Ala Glu Glu Leu Arg Lys Asn Ala Leu Lys Trp Lys
435 440 445

Ala Glu Ala Glu Ala Ala Val Ala Pro Gly Gly Ser Ser Asp Lys Asn
450 455 460

Phe Arg Glu Phe Val Glu Lys Leu Gly Ala Gly Val Thr Lys Thr Lys
465 470 475 480

Asp Asn Gly Tyr

<210> SEQ ID NO 9
<211> LENGTH: 1473
<212> TYPE: DNA
<213> ORGANISM: Arabidopsis thaliana

<400> SEQUENCE: 9
ctagtatcca ttatctttag tcttcgttac tcccgcacct aacttctcca caaactccct 60
aaaattctta tccgacgaac ctcctggagc caccgctgct tccgcctccg ccttccattt 120
caaagcgttc tttctcaact cctctgcctt ctccccaact gtcgcttcca aaagcttctc 180
cgccacttcc tcccttggca ctaccctctc ctcggtcgct ccacggccta gtctaacccc 240
ggtcttgaaa acatcgatca aatacactgc atcagtcact tgatctcccc attgcggaca 300
acaaaccacc ggaacacctg aagacaaaga ttccattgtc gagttccatc cacaatgagt 360
cacgaagcat gccactgaag gatgagacaa gacttgctct tgtgggcacc aatccacaat 420
catcccttta cctttagcac tactctcttt aagttcttga ggcaagacat gtgtctcgac 480
cttcagatcg tgtggtggag gtctaatcac ccacaagaac gataaacccg acttcaaaac 540
tccgtgagcg atctcttcga tctgttcttg cttcaaatat gcaactgtcc cgaacgaaat 600
gtagacaact gacgatttag gcctcgagtc taaccactcg aggcatttat ctgttgattt 660
gcaaatgtca ccgcttacgt cagaagtaac tgtcctagca actttgaaaa gcggtccaac 720
ggttttaacc ggacaaagac ttgacatgta atcgataact tcttgttcca atgagtcaaa 780
agaatcgatt agaacacaga aggacttgct cagattcttg aattgcccaa gaatcgcttg 840
tcgaaaaccc gtgaacctag aagaaggatg gagaaagcta ggaatctcgt cgttcttcaa 900
gacaggaaca caaggaagct tcacatcgag ctcaggctct gtttccgtag ggaatgaaac 960
agagccatct tggtaatggt aataagcaga gaaacaagca caagactgaa cccagagaac 1020
cgcacaagga atgttgaact cttccgccac gtggcagacc catgggataa acgggttatt 1080

-continued gataagacac gagacaggct cgttcgcttc ctcgtatctt ctcacaagct tagacacttc 1140
tcgtatccca acgctctcta ggtgagcaat gtacaaagag aaatcagctc tccggtcatc 1200
atcctctgcc cattcttcat caaagaactc aaaccggatt gaaccggaac caaccggttt 1260
aagttcaccg tcaacgattt tgttggcttg tctcattttc ttgccccaaa gctccgttgt 1320
aacgaaggta acgagtaaac cctttgaagc aattaacttg ccgagacgaa gaagagggtt 1380
gacgtggcct tgtccttgaa acgagacgag cattacatga attgggtttg gagatggaca 1440
agtttcgaac accatttctg atatggatcc cat 1473

<210> SEQ ID NO 10
<211> LENGTH: 1440
<212> TYPE: DNA
<213> ORGANISM: Arabidopsis thaliana

<400> SEQUENCE: 10
atggacccgt ctcgtcatac tcatgtgatg ctcgtatctt tccccggcca aggtcacgta 60
aaccctctac ttcgtctcgg aaagctcata gcctctaaag gcttactcgt cacctttgtc 120
accacagaga agccatgggg caagaagatg cgtcaagcca acaagattca agacggtgtg 180
ctcaaaccgg tcggtctagg tttcatccgg tttgagttct tctctgacgg cttcgccgac 240
gacgatgaaa aaagattcga cttcgatgcc ttccgaccac accttgaagc tgtcggaaaa 300
caagagatca agaatctcgt taagagatat aacaaggagc cggtgacgtg tctcataaac 360
aacgcttttg tcccatgggt atgtgatgtc gccgaggagc ttcacatccc ttcggctgtt 420
ctatgggtcc agtcttgtgc ttgtctcacg gcttattact attaccacca ccggttagtt 480
aagttcccga ccaaaaccga gccggacatc agcgttgaaa tcccttgctt gccattgtta 540
aagcatgacg agatcccaag ctttcttcac ccttcgtctc cgtatacagc ttttggagat 600
atcattttag accagttaaa gagattcgaa aaccacaagt ctttctatct tttcatcgac 660
acttttcgcg aactagaaaa agacatcatg gaccacatgt cacaactttg tcctcaagcc 720
atcatcagtc ctgtcggtcc gctcttcaag atggctcaaa ccttgagttc tgacgttaag 780
ggagatatat ccgagccagc gagtgactgc atggaatggc ttgactcaag agaaccatcc 840
tcagtcgttt acatctcctt tgggactata gccaacttga agcaagagca gatggaggag 900
atcgctcatg gcgttttgag ctctggcttg tcggtcttat gggtggttcg gcctcccatg 960
gaagggacat ttgtagaacc acatgttttg cctcgagagc tcgaagaaaa gggtaaaatc 1020
gtggaatggt gtccccaaga gagagtcttg gctcatcctg cgattgcttg tttcttaagt 1080
cactgcggat ggaactcgac aatggaggct ttaactgccg gagtccccgt tgtttgtttt 1140
ccgcaatggg gagatcaagt gactgatgcg gtgtacttgg ctgatgtttt caagacagga 1200
gtgagactag gccgcggagc cgctgaggag atgattgttt cgagggaggt tgtagcagag 1260
aagctgcttg aggccacagt tggggaaaag gcggtggagc tgagagaaaa cgctcggagg 1320
tggaaggcgg aggccgaggc cgccgtggcg gacggtggat catctgatat gaactttaaa 1380
gagtttgtgg acaagttggt tacgaaacat gtgacgagag aagacaacgg agaacactag 1440

<210> SEQ ID NO 11
<211> LENGTH: 479
<212> TYPE: PRT
<213> ORGANISM: Arabidopsis thaliana

<400> SEQUENCE: 11

-continued

```
Met Asp Pro Ser Arg His Thr His Val Met Leu Val Ser Phe Pro Gly
1               5                   10                  15

Gln Gly His Val Asn Pro Leu Leu Arg Leu Gly Lys Leu Ile Ala Ser
            20                  25                  30

Lys Gly Leu Leu Val Thr Phe Val Thr Thr Glu Lys Pro Trp Gly Lys
        35                  40                  45

Lys Met Arg Gln Ala Asn Lys Ile Gln Asp Gly Val Leu Lys Pro Val
    50                  55                  60

Gly Leu Gly Phe Ile Arg Phe Glu Phe Phe Ser Asp Gly Phe Ala Asp
65                  70                  75                  80

Asp Asp Glu Lys Arg Phe Asp Phe Asp Ala Phe Arg Pro His Leu Glu
                85                  90                  95

Ala Val Gly Lys Gln Glu Ile Lys Asn Leu Val Lys Arg Tyr Asn Lys
            100                 105                 110

Glu Pro Val Thr Cys Leu Ile Asn Asn Ala Phe Val Pro Trp Val Cys
        115                 120                 125

Asp Val Ala Glu Glu Leu His Ile Pro Ser Ala Val Leu Trp Val Gln
    130                 135                 140

Ser Cys Ala Cys Leu Thr Ala Tyr Tyr Tyr Tyr His His Arg Leu Val
145                 150                 155                 160

Lys Phe Pro Thr Lys Thr Glu Pro Asp Ile Ser Val Glu Ile Pro Cys
                165                 170                 175

Leu Pro Leu Leu Lys His Asp Glu Ile Pro Ser Phe Leu His Pro Ser
            180                 185                 190

Ser Pro Tyr Thr Ala Phe Gly Asp Ile Ile Leu Asp Gln Leu Lys Arg
        195                 200                 205

Phe Glu Asn His Lys Ser Phe Tyr Leu Phe Ile Asp Thr Phe Arg Glu
    210                 215                 220

Leu Glu Lys Asp Ile Met Asp His Met Ser Gln Leu Cys Pro Gln Ala
225                 230                 235                 240

Ile Ile Ser Pro Val Gly Pro Leu Phe Lys Met Ala Gln Thr Leu Ser
                245                 250                 255

Ser Asp Val Lys Gly Asp Ile Ser Glu Pro Ala Ser Asp Cys Met Glu
            260                 265                 270

Trp Leu Asp Ser Arg Glu Pro Ser Ser Val Val Tyr Ile Ser Phe Gly
        275                 280                 285

Thr Ile Ala Asn Leu Lys Gln Glu Gln Met Glu Glu Ile Ala His Gly
    290                 295                 300

Val Leu Ser Ser Gly Leu Ser Val Leu Trp Val Val Arg Pro Pro Met
305                 310                 315                 320

Glu Gly Thr Phe Val Glu Pro His Val Leu Pro Arg Glu Leu Glu Glu
                325                 330                 335

Lys Gly Lys Ile Val Glu Trp Cys Pro Gln Glu Arg Val Leu Ala His
            340                 345                 350

Pro Ala Ile Ala Cys Phe Leu Ser His Cys Gly Trp Asn Ser Thr Met
        355                 360                 365

Glu Ala Leu Thr Ala Gly Val Pro Val Val Cys Phe Pro Gln Trp Gly
    370                 375                 380

Asp Gln Val Thr Asp Ala Val Tyr Leu Ala Asp Val Phe Lys Thr Gly
385                 390                 395                 400

Val Arg Leu Gly Arg Gly Ala Ala Glu Glu Met Ile Val Ser Arg Glu
                405                 410                 415

Val Val Ala Glu Lys Leu Leu Glu Ala Thr Val Gly Glu Lys Ala Val
```

-continued

```
            420                 425                 430

Glu Leu Arg Glu Asn Ala Arg Arg Trp Lys Ala Glu Ala Glu Ala Ala
        435                 440                 445

Val Ala Asp Gly Gly Ser Ser Asp Met Asn Phe Lys Glu Phe Val Asp
    450                 455                 460

Lys Leu Val Thr Lys His Val Thr Arg Glu Asp Asn Gly Glu His
465                 470                 475


<210> SEQ ID NO 12
<211> LENGTH: 1440
<212> TYPE: DNA
<213> ORGANISM: Arabidopsis thaliana

<400> SEQUENCE: 12

ctagtgttct ccgttgtctt ctctcgtcac atgtttcgta accaacttgt ccacaaactc     60

tttaaagttc atatcagatg atccaccgtc cgccacggcg gcctcggcct ccgccttcca    120

cctccgagcg ttttctctca gctccaccgc cttttcccca actgtggcct caagcagctt    180

ctctgctaca acctccctcg aaacaatcat ctcctcagcg gctccgcggc ctagtctcac    240

tcctgtcttg aaaacatcag ccaagtacac cgcatcagtc acttgatctc cccattgcgg    300

aaaacaaaca acggggactc cggcagttaa agcctccatt gtcgagttcc atccgcagtg    360

acttaagaaa caagcaatcg caggatgagc caagactctc tcttggggac accattccac    420

gattttaccc ttttcttcga gctctcgagg caaaacatgt ggttctacaa atgtcccttc    480

catgggaggc cgaaccaccc ataagaccga caagccagag ctcaaaacgc catgagcgat    540

ctcctccatc tgctcttgct tcaagttggc tatagtccca aaggagatgt aaacgactga    600

ggatggttct cttgagtcaa gccattccat gcagtcactc gctggctcgg atatatctcc    660

cttaacgtca gaactcaagg tttgagccat cttgaagagc ggaccgacag gactgatgat    720

ggcttgagga caaagttgtg acatgtggtc catgatgtct ttttctagtt cgcgaaaagt    780

gtcgatgaaa agatagaaag acttgtggtt ttcgaatctc tttaactggt ctaaaatgat    840

atctccaaaa gctgtatacg gagacgaagg gtgaagaaag cttgggatct cgtcatgctt    900

taacaatggc aagcaaggga tttcaacgct gatgtccggc tcggttttgg tcgggaactt    960

aactaaccgg tggtggtaat agtaataagc cgtgagacaa gcacaagact ggacccatag   1020

aacagccgaa gggatgtgaa gctcctcggc gacatcacat acccatggga caaaagcgtt   1080

gtttatgaga cacgtcaccg gctccttgtt atatctctta acgagattct tgatctcttg   1140

ttttccgaca gcttcaaggt gtggtcggaa ggcatcgaag tcgaatcttt tttcatcgtc   1200

gtcggcgaag ccgtcagaga agaactcaaa ccggatgaaa cctagaccga ccggtttgag   1260

cacaccgtct tgaatcttgt tggcttgacg catcttcttg ccccatggct tctctgtggt   1320

gacaaaggtg acgagtaagc ctttagaggc tatgagcttt ccgagacgaa gtagagggtt   1380

tacgtgacct tggccgggga aagatacgag catcacatga gtatgacgag acgggtccat   1440


<210> SEQ ID NO 13
<211> LENGTH: 1430
<212> TYPE: DNA
<213> ORGANISM: Arabidopsis thaliana

<400> SEQUENCE: 13

atggagatgg aatcgtcgtt acctcatgtg atgctcgtat cattcccagg gcaaggtcac     60

ataagccctc ttcttcgtct cggaaagatc attgcctcta aaggcttaat cgtcaccttt    120
```

-continued

```
gtaaccacag aggaaccatt gggcaagaag atgcgtcaag ccaacaatat tcaagacggt    180

gtgctcaaac cggtcgggct aggttttctc cggttcgagt tcttcgagga tggatttgtc    240

tacaaagaag actttgattt gttacaaaaa tcacttgaag tttccggaaa acgagagatc    300

aagaatcttg tcaagaaata tgagaagcaa ccagtgagat gtctcataaa taatgccttt    360

gttccatggg tttgtgacat agccgaggag cttcaaatcc catcagctgt tctttgggtc    420

cagtcttgtg cttgcctcgc cgcttattac tattaccacc accagttagt taagtttccg    480

accgaaaccg agccggaaat aaccgttgac gtccctttca agccattaac attgaagcat    540

gacgagatcc ctagctttct tcacccttcc tctccgctgt cctctatagg aggtaccatt    600

ttagagcaga tcaagcgact tcacaagcct ttctctgttc tcatcgaaac ttttcaagaa    660

cttgaaaaag ataccattga ccacatgtcc cagctctgcc ctcaagtcaa cttcaacccc    720

atcggtccgc tttttactat ggctaaaacc ataaggtctg acatcaaggg agacatctcc    780

aagccagata gtgactgcat agagtggctt gactcgagag aaccatcctc cgttgtttac    840

atctcttttg ggactttggc tttcttgaag caaaaccaga tcgacgagat tgctcacggc    900

attctcaact ccgggttgtc ctgcttatgg gttttgcggc ctcccttaga aggcttagcc    960

atagaaccgc atgtcttgcc tctagagctt gaagagaaag ggaagattgt ggaatggtgt   1020

caacaagaga aagttttggc tcatcctgcg gttgcttgct tcttaagtca ctgtggatgg   1080

aactcaacca tggaggcttt aacttcagga gttcccgtta tttgtttccc gcagtgggga   1140

gatcaggtga caaatgcggt gtacatgatt gatgttttca agacaggatt gagactcagc   1200

cgtggagctt ccgatgagag gattgttcca agggaggagg ttgctgagcg actgcttgag   1260

gccaccgttg gagagaaggc ggtggagctg agagaaaacg ctcggaggtg gaaggaggag   1320

gcggagtctg ccgtggctta cggtggaaca tcggaaagga attttcaaga gtttgttgac   1380

aagttggttg atgtcaagac aatgacaaac attaataatg tcgtgtaagt              1430
```

<210> SEQ ID NO 14
<211> LENGTH: 475
<212> TYPE: PRT
<213> ORGANISM: Arabidopsis thaliana

<400> SEQUENCE: 14

```
Met Glu Met Glu Ser Ser Leu Pro His Val Met Leu Val Ser Phe Pro
  1               5                  10                  15

Gly Gln Gly His Ile Ser Pro Leu Leu Arg Leu Gly Lys Ile Ile Ala
             20                  25                  30

Ser Lys Gly Leu Ile Val Thr Phe Val Thr Thr Glu Glu Pro Leu Gly
         35                  40                  45

Lys Lys Met Arg Gln Ala Asn Asn Ile Gln Asp Gly Val Leu Lys Pro
     50                  55                  60

Val Gly Leu Gly Phe Leu Arg Phe Glu Phe Phe Glu Asp Gly Phe Val
 65                  70                  75                  80

Tyr Lys Glu Asp Phe Asp Leu Leu Gln Lys Ser Leu Glu Val Ser Gly
                 85                  90                  95

Lys Arg Glu Ile Lys Asn Leu Val Lys Lys Tyr Glu Lys Gln Pro Val
            100                 105                 110

Arg Cys Leu Ile Asn Asn Ala Phe Val Pro Trp Val Cys Asp Ile Ala
        115                 120                 125

Glu Glu Leu Gln Ile Pro Ser Ala Val Leu Trp Val Gln Ser Cys Ala
    130                 135                 140
```

-continued

```
Cys Leu Ala Ala Tyr Tyr Tyr Tyr His His Gln Leu Val Lys Phe Pro
145                 150                 155                 160

Thr Glu Thr Glu Pro Glu Ile Thr Val Asp Val Pro Phe Lys Pro Leu
                165                 170                 175

Thr Leu Lys His Asp Glu Ile Pro Ser Phe Leu His Pro Ser Ser Pro
            180                 185                 190

Leu Ser Ser Ile Gly Gly Thr Ile Leu Glu Gln Ile Lys Arg Leu His
        195                 200                 205

Lys Pro Phe Ser Val Leu Ile Glu Thr Phe Gln Glu Leu Glu Lys Asp
    210                 215                 220

Thr Ile Asp His Met Ser Gln Leu Cys Pro Gln Val Asn Phe Asn Pro
225                 230                 235                 240

Ile Gly Pro Leu Phe Thr Met Ala Lys Thr Ile Arg Ser Asp Ile Lys
                245                 250                 255

Gly Asp Ile Ser Lys Pro Asp Ser Asp Cys Ile Glu Trp Leu Asp Ser
            260                 265                 270

Arg Glu Pro Ser Ser Val Val Tyr Ile Ser Phe Gly Thr Leu Ala Phe
        275                 280                 285

Leu Lys Gln Asn Gln Ile Asp Glu Ile Ala His Gly Ile Leu Asn Ser
    290                 295                 300

Gly Leu Ser Cys Leu Trp Val Leu Arg Pro Pro Leu Glu Gly Leu Ala
305                 310                 315                 320

Ile Glu Pro His Val Leu Pro Leu Glu Leu Glu Glu Lys Gly Lys Ile
                325                 330                 335

Val Glu Trp Cys Gln Gln Glu Lys Val Leu Ala His Pro Ala Val Ala
            340                 345                 350

Cys Phe Leu Ser His Cys Gly Trp Asn Ser Thr Met Glu Ala Leu Thr
        355                 360                 365

Ser Gly Val Pro Val Ile Cys Phe Pro Gln Trp Gly Asp Gln Val Thr
    370                 375                 380

Asn Ala Val Tyr Met Ile Asp Val Phe Lys Thr Gly Leu Arg Leu Ser
385                 390                 395                 400

Arg Gly Ala Ser Asp Glu Arg Ile Val Pro Arg Glu Glu Val Ala Glu
                405                 410                 415

Arg Leu Leu Glu Ala Thr Val Gly Glu Lys Ala Val Glu Leu Arg Glu
            420                 425                 430

Asn Ala Arg Arg Trp Lys Glu Glu Ala Glu Ser Ala Val Ala Tyr Gly
        435                 440                 445

Gly Thr Ser Glu Arg Asn Phe Gln Glu Phe Val Asp Lys Leu Val Asp
    450                 455                 460

Val Lys Thr Met Thr Asn Ile Asn Asn Val Val
465                 470                 475
```

<210> SEQ ID NO 15
<211> LENGTH: 1430
<212> TYPE: DNA
<213> ORGANISM: Arabidopsis thaliana

<400> SEQUENCE: 15

```
acttacacga cattattaat gtttgtcatt gtcttgacat caaccaactt gtcaacaaac      60

tcttgaaaat tcctttccga tgttccaccg taagccacgg cagactccgc ctcctccttc     120

cacctccgag cgttttctct cagctccacc gccttctctc caacggtggc ctcaagcagt     180

cgctcagcaa cctcctccct tggaacaatc ctctcatcgg aagctccacg gctgagtctc     240
```

-continued

```
aatcctgtct tgaaaacatc aatcatgtac accgcatttg tcacctgatc tccccactgc    300

gggaaacaaa taacgggaac tcctgaagtt aaagcctcca tggttgagtt ccatccacag    360

tgacttaaga agcaagcaac cgcaggatga gccaaaactt tctcttgttg acaccattcc    420

acaatcttcc ctttctcttc aagctctaga ggcaagacat gcggttctat ggctaagcct    480

tctaagggag gccgcaaaac ccataagcag gacaacccgg agttgagaat gccgtgagca    540

atctcgtcga tctggttttg cttcaagaaa gccaaagtcc caaaagagat gtaaacaacg    600

gaggatggtt ctctcgagtc aagccactct atgcagtcac tatctggctt ggagatgtct    660

cccttgatgt cagaccttat ggttttagcc atagtaaaaa gcggaccgat ggggttgaag    720

ttgacttgag ggcagagctg ggacatgtgg tcaatggtat ctttttcaag ttcttgaaaa    780

gtttcgatga gaacagagaa aggcttgtga agtcgcttga tctgctctaa aatggtacct    840

cctatagagg acagcggaga ggaagggtga agaaagctag ggatctcgtc atgcttcaat    900

gttaatggct tgaaagggac gtcaacggtt atttccggct cggtttcggt cggaaactta    960

actaactggt ggtggtaata gtaataagcg gcgaggcaag cacaagactg gacccaaaga   1020

acagctgatg ggatttgaag ctcctcggct atgtcacaaa cccatggaac aaaggcatta   1080

tttatgagac atctcactgg ttgcttctca tatttcttga caagattctt gatctctcgt   1140

tttccggaaa cttcaagtga tttttgtaac aaatcaaagt cttctttgta gacaaatcca   1200

tcctcgaaga actcgaaccg gagaaaacct agcccgaccg gtttgagcac accgtcttga   1260

atattgttgg cttgacgcat cttcttgccc aatggttcct ctgtggttac aaaggtgacg   1320

attaagcctt tagaggcaat gatctttccg agacgaagaa gagggcttat gtgaccttgc   1380

cctgggaatg atacgagcat cacatgaggt aacgacgatt ccatctccat              1430
```

<210> SEQ ID NO 16
<211> LENGTH: 1437
<212> TYPE: DNA
<213> ORGANISM: Arabidopsis thaliana

<400> SEQUENCE: 16

```
atgggcagta gtgagggtca agaaacacat gtcctaatgg taacactacc attccaaggt     60

cacatcaatc caatgctcaa actcgcaaaa catctctcgt tatcatcaaa gaacctacac    120

atcaatctcg ccactattga gtcagcccgt gatctcctct ccaccgtaga aaaacctcgt    180

tatccggtgg acctcgtgtt cttctccgat ggtctaccta aagaagatcc aaaggcccct    240

gaaactcttt tgaagtcatt gaataaagtc ggagccatga acttgtctaa aatcatcgaa    300

gaaaagagat actcttgtat catctcttcg ccttttactc catgggttcc agctgttgca    360

gcctctcata acatctcttg tgcaatactt tggatccaag cttgtggagc ttactcggtt    420

tattaccgtt actacatgaa gacaaactct ttccctgatc ttgaagatct gaatcaaacg    480

gtggagttac cagctttacc attgttggaa gttcgagatc ttccatcgtt tatgttacct    540

tctggtggtg ctcacttcta taatctaatg gcggaatttg cagattgttt gaggtatgtg    600

aaatgggttt tggttaattc attctatgaa ctcgaatcag agataatcga atcgatggct    660

gatttaaaac ctgtaattcc aattggtcct ctggtttctc catttctgtt gggcgatggt    720

gaggaggaaa ccctagacgg taaaaaccta gatttttgta aatctgatga ttgttgtatg    780

gagtggcttg acaagcaagc taggtcttct gttgtgtaca tatctttcgg aagtatgctc    840

gaaacattgg agaatcaggt cgagaccata gcgaaggcgc tgaagaacag aggacttcca    900

tttctttggg tgataaggcc aaaggagaaa gcccaaaacg ttgctgtttt gcaggagatg    960
```

-continued

```
gtgaaagaag gacaaggggt tgttctcgag tggagtccac aagagaagat tttgagccac   1020

gaggcaatct cttgttttgt cacgcattgc ggctggaact cgactatgga gacggtggtg   1080

gctggtgttc ctgtggtagc gtaccctagc tggacggatc agcccattga cgcgcggttg   1140

cttgttgatg tgtttggaat cggagtaagg atgaggaatg acagtgtcga tggcgagctt   1200

aaggtcgaag aagtagaaag atgcattgag gccgtgacgg agggacccgc tgccgtggat   1260

ataagaagga gagcggcgga gctaaagcgc gtggcgagat tggcgttggc acctggtgga   1320

tcttcgacac ggaatttaga cttgttcatt agtgatatca caatcgccta actctttact   1380

tcaactagta caaaatgtat gaatacaagg tttgatataa ccactatcaa ttgttag      1437
```

<210> SEQ ID NO 17
<211> LENGTH: 456
<212> TYPE: PRT
<213> ORGANISM: Arabidopsis thaliana

<400> SEQUENCE: 17

```
Met Gly Ser Ser Glu Gly Gln Glu Thr His Val Leu Met Val Thr Leu
  1               5                  10                  15

Pro Phe Gln Gly His Ile Asn Pro Met Leu Lys Leu Ala Lys His Leu
             20                  25                  30

Ser Leu Ser Ser Lys Asn Leu His Ile Asn Leu Ala Thr Ile Glu Ser
         35                  40                  45

Ala Arg Asp Leu Leu Ser Thr Val Glu Lys Pro Arg Tyr Pro Val Asp
     50                  55                  60

Leu Val Phe Phe Ser Asp Gly Leu Pro Lys Glu Asp Pro Lys Ala Pro
 65                  70                  75                  80

Glu Thr Leu Leu Lys Ser Leu Asn Lys Val Gly Ala Met Asn Leu Ser
                 85                  90                  95

Lys Ile Ile Glu Glu Lys Arg Tyr Ser Cys Ile Ile Ser Ser Pro Phe
            100                 105                 110

Thr Pro Trp Val Pro Ala Val Ala Ala Ser His Asn Ile Ser Cys Ala
        115                 120                 125

Ile Leu Trp Ile Gln Ala Cys Gly Ala Tyr Ser Val Tyr Tyr Arg Tyr
    130                 135                 140

Tyr Met Lys Thr Asn Ser Phe Pro Asp Leu Glu Asp Leu Asn Gln Thr
145                 150                 155                 160

Val Glu Leu Pro Ala Leu Pro Leu Leu Glu Val Arg Asp Leu Pro Ser
                165                 170                 175

Phe Met Leu Pro Ser Gly Gly Ala His Phe Tyr Asn Leu Met Ala Glu
            180                 185                 190

Phe Ala Asp Cys Leu Arg Tyr Val Lys Trp Val Leu Val Asn Ser Phe
        195                 200                 205

Tyr Glu Leu Glu Ser Glu Ile Ile Glu Ser Met Ala Asp Leu Lys Pro
    210                 215                 220

Val Ile Pro Ile Gly Pro Leu Val Ser Pro Phe Leu Leu Gly Asp Gly
225                 230                 235                 240

Glu Glu Glu Thr Leu Asp Gly Lys Asn Leu Asp Phe Cys Lys Ser Asp
                245                 250                 255

Asp Cys Cys Met Glu Trp Leu Asp Lys Gln Ala Arg Ser Ser Val Val
            260                 265                 270

Tyr Ile Ser Phe Gly Ser Met Leu Glu Thr Leu Glu Asn Gln Val Glu
        275                 280                 285
```

-continued

```
Thr Ile Ala Lys Ala Leu Lys Asn Arg Gly Leu Pro Phe Leu Trp Val
    290                 295                 300

Ile Arg Pro Lys Glu Lys Ala Gln Asn Val Ala Val Leu Gln Glu Met
305                 310                 315                 320

Val Lys Glu Gly Gln Gly Val Val Leu Glu Trp Ser Pro Gln Glu Lys
                325                 330                 335

Ile Leu Ser His Glu Ala Ile Ser Cys Phe Val Thr His Cys Gly Trp
            340                 345                 350

Asn Ser Thr Met Glu Thr Val Val Ala Gly Val Pro Val Val Ala Tyr
        355                 360                 365

Pro Ser Trp Thr Asp Gln Pro Ile Asp Ala Arg Leu Leu Val Asp Val
    370                 375                 380

Phe Gly Ile Gly Val Arg Met Arg Asn Asp Ser Val Asp Gly Glu Leu
385                 390                 395                 400

Lys Val Glu Glu Val Glu Arg Cys Ile Glu Ala Val Thr Glu Gly Pro
                405                 410                 415

Ala Ala Val Asp Ile Arg Arg Arg Ala Ala Glu Leu Lys Arg Val Ala
            420                 425                 430

Arg Leu Ala Leu Ala Pro Gly Gly Ser Ser Thr Arg Asn Leu Asp Leu
        435                 440                 445

Phe Ile Ser Asp Ile Thr Ile Ala
    450                 455


<210> SEQ ID NO 18
<211> LENGTH: 1437
<212> TYPE: DNA
<213> ORGANISM: Arabidopsis thaliana

<400> SEQUENCE: 18

ctaacaattg atagtggtta tatcaaacct tgtattcata cattttgtac tagttgaagt     60

aaagagttag gcgattgtga tatcactaat gaacaagtct aaattccgtg tcgaagatcc    120

accaggtgcc aacgccaatc tcgccacgcg ctttagctcc gccgctctcc ttcttatatc    180

cacggcagcg ggtccctccg tcacggcctc aatgcatctt tctacttctt cgaccttaag    240

ctcgccatcg acactgtcat tcctcatcct tactccgatt ccaaacacat caacaagcaa    300

ccgcgcgtca atgggctgat ccgtccagct agggtacgct accacaggaa caccagccac    360

caccgtctcc atagtcgagt tccagccgca atgcgtgaca aaacaagaga ttgcctcgtg    420

gctcaaaatc ttctcttgtg gactccactc gagaacaacc ccttgtcctt ctttcaccat    480

ctcctgcaaa acagcaacgt tttgggcttt ctcctttggc cttatcaccc aaagaaatgg    540

aagtcctctg ttcttcagcg ccttcgctat ggtctcgacc tgattctcca atgtttcgag    600

catacttccg aaagatatgt acacaacaga agacctagct tgcttgtcaa gccactccat    660

acaacaatca tcagatttac aaaaatctag gtttttaccg tctagggttt cctcctcacc    720

atcgcccaac agaaatggag aaaccagagg accaattgga attacaggtt ttaaatcagc    780

catcgattcg attatctctg attcgagttc atagaatgaa ttaaccaaaa cccatttcac    840

atacctcaaa caatctgcaa attccgccat tagattatag aagtgagcac caccagaagg    900

taacataaac gatggaagat ctcgaacttc caacaatggt aaagctggta actccaccgt    960

ttgattcaga tcttcaagat cagggaaaga gtttgtcttc atgtagtaac ggtaataaac   1020

cgagtaagct ccacaagctt ggatccaaag tattgcacaa gagatgttat gagaggctgc   1080

aacagctgga acccatggag taaaaggcga agagatgata caagagtatc tcttttcttc   1140
```

-continued

```
gatgatttta gacaagttca tggctccgac tttattcaat gacttcaaaa gagtttcagg   1200

ggcctttgga tcttctttag gtagaccatc ggagaagaac acgaggtcca ccggataacg   1260

aggtttttct acggtggaga ggagatcacg ggctgactca atagtggcga gattgatgtg   1320

taggttcttt gatgataacg agagatgttt tgcgagtttg agcattggat tgatgtgacc   1380

ttggaatggt agtgttacca ttaggacatg tgtttcttga ccctcactac tgcccat      1437
```

<210> SEQ ID NO 19
<211> LENGTH: 1446
<212> TYPE: DNA
<213> ORGANISM: Arabidopsis thaliana

<400> SEQUENCE: 19

```
atgcatatca caaaaccaca cgccgccatg ttttccagtc ccggaatggg ccatgtcatc     60

ccggtgatcg agcttggaaa gcgtctctcc gctaacaacg gcttccacgt caccgtcttc    120

gtcctcgaaa ccgacgcagc ctccgctcaa tccaagttcc taaactcaac cggcgtcgac    180

atcgtcaaac ttccatcgcc ggacatttat ggtttagtgg accccgacga ccatgtagtg    240

accaagatcg gagtcattat gcgtgcagca gttccagccc tccgatccaa gatcgctgcc    300

atgcatcaaa agccaacggc tctgatcgtt gacttgtttg gcacagatgc gttatgtctc    360

gcaaaggaat ttaacatgtt gagttatgtg tttatcccta ccaacgcacg ttttctcgga    420

gtttcgattt attatccaaa tttggacaaa gatatcaagg aagagcacac agtgcaaaga    480

aacccactcg ctataccggg gtgtgaaccg gttaggttcg aagatactct ggatgcatat    540

ctggttcccg acgaaccggt gtaccgggat tttgttcgtc atggtctggc ttacccaaaa    600

gccgatggaa ttttggtaaa tacatgggaa gagatggagc ccaaatcatt gaagtccctt    660

ctaaacccaa agctcttggg ccgggttgct cgtgtaccgg tctatccaat cggtccctta    720

tgcagaccga tacaatcatc cgaaaccgat cacccggttt tggattggtt aaacgaacaa    780

ccgaacgagt cggttctcta tatctccttc gggagtggtg gttgtctatc ggcgaaacag    840

ttaactgaat tggcgtgggg actcgagcag agccagcaac ggttcgtatg ggtggttcga    900

ccaccggtcg acggttcgtg ttgtagcgag tatgtctcgg ctaacggtgg tggaaccgaa    960

gacaacacgc cagagtatct accggaaggg ttcgtgagtc gtactagtga tagaggtttc   1020

gtggtcccct catgggcccc acaagctgaa atcctgtccc atcgggccgt tggtgggttt   1080

ttgacccatt gcggttggag ctcgacgttg gaaagcgtcg ttggcggcgt tccgatgatc   1140

gcatggccac tttttgccga gcagaatatg aatgcggcgt tgctcagcga cgaactggga   1200

atcgcagtca gattggatga tccaaaggag gatatttcta ggtggaagat tgaggcgttg   1260

gtgaggaagg ttatgactga gaaggaaggt gaagcgatga gaaggaaagt gaagaagttg   1320

agagactcgg cggagatgtc actgagcatt gacggtggtg gtttggcgca cgagtcgctt   1380

tgcagagtca ccaaggagtg tcaacggttt ttggaacgtg tcgtggactt gtcacgtggt   1440

gcttag                                                              1446
```

<210> SEQ ID NO 20
<211> LENGTH: 481
<212> TYPE: PRT
<213> ORGANISM: Arabidopsis thaliana

<400> SEQUENCE: 20

```
Met His Ile Thr Lys Pro His Ala Ala Met Phe Ser Ser Pro Gly Met
  1               5                  10                  15
```

-continued

```
Gly His Val Ile Pro Val Ile Glu Leu Gly Lys Arg Leu Ser Ala Asn
                20                  25                  30

Asn Gly Phe His Val Thr Val Phe Val Leu Glu Thr Asp Ala Ala Ser
        35                  40                  45

Ala Gln Ser Lys Phe Leu Asn Ser Thr Gly Val Asp Ile Val Lys Leu
    50                  55                  60

Pro Ser Pro Asp Ile Tyr Gly Leu Val Asp Pro Asp Asp His Val Val
 65                 70                  75                  80

Thr Lys Ile Gly Val Ile Met Arg Ala Ala Val Pro Ala Leu Arg Ser
                85                  90                  95

Lys Ile Ala Ala Met His Gln Lys Pro Thr Ala Leu Ile Val Asp Leu
            100                 105                 110

Phe Gly Thr Asp Ala Leu Cys Leu Ala Lys Glu Phe Asn Met Leu Ser
        115                 120                 125

Tyr Val Phe Ile Pro Thr Asn Ala Arg Phe Leu Gly Val Ser Ile Tyr
    130                 135                 140

Tyr Pro Asn Leu Asp Lys Asp Ile Lys Glu Glu His Thr Val Gln Arg
145                 150                 155                 160

Asn Pro Leu Ala Ile Pro Gly Cys Glu Pro Val Arg Phe Glu Asp Thr
                165                 170                 175

Leu Asp Ala Tyr Leu Val Pro Asp Glu Pro Val Tyr Arg Asp Phe Val
            180                 185                 190

Arg His Gly Leu Ala Tyr Pro Lys Ala Asp Gly Ile Leu Val Asn Thr
        195                 200                 205

Trp Glu Glu Met Glu Pro Lys Ser Leu Lys Ser Leu Leu Asn Pro Lys
    210                 215                 220

Leu Leu Gly Arg Val Ala Arg Val Pro Val Tyr Pro Ile Gly Pro Leu
225                 230                 235                 240

Cys Arg Pro Ile Gln Ser Ser Glu Thr Asp His Pro Val Leu Asp Trp
                245                 250                 255

Leu Asn Glu Gln Pro Asn Glu Ser Val Leu Tyr Ile Ser Phe Gly Ser
            260                 265                 270

Gly Gly Cys Leu Ser Ala Lys Gln Leu Thr Glu Leu Ala Trp Gly Leu
        275                 280                 285

Glu Gln Ser Gln Gln Arg Phe Val Trp Val Val Arg Pro Pro Val Asp
    290                 295                 300

Gly Ser Cys Cys Ser Glu Tyr Val Ser Ala Asn Gly Gly Gly Thr Glu
305                 310                 315                 320

Asp Asn Thr Pro Glu Tyr Leu Pro Glu Gly Phe Val Ser Arg Thr Ser
                325                 330                 335

Asp Arg Gly Phe Val Val Pro Ser Trp Ala Pro Gln Ala Glu Ile Leu
            340                 345                 350

Ser His Arg Ala Val Gly Gly Phe Leu Thr His Cys Gly Trp Ser Ser
        355                 360                 365

Thr Leu Glu Ser Val Val Gly Gly Val Pro Met Ile Ala Trp Pro Leu
    370                 375                 380

Phe Ala Glu Gln Asn Met Asn Ala Ala Leu Leu Ser Asp Glu Leu Gly
385                 390                 395                 400

Ile Ala Val Arg Leu Asp Asp Pro Lys Glu Asp Ile Ser Arg Trp Lys
                405                 410                 415

Ile Glu Ala Leu Val Arg Lys Val Met Thr Glu Lys Glu Gly Glu Ala
            420                 425                 430

Met Arg Arg Lys Val Lys Lys Leu Arg Asp Ser Ala Glu Met Ser Leu
```

-continued

```
        435                 440                 445

Ser Ile Asp Gly Gly Gly Leu Ala His Glu Ser Leu Cys Arg Val Thr
    450                 455                 460

Lys Glu Cys Gln Arg Phe Leu Glu Arg Val Val Asp Leu Ser Arg Gly
465                 470                 475                 480

Ala


<210> SEQ ID NO 21
<211> LENGTH: 1446
<212> TYPE: DNA
<213> ORGANISM: Arabidopsis thaliana

<400> SEQUENCE: 21

ctaagcacca cgtgacaagt ccacgacacg ttccaaaaac cgttgacact ccttggtgac      60

tctgcaaagc gactcgtgcg ccaaaccacc accgtcaatg ctcagtgaca tctccgccga     120

gtctctcaac ttcttcactt tccttctcat cgcttcacct tccttctcag tcataacctt     180

cctcaccaac gcctcaatct tccacctaga aatatcctcc tttggatcat ccaatctgac     240

tgcgattccc agttcgtcgc tgagcaacgc cgcattcata ttctgctcgg caaaaagtgg     300

ccatgcgatc atcggaacgc cgccaacgac gctttccaac gtcgagctcc aaccgcaatg     360

ggtcaaaaac ccaccaacgg cccgatggga caggatttca gcttgtgggg cccatgaggg     420

gaccacgaaa cctctatcac tagtacgact cacgaaccct tccggtagat actctggcgt     480

gttgtcttcg gttccaccac cgttagccga gacatactcg ctacaacacg aaccgtcgac     540

cggtggtcga accacccata cgaaccgttg ctggctctgc tcgagtcccc acgccaattc     600

agttaactgt ttcgccgata gacaaccacc actcccgaag gagatataga gaaccgactc     660

gttcggttgt tcgtttaacc aatccaaaac cgggtgatcg gtttcggatg attgtatcgg     720

tctgcataag ggaccgattg gatagaccgg tacacgagca acccggccca agagctttgg     780

gtttagaagg gacttcaatg atttgggctc catctcttcc catgtattta ccaaaattcc     840

atcggctttt gggtaagcca gaccatgacg aacaaaatcc cggtacaccg gttcgtcggg     900

aaccagatat gcatccagag tatcttcgaa cctaaccggt tcacaccccg gtatagcgag     960

tgggtttctt tgcactgtgt gctcttcctt gatatctttg tccaaatttg gataataaat    1020

cgaaactccg agaaaacgtg cgttggtagg gataaacaca taactcaaca tgttaaattc    1080

ctttgcgaga cataacgcat ctgtgccaaa caagtcaacg atcagagccg ttggcttttg    1140

atgcatggca gcgatcttgg atcggagggc tggaactgct gcacgcataa tgactccgat    1200

cttggtcact acatggtcgt cggggtccac taaaccataa atgtccggcg atggaagttt    1260

gacgatgtcg acgccggttg agtttaggaa cttggattga gcggaggctg cgtcggtttc    1320

gaggacgaag acggtgacgt ggaagccgtt gttagcggag agacgctttc caagctcgat    1380

caccgggatg acatggccca ttccgggact ggaaaacatg gcggcgtgtg gttttgtgat    1440

atgcat                                                               1446


<210> SEQ ID NO 22
<211> LENGTH: 1446
<212> TYPE: DNA
<213> ORGANISM: Arabidopsis thaliana

<400> SEQUENCE: 22

atgagtagtg atcctcatcg taagctccat gttgtgttct tccctttcat ggcttatggt      60

cacatgatac caactctaga catggctaag cttttctcta gcagaggagc caaatctaca     120
```

-continued

```
atcctcacca cacctctcaa ctccaagatc ttccaaaaac ccatcgaaag attcaagaac    180

ctgaatccga gtttcgaaat cgacatccag atcttcgatt tcccttgcgt ggatctcggg    240

ttaccagaag gatgcgaaaa cgtcgatttc ttcacctcaa acaacaatga tgatagacag    300

tatctgacct tgaagttctt taagtcgaca aggtttttca aagatcagct tgagaagctc    360

ctcgagacaa cgagaccaga ctgtcttatc gccgacatgt tcttcccctg ggctacggaa    420

gctgctgaga agttcaatgt gccaagactt gtgttccacg gtactggcta cttttcttta    480

tgctctgaat attgcatcag agtgcataac ccacaaaaca tagtagcttc aaggtacgag    540

ccatttgtga ttcctgatct cccggggaac atagtgataa ctcaagaaca gatagcagac    600

cgtgacgaag aaagcgagat ggggaagttt atgattgagg tcaaagaatc tgatgtgaag    660

agctcaggtg ttattgtaaa cagcttctac gagcttgaac ctgattacgc cgacttttac    720

aagagtgttg tactgaagag agcgtggcat atcggtccgc tttcggttta caacagagga    780

tttgaggaga aggctgagag aggaaagaaa gcaagcatta atgaggttga atgcctcaaa    840

tggcttgact ccaagaaacc agattcagtc atttacattt cttttgggag cgtggcttgc    900

ttcaagaacg agcagctatt cgagatcgct gcaggattag aaacttctgg agcaaatttc    960

atctgggttg ttaggaaaaa cataggtatt gaaaaagaag aatggttacc agaagggttc   1020

gaagagaggg tgaaaggaaa agggatgatt ataagaggat gggcaccaca ggtgctcata   1080

cttgatcatc aagcaacttg tgggtttgtg acccattgcg gctggaactc gcttctggaa   1140

ggagtggctg cagggctacc aatggtgaca tggcctgtag cagcggagca attctacaat   1200

gagaaattgg ttacgcaagt gctcagaaca ggagtgagcg tgggagcgaa aaagaatgta   1260

agaactacgg gagatttcat tagcagagag aaagtggtta aagcggtgag ggaggtgttg   1320

gttggggaag aggcggatga gaggcgggag agggcaaaga agttggcaga gatggctaaa   1380

gctgccgtgg aaggagggtc ttctttcaac gatctaaaca gcttcataga agagtttacc   1440

tcgtaa                                                              1446
```

<210> SEQ ID NO 23
<211> LENGTH: 481
<212> TYPE: PRT
<213> ORGANISM: Arabidopsis thaliana

<400> SEQUENCE: 23

```
Met Ser Ser Asp Pro His Arg Lys Leu His Val Val Phe Phe Pro Phe
  1               5                  10                  15

Met Ala Tyr Gly His Met Ile Pro Thr Leu Asp Met Ala Lys Leu Phe
             20                  25                  30

Ser Ser Arg Gly Ala Lys Ser Thr Ile Leu Thr Thr Pro Leu Asn Ser
         35                  40                  45

Lys Ile Phe Gln Lys Pro Ile Glu Arg Phe Lys Asn Leu Asn Pro Ser
     50                  55                  60

Phe Glu Ile Asp Ile Gln Ile Phe Asp Phe Pro Cys Val Asp Leu Gly
 65                  70                  75                  80

Leu Pro Glu Gly Cys Glu Asn Val Asp Phe Phe Thr Ser Asn Asn Asn
                 85                  90                  95

Asp Asp Arg Gln Tyr Leu Thr Leu Lys Phe Phe Lys Ser Thr Arg Phe
            100                 105                 110

Phe Lys Asp Gln Leu Glu Lys Leu Leu Glu Thr Thr Arg Pro Asp Cys
        115                 120                 125
```

-continued

```
Leu Ile Ala Asp Met Phe Phe Pro Trp Ala Thr Glu Ala Ala Glu Lys
    130                 135                 140

Phe Asn Val Pro Arg Leu Val Phe His Gly Thr Gly Tyr Phe Ser Leu
145                 150                 155                 160

Cys Ser Glu Tyr Cys Ile Arg Val His Asn Pro Gln Asn Ile Val Ala
                165                 170                 175

Ser Arg Tyr Glu Pro Phe Val Ile Pro Asp Leu Pro Gly Asn Ile Val
            180                 185                 190

Ile Thr Gln Glu Gln Ile Ala Asp Arg Asp Glu Glu Ser Glu Met Gly
        195                 200                 205

Lys Phe Met Ile Glu Val Lys Glu Ser Asp Val Lys Ser Ser Gly Val
    210                 215                 220

Ile Val Asn Ser Phe Tyr Glu Leu Glu Pro Asp Tyr Ala Asp Phe Tyr
225                 230                 235                 240

Lys Ser Val Val Leu Lys Arg Ala Trp His Ile Gly Pro Leu Ser Val
                245                 250                 255

Tyr Asn Arg Gly Phe Glu Glu Lys Ala Glu Arg Gly Lys Lys Ala Ser
            260                 265                 270

Ile Asn Glu Val Glu Cys Leu Lys Trp Leu Asp Ser Lys Lys Pro Asp
        275                 280                 285

Ser Val Ile Tyr Ile Ser Phe Gly Ser Val Ala Cys Phe Lys Asn Glu
    290                 295                 300

Gln Leu Phe Glu Ile Ala Ala Gly Leu Glu Thr Ser Gly Ala Asn Phe
305                 310                 315                 320

Ile Trp Val Val Arg Lys Asn Ile Gly Ile Glu Lys Glu Glu Trp Leu
                325                 330                 335

Pro Glu Gly Phe Glu Glu Arg Val Lys Gly Lys Gly Met Ile Ile Arg
            340                 345                 350

Gly Trp Ala Pro Gln Val Leu Ile Leu Asp His Gln Ala Thr Cys Gly
        355                 360                 365

Phe Val Thr His Cys Gly Trp Asn Ser Leu Leu Glu Gly Val Ala Ala
    370                 375                 380

Gly Leu Pro Met Val Thr Trp Pro Val Ala Ala Glu Gln Phe Tyr Asn
385                 390                 395                 400

Glu Lys Leu Val Thr Gln Val Leu Arg Thr Gly Val Ser Val Gly Ala
                405                 410                 415

Lys Lys Asn Val Arg Thr Thr Gly Asp Phe Ile Ser Arg Glu Lys Val
            420                 425                 430

Val Lys Ala Val Arg Glu Val Leu Val Gly Glu Glu Ala Asp Glu Arg
        435                 440                 445

Arg Glu Arg Ala Lys Lys Leu Ala Glu Met Ala Lys Ala Ala Val Glu
    450                 455                 460

Gly Gly Ser Ser Phe Asn Asp Leu Asn Ser Phe Ile Glu Glu Phe Thr
465                 470                 475                 480

Ser


<210> SEQ ID NO 24
<211> LENGTH: 1446
<212> TYPE: DNA
<213> ORGANISM: Arabidopsis thaliana

<400> SEQUENCE: 24

ttacgaggta aactcttcta tgaagctgtt tagatcgttg aaagaagacc ctccttccac      60

ggcagcttta gccatctctg ccaacttctt tgccctctcc cgcctctcat ccgcctcttc     120
```

-continued cccaaccaac acctccctca ccgctttaac cactttctct ctgctaatga aatctcccgt 180
agttcttaca ttctttttcg ctcccacgct cactcctgtt ctgagcactt gcgtaaccaa 240
tttctcattg tagaattgct ccgctgctac aggccatgtc accattggta gccctgcagc 300
cactccttcc agaagcgagt tccagccgca atgggtcaca aacccacaag ttgcttgatg 360
atcaagtatg agcacctgtg gtgcccatcc tcttataatc atccctttc ctttcaccct 420 ctcttcgaac ccttctggta accattcttc tttttcaata cctatgtttt tcctaacaac 480
ccagatgaaa tttgctccag aagtttctaa tcctgcagcg atctcgaata gctgctcgtt 540
cttgaagcaa gccacgctcc caaaagaaat gtaaatgact gaatctggtt tcttggagtc 600
aagccatttg aggcattcaa cctcattaat gcttgctttc tttcctctct cagccttctc 660
ctcaaatcct ctgttgtaaa ccgaaagcgg accgatatgc cacgctctct tcagtacaac 720
actcttgtaa aagtcggcgt aatcaggttc aagctcgtag aagctgttta caataacacc 780
tgagctcttc acatcagatt ctttgacctc aatcataaac ttccccatct cgctttcttc 840
gtcacggtct gctatctgtt cttgagttat cactatgttc cccgggagat caggaatcac 900
aaatggctcg taccttgaag ctactatgtt ttgtgggtta tgcactctga tgcaatattc 960
agagcataaa gaaaagtagc cagtaccgtg gaacacaagt cttggcacat tgaacttctc 1020
agcagcttcc gtagcccagg ggaagaacat gtcggcgata agacagtctg gtctcgttgt 1080
ctcgaggagc ttctcaagct gatctttgaa aaaccttgtc gacttaaaga acttcaaggt 1140
cagatactgt ctatcatcat tgttgtttga ggtgaagaaa tcgacgtttt cgcatccttc 1200
tggtaacccg agatccacgc aagggaaatc gaagatctgg atgtcgattt cgaaactcgg 1260
attcaggttc ttgaatcttt cgatgggttt ttggaagatc ttggagttga gaggtgtggt 1320
gaggattgta gatttggctc ctctgctaga gaaaagctta gccatgtcta gagttggtat 1380
catgtgacca taagccatga aagggaagaa cacaacatgg agcttacgat gaggatcact 1440
actcat 1446

<210> SEQ ID NO 25
<211> LENGTH: 1446
<212> TYPE: DNA
<213> ORGANISM: Arabidopsis thaliana

<400> SEQUENCE: 25
atgcatatca caaaaccaca cgccgccatg ttttccagtc ccggaatggg ccatgtcctc 60
ccggtgatcg agctagctaa gcgtctctcc gctaaccacg gcttccacgt caccgtcttc 120
gtccttgaaa ctgacgcagc ctccgttcag tccaagctcc ttaactcaac cggtgttgac 180
atcgtcaacc ttccatcgcc cgacatttct ggcttggtag accccaacgc ccatgtggtg 240
accaagatcg gagtcattat gcgtgaagct gttccaaccc tccgatccaa gatcgttgcc 300
atgcatcaaa acccaacggc tctgatcatt gacttgtttg gcacagatgc gttatgtctt 360
gcagcggagt taaacatgtt gacttatgtc tttatcgctt ccaacgcgcg ttatctcgga 420
gtttcgatat attatccaac tttggacgaa gttatcaaag aagagcacac agtgcaacga 480
aaaccgctca ctataccggg gtgtgaaccg gttagatttg aagatattat ggatgcatat 540
ctggttccgg acgaaccggt gtaccacgat ttggttcgtc actgtctggc ctacccaaaa 600
gcggatggaa tcttggtgaa tacatgggaa gagatggagc ccaaatcatt aaagtccctt 660
caagacccga aacttttggg ccgggtcgct cgtgtaccgg tttatccggt tggtccgtta 720

-continued

```
tgcagaccga tacaatcatc cacgaccgat cacccggttt ttgattggtt aaacaaacaa    780

ccaaacgagt cggttctcta catttccttc gggagtggtg gttctctaac ggctcaacag    840

ttaaccgaat tggcgtgggg gctcgaggag agccagcaac ggtttatatg ggtggttcga    900

ccgcccgttg acggctcgtc ttgcagtgat tatttctcgg ctaaaggcgg tgtaaccaaa    960

gacaacacgc cagagtatct accagaaggg ttcgtgactc gtacttgcga tagaggtttc   1020

atgatcccat catgggcacc gcaagctgaa atcctagccc atcaggccgt tggtgggttt   1080

ttaacacatt gtggttggag ctcgacgttg gaaagcgtcc tttgcggcgt tccaatgata   1140

gcgtggccgc ttttcgccga gcagaatatg aacgcggcgt tgcttagcga tgaactggga   1200

atctctgtta gagtggatga tccaaaggag gcgatttcta ggtcgaagat tgaggcgatg   1260

gtgaggaagg ttatggctga ggacgaaggt gaagagatga gaaggaaagt gaagaagttg   1320

agagacacgg cggagatgtc acttagtatt cacggtggtg gttcggcgca tgagtcgctt   1380

tgcagagtca cgaaggagtg tcaacggttt ttggaatgtg tcggggactt gggacgtggt   1440

gcttag                                                              1446
```

<210> SEQ ID NO 26
<211> LENGTH: 381
<212> TYPE: PRT
<213> ORGANISM: Arabidopsis thaliana

<400> SEQUENCE: 26

```
Met His Gln Asn Pro Thr Ala Leu Ile Ile Asp Leu Phe Gly Thr Asp
  1               5                  10                  15

Ala Leu Cys Leu Ala Ala Glu Leu Asn Met Leu Thr Tyr Val Phe Ile
             20                  25                  30

Ala Ser Asn Ala Arg Tyr Leu Gly Val Ser Ile Tyr Tyr Pro Thr Leu
         35                  40                  45

Asp Glu Val Ile Lys Glu Glu His Thr Val Gln Arg Lys Pro Leu Thr
     50                  55                  60

Ile Pro Gly Cys Glu Pro Val Arg Phe Glu Asp Ile Met Asp Ala Tyr
 65                  70                  75                  80

Leu Val Pro Asp Glu Pro Val Tyr His Asp Leu Val Arg His Cys Leu
                 85                  90                  95

Ala Tyr Pro Lys Ala Asp Gly Ile Leu Val Asn Thr Trp Glu Glu Met
            100                 105                 110

Glu Pro Lys Ser Leu Lys Ser Leu Gln Asp Pro Lys Leu Leu Gly Arg
        115                 120                 125

Val Ala Arg Val Pro Val Tyr Pro Val Gly Pro Leu Cys Arg Pro Ile
    130                 135                 140

Gln Ser Ser Thr Thr Asp His Pro Val Phe Asp Trp Leu Asn Lys Gln
145                 150                 155                 160

Pro Asn Glu Ser Val Leu Tyr Ile Ser Phe Gly Ser Gly Gly Ser Leu
                165                 170                 175

Thr Ala Gln Gln Leu Thr Glu Leu Ala Trp Gly Leu Glu Glu Ser Gln
            180                 185                 190

Gln Arg Phe Ile Trp Val Val Arg Pro Pro Val Asp Gly Ser Ser Cys
        195                 200                 205

Ser Asp Tyr Phe Ser Ala Lys Gly Gly Val Thr Lys Asp Asn Thr Pro
    210                 215                 220

Glu Tyr Leu Pro Glu Gly Phe Val Thr Arg Thr Cys Asp Arg Gly Phe
225                 230                 235                 240
```

-continued

```
Met Ile Pro Ser Trp Ala Pro Gln Ala Glu Ile Leu Ala His Gln Ala
                245                 250                 255

Val Gly Gly Phe Leu Thr His Cys Gly Trp Ser Ser Thr Leu Glu Ser
            260                 265                 270

Val Leu Cys Gly Val Pro Met Ile Ala Trp Pro Leu Phe Ala Glu Gln
        275                 280                 285

Asn Met Asn Ala Ala Leu Leu Ser Asp Glu Leu Gly Ile Ser Val Arg
    290                 295                 300

Val Asp Asp Pro Lys Glu Ala Ile Ser Arg Ser Lys Ile Glu Ala Met
305                 310                 315                 320

Val Arg Lys Val Met Ala Glu Asp Glu Gly Glu Glu Met Arg Arg Lys
                325                 330                 335

Val Lys Lys Leu Arg Asp Thr Ala Glu Met Ser Leu Ser Ile His Gly
            340                 345                 350

Gly Gly Ser Ala His Glu Ser Leu Cys Arg Val Thr Lys Glu Cys Gln
        355                 360                 365

Arg Phe Leu Glu Cys Val Gly Asp Leu Gly Arg Gly Ala
    370                 375                 380


<210> SEQ ID NO 27
<211> LENGTH: 1446
<212> TYPE: DNA
<213> ORGANISM: Arabidopsis thaliana

<400> SEQUENCE: 27

ctaagcacca cgtcccaagt ccccgacaca ttccaaaaac cgttgacact ccttcgtgac      60

tctgcaaagc gactcatgcg ccgaaccacc accgtgaata ctaagtgaca tctccgccgt     120

gtctctcaac ttcttcactt tccttctcat ctcttcacct tcgtcctcag ccataacctt     180

cctcaccatc gcctcaatct tcgacctaga aatcgcctcc tttggatcat ccactctaac     240

agagattccc agttcatcgc taagcaacgc cgcgttcata ttctgctcgg cgaaaagcgg     300

ccacgctatc attggaacgc cgcaaaggac gctttccaac gtcgagctcc aaccacaatg     360

tgttaaaaac ccaccaacgg cctgatgggc taggatttca gcttgcggtg cccatgatgg     420

gatcatgaaa cctctatcgc aagtacgagt cacgaaccct tctggtagat actctggcgt     480

gttgtctttg gttacaccgc ctttagccga gaaataatca ctgcaagacg agccgtcaac     540

gggcggtcga accacccata taaaccgttg ctggctctcc tcgagccccc acgccaattc     600

ggttaactgt tgagccgtta gagaaccacc actcccgaag gaaatgtaga gaaccgactc     660

gtttggttgt ttgtttaacc aatcaaaaac cgggtgatcg gtcgtggatg attgtatcgg     720

tctgcataac ggaccaaccg gataaaccgg tacacgagcg acccggccca aaagtttcgg     780

gtcttgaagg gactttaatg atttgggctc catctcttcc catgtattca ccaagattcc     840

atccgctttt gggtaggcca gacagtgacg aaccaaatcg tggtacaccg gttcgtccgg     900

aaccagatat gcatccataa tatcttcaaa tctaaccggt tcacaccccg gtatagtgag     960

cggttttcgt tgcactgtgt gctcttcttt gataacttcg tccaaagttg gataatatat    1020

cgaaactccg agataacgcg cgttggaagc gataaagaca taagtcaaca tgtttaactc    1080

cgctgcaaga cataacgcat ctgtgccaaa caagtcaatg atcagagccg ttgggttttg    1140

atgcatggca acgatcttgg atcggagggt tggaacagct tcacgcataa tgactccgat    1200

cttggtcacc acatgggcgt tggggtctac caagccagaa atgtcgggcg atggaaggtt    1260

gacgatgtca acaccggttg agttaaggag cttggactga acggaggctg cgtcagtttc    1320
```

-continued

```
aaggacgaag acggtgacgt ggaagccgtg gttagcggag agacgcttag ctagctcgat   1380

caccgggagg acatggccca ttccgggact ggaaaacatg gcggcgtgtg gttttgtgat   1440

atgcat                                                              1446
```

<210> SEQ ID NO 28
<211> LENGTH: 1446
<212> TYPE: DNA
<213> ORGANISM: Arabidopsis thaliana

<400> SEQUENCE: 28

```
atggggaagc aagaagatgc agagctcgtc atcatacctt tccctttctc cggacacatt     60

ctcgcaacaa tcgaactcgc caaacgtctc ataagtcaag acaatcctcg gatccacacc    120

atcaccatcc tctattgggg attacctttt attcctcaag ctgacacaat cgctttcctc    180

cgatccctag tcaaaaatga gcctcgtatc cgtctcgtta cgttgcccga agtccaagac    240

cctccaccaa tggaactctt tgtggaattt gccgaatctt acattcttga atacgtcaag    300

aaaatggttc ccatcatcag agaagctctc tccactctct tgtcttcccg cgatgaatcg    360

ggttcagttc gtgtggctgg attggttctt gacttcttct gcgtccctat gatcgatgta    420

ggaaacgagt ttaatctccc ttcttacatt ttcttgacgt gtagcgcagg gttcttgggt    480

atgatgaagt atcttccaga gagacaccgc gaaatcaaat cggaattcaa ccggagcttc    540

aacgaggagt tgaatctcat tcctggttat gtcaactctg ttcctactaa ggttttgccg    600

tcaggtctat tcatgaaaga gacctacgag ccttgggtcg aactagcaga gaggtttcct    660

gaagctaagg gtattttggt taattcatac acagctctcg agccaaacgg ttttaaatat    720

ttcgatcgtt gtccggataa ctacccaacc atttacccaa tcgggccgat attatgctcc    780

aacgaccgtc cgaatttgga ctcatcggaa cgagatcgga tcataacttg gctagatgac    840

caacccgagt catcggtcgt gttcctctgt ttcgggagct tgaagaatct cagcgctact    900

cagatcaacg agatagctca agccttagag atcgttgact gcaaattcat ctggtcgttt    960

cgaaccaacc cgaaggagta cgcgagccct tacgaggctc taccacacgg gttcatggac   1020

cgggtcatgg atcaaggcat tgtttgtggt tgggctcctc aagttgaaat cctagcccat   1080

aaagctgtgg gaggattcgt atctcattgt ggttggaact cgatattgga gagtttgggt   1140

ttcggcgttc caatcgccac gtggccgatg tacgcggaac aacaactaaa cgcgttcacg   1200

atggtgaagg agcttggttt agccttggag atgcggttgg attacgtgtc ggaagatgga   1260

gatatagtga aagctgatga gatcgcagga accgttagat ctttaatgga cggtgtggat   1320

gtgccgaaga gtaaagtgaa ggagattgct gaggcgggaa aagaagctgt ggacggtgga   1380

tcttcgtttc ttgcggttaa aagattcatc ggtgacttga tcgacggcgt ttctataagt   1440

aagtag                                                              1446
```

<210> SEQ ID NO 29
<211> LENGTH: 481
<212> TYPE: PRT
<213> ORGANISM: Arabidopsis thaliana

<400> SEQUENCE: 29

```
Met Gly Lys Gln Glu Asp Ala Glu Leu Val Ile Ile Pro Phe Pro Phe
  1               5                  10                  15

Ser Gly His Ile Leu Ala Thr Ile Glu Leu Ala Lys Arg Leu Ile Ser
             20                  25                  30

Gln Asp Asn Pro Arg Ile His Thr Ile Thr Ile Leu Tyr Trp Gly Leu
```

-continued

```
        35                  40                  45

Pro Phe Ile Pro Gln Ala Asp Thr Ile Ala Phe Leu Arg Ser Leu Val
    50                  55                  60

Lys Asn Glu Pro Arg Ile Arg Leu Val Thr Leu Pro Glu Val Gln Asp
65                  70                  75                  80

Pro Pro Pro Met Glu Leu Phe Val Glu Phe Ala Glu Ser Tyr Ile Leu
                85                  90                  95

Glu Tyr Val Lys Lys Met Val Pro Ile Ile Arg Glu Ala Leu Ser Thr
            100                 105                 110

Leu Leu Ser Ser Arg Asp Glu Ser Gly Ser Val Arg Val Ala Gly Leu
        115                 120                 125

Val Leu Asp Phe Phe Cys Val Pro Met Ile Asp Val Gly Asn Glu Phe
    130                 135                 140

Asn Leu Pro Ser Tyr Ile Phe Leu Thr Cys Ser Ala Gly Phe Leu Gly
145                 150                 155                 160

Met Met Lys Tyr Leu Pro Glu Arg His Arg Glu Ile Lys Ser Glu Phe
                165                 170                 175

Asn Arg Ser Phe Asn Glu Glu Leu Asn Leu Ile Pro Gly Tyr Val Asn
            180                 185                 190

Ser Val Pro Thr Lys Val Leu Pro Ser Gly Leu Phe Met Lys Glu Thr
        195                 200                 205

Tyr Glu Pro Trp Val Glu Leu Ala Glu Arg Phe Pro Glu Ala Lys Gly
    210                 215                 220

Ile Leu Val Asn Ser Tyr Thr Ala Leu Glu Pro Asn Gly Phe Lys Tyr
225                 230                 235                 240

Phe Asp Arg Cys Pro Asp Asn Tyr Pro Thr Ile Tyr Pro Ile Gly Pro
                245                 250                 255

Ile Leu Cys Ser Asn Asp Arg Pro Asn Leu Asp Ser Ser Glu Arg Asp
            260                 265                 270

Arg Ile Ile Thr Trp Leu Asp Asp Gln Pro Glu Ser Ser Val Val Phe
        275                 280                 285

Leu Cys Phe Gly Ser Leu Lys Asn Leu Ser Ala Thr Gln Ile Asn Glu
    290                 295                 300

Ile Ala Gln Ala Leu Glu Ile Val Asp Cys Lys Phe Ile Trp Ser Phe
305                 310                 315                 320

Arg Thr Asn Pro Lys Glu Tyr Ala Ser Pro Tyr Glu Ala Leu Pro His
                325                 330                 335

Gly Phe Met Asp Arg Val Met Asp Gln Gly Ile Val Cys Gly Trp Ala
            340                 345                 350

Pro Gln Val Glu Ile Leu Ala His Lys Ala Val Gly Gly Phe Val Ser
        355                 360                 365

His Cys Gly Trp Asn Ser Ile Leu Glu Ser Leu Gly Phe Gly Val Pro
    370                 375                 380

Ile Ala Thr Trp Pro Met Tyr Ala Glu Gln Gln Leu Asn Ala Phe Thr
385                 390                 395                 400

Met Val Lys Glu Leu Gly Leu Ala Leu Glu Met Arg Leu Asp Tyr Val
                405                 410                 415

Ser Glu Asp Gly Asp Ile Val Lys Ala Asp Glu Ile Ala Gly Thr Val
            420                 425                 430

Arg Ser Leu Met Asp Gly Val Asp Val Pro Lys Ser Lys Val Lys Glu
        435                 440                 445

Ile Ala Glu Ala Gly Lys Glu Ala Val Asp Gly Gly Ser Ser Phe Leu
    450                 455                 460
```

-continued

Ala Val Lys Arg Phe Ile Gly Asp Leu Ile Asp Gly Val Ser Ile Ser
465 470 475 480

Lys

<210> SEQ ID NO 30
<211> LENGTH: 1446
<212> TYPE: DNA
<213> ORGANISM: Arabidopsis thaliana

<400> SEQUENCE: 30
ctacttactt atagaaacgc cgtcgatcaa gtcaccgatg aatcttttaa ccgcaagaaa 60
cgaagatcca ccgtccacag cttcttttcc cgcctcagca atctccttca ctttactctt 120
cggcacatcc acaccgtcca ttaaagatct aacggttcct gcgatctcat cagctttcac 180
tatatctcca tcttccgaca cgtaatccaa ccgcatctcc aaggctaaac caagctcctt 240
caccatcgtg aacgcgttta gttgttgttc cgcgtacatc ggccacgtgg cgattggaac 300
gccgaaaccc aaactctcca atatcgagtt ccaaccacaa tgagatacga atcctcccac 360
agctttatgg gctaggattt caacttgagg agcccaacca caaacaatgc cttgatccat 420
gacccggtcc atgaacccgt gtggtagagc ctcgtaaggg ctcgcgtact ccttcgggtt 480
ggttcgaaac gaccagatga atttgcagtc aacgatctct aaggcttgag ctatctcgtt 540
gatctgagta gcgctgagat tcttcaagct cccgaaacag aggaacacga ccgatgactc 600
gggttggtca tctagccaag ttatgatccg atctcgttcc gatgagtcca aattcggacg 660
gtcgttggag cataatatcg gcccgattgg gtaaatggtt gggtagttat ccggacaacg 720
atcgaaatat ttaaaaccgt ttggctcgag agctgtgtat gaattaacca aaataccctt 780
agcttcagga aacctctctg ctagttcgac ccaaggctcg taggtctctt tcatgaatag 840
acctgacggc aaaaccttag taggaacaga gttgacataa ccaggaatga gattcaactc 900
ctcgttgaag ctccggttga attccgattt gatttcgcgg tgtctctctg gaagatactt 960
catcataccc aagaaccctg cgctacacgt caagaaaatg taagaaggga gattaaactc 1020
gtttcctaca tcgatcatag ggacgcagaa gaagtcaaga accaatccag ccacacgaac 1080
tgaacccgat tcatcgcggg aagacaagag agtggagaga gcttctctga tgatgggaac 1140
cattttcttg acgtattcaa gaatgtaaga ttcggcaaat tccacaaaga gttccattgg 1200
tggagggtct tggacttcgg gcaacgtaac gagacggata cgaggctcat ttttgactag 1260
ggatcggagg aaagcgattg tgtcagcttg aggaataaaa ggtaatcccc aatagaggat 1320
ggtgatggtg tggatccgag gattgtcttg acttatgaga cgtttggcga gttcgattgt 1380
tgcgagaatg tgtccggaga aagggaaagg tatgatgacg agctctgcat cttcttgctt 1440
ccccat 1446

<210> SEQ ID NO 31
<211> LENGTH: 1425
<212> TYPE: DNA
<213> ORGANISM: Arabidopsis thaliana

<400> SEQUENCE: 31
atggcgaagc agcaagaagc agagctcatc ttcatcccat ttccaatccc cggacacatt 60
ctcgccacaa tcgaactcgc gaaacgtctc atcagtcacc aacctagtcg gatccacacc 120
atcaccatcc tccattggag cttacctttt cttcctcaat ctgacactat cgccttcctc 180
aaatccctaa tcgaaacaga gtctcgtatc cgtctcatta ccttacccga tgtccaaaac 240

-continued

```
cctccaccaa tggagctatt tgtgaaagct tccgaatctt acattcttga atacgtcaag    300

aaaatggttc ctttggtcag aaacgctctc tccactctct tgtcttctcg tgatgaatcg    360

gattcagttc atgtcgccgg attagttctt gatttcttct gtgtcccttt gatcgatgtc    420

ggaaacgagt ttaatctccc ttcttacatc ttcttgacgt gtagcgcaag tttcttgggt    480

atgatgaagt atcttctgga gagaaaccgc gaaaccaaac cggaacttaa ccggagctct    540

gacgaggaaa caatatcagt tcctggtttt gttaactccg ttccggttaa agttttgcca    600

ccgggtttgt tcacgactga gtcttacgaa gcttgggtcg aaatggcgga aaggttccct    660

gaagccaagg gtattttggt caattcattt gaatctctag aacgtaacgc ttttgattat    720

ttcgatcgtc gtccggataa ttacccaccc gtttacccaa tcgggccaat tctatgctcc    780

aacgatcgtc cgaatttgga tttatcggaa cgagaccgga tcttgaaatg gctcgatgac    840

caacccgagt catctgttgt gtttctctgc ttcgggagct tgaagagtct cgctgcgtct    900

cagattaaag agatcgctca agccttagag ctcgtcggaa tcagattcct ctggtcgatt    960

cgaacggacc cgaaggagta cgcgagcccg aacgagattt taccggacgg gtttatgaac   1020

cgagtcatgg gtttgggcct tgtttgtggt tgggctcctc aagttgaaat tctggcccat   1080

aaagcaattg gagggttcgt gtcacactgc ggttggaact cgatattgga gagtttgcgt   1140

ttcggagttc caattgccac gtggccaatg tacgcggaac aacaactaaa cgcgttcacg   1200

attgtgaagg agcttggttt ggcgttggag atgcggttgg attacgtgtc ggaatatgga   1260

gaaatcgtga aagctgatga aatcgcagga gccgtacgat ctttgatgga cggtgaggat   1320

gtgccgagga ggaaactgaa ggagattgcg gaggcgggaa aagaggctgt gatggacggt   1380

ggatcttcgt ttgttgcggt taaaagattc atagatgggc tttga                   1425
```

<210> SEQ ID NO 32
<211> LENGTH: 474
<212> TYPE: PRT
<213> ORGANISM: Arabidopsis thaliana

<400> SEQUENCE: 32

```
Met Ala Lys Gln Gln Glu Ala Glu Leu Ile Phe Ile Pro Phe Pro Ile
  1               5                  10                  15

Pro Gly His Ile Leu Ala Thr Ile Glu Leu Ala Lys Arg Leu Ile Ser
             20                  25                  30

His Gln Pro Ser Arg Ile His Thr Ile Thr Ile Leu His Trp Ser Leu
         35                  40                  45

Pro Phe Leu Pro Gln Ser Asp Thr Ile Ala Phe Leu Lys Ser Leu Ile
     50                  55                  60

Glu Thr Glu Ser Arg Ile Arg Leu Ile Thr Leu Pro Asp Val Gln Asn
 65                  70                  75                  80

Pro Pro Pro Met Glu Leu Phe Val Lys Ala Ser Glu Ser Tyr Ile Leu
                 85                  90                  95

Glu Tyr Val Lys Lys Met Val Pro Leu Val Arg Asn Ala Leu Ser Thr
            100                 105                 110

Leu Leu Ser Ser Arg Asp Glu Ser Asp Ser Val His Val Ala Gly Leu
        115                 120                 125

Val Leu Asp Phe Phe Cys Val Pro Leu Ile Asp Val Gly Asn Glu Phe
    130                 135                 140

Asn Leu Pro Ser Tyr Ile Phe Leu Thr Cys Ser Ala Ser Phe Leu Gly
145                 150                 155                 160
```

-continued

```
Met Met Lys Tyr Leu Leu Glu Arg Asn Arg Glu Thr Lys Pro Glu Leu
                165                 170                 175

Asn Arg Ser Ser Asp Glu Glu Thr Ile Ser Val Pro Gly Phe Val Asn
            180                 185                 190

Ser Val Pro Val Lys Val Leu Pro Pro Gly Leu Phe Thr Thr Glu Ser
        195                 200                 205

Tyr Glu Ala Trp Val Glu Met Ala Glu Arg Phe Pro Glu Ala Lys Gly
    210                 215                 220

Ile Leu Val Asn Ser Phe Glu Ser Leu Glu Arg Asn Ala Phe Asp Tyr
225                 230                 235                 240

Phe Asp Arg Arg Pro Asp Asn Tyr Pro Pro Val Tyr Pro Ile Gly Pro
                245                 250                 255

Ile Leu Cys Ser Asn Asp Arg Pro Asn Leu Asp Leu Ser Glu Arg Asp
            260                 265                 270

Arg Ile Leu Lys Trp Leu Asp Asp Gln Pro Glu Ser Ser Val Val Phe
        275                 280                 285

Leu Cys Phe Gly Ser Leu Lys Ser Leu Ala Ala Ser Gln Ile Lys Glu
    290                 295                 300

Ile Ala Gln Ala Leu Glu Leu Val Gly Ile Arg Phe Leu Trp Ser Ile
305                 310                 315                 320

Arg Thr Asp Pro Lys Glu Tyr Ala Ser Pro Asn Glu Ile Leu Pro Asp
                325                 330                 335

Gly Phe Met Asn Arg Val Met Gly Leu Gly Leu Val Cys Gly Trp Ala
            340                 345                 350

Pro Gln Val Glu Ile Leu Ala His Lys Ala Ile Gly Gly Phe Val Ser
        355                 360                 365

His Cys Gly Trp Asn Ser Ile Leu Glu Ser Leu Arg Phe Gly Val Pro
    370                 375                 380

Ile Ala Thr Trp Pro Met Tyr Ala Glu Gln Gln Leu Asn Ala Phe Thr
385                 390                 395                 400

Ile Val Lys Glu Leu Gly Leu Ala Leu Glu Met Arg Leu Asp Tyr Val
                405                 410                 415

Ser Glu Tyr Gly Glu Ile Val Lys Ala Asp Glu Ile Ala Gly Ala Val
            420                 425                 430

Arg Ser Leu Met Asp Gly Glu Asp Val Pro Arg Arg Lys Leu Lys Glu
        435                 440                 445

Ile Ala Glu Ala Gly Lys Glu Ala Val Met Asp Gly Gly Ser Ser Phe
    450                 455                 460

Val Ala Val Lys Arg Phe Ile Asp Gly Leu
465                 470
```

<210> SEQ ID NO 33
<211> LENGTH: 1425
<212> TYPE: DNA
<213> ORGANISM: Arabidopsis thaliana

<400> SEQUENCE: 33

```
tcaaagccca tctatgaatc ttttaaccgc aacaaacgaa gatccaccgt ccatcacagc      60

ctcttttccc gcctccgcaa tctccttcag tttcctcctc ggcacatcct caccgtccat     120

caaagatcgt acggctcctg cgatttcatc agctttcacg atttctccat attccgacac     180

gtaatccaac cgcatctcca acgccaaacc aagctccttc acaatcgtga acgcgtttag     240

ttgttgttcc gcgtacattg gccacgtggc aattggaact ccgaaacgca aactctccaa     300

tatcgagttc caaccgcagt gtgacacgaa ccctccaatt gctttatggg ccagaatttc     360
```

-continued

```
aacttgagga gcccaaccac aaacaaggcc caaacccatg actcggttca taaacccgtc    420
cggtaaaatc tcgttcgggc tcgcgtactc cttcgggtcc gttcgaatcg accagaggaa    480
tctgattccg acgagctcta aggcttgagc gatctcttta atctgagacg cagcgagact    540
cttcaagctc ccgaagcaga gaaacacaac agatgactcg ggttggtcat cgagccattt    600
caagatccgg tctcgttccg ataaatccaa attcggacga tcgttggagc atagaattgg    660
cccgattggg taaacgggtg ggtaattatc cggacgacga tcgaaataat caaaagcgtt    720
acgttctaga gattcaaatg aattgaccaa aatacccttg gcttcaggga acctttccgc    780
catttcgacc caagcttcgt aagactcagt cgtgaacaaa cccggtggca aaactttaac    840
cggaacggag ttaacaaaac caggaactga tattgtttcc tcgtcagagc tccggttaag    900
ttccggtttg gtttcgcggt ttctctccag aagatacttc atcataccca agaaacttgc    960
gctacacgtc aagaagatgt aagaagggag attaaactcg tttccgacat cgatcaaagg   1020
gacacagaag aaatcaagaa ctaatccggc gacatgaact gaatccgatt catcacgaga   1080
agacaagaga gtggagagag cgtttctgac caaaggaacc attttcttga cgtattcaag   1140
aatgtaagat tcggaagctt tcacaaatag ctccattggt ggagggtttt ggacatcggg   1200
taaggtaatg agacggatac gagactctgt ttcgattagg gatttgagga aggcgatagt   1260
gtcagattga ggaagaaaag gtaagctcca atggaggatg gtgatggtgt ggatccgact   1320
aggttggtga ctgatgagac gtttcgcgag ttcgattgtg gcgagaatgt gtccggggat   1380
tggaaatggg atgaagatga gctctgcttc ttgctgcttc gccat                   1425
```

<210> SEQ ID NO 34
<211> LENGTH: 1437
<212> TYPE: DNA
<213> ORGANISM: Arabidopsis thaliana

<400> SEQUENCE: 34

```
atgaagattg agcttgtgtt catacctttg ccggggattg gtcatctcag gccaaccgtg     60
aagctagcga agcaactcat aggcagcgaa aaccgtcttt cgatcaccat aatcatcatc    120
ccttcaagat ttgacgccgg tgatgcatcc gcctgtatcg catctctcac cacgttgtct    180
caagatgatc gcctccatta cgaatccata tccgtcgcaa aacaaccacc aacctccgac    240
ccggatcctg ttccggctca agtgtacata gagaaacaaa agacgaaagt gagagatgca    300
gtcgcggcga gaatcgtcga tccaacaaga aagctcgcgg gattcgtggt ggacatgttc    360
tgttcctcga tgatcgatgt agctaacgag tttggagttc cgtgttatat ggtatacaca    420
tcgaacgcta cgtttttagg aaccatgctt cacgttcaac aaatgtacga tcaaaagaag    480
tatgacgtca gcgagttaga aaactcggtc accgagttgg agtttccgtc tctgactcgt    540
ccttatccag tgaagtgtct tcctcatatc ctcacttcaa aggagtggtt acctctctct    600
ctagctcaag ctaggtgttt ccggaagatg aagggtattt tggtaaatac agttgctgag    660
cttgaacctc acgctttgaa aatgttcaat attaatggtg acgatcttcc tcaagtttat    720
cctgttggac cagtgttgca tctcgaaaac ggcaatgacg atgatgagaa gcaatcggaa    780
attttgcggt ggctcgacga gcaaccgtct aaatctgttg tgtttctctg ctttgggagc    840
ttgggaggtt tcactgaaga acaaacaaga gaaaccgctg tggccctaga tagaagcggt    900
cagcggtttc tttggtgtct tcgtcacgca tcgccaaata taaaaacaga tcgtcccaga    960
gattacacga atcttgagga ggttttaccg gaggggttct tggaacggac tttggataga   1020
```

-continued

```
gggaaagtga ttggatgggc accacaagtg gcggtactag agaagccggc gataggaggg   1080

tttgtcactc actgcggttg gaactctatt ttagagagct tgtggttcgg tgttccaatg   1140

gtgacgtggc cgctatacgc ggaacagaag gttaacgcgt ttgagatggt tgaggagctg   1200

ggtttggcgg tggagatacg gaagtactta aaaggagatt tgttcgccgg agagatggag   1260

acggttaccg cggaggatat agagagagcc attaggcgtg tgatggagca agacagtgac   1320

gttaggaaca acgtgaaaga gatggcggag aagtgccact tcgcgttaat ggacggtgga   1380

tcttcgaagg cggctttgga aaagtttatt caagacgtga tagagaatat ggattaa      1437
```

```
<210> SEQ ID NO 35
<211> LENGTH: 1431
<212> TYPE: DNA
<213> ORGANISM: Arabidopsis thaliana

<400> SEQUENCE: 35

atgaaagcag aagcagagat catcttcgtt acatatccat cccctggtca tcttcttgtc     60

tccattgaat tcgctaaatc tctcatcaaa cgtgatgatc gcatccacac catcaccatc    120

ctctactggg ctttacctct cgctcctcaa gcccaccttt tcgctaagtc cctcgttgct    180

tcacagcctc gaatccgtct ccttgcgttg cctgatgttc aaaaccctcc accattggaa    240

ctcttcttta aagctcccga agcttatatt cttgagtcca ccaagaaaac agttccttta    300

gtcagagacg ctctctccac tctagtttct tcacgtaaag aatccggttc ggttcgtgta    360

gtcggtttgg ttatcgattt tttttgtgtt ccaatgatcg aagtggcaaa cgagcttaac    420

cttccttctt acatcttcct aacgtgtaac gctgggtttt taagtatgat gaagtatctc    480

cctgagagac atcgcataac cacttctgag ctagatttaa gctccggcaa cgtagaacat    540

ccaattcctg gctacgtctg ctccgtgccg acgaaggttt tgcctccagg tctattcgtg    600

agagagtcct acgaggcttg ggtcgagatt gcagagaagt tccctggagc caagggcatt    660

ttggtaaact cagtcacatg tcttgagcag aatgcatttg attacttcgc tcgtcttgat    720

gagaactatc ctccggttta cccggtcgga ccggttctta gtttgaagga tcgtccgtct    780

ccaaatctgg acgcatcgga ccgggatcgg atcatgagat ggctcgagga ccagccggag    840

tcgtcaattg tgtatatctg cttcggaagc ctcggaatca ttggcaagct gcagattgaa    900

gagatagctg aagccttgga actcaccggc cacaggtttc tttggtcaat acgtacaaat    960

ccgacggaga aagcgagccc gtacgatctg ttgccggagg gatttctcga tcggacggcc   1020

agtaagggat tggtgtgtga ttgggccccg caagtagaag ttctggccca taaagcgctc   1080

ggaggattcg tgtctcactg cggttggaac tctgtactgg agagcttatg gttcggtgtt   1140

ccgatcgcca cgtggccaat gtacgctgag caacagttaa acgcattctc gatggtgaag   1200

gagttagggt tagccgtgga gctgcgttta gactacgttt cggcgtacgg agagatagta   1260

aaagctgagg agatcgcggg agccatacga tcattgatgg acggtgagga tacgccgagg   1320

aagagagtga aggagatggc ggaagcggcg aggaatgctt tgatggacgg aggatcttcg   1380

tttgttgcgg ttaaacgatt tctcgacgag ttgatcggcg gagatgttta g            1431
```

```
<210> SEQ ID NO 36
<211> LENGTH: 1443
<212> TYPE: DNA
<213> ORGANISM: Arabidopsis thaliana

<400> SEQUENCE: 36

atgaagacag cagagctcat attcgttcct ctgccggaga ccggccatct cttgtcaacg     60
```

-continued

```
atcgagtttg gaaagcgtct actcaatcta gaccgtcgga tttctatgat tacaatcctc    120
tccatgaatc ttccttacgc tcctcacgcc gacgcttctc ttgcttcgct aacagcctcc    180
gagcctggta tccgaatcat cagtctcccg gagatccacg atccacctcc gatcaagctt    240
cttgacactt cctccgagac ttacatcctc gatttcatcc ataaaaacat accttgtctc    300
agaaaaacca tccaagattt agtctcatca tcatcatctt ccggaggtgg tagtagtcat    360
gtcgccggct tgattcttga tttcttctgc gttggtttga tcgacatcgg ccgtgaggta    420
aaccttcctt cctatatctt catgacttcc aactttggtt tcttaggggt tctacagtat    480
ctcccggaac gacaacgttt gactccgtcg gagttcgatg agagctccgg cgaggaagag    540
ttacatattc cggcgtttgt gaaccgtgtt cccgccaagg ttctgccgcc aggtgtgttc    600
gataaactct cttacgggtc tctggtcaaa atcggcgagc gattacatga agccaagggt    660
attttggtta attcatttac ccaagtggag ccttatgctg ctgaacattt ttctcaagga    720
cgagattacc ctcacgtgta tcctgttggg ccggttctca acttaacggg ccgtacaaat    780
ccgggtctag cttcggccca atataaagag atgatgaagt ggcttgacga gcaaccagac    840
tcgtcggttt tgttcctgtg tttcgggagc atgggagtct tccctgcacc tcagatcaca    900
gagattgctc acgcgctcga gcttatcggg tgcaggttca tctgggcgat ccgtacgaac    960
atggcgggag atggcgatcc tcaggagccg cttccagaag gatttgtcga tcgaacaatg   1020
ggccgtggaa ttgtgtgtag ttgggctcca caagtggata tcttggccca caaggcaaca   1080
ggtggattcg tttctcactg cgggtggaat tccgtccaag agagtctatg gtacggtgta   1140
cctattgcaa cgtggccaat gtatgcggag caacaactga acgcatttga gatggtgaag   1200
gagttgggct tagcagtgga gataaggctt gactacgtgg cggatggtga tagggttact   1260
ttggagatcg tgtcagccga tgaaatagcc acagccgtcc gatcattgat ggatagtgat   1320
aaccccgtga gaaagaaggt tatagaaaaa tcttcagtgg cgaggaaagc tgttggtgat   1380
ggtgggtctt ctacggtggc cacatgtaat tttatcaaag atattcttgg ggatcacttt   1440
tga                                                                 1443
```

<210> SEQ ID NO 37
<211> LENGTH: 1404
<212> TYPE: DNA
<213> ORGANISM: Arabidopsis thaliana

<400> SEQUENCE: 37

```
atgcggaatg tagagctcat cttcatcccc acaccaaccg ttggtcatct tgttccgttt     60
cttgaatttg ctaggcgtct cattgagcaa gatgatagga tccgtatcac aatcctcttg    120
atgaaactac aaggtcagtc tcatctagac acttatgtta aatcaattgc ctcctctcaa    180
ccgtttgtta gattcattga tgtccctgag ttagaggaga aacctacact tggtagtaca    240
caatctgtgg aagcttatgt gtatgatgtt attgagagaa atatccctct tgtgaggaat    300
atagtcatgg atattttaac ttctcttgca ttggatggag ttaaggtcaa gggattagtt    360
gttgactttt tctgtctccc tatgattgac gttgctaaag atataagtct ccctttctat    420
gtgttcttga ctacaaattc cgggttctta gctatgatgc agtatctagc agatcgacat    480
agtagagata catcggtttt tgtaagaaac tcggaagaaa tgttgtcgat acctggattt    540
gtaaaccctg tcccagccaa tgttctgccg tcagctctgt ttgttgaaga tggttatgat    600
gcttacgtta agctggccat attgtttaca aaggccaatg gaatcctagt gaatagctcc    660
```

-continued tttgatattg agccttactc tgtgaatcat tttcttcaag aacagaatta tccttctgtt 720
tatgctgttg gccccatatt tgacttgaaa gcccagcctc atccagagca ggacctaacc 780
cgtcgtgacg agttgatgaa atggcttgat gatcaacccg aggcatcggt tgtattcctt 840
tgttttggga gtatggcaag gttaagaggt tctctagtga aggaaatagc tcatggactt 900
gagctatgtc aatatagatt cctctggtca ctccgtaaag aagaggtgac aaaggatgat 960
ttgccagagg ggttccttga ccgtgtcgat ggacgtggaa tgatatgtgg ttggtctcct 1020
caggtagaaa tactggccca taaggcagtg ggaggctttg tttctcactg tggatggaac 1080
tcaatagtag agagtttgtg gtttggcgtg ccaattgtga catggccaat gtatgcagag 1140
caacaactca atgcgtttct gatggtgaag gaactgaagc tagctgtgga gctgaagctt 1200
gattacaggg tacatagtga tgagatagta aacgcaaacg agatagagac cgctattcgt 1260
tatgtaatgg acacggataa taatgttgtg aggaaacgag tgatggatat ctcgcagatg 1320
atccagagag ctacgaagaa tggtggatct tcgtttgccg caattgagaa attcatatat 1380
gacgtgatag gaattaagcc ctag 1404

<210> SEQ ID NO 38
<211> LENGTH: 1592
<212> TYPE: DNA
<213> ORGANISM: Arabidopsis thaliana

<400> SEQUENCE: 38
atgggaactc ctgtcgaagt ctctaagctc catttcttgc tcttcccttt catggctcat 60
ggccatatga taccaactct agacatggct aagctctttg ccaccaaagg agctaaatcc 120
actatcctca ctacacctct caatgccaag ctcttcttcg agaaacccat caaatcattc 180
aaccaagaca acccgggact cgaagacatc accatccaga tccttaattt cccttgcaca 240
gagcttggtt tgcctgatgg ctgtgagaat actgatttca tcttctccac acctgaccta 300
aacgtaggtg acttgagtca aaagttttta ctcgcaatga aatatttcga agagccacta 360
gaggagctcc tcgtgacaat gagaccagac tgtcttgtcg gtaacatgtt cttcccttgg 420
tccactaaag ttgctgagaa gttcggagta ccgagacttg tgttccacgg cacaggctac 480
ttctctttat gtgcttctca ttgcataagg ctccctaaga atgtggcaac aagttctgag 540
ccctttgtga ttcctgatct cccgggagac attttgatta cagaggaaca ggtcatggag 600
acagaagaag agtctgtaat ggggaggttt atgaaggcaa taagagactc agagagagat 660
agctttggcg tgttggtgaa cagcttctac gagcttgaac aggcttactc agattatttc 720
aagagctttg tggcgaaaag agcgtggcat atcggtccgc tttccttagg aaatagaaag 780
ttcgaggaga aagcagaaag aggcaaaaag gcaagcattg atgagcatga atgtttgaaa 840
tggctcgact ccaagaaatg tgattcagtg atttacatgg cctttggaac catgtctagc 900
tttaaaaacg agcagctgat agagattgca gctggtttag atatgtcagg acatgatttt 960
gtctgggtgg ttaacagaaa aggcagccaa ggtaccatag acatcactct ctttgcagca 1020
aaatcctctg tttttgtttt agagaaaaac caatgatcta attaggattc tactgtttca 1080
aactctaact tttgcgtttg cattacatat aaatagttga gaaggaagat tggttaccag 1140
aggggtttga agagaagacc aagggaaaag gattgataat ccgagggtgg gcgccacaag 1200
tgctgatact tgagcacaaa gcaattggcg gatttttgac gcattgtgga tggaactcgt 1260
tattagaagg ggtggcagcg ggcctgccaa tggtgacatg gcccgtggga gccgagcagt 1320
tctacaacga gaaattggtg acacaagtgt tgaaaacagg agtgagtgtg ggagtgaaga 1380

-continued agatgatgca agtagttgga gacttcatta gcagagagaa agtggaggga gcggtgaggg 1440
aagtgatggt tggagaagag aggaggaaac gggccaagga gttagcagaa atggcgaaaa 1500
atgcggtgaa agaaggagga tcttcagatc tagaggtaga taggttgatg gaagagctta 1560
cgttagttaa actgcaaaaa gagaaggtat aa 1592

<210> SEQ ID NO 39
<211> LENGTH: 1541
<212> TYPE: DNA
<213> ORGANISM: Arabidopsis thaliana

<400> SEQUENCE: 39
atgggtagtg atcatcatca tcgaaagctc cacgttatgt tcttcccttt catggcttat 60
ggtcacatga taccaactct agacatggct aagcttttct ctagcagagg agccaaatcc 120
acaatcctca ccacatctct caactccaag atcctccaaa aacccatcga cacattcaag 180
aatctgaatc cgggtctcga aatcgacatc cagatcttca atttcccttg cgtggagctg 240
gggttaccag aaggatgtga aaacgttgat ttcttcactt caaacaacaa tgatgataaa 300
aacgagatga tcgtgaaatt ctttttctcg acaaggtttt tcaaagacca gcttgagaaa 360
ctcctcggga caacgagacc agactgtctt atcgccgaca tgttcttccc ctgggctact 420
gaagctgctg ggaagttcaa tgtgccaaga cttgtgttcc acggcactgg ctacttctct 480
ttatgcgctg gttattgcat cggagtgcat aaaccacaga agagagtggc ttcaagctct 540
gagccatttg tgattcccga gctccctggg aacattgtga taactgaaga acagatcata 600
gatggcgatg gagaatccga catgggaaag tttatgactg aagttaggga atcggaagtg 660
aagagctcag gagttgtttt gaatagtttc tacgagctag aacatgatta cgccgatttt 720
tacaaaagtt gtgtacaaaa gagagcgtgg catatcggtc cgctatcggt ttacaacagg 780
ggatttgagg agaaggctga gagaggaaag aaagcgaaca ttgatgaggc tgaatgcctc 840
aaatggcttg actccaagaa accaaattca gtcatttatg tttcctttgg gagcgtggct 900
ttcttcaaga atgaacagtt attcgagatc gctgcagggt tagaagcttc cggtacaagt 960
ttcatttggg ttgttaggaa aaccaaaggt attgaaattg acgtttgaag cctatattat 1020
atagctgtaa tttgggtagc tttgatttta atctgacaca agatttggtg tgaacagatg 1080
atagagaaga atggttacca gaagggttcg aagagagggt gaaagggaaa ggtatgataa 1140
taagaggatg ggcaccacag gtgctgatac ttgaccacca agcaaccggt gggtttgtga 1200
cccattgcgg ctggaactcg cttcttgaag gagtggctgc agggctacca atggtgacat 1260
ggcctgtagg agcggagcaa ttctacaatg agaaattggt tacgcaagtg ctcagaacag 1320
gagtgagcgt gggagcgagc aagcatatga aagttatgat gggagatttc attagcagag 1380
agaaagtgga taaagcggtg agggaggttt tggctgggga agcagcagag gagaggcgga 1440
gacgggcaaa gaagctagcg gcgatggcta aagctgccgt ggaagaagga gggtcttcct 1500
tcaacgatct aaacagcttc atggaagagt ttagttcata a 1541

<210> SEQ ID NO 40
<211> LENGTH: 1649
<212> TYPE: DNA
<213> ORGANISM: Arabidopsis thaliana

<400> SEQUENCE: 40
atgaacagag agcaaattca tattttgttc ttccccttca tggctcatgg ccacatgatt 60

-continued

```
ccactcttag acatggccaa gcttttcgct agaagaggag ccaaatcaac tctcctcaca    120

accccaataa atgctaagat cttggagaaa cccattgaag cattcaaagt tcaaaatcct    180

gatctcgaaa tcggaatcaa gatcctcaat ttcccttgtg tagagcttgg attgccagaa    240

ggatgcgaga accgtgactt cattaactca taccaaaaat ctgactcatt tgacttgttc    300

ttgaagtttc ttttctctac caagtatatg aaacagcagt tggagagttt cattgaaaca    360

accaaaccga gtgctcttgt agccgatatg ttcttccctt gggcaacaga atccgcggag    420

aagatcggtg ttccaagact tgtgttccac ggcacatcat cctttgcctt gtgttgttcg    480

tataacatga ggattcataa gccacacaag aaagtcgctt cgagttctac tccatttgta    540

atccctggtc tccctggaga catagttatt acagaagacc aagccaatgt caccaacgaa    600

gaaactccat tcggaaagtt ttggaaagaa gtcagggaat cagagaccag tagctttggt    660

gttttggtga atagcttcta cgagctggaa tcatcttatg ctgattttta ccgtagtttt    720

gtggcgaaaa aagcgtggca tataggtcca ctttcactat ccaacagagg gattgcagag    780

aaagccggaa gagggaaaaa ggcaaacatt gatgagcaag aatgcctcaa atggcttgac    840

tctaagacac ctggctcagt agtttacttg tcctttggta gcggaaccgg cttacccaac    900

gaacagctgt tagagattgc tttcggcctt gaaggctctg gacaaaattt catttgggtg    960

gttagcaaaa atgaaaacca aggtaatttt tttcctcctt aaccattatt aatcaatgta   1020

gtctttatta gtatatttcc aaaaatatta acatttgtgt atacattttc ctattgccaa   1080

atatgctatg atgccatagc aatgagtaga ttggtttgtg tactttatat attactttgt   1140

agaacttcta acaattatga cttggtgttg gtgtagttgg gacaggtgaa aatgaagatt   1200

ggttgcctaa agggtttgaa gagaggaata aaggaaaagg gctgataata cgcggatggg   1260

ccccgcaagt gctgatactt gaccacaaag caatcggagg atttgtgacg cattgcggat   1320

ggaactcgac tttggagggc attgccgcag ggctgcctat ggtgacttgg ccgatggggg   1380

cagaacagtt ctacaacgag aagttattga caaaagtgtt gagaatagga gtgaacgttg   1440

gagctaccga gttggtgaaa aaaggaaagt tgattagtag agcacaagtg gagaaggcag   1500

taagggaagt gattggtggt gagaaggcag aggaaaggcg gctaagggct aaggagctgg   1560

gcgagatggc taaagccgct gtggaagaag gagggtcttc ttataatgat gtgaacaagt   1620

ttatggaaga gctgaatggt agaaagtag                                     1649
```

<210> SEQ ID NO 41
<211> LENGTH: 1636
<212> TYPE: DNA
<213> ORGANISM: Arabidopsis thaliana

<400> SEQUENCE: 41

```
atgaacagag aagtctctga gagaattcat attttgttct tccccttcat ggctcaaggc     60

cacatgattc caattttgga catggccaag cttttctcga ggagaggagc caagtcaacc    120

cttctcacaa ccccaatcaa cgctaagatc ttcgagaaac ctattgaagc attcaaaaat    180

caaaaccctg atctcgaaat cggaatcaag atcttcaatt tcccttgtgt agagcttgga    240

ttgcctgaag gatgcgagaa cgctgacttt atcaactcat accaaaaatc tgactcaggt    300

gacttgttct tgaagtttct tttctctacc aagtatatga aacaacagtt ggagagtttc    360

attgaaacaa ccaaaccaag tgctcttgtt gccgatatgt tcttcccttg ggcgacagaa    420

tctgctgaga agctcggtgt accaagactt gtgttccacg gtacatcttt cttttctttg    480

tgttgttcgt ataacatgag gattcataag ccacacaaga aagtcgctac gagttctact    540
```

-continued

```
ccttttgtaa tccctggtct cccaggagac atagttatta cagaagacca agccaatgtt    600
gccaaagaag aaacgccaat gggaaagttt atgaaagagg ttagggaatc agagaccaat    660
agctttggtg tattggttaa tagcttctac gagctggaat cagcttatgc tgatttttat    720
cgtagttttg tggcgaaaag agcttggcat atcggtccgc tttcgctatc taacagagag    780
ttaggagaga aagccagaag agggaaaaag gctaacattg atgagcaaga atgcctaaaa    840
tggctggact ctaagacacc tggttcagta gtttacttgt cctttgggag cggaactaat    900
ttcaccaacg accagctgtt agagatcgct tttggtcttg aaggttctgg acaaagtttc    960
atctgggtgg ttaggaaaaa tgaaaaccaa ggtaaattgt ttctccccag ccattattaa   1020
ccaacatagt aatgttaata tttgtgtata tattcgtatt gccaaatatg ctctgatacc   1080
atggcaagta atagattggc tcatgtattt tatttgtgat catgtagaat tttcttaaca   1140
gttatgactt ggtgttggta tggttgggac aggtgacaat gaagagtggt tgcctgaagg   1200
gtttaaagag aggacaacag ggaaagggct aataatacct ggatgggcgc cgcaagtgct   1260
gatacttgac cataaagcaa ttggaggatt tgtgactcat tgcggatgga actcggctat   1320
agagggcatt gccgcggggc tgcctatggt aacatggcca atgggggcag aacagttcta   1380
caatgagaag ctattgacaa aagtgttgag aataggagtg aacgttggag ctaccgagtt   1440
ggtgaaaaaa ggaaagttga ttagtagagc acaagtggag aaggcagtaa gggaagtgat   1500
tggtggtgag aaggcagagg aaaggcggct atgggctaag aagctgggcg agatggctaa   1560
agccgctgtg gaagaaggag ggtcctctta taatgatgtg aacaagttta tggaagagct   1620
gaatggtaga aagtag                                                   1636
```

<210> SEQ ID NO 42
<211> LENGTH: 1476
<212> TYPE: DNA
<213> ORGANISM: Arabidopsis thaliana

<400> SEQUENCE: 42

```
atggcatcgg aatttcgtcc tcctcttcat tttgttctct tccctttcat ggctcaaggc     60
cacatgatcc caatggtaga tattgcaagg ctcctggctc agcgcggggt gactataacc    120
attgtcacta cacctcaaaa cgcaggccgg ttcaagaacg ttcttagccg ggctatccaa    180
tccggcttgc ccatcaatct cgtgcaagta aagtttccat ctcaagaatc gggttcaccg    240
gaaggacagg agaatttgga cttgctcgat tcattggggg cttcattaac cttcttcaaa    300
gcatttagcc tgctcgagga accagtcgag aagctcttga aagagattca acctaggcca    360
aactgcataa tcgctgacat gtgtttgcct tatacaaaca gaattgccaa gaatcttggt    420
ataccaaaaa tcatctttca tggcatgtgt tgcttcaatc ttctttgtac gcacataatg    480
caccaaaacc acgagttctt ggaaactata gagtctgaca aggaatactt ccccattcct    540
aatttccctg acagagttga gttcacaaaa tctcagcttc caatggtatt agttgctgga    600
gattggaaag acttccttga cggaatgaca gaaggggata acacttctta tggtgtgatt    660
gttaacacgt ttgaagagct cgagccagct tatgttagag actacaagaa ggttaaagcg    720
ggtaagatat ggagcatcgg accggtttcc ttgtgcaaca agttaggaga agaccaagct    780
gagaggggaa acaaggcgga cattgatcaa gacgagtgta ttaaatggct tgattctaaa    840
gaagaagggt cggtgctata tgtttgcctt ggaagtatat gcaatcttcc tctgtctcag    900
ctcaaagagc tcggcttagg cctcgaggaa tcccaaagac ctttcatttg ggtcataaga    960
```

-continued

```
ggttgggaga agtataacga gttacttgaa tggatctcag agagcggtta taaggaaaga   1020

atcaaagaaa gaggccttct cataacagga tggtcgcctc aaatgcttat ccttacacat   1080

cctgccgttg gaggattctt gacacattgt ggatggaact ctactcttga aggaatcact   1140

tcaggcgttc cattactcac gtggccactg tttggagacc aattctgcaa tgagaaattg   1200

gcggtgcaga tactaaaagc cggtgtgaga gctggggttg aagagtccat gagatgggga   1260

gaagaggaga aaataggagt actggtggat aaagaaggag taaagaaggc agtggaggaa   1320

ttgatgggtg atagtaatga tgctaaggag agaagaaaaa gagtgaaaga gcttggagaa   1380

ttagctcaca aggctgtgga agaaggaggc tcttctcatt ccaacatcac attcttgcta   1440

caagacataa tgcaattaga acaacccaag aaatga                             1476
```

```
<210> SEQ ID NO 43
<211> LENGTH: 1491
<212> TYPE: DNA
<213> ORGANISM: Arabidopsis thaliana

<400> SEQUENCE: 43

atggctacgg aaaaaaccca ccaatttcat ccttctcttc actttgtcct cttccctttc     60

atggctcaag gccacatgat tcccatgatt gatattgcaa gactcttggc tcagcgtggt    120

gtgaccataa caattgtcac gacacctcac aacgcagcaa ggtttaagaa tgtcctaaac    180

cgagcgatcg agtctggctt ggccatcaac atactgcatg tgaagtttcc atatcaagag    240

tttggtttgc cagaaggaaa agagaatata gattcgttag actcaacgga gttgatggta    300

cctttcttca aagcggtgaa cttgcttgaa gatccggtca tgaagctcat ggaagagatg    360

aaacctagac ctagctgtct aatttctgat tggtgtttgc cttatacaag cataatcgcc    420

aagaacttca atataccaaa gatagttttc cacggcatgg gttgctttaa tcttttgtgt    480

atgcatgttc tacgcagaaa cttagagatc ctagagaatg taaagtcgga tgaagagtat    540

ttcttggttc ctagttttcc tgatagagtt gaatttacaa agcttcaact tcctgtgaaa    600

gcaaatgcaa gtggagattg gaaagagata atggatgaaa tggtaaaagc agaatacaca    660

tcctatggtg tgatcgtcaa cacatttcag gagttggagc caccttatgt caaagactac    720

aaagaggcaa tggatggaaa agtatggtcc attggacccg tttccttgtg taacaaggca    780

ggtgcagaca aagctgagag gggaagcaag gccgccattg atcaagatga gtgtcttcaa    840

tggcttgatt ctaaagaaga aggttcggtg ctctatgttt gccttggaag tatatgtaat    900

cttcctttgt ctcagctcaa ggagctgggg ctaggccttg aggaatctcg aagatctttt    960

atttgggtca taagaggttc ggaaaagtat aaagaactat ttgagtggat gttggagagc   1020

ggttttgaag aaagaatcaa agagagagga cttctcatta aagggtgggc acctcaagtc   1080

cttatccttt cacatccttc cgttggagga ttcctgacac actgtggatg gaactcgact   1140

ctcgaaggaa tcacctcagg cattccactg atcacttggc cgctgtttgg agaccaattc   1200

tgcaaccaaa aactggtcgt tcaagtacta aaagccggtg taagtgccgg ggttgaagaa   1260

gtcatgaaat ggggagaaga agataaaata ggagtgttag tggataaaga aggagtgaaa   1320

aaggctgtgg aagaattgat gggtgatagt gatgatgcaa aagagaggag aagaagagtc   1380

aaagagcttg gagaattagc tcacaaagct gtggaaaaag gaggctcttc tcattctaac   1440

atcacactct tgctacaaga cataatgcaa ctagcacaat tcaagaattg a            1491

<210> SEQ ID NO 44
<211> LENGTH: 1488
```

-continued

<212> TYPE: DNA
<213> ORGANISM: Arabidopsis thaliana

<400> SEQUENCE: 44
atggtttccg aaacaaccaa atcttctcca cttcactttg ttctcttccc tttcatggct 60
caaggccaca tgattcccat ggttgatatt gcaaggctct tggctcagcg tggtgtgatc 120
ataacaattg tcacgacgcc tcacaatgca gcgaggttca agaatgtcct aaaccgtgcc 180
attgagtctg gcttgcccat caacttagtg caagtcaagt ttccatatct agaagctggt 240
ttgcaagaag gacaagagaa tatcgattct cttgacacaa tggagcggat gatacctttc 300
tttaaagcgg ttaactttct cgaagaacca gtccagaagc tcattgaaga gatgaaccct 360
cgaccaagct gtctaatttc tgatttttgt ttgccttata caagcaaaat cgccaagaag 420
ttcaatatcc caaagatcct cttccatggc atgggttgct tttgtcttct gtgtatgcat 480
gttttacgca agaaccgtga gatcttggac aatttaaagt cagataagga gcttttcact 540
gttcctgatt ttcctgatag agttgaattc acaagaacgc aagttccggt agaaacatat 600
gttccagctg gagactggaa agatatcttt gatggtatgg tagaagcgaa tgagacatct 660
tatggtgtga tcgtcaactc atttcaagag ctcgagcctg cttatgccaa agactacaag 720
gaggtaaggt ccggtaaagc atggaccatt ggacccgttt ccttgtgcaa caaggtagga 780
gccgacaaag cagagagggg aaacaaatca gacattgatc aagatgagtg ccttaaatgg 840
ctcgattcta agaaacatgg ctcggtgctt tacgtttgtc ttggaagtat ctgtaatctt 900
cctttgtctc aactcaagga gctgggacta ggcctagagg aatcccaaag acctttcatt 960
tgggtcataa gaggttggga gaagtacaaa gagttagttg agtggttctc ggaaagcggc 1020
tttgaagata gaatccaaga tagaggactt ctcatcaaag gatggtcccc tcaaatgctt 1080
atcctttcac atccatcagt tggagggttc ctaacacact gtggttggaa ctcgactctt 1140
gaggggataa ctgctggtct accgctactt acatggccgc tattcgcaga ccaattctgc 1200
aatgagaaat tggtcgttga ggtactaaaa gccggtgtaa gatccggggt tgaacagcct 1260
atgaaatggg gagaagagga gaaaatagga gtgttggtgg ataaagaagg agtgaagaag 1320
gcagtggaag aattaatggg tgagagtgat gatgcaaaag agagaagaag aagagccaaa 1380
gagcttggag attcagctca caaggctgtg gaagaaggag gctcttctca ttctaacatc 1440
tctttcttgc tacaagacat aatggaactg gcagaaccca ataattga 1488

<210> SEQ ID NO 45
<211> LENGTH: 1488
<212> TYPE: DNA
<213> ORGANISM: Arabidopsis thaliana

<400> SEQUENCE: 45
atggctttcg aaaaaaacaa cgaacctttt cctcttcact ttgttctctt ccctttcatg 60
gctcaaggcc acatgattcc catggttgat attgcaaggc tcttggctca gcgaggtgtg 120
cttataacaa ttgtcacgac gcctcacaat gcagcaaggt tcaagaatgt cctaaaccgt 180
gccattgagt ctggtttgcc catcaaccta gtgcaagtca agtttccata tcaagaagct 240
ggtctgcaag aaggacaaga aaatatggat ttgcttacca cgatggagca gataacatct 300
ttctttaaag cggttaactt actcaaagaa ccagtccaga accttattga agagatgagc 360
ccgcgaccaa gctgtctaat ctctgatatg tgtttgtcgt atacaagcga aatcgccaag 420
aagttcaaaa taccaaagat cctcttccat ggcatgggtt gcttttgtct tctgtgtgtt 480

-continued

```
aacgttctgc gcaagaaccg tgagatcttg gacaatttaa agtctgataa ggagtacttc    540

attgttcctt attttcctga tagagttgaa ttcacaagac ctcaagttcc ggtggaaaca    600

tatgttcctg caggctggaa agagatcttg gaggatatgg tagaagcgga taagacatct    660

tatggtgtta tagtcaactc atttcaagag ctcgaacctg cgtatgccaa agacttcaag    720

gaggcaaggt ctggtaaagc atggaccatt ggacctgttt ccttgtgcaa caaggtagga    780

gtagacaaag cagagagggg aaacaaatca gatattgatc aagatgagtg ccttgaatgg    840

ctcgattcta aggaaccggg atctgtgctc tacgtttgcc ttggaagtat ttgtaatctt    900

cctctgtctc agctccttga gctgggacta ggcctagagg aatcccaaag acctttcatc    960

tgggtcataa gaggttggga gaaatacaaa gagttagttg agtggttctc ggaaagcggc   1020

tttgaagata gaatccaaga tagaggactt ctcatcaaag gatggtcccc tcaaatgctt   1080

atcctttcac atccttctgt tggagggttc ttaacgcact gcggatggaa ctcgactctt   1140

gaggggataa ctgctggtct accaatgctt acatggccac tatttgcaga ccaattctgc   1200

aacgagaaac tggtcgtaca aatactaaaa gtcggtgtaa gtgccgaggt taaagaggtc   1260

atgaaatggg gagaagaaga gaagatagga gtgttggtgg ataaagaagg agtgaagaag   1320

gcagtggaag aactaatggg tgagagtgat gatgcaaaag agagaagaag aagagccaaa   1380

gagcttggag aatcagctca caaggctgtg gaagaaggag gctcctctca ttctaatatc   1440

actttcttgc tacaagacat aatgcaacta gcacagtcca ataattga                1488
```

<210> SEQ ID NO 46
<211> LENGTH: 1473
<212> TYPE: DNA
<213> ORGANISM: Arabidopsis thaliana

<400> SEQUENCE: 46

```
atgtgttctc atgatcctct tcacttcgtc gtaataccct ttatggccca aggccatatg     60

atcccattgg tcgacatctc taggctcttg tcccagcgcc aaggcgtgac tgtctgcatc    120

atcacaacta ctcaaaatgt agccaagatc aagacttcac tctcattttc ctctttgttt    180

gcgactatca acatcgttga agttaagttt ctgtctcaac aaacgggttt gccagaaggg    240

tgcgagagtt tagatatgtt ggcttcaatg ggcgatatgg tgaagttctt tgatgctgcc    300

aactcacttg aggagcaagt tgagaaagct atggaagaga tggttcagcc gcggccaagc    360

tgcatcattg gagacatgag ccttcctttc acttcaagac ttgccaagaa attcaagatc    420

cccaaactta tcttccatgg gttttcttgt ttcagcctca tgtctataca agtggttcga    480

gaaagcggga tcttgaaaat gatagaatca aacgacgagt attttgattt gcccggcttg    540

cctgacaaag ttgagttcac gaaacctcag gtctctgtgt tgcaacctgt tgaaggaaat    600

atgaaagaga gtacggccaa gattattgaa gctgataatg actcttatgg tgttattgtg    660

aacacttttg aagagttaga ggttgattat gcaagagaat ataggaaagc aagggctgga    720

aaagtttggt gcgttggacc tgtttccttg tgcaataggt tagggttaga caaagctaaa    780

agaggagata aggcttctat tggtcaagac caatgtcttc aatggcttga ctctcaagaa    840

actggttcag tgctctacgt ttgccttgga agtctatgta atcttccctt ggctcagctc    900

aaagagctgg gactaggcct tgaggcatct aataaacctt tcatatgggt tataagagaa    960

tggggaaaat atggagattt agcaaattgg atgcaacaaa gcggatttga agagcggatc   1020

aaagatagag gactggtgat caaaggttgg gcgccgcaag ttttcatcct ctcacacgca   1080

tccattggag ggtttttgac tcactgtgga tggaactcga cactagaagg aattactgca   1140
```

-continued

```
ggagttccat tattgacatg gcctttgttt gctgaacaat tcttgaatga gaagttagtt   1200

gtgcagatac taaaagcagg gttaaagata ggagtagaga aattgatgaa atatggaaaa   1260

gaagaggaga taggagcgat ggtgagcaga gaatgtgtga gaaaagctgt ggatgagcta   1320

atgggtgata gtgaagaagc agaagagaga agaagaaaag ttacagaact tagtgacttg   1380

gcaaataagg ctttggaaaa aggaggatct tcagattcta atatcacatt gctcattcaa   1440

gatattatgg agcaatcaca aaatcaattt taa                                1473
```

<210> SEQ ID NO 47
<211> LENGTH: 1437
<212> TYPE: DNA
<213> ORGANISM: Arabidopsis thaliana

<400> SEQUENCE: 47

```
atggagcata agagaggaca tgtattagca gtgccgtacc caacgcaagg acacatcaca     60

ccattccgcc aattctgcaa acgacttcac ttcaaaggtc tcaaaaccac tctcgctctc    120

accactttcg tcttcaactc catcaatcct gacctatccg gtccaatctc catagccacc    180

atctccgatg gctatgacca tggggggtttc gagacagctg actccatcga cgactacctc    240

aaagacttta aaacttccgg ctcgaaaacc attgcagaca tcatccaaaa acaccagact    300

agtgataacc ccatcacttg tatcgtctat gatgctttcc tgccttgggc acttgacgtt    360

gctagagagt ttggtttagt tgcgactcct ttctttacgc agccttgtgc tgttaactat    420

gtttattatc tttcttacat aaacaatgga agcttgcaac ttcccattga ggaattgcct    480

tttcttgagc tccaagattt gccttctttc ttctctgttt ctggctctta tcctgcttac    540

tttgagatgg tgcttcaaca gttcataaat ttcgaaaaag ctgatttcgt tctcgttaat    600

agcttccaag agttggaact gcatgttaga tctctctcta tctctttctt acaattctta    660

aaccatctct tgttcttgtg catgtactaa ctgctctttt tttgtttaca ggagaatgaa    720

ttgtggtcga aagcttgtcc tgtgttgaca attggtccaa ctattccatc aatttactta    780

gaccaacgta tcaaatcaga caccggctat gatcttaatc tctttgaatc gaaagatgat    840

tccttctgca ttaactggct cgacacaagg ccacaagggt cggtggtgta cgtagcattc    900

ggaagcatgg ctcagctgac taatgtgcag atggaggagc ttgcttcagc agtaagcaac    960

ttcagcttcc tgtgggtggt cagatcttca gaggaggaaa aactcccatc agggtttctt   1020

gagacagtga ataaagaaaa gagcttggtc ttgaaatgga gtcctcagct tcaagttctg   1080

tcaaacaaag ccatcggttg tttcttgact cactgtggct ggaactcaac catggaggct   1140

ttgaccttcg ggttcccat ggtggcaatg ccccaatgga ctgatcaacc gatgaacgca    1200

aagtacatac aagatgtgtg gaaggctgga gttcgtgtga agacagagaa ggagagtggg   1260

attgccaaga gagaggagat tgagtttagc attaaggaag tgatggaagg agagaggagc   1320

aaagagatga agaagaacgt gaagaaatgg agagacttgg ctgtcaagtc actcaatgaa   1380

ggaggttcta cggatactaa cattgataca tttgtatcaa gggttcagag caaatag      1437
```

<210> SEQ ID NO 48
<211> LENGTH: 1451
<212> TYPE: DNA
<213> ORGANISM: Arabidopsis thaliana

<400> SEQUENCE: 48

```
atggaagaac taggagtgaa gagaaggata gtattggttc cagttccagc acaaggtcat     60
```

-continued

```
gtaactccga ttatgcaact cgggaaggct ctttactcca agggcttctc catcactgtt    120

gttctcacac agtataatcg agttagctca tccaaggact tctctgattt tcatttcctc    180

accatcccag gcagcttgac cgagtctgat ctcaaaaacc ttggaccatt caagtttctc    240

ttcaagctca atcaaatttg cgaggcaagc ttcaagcaat gtattggtca actattgcag    300

gagcaaggta atgatatcgc ttgtgtcgtc tacgatgagt acatgtactt ctcccaagct    360

gcagttaaag agtttcaact tcctagcgtc ctcttcagca cgacaagtgc tactgccttt    420

gtctgtcgct ctgttttgtc tagagtcaac gcagagtcat tcttgcttga catgaaaggt    480

actcaagatt ttttagcttg ttaactcaaa ctttaaaagt gcatttaggt atataaacca    540

atccaaatgc tgttgtttgc tttgcagatc ccaaagtgtc agacaaggaa tttccagggt    600

tgcatccgct aaggtacaag gacctgccaa cttcagcatt tgggccatta gagagtatac    660

tcaaggttta cagtgagact gtcaacattc gaacagcttc ggcagttatc atcaactcaa    720

caagctgtct agagagctca tctttggcat ggttacaaaa acaactgcaa gttccagtgt    780

atcctatagg cccacttcac attgcagctt cagcgccttc tagtttactt gaagaggaca    840

ggagttgcct tgagtggttg aacaagcaaa aaataggctc agtgatttac ataagtttgg    900

gaagcttggc tctaatggaa actaaagaca tgttggagat ggcttggggt ttacgtaata    960

gcaaccaacc tttcttatgg gtgatccgac cgggttctat tcccggctcg gaatggacag   1020

agtctttacc ggaggaattc agtaggttgg tttcagaaag aggttacatt gtgaaatggg   1080

caccacagat agaagttctc agacatcctg cagtgggagg gttttggagt cactgcggat   1140

ggaactcgac cctagagagc atcggggaag gagttccgat gatctgtagg ccttttacgg   1200

gagatcagaa agtcaatgcg aggtacttag agagagtttg gagaattggg gttcaattgg   1260

aaggagagct ggataaagga acagtggaga gagctgtaga gagattgatt atggatgaag   1320

aaggagcaga aatgaggaag agagttatca acttgaaaga gaagcttcaa gcctctgtca   1380

agagtagagg ttcctcattc agctcattag acaactttgt caattcctta aaaatgatga   1440

atttcatgta g                                                        1451
```

<210> SEQ ID NO 49
<211> LENGTH: 1433
<212> TYPE: DNA
<213> ORGANISM: Arabidopsis thaliana

<400> SEQUENCE: 49

```
atggaggaaa agccggcggg cagaagagta gtgttggttg cagttccagc tcaaggacat     60

atctctccaa taatgcaact tgcaaaaaca cttcacttga agggtttctc aatcacaatc    120

gctcagacaa agttcaatta ctttagccct tcagatgact tcactgattt tcagtttgtc    180

accattccag aaagcttacc agagtctgat tttgaggatc tcgggccaat agagtttctg    240

cataagctca acaaagagtg tcaggtgagc ttcaaagact gtttgggtca gttgttgctg    300

caacaaggta atgagatagc ctgtgttgtc tacgacgagt tcatgtactt tgctgaagct    360

gcagccaaag agtttaagct tccaaacgtc attttcagca ccacaagtgc cacggctttt    420

gtttgccgct ctgcattcga caaactttat gcaaacagta tcctgactcc cttgaaaggt    480

actcttgaat tctctgtctt ctattcttgc tggtttctat aatctgtaac agcatggttc    540

ttgacctttt tgcagaaccc aaaggacaac aaaacgagct agtgccagag tttcatcccc    600

tgagatgcaa agactttccg gtttcacatt gggcatcatt agaaagcatg atggagctgt    660

ataggaatac agttgacaaa cggacagctt cctcggtgat aatcaacaca gcgagctgtc    720
```

-continued

```
tagagagctc atctctgtct cgtctgcagc aacagctaca aattccagtt tatcctatag    780

gccctcttca cctggtggca tcagcttcta cgagtcttct tgaagagaac aagagctgta    840

ttgaatggtt gaacaaacaa aagaaaaact ctgtgatatt cgtaagcttg ggaagcttag    900

ctttgatgga aatcaatgag gtgatagaaa ctgctttggg attggatagt agcaagcaac    960

agttcttgtg ggtcattcgg ccagggtcag tacgtggttc ggaatggata gagaacttgc   1020

ctaaggagtt tagtaagata atttcgggtc gaggttacat tgtgaaatgg gctccacaga   1080

aggaagtact ttctcatcct gcagtaggag gatttttggag ccattgcgga tggaactcga   1140

cactagagag catcggggaa ggagttccaa tgatttgcaa gccgttttcc agtgatcaaa   1200

tggtgaatgc gagatacttg gagtgtgtat ggaaaattgg gattcaagtt gagggtgatc   1260

tagacagagg agcggtcgag agagctgtga ggaggttaat ggtggaggaa gaaggggagg   1320

ggatgaggaa gagagctatc agtttgaaag agcaacttag agcctctgtt ataagtggag   1380

gttcttcaca caactcgcta gaggagtttg tacactacat gaggactcta tga          1433
```

<210> SEQ ID NO 50
<211> LENGTH: 1457
<212> TYPE: DNA
<213> ORGANISM: Arabidopsis thaliana

<400> SEQUENCE: 50

```
atgcaggttt tgggaatgga ggaaaagcct gcaaggagaa gcgtagtgtt ggttccattt     60

ccagcacaag gacatatatc tccaatgatg caacttgcca aaacccttca cttaaagggt    120

ttctcgatca cagttgttca gactaagttc aattacttta gcccttcaga tgacttcact    180

catgattttc agttcgtcac cattccagaa agcttaccag agtctgattt caagaatctc    240

ggaccaatac agtttctgtt taagctcaac aaagagtgta aggtgagctt caaggactgt    300

ttgggtcagt tggtgctgca acaaagtaat gagatctcat gtgtcatcta cgatgagttc    360

atgtactttg ctgaagctgc agccaaagag tgtaagcttc caaacatcat tttcagcaca    420

acaagtgcca cggctttcgc ttgccgctct gtatttgaca aactatatgc aaacaatgtc    480

caagctccct tgaaaggtac tctaaaactc tctgtttcgt ggtttccgcg agtggctata    540

agattgaaac agcattgttt ttgacctttt ttgcagaaac taaaggacaa caagaagagc    600

tagttccgga gttttatccc ttgagatata aagactttcc agtttcacgg tttgcatcat    660

tagagagcat aatggaggtg tataggaata cagttgacaa acggacagct tcctcggtga    720

taatcaacac tgcgagctgt ctagagagct catctctgtc ttttctgcaa caacaacagc    780

tacaaattcc agtgtatcct ataggccctc ttcacatggt ggcctcagct cctacaagtc    840

tgcttgaaga gaacaagagc tgcatcgaat ggttgaacaa acaaaaggta aactcggtga    900

tatacataag catgggaagc atagctttaa tggaaatcaa cgagataatg gaagtcgcgt    960

caggattggc tgctagcaac caacacttct tatgggtgat ccgaccaggg tcaatacctg   1020

gttccgagtg gatagagtcc atgcctgaag agtttagtaa gatggttttg gaccgaggtt   1080

acattgtgaa atgggctcca cagaaggaag tactttctca tcctgcagta ggagggtttt   1140

ggagccattg tggatggaac tcgacactag aaagcatcgg ccaaggagtt ccaatgatct   1200

gcaggccatt ttcgggtgat caaaaggtga acgctagata cttggagtgt gtatggaaaa   1260

ttgggattca agtggagggt gagctagaca gaggagtggt cgagagagct gtgaagaggt   1320

taatggttga cgaagaagga gaggagatga ggaagagagc tttcagttta aaagagcaac   1380
```

-continued

```
ttagagcctc tgttaaaagt ggaggctctt cacacaactc gctagaagag tttgtacact   1440

tcataaggac tctatga                                                  1457
```

<210> SEQ ID NO 51
<211> LENGTH: 1434
<212> TYPE: DNA
<213> ORGANISM: Arabidopsis thaliana

<400> SEQUENCE: 51

```
atggaggaaa agcaagtgaa ggagacaagg atagtgttgg ttccagttcc agctcaaggt     60

catgtaactc cgatgatgca actaggaaaa gctcttcact caaagggttt ctccatcact    120

gttgttctga cacagtctaa tcgagttagc tcttccaaag acttctctga tttccatttc    180

ctcaccatcc caggcagctt aactgagtct gatctccaaa acctaggacc acaaaagttt    240

gtgctcaagc tcaatcaaat ttgtgaggca agcttcaagc agtgtatagg tcaactattg    300

catgaacaat gtaataatga tattgcttgt gtcgtctacg atgagtacat gtacttctct    360

catgctgcag taaaagagtt tcaacttcct agtgtcgtct ttagcacgac aagtgctact    420

gcttttgtct gtcgctctgt tttgtctaga gtcaacgcag agtcgttctt gatcgacatg    480

aaaggtattc aagattctag cttgttttat cttaattcaa aatcctattt atagaaacta    540

atccaaatga tcgatgttat cttttcagat cctgaaacac aagacaaagt atttccaggg    600

ttgcatcctc tgaggtacaa ggatctacca acttcagtat ttgggccaat agagagtacg    660

ctcaaggttt acagtgagac tgtgaacact cgaacagctt ccgctgttat catcaactca    720

gcaagctgtt tagagagctc atctttggca aggttgcaac aacaactgca agttccggtg    780

tatcctatag gcccacttca tattacagct tcagcgcctt ctagtttact agaagaagac    840

aggagttgcg ttgagtggtt gaacaagcaa aaatcaaatt cagttattta cataagcttg    900

ggaagcttgg ctctaatgga caccaaagac atgttggaga tggcttgggg attaagtaat    960

agcaaccaac ctttcttatg ggtggtcaga ccgggctcta ttccggggtc agaatggaca   1020

gagtccttac cagaggaatt caataggttg gtttcagaaa gaggttacat tgtgaaatgg   1080

gctccgcaga tggaagttct cagacatcct gcagtaggag ggttttggag tcactgtgga   1140

tggaactcaa cagtagagag catcggggaa ggagttccga tgatatgtag gcctttcacc   1200

ggggatcaga aagtcaatgc gaggtactta gagagagttt ggagaattgg ggttcaattg   1260

gagggagatc tggataaaga aactgtggag agagctgtag agtggttgct tgtggatgaa   1320

gaaggagcag aaatgaggaa gagagccatt gacttgaaag aaaagattga aacctctgtt   1380

agaagtggag gttcctcatg cagctcacta gacgactttg ttaattccat gtga         1434
```

<210> SEQ ID NO 52
<211> LENGTH: 1458
<212> TYPE: DNA
<213> ORGANISM: Arabidopsis thaliana

<400> SEQUENCE: 52

```
atgaccaaat tctccgagcc aatcagagac tcccacgtgg cagttctcgc gtttttcccc     60

gttggcgctc atgccggtcc tctcttagcc gtcactcgcc gtctcgccgc cgcttctccc    120

tccaccatct tttctttctt caacaccgca agatcaaacg cgtcgttgtt ctcctctgat    180

catcccgaga acatcaaggt ccacgacgtc tctgacggtg ttccggaggg aaccatgctc    240

gggaatccac tggagatggt cgagctgttt ctcgaagcgg ctccacgtat tttccggagc    300

gaaatcgcgg cggcagagat agaagttgga aagaaagtga catgcatgct aacagatgcc    360
```

-continued

```
ttcttctggt tcgcagcgga catagcggct gagctgaacg cgacttgggt tgccttctgg    420
gccggcggag caaactcact ctgtgctcat ctctacactg atctcatcag agaaaccatc    480
ggtctcaaag gtaactagct ttttagcgtt tagtgattat tccacaaatt cagctactac    540
actttgtatg tatttatggt tattattatt atttatctcc tggtagatgt gagtatggaa    600
gagacattag ggtttatacc aggaatggag aattacagag ttaaagatat accagaggaa    660
gttgtatttg aagatttgga ctctgttttc ccaaaggctt tataccaaat gagtcttgct    720
ttacctcgtg cctctgctgt tttcatcagt tcctttgaag agttagaacc tacattgaac    780
tataacctaa gatccaaact taaacgtttc ttgaacatcg cccctctcac gttattatct    840
tctacatcgg agaaagagat gcgtgatcct catggctgct ttgcttggat ggggaagaga    900
tcagctgctt ctgtagcgta cattagcttc ggcaccgtca tggaacctcc tcctgaagag    960
cttgtggcga tagcacaagg gttggaatca agcaaagtgc cgtttgtttg gtcgctgaag   1020
gagaagaaca tggttcatct accaaaaggg tttttggatc ggacaagaga gcaagggata   1080
gtggttcctt gggctccaca agtggaactg ctgaaacacg aggcaatggg tgtgaatgtg   1140
acacattgtg gatggaactc agtgttggag agtgtgtcgg caggtgtacc gatgatcggc   1200
agaccgattt tggcggataa taggctcaac ggaagagcag tggaggttgt gtggaaggtt   1260
ggagtgatga tggataatgg agtcttcacg aaagaaggat ttgagaagtg tttgaatgat   1320
gtttttgttc atgatgatgg taagacgatg aaggctaatg ccaagaagct taaagaaaaa   1380
ctccaagaag atttctccat gaaaggaagc tctttagaga atttcaaaat attgttggac   1440
gaaattgtga aagtttag                                                 1458
```

<210> SEQ ID NO 53
<211> LENGTH: 1420
<212> TYPE: DNA
<213> ORGANISM: Arabidopsis thaliana

<400> SEQUENCE: 53

```
atgaaagtga acgaggaaaa caacaagccg acaaagaccc atgtcttaat cttcccattt     60
ccggcgcaag gtcacatgat tcccctcctc gacttcaccc accgccttgc tctccgcggc    120
ggcgccgcct taaaaataac cgtcctagtc actccaaaaa accttccttt tctctctccg    180
cttctctccg ccgtagttaa catcgaacca cttatcctcc cttttccctc ccacccttca    240
atcccctccg gcgtcgaaaa cgtccaagac ttacctcctt caggcttccc tttaatgatc    300
cacgcgcttg gtaatctcca cgcgccgctt atctcttgga ttacttctca cccttctcct    360
ccagtagcca tcgtatctga tttcttcctt ggttggacca aaaacctcgg aatccctcgt    420
ttcgatttct ctccctccgc tgctatcact tgctgcatac tcaatactct ctggatcgaa    480
atgcccacca agatcaacga agatgacgat aacgagatcc tccactttcc caagatcccg    540
aattgtccaa aataccgttt tgatcagatc tcctctcttt acagaagtta cgttcacgga    600
gatccagctt gggagttcat aagagactcc tttagagata acgtggcgag ttggggactc    660
gtcgtgaact cgttcaccgc catggaaggt gtttatctcg aacatcttaa gcgagagatg    720
ggccatgatc gtgtatgggc tgtaggccca attattccgt tatctgggga taaccgtggt    780
ggcccgactt ctgtttctgt tgatcacgtg atgtcgtggc ttgacgcacg tgaggataac    840
cacgtggtgt acgtgtgctt tggaagtcaa gtagttttga ctaaagagca gactcttgca    900
ctcgcctctg ggcttgagaa aagcggcgtc catttcatat gggccgtaaa ggagcccgtt    960
```

-continued

```
gagaaagact caacacgtgg caacatcctg gacggtttcg acgatcgcgt ggctgggaga   1020

ggtctggtga tcagaggatg ggctccacaa gtagctgtgc tacgtcaccg agccgttggc   1080

gcgtttttaa cgcactgtgg ttggaactct gtggtggagg cggttgtcgc cggcgttttg   1140

atgctgacgt ggccgatgag agctgaccag tacactgacg cgtctctggt ggttgatgag   1200

ttgaaagtag gtgtgcgtgc ttgcgaagga cctgacacgg tgcctgaccc ggacgagtta   1260

gctcgagttt tcgctgattc cgtgaccgga aatcaaacgg agaggatcaa agccgtggag   1320

ctgaggaaag cagcgttgga tgcgattcaa gaacgtggga gctcagtgaa tgatttagat   1380

ggatttatcc aacatgtcgt tagtttagga ctaaacaaat                          1420
```

<210> SEQ ID NO 54
<211> LENGTH: 1494
<212> TYPE: DNA
<213> ORGANISM: Arabidopsis thaliana

<400> SEQUENCE: 54

```
atgagcatag atatttttca agaaataaga ataaagaaaa ttctactctt aatggcggaa     60

gcaaacactc cacacatagc aatcatgccg agtcccggta tgggtcacct tatcccattc    120

gtcgagttag caaagcgact cgttcagcac gactgtttca ccgtcacaat gatcatctcc    180

ggtgaaactt cgccgtctaa ggcacaaaga tccgttctca actctctccc ttcctccata    240

gcctccgtat ttctccctcc cgccgatctt tccgatgttc cctccacagc gcgaatcgaa    300

actcgggcca tgctcaccat gactcgttcc aatccggcgc tccgggagct tttggctct     360

ttatcaacga agaaaagtct cccggcggtt ctcgtcgtcg atatgtttgg tgcggatgcg    420

ttcgacgtgg ccgttgactt ccacgtgtca ccatacattt tctatgcatc caatgcaaac    480

gtcttgtcgt tttttcttca cttgccgaaa ctagacaaaa cggtgtcgtg tgagtttagg    540

tacttaaccg aaccgcttaa gattcccggc tgtgtcccga taaccggtaa ggactttctt    600

gatacggttc aagaccgaaa cgacgacgca tacaaattgc ttctccataa caccaagagg    660

tacaaagaag ctaaagggat tctagtgaat tccttcgttg atttagagtc gaatgcaata    720

aaggccttac aagaaccggc tcctgataaa ccaacggtat acccgattgg gccgctggtt    780

aacacaagtt catctaatgt taacttggaa gacaagttcg gatgtttaag ttggctagac    840

aaccaaccat tcggctcggt tctatacata tcatttggaa gcggcggaac acttacatgt    900

gagcagttta atgagcttgc tattggtctt gcggagagcg gaaaacggtt tatttgggtc    960

atacgaagtc caagcgagat agttagttcg tcgtatttca atccacacag cgagacagac   1020

ccctttcgt ttttaccaat tgggttctta gaccgaacca aagagaaagg tttggtggtt    1080

ccatcatggg ctccacaggt tcaaatcctg gctcatccat ccacatgcgg gtttttaaca   1140

cactgtggat ggaattcgac cttagaaagc attgtaaacg gtgtaccact catagcgtgg   1200

cctttattcg cggagcaaaa gatgaataca ttgctactcg tggaggatgt tggagcggct   1260

ctaagaatcc atgcgggtga agatgggatt gtacggaggg aagaagtggt gagagtggtg   1320

aaggcactga tggaaggtga agagggaaaa gccataggaa ataaagtgaa ggagttgaaa   1380

gaaggagttg ttagagtctt gggtgacgat ggattgtcca gcaagtcatt tggtgaagtt   1440

ttgttaaagt ggaaaacgca ccagcgagat atcaaccaag agacgtccca ctaa         1494
```

<210> SEQ ID NO 55
<211> LENGTH: 35
<212> TYPE: DNA
<213> ORGANISM: Artificial Sequence -continued
<220> FEATURE:
<223> OTHER INFORMATION: Description of Artificial Sequence: Synthetic
primer

<400> SEQUENCE: 55
cgggtgatca ggtaccatgg cgccaccgca ttttc 35

<210> SEQ ID NO 56
<211> LENGTH: 35
<212> TYPE: DNA
<213> ORGANISM: Artificial Sequence
<220> FEATURE:
<223> OTHER INFORMATION: Description of Artificial Sequence: Synthetic
primer

<400> SEQUENCE: 56
cggaattcgt cgacttactt tacttttacc tcctc 35

<210> SEQ ID NO 57
<211> LENGTH: 34
<212> TYPE: DNA
<213> ORGANISM: Artificial Sequence
<220> FEATURE:
<223> OTHER INFORMATION: Description of Artificial Sequence: Synthetic
primer

<400> SEQUENCE: 57
cccccgggta ccatggagct agaatcttct ctcc 34

<210> SEQ ID NO 58
<211> LENGTH: 34
<212> TYPE: DNA
<213> ORGANISM: Artificial Sequence
<220> FEATURE:
<223> OTHER INFORMATION: Description of Artificial Sequence: Synthetic
primer

<400> SEQUENCE: 58
cggaattctc gagttaaaag cttttgattg atcc 34

<210> SEQ ID NO 59
<211> LENGTH: 26
<212> TYPE: DNA
<213> ORGANISM: Artificial Sequence
<220> FEATURE:
<223> OTHER INFORMATION: Description of Artificial Sequence: Synthetic
primer

<400> SEQUENCE: 59
tgggatccat atcagaaatg gtgttc 26

<210> SEQ ID NO 60
<211> LENGTH: 30
<212> TYPE: DNA
<213> ORGANISM: Artificial Sequence
<220> FEATURE:
<223> OTHER INFORMATION: Description of Artificial Sequence: Synthetic
primer

<400> SEQUENCE: 60
gggaattcct agtatccatt atctttagtc 30

<210> SEQ ID NO 61
<211> LENGTH: 30
<212> TYPE: DNA
<213> ORGANISM: Artificial Sequence
<220> FEATURE:

-continued

<223> OTHER INFORMATION: Description of Artificial Sequence: Synthetic
      primer

<400> SEQUENCE: 61
ggggatccat ggacccgtct cgtcatactc 30

<210> SEQ ID NO 62
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
gggaattcca ctagtgttct ccgttgtctt c 31

<210> SEQ ID NO 63
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
ggggatccaa tatggagatg gaatcgtcgt tac 33

<210> SEQ ID NO 64
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
gggaattcct tacacgacat tattaatgtt tg 32

<210> SEQ ID NO 65
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
ggggtacctg atcaataatg ggcagtagtg aggg 34

<210> SEQ ID NO 66
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
cggaattcgt cgacgagtta ggcgattgtg atatc 35

<210> SEQ ID NO 67
<211> LENGTH: 35
<212> TYPE: DNA
<213> ORGANISM: Artificial Sequence
<220> FEATURE:
<223> OTHER INFORMATION: Description of Artificial Sequence: Synthetic -continued primer

<400> SEQUENCE: 67
cgggatccgg taccatgcat atcacaaaac cacac 35

<210> SEQ ID NO 68
<211> LENGTH: 35
<212> TYPE: DNA
<213> ORGANISM: Artificial Sequence
<220> FEATURE:
<223> OTHER INFORMATION: Description of Artificial Sequence: Synthetic
primer

<400> SEQUENCE: 68
cggaattcgc tagctaagca ccacgtgaca agtcc 35

<210> SEQ ID NO 69
<211> LENGTH: 35
<212> TYPE: DNA
<213> ORGANISM: Artificial Sequence
<220> FEATURE:
<223> OTHER INFORMATION: Description of Artificial Sequence: Synthetic
primer

<400> SEQUENCE: 69
cgggatccgg taccatgagt agtgatcctc atcgt 35

<210> SEQ ID NO 70
<211> LENGTH: 35
<212> TYPE: DNA
<213> ORGANISM: Artificial Sequence
<220> FEATURE:
<223> OTHER INFORMATION: Description of Artificial Sequence: Synthetic
primer

<400> SEQUENCE: 70
cgggatccga attctacgag gtaaactctt ctatg 35

<210> SEQ ID NO 71
<211> LENGTH: 35
<212> TYPE: DNA
<213> ORGANISM: Artificial Sequence
<220> FEATURE:
<223> OTHER INFORMATION: Description of Artificial Sequence: Synthetic
primer

<400> SEQUENCE: 71
cgggatccgg taccatgcat atcacaaaac cacac 35

<210> SEQ ID NO 72
<211> LENGTH: 33
<212> TYPE: DNA
<213> ORGANISM: Artificial Sequence
<220> FEATURE:
<223> OTHER INFORMATION: Description of Artificial Sequence: Synthetic
primer

<400> SEQUENCE: 72
cggaattcgt cgacctaagc accacgtccc aag 33

<210> SEQ ID NO 73
<211> LENGTH: 34
<212> TYPE: DNA
<213> ORGANISM: Artificial Sequence
<220> FEATURE:
<223> OTHER INFORMATION: Description of Artificial Sequence: Synthetic
primer -continued

```
<400> SEQUENCE: 73

gggtgatcag gtaccatggg gaagcaagaa gatg                              34


<210> SEQ ID NO 74
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74

cggaattcgt cgactactta cttatagaaa cgccg                             35


<210> SEQ ID NO 75
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75

gaagatctgg taccatggcg aagcagcaag aag                               33


<210> SEQ ID NO 76
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76

cggaattcgt cgaccgatca aagcccatct atg                               33
```